United States Patent
Nowak et al.

(10) Patent No.: US 11,505,560 B2
(45) Date of Patent: Nov. 22, 2022

(54) HETEROBIFUNCTIONAL COMPOUNDS WITH IMPROVED SPECIFICITY

(71) Applicant: DANA-FARBER CANCER INSTITUTE, INC., Boston, MA (US)

(72) Inventors: Radoslaw P. Nowak, Boston, MA (US); Eric S. Fischer, Newton, MA (US); Nathanael S. Gray, Boston, MA (US); Tinghu Zhang, Brookline, MA (US); Zhixiang He, Brookline, MA (US); Brian Groendyke, Chestnut Hill, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 16/755,502

(22) PCT Filed: Oct. 19, 2018

(86) PCT No.: PCT/US2018/056680
§ 371 (c)(1),
(2) Date: Apr. 10, 2020

(87) PCT Pub. No.: WO2019/079701
PCT Pub. Date: Apr. 25, 2019

(65) Prior Publication Data
US 2021/0130368 A1 May 6, 2021

Related U.S. Application Data

(60) Provisional application No. 62/575,156, filed on Oct. 20, 2017.

(51) Int. Cl.
| | | |
|---|---|---|
| *C07D 495/14* | (2006.01) |
| *C07D 487/04* | (2006.01) |
| *A61K 47/55* | (2017.01) |
| *A61P 35/00* | (2006.01) |
| *C07D 211/56* | (2006.01) |
| *C07D 401/04* | (2006.01) |
| *C07D 401/12* | (2006.01) |

(52) U.S. Cl.
CPC ............ *C07D 495/14* (2013.01); *A61K 47/55* (2017.08); *A61P 35/00* (2018.01); *C07D 211/56* (2013.01); *C07D 401/04* (2013.01); *C07D 401/12* (2013.01); *C07D 487/04* (2013.01)

(58) Field of Classification Search
CPC ............................ C07D 487/04; C07D 495/14
See application file for complete search history.

(56) References Cited

U.S. PATENT DOCUMENTS

2015/0291562 A1* 10/2015 Crew ................. A61P 9/00
424/94.3

FOREIGN PATENT DOCUMENTS

| WO | 2016105518 A1 | 6/2016 |
| WO | 2017007612 A1 | 1/2017 |
| WO | 2017197056 A1 | 11/2017 |

OTHER PUBLICATIONS

PubChem CID 118912829—National Center for Biotechnology Information. PubChem Compound Summary for CID 118912829. https://pubchem.ncbi.nlm.nih.gov/compound/118912829. Accessed Jun. 10, 2021, create date Apr. 9, 2016. (Year: 2016).*

* cited by examiner

*Primary Examiner* — Laura L Stockton
(74) *Attorney, Agent, or Firm* — Burns & Levinson, LLP; Daniel W. Clarke; Shawn P. Foley

(57) ABSTRACT

Disclosed are heterobifunctional compounds that effectuate selective degradation of a target protein, and which include a targeting ligand that binds a target protein and at least one other protein, a ligand that binds an E3 ubiquitin ligase or a component of E3 ubiquitin ligase, and a specificity modulating linker that links the first ligand and the second ligand. Pharmaceutical compositions containing the compounds, and methods of using and making the compounds are also disclosed.

16 Claims, 63 Drawing Sheets

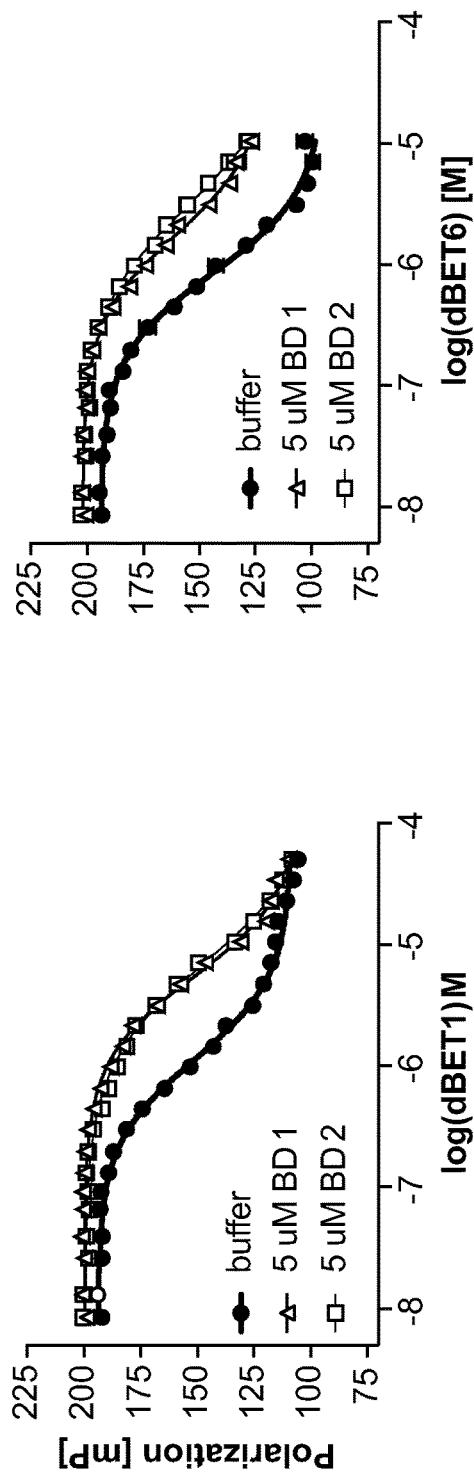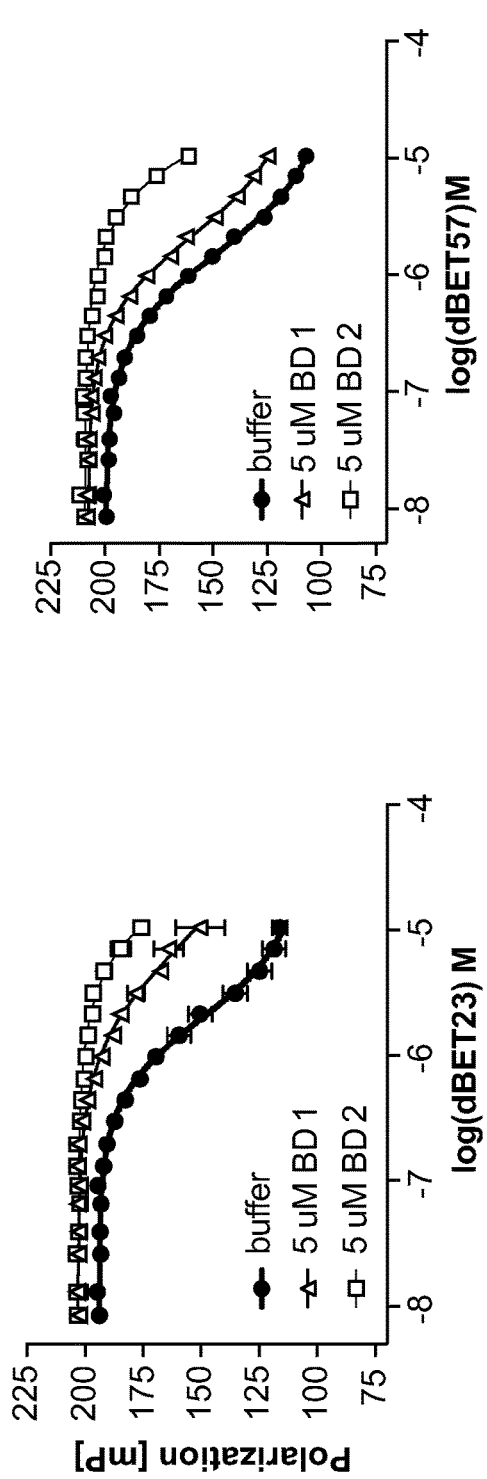
FIG. 2C
FIG. 2D
FIG. 2E
FIG. 2F

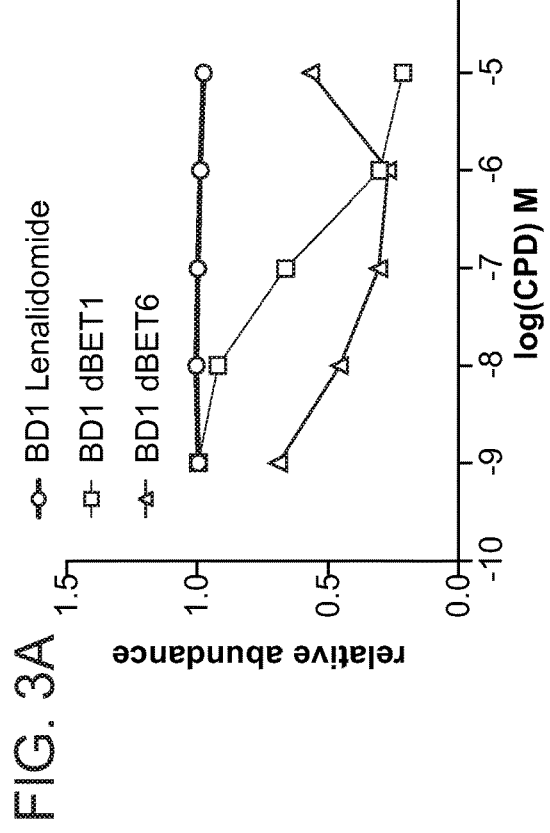
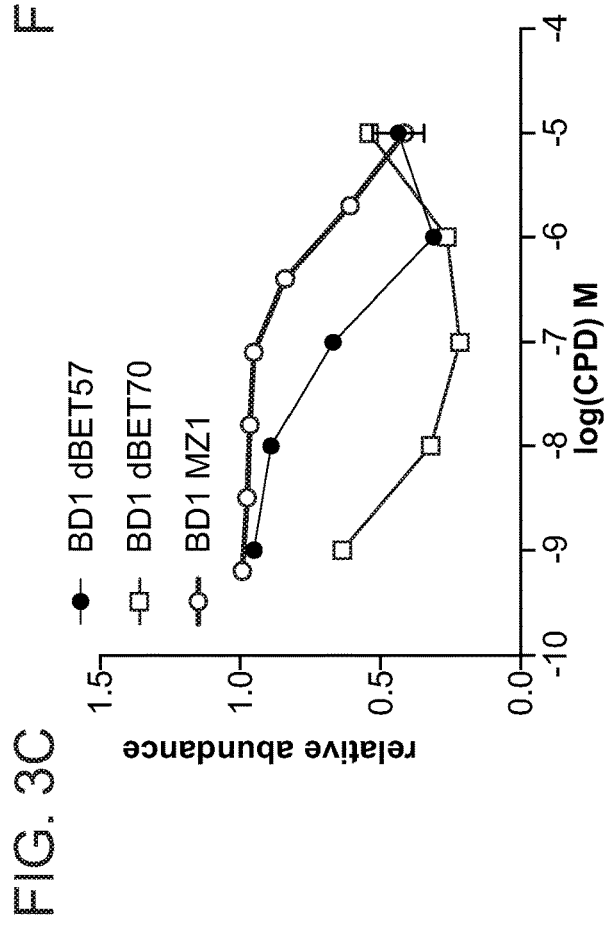
FIG. 3A, FIG. 3B, FIG. 3C, FIG. 3D dBET57

Cluster 19
N=7

ZXH-3-26

| | | |
|---|---|---|
| BRD2 (BD1) | 91-16 | SEQ ID NO: 1 |
| BRDT (BD1) | 44-11 | SEQ ID NO: 2 |
| BRD3 (BD1) | 51-12 | SEQ ID NO: 3 |
| BRD4 (BD1) | 75-14 | SEQ ID NO: 4 |
| BRD2 (BD2) | 364-4 | SEQ ID NO: 5 |
| BRDT (BD2) | 287-3 | SEQ ID NO: 6 |
| BRD3 (BD2) | 326-3 | SEQ ID NO: 7 |
| BRD4 (BD2) | 368-4 | SEQ ID NO: 8 |

| | | |
|---|---|---|
| BRD4 (BD1) | 75-14 | SEQ ID NO: 9 |
| BRD4 (BD2) | 368-4 | SEQ ID NO: 10 |

BD1 — A — BD2 — B — ET SEED — CTM dBET6

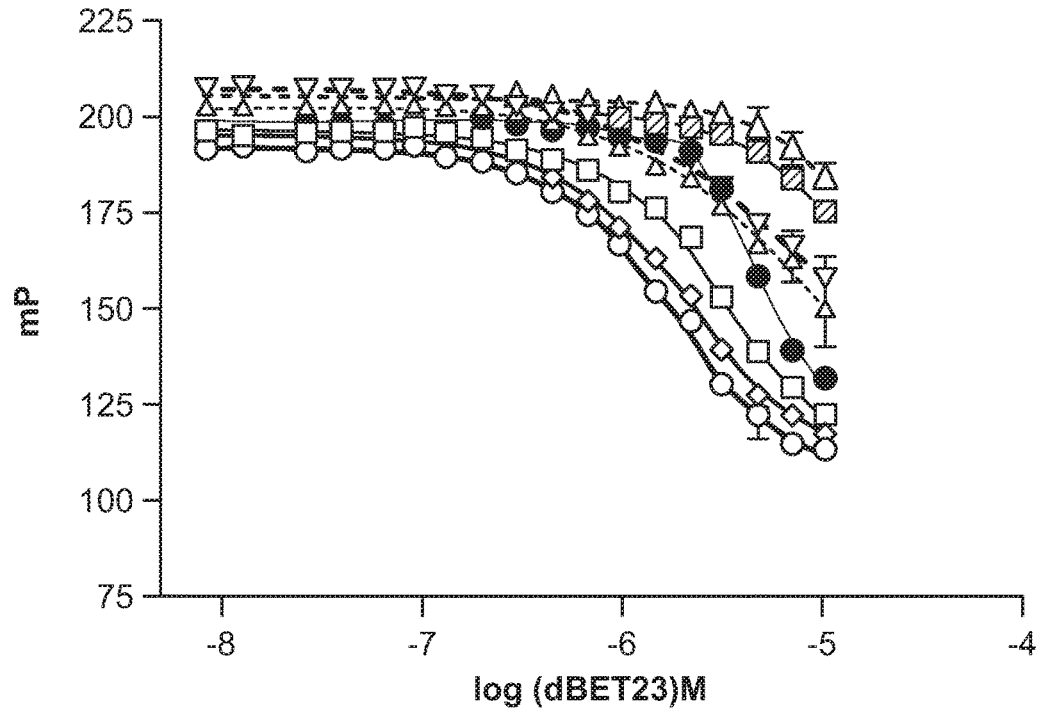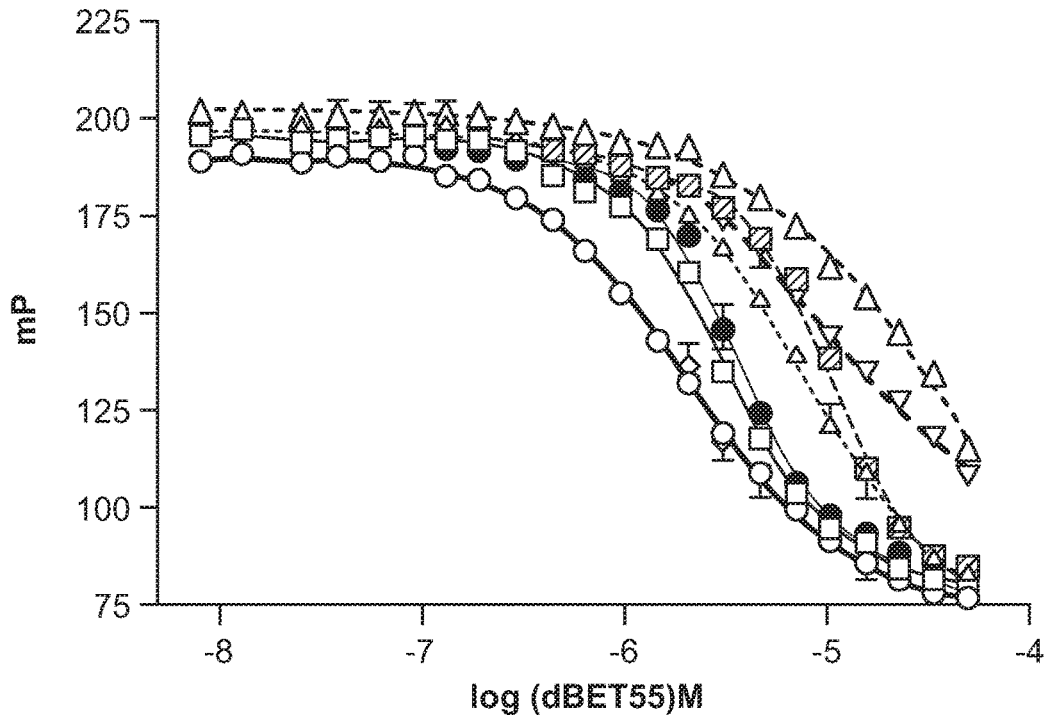

|  | dBET1 | dBET6 | dBET23 | dBET55 | dBET57 |
|---|---|---|---|---|---|
| BD1 $\alpha_{app}$ | 0.2 | 0.6 | 0.4 | 0.2 | 0.8 |
| BD2 $\alpha_{app}$ | 0.1 | 0.1 | < 0.1 | 0.2 | < 0.1 |

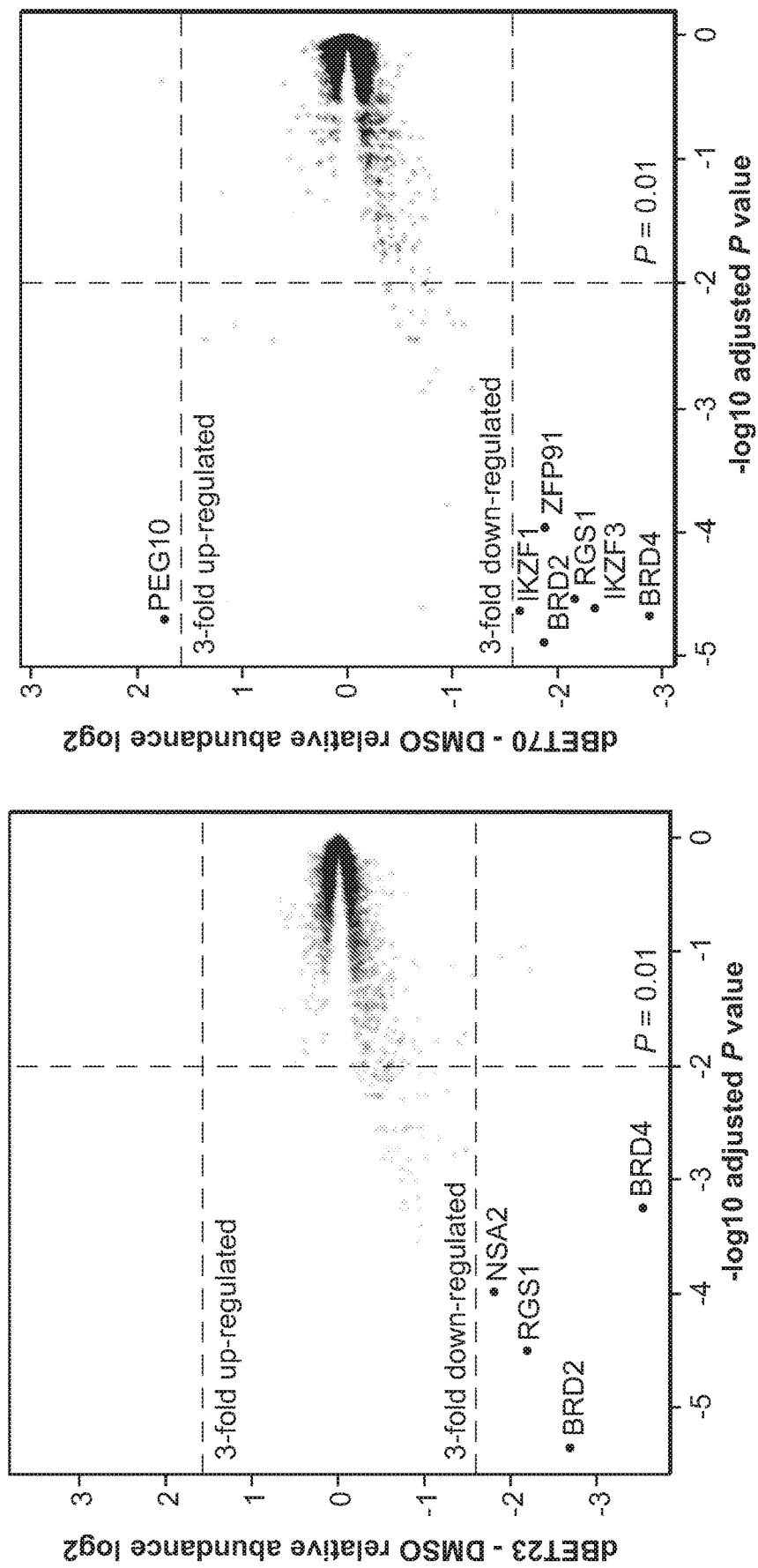

FIG. 16I ZXH-3-26

FIG. 16K ZXH-3-82

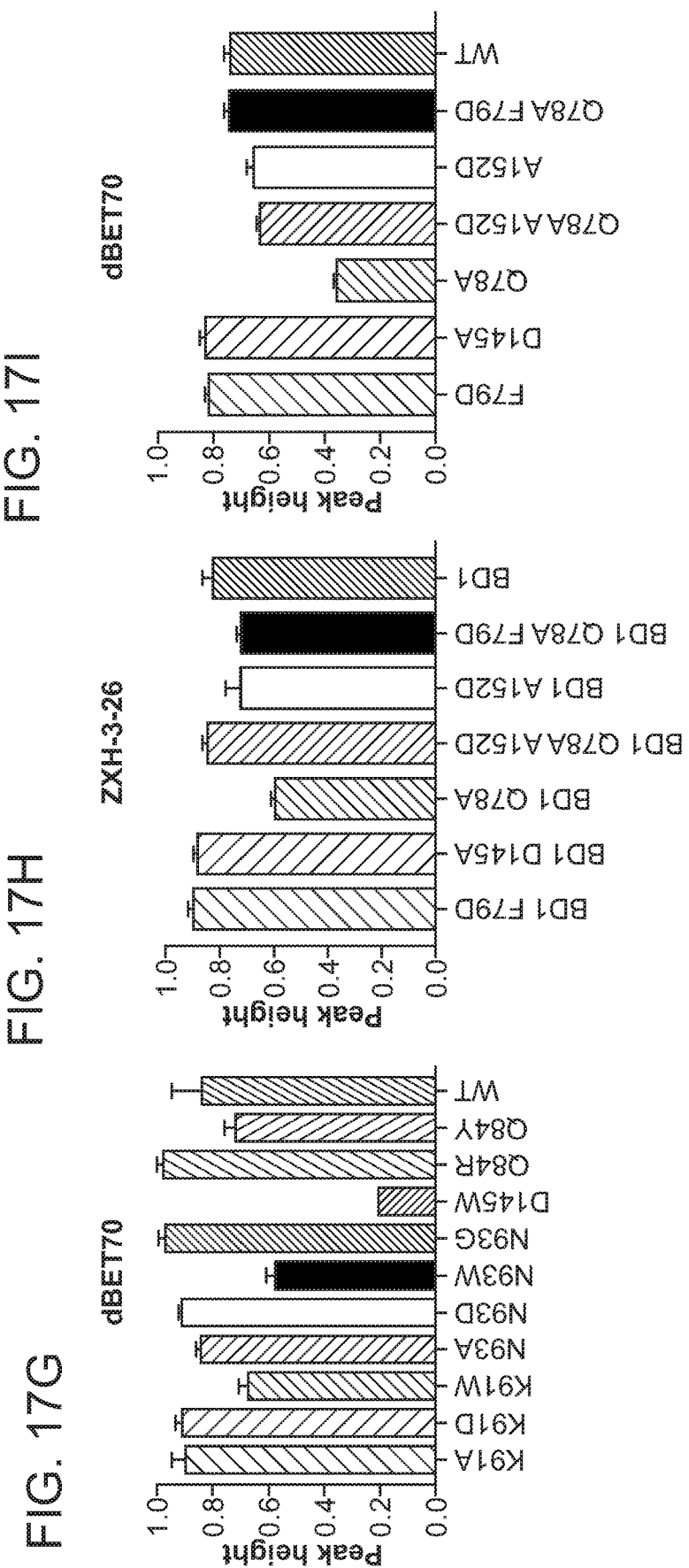

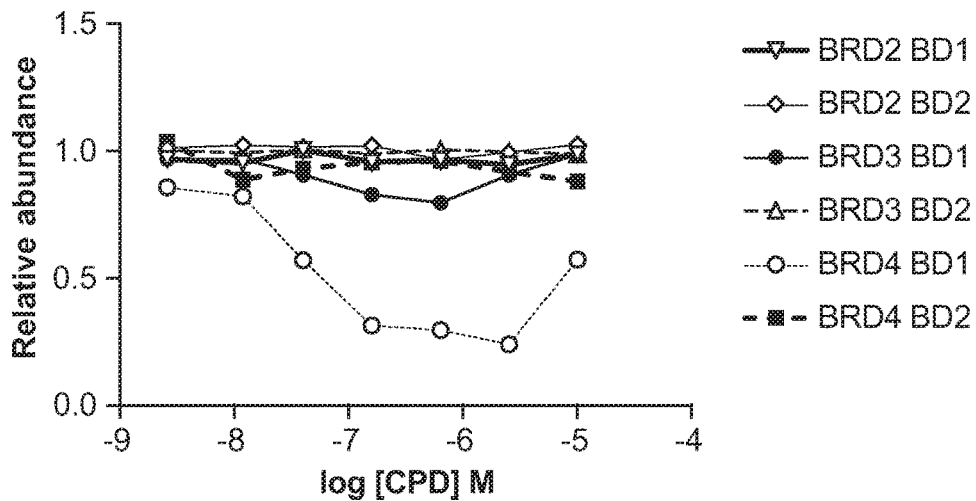
FIG. 19A  BJG-02-030
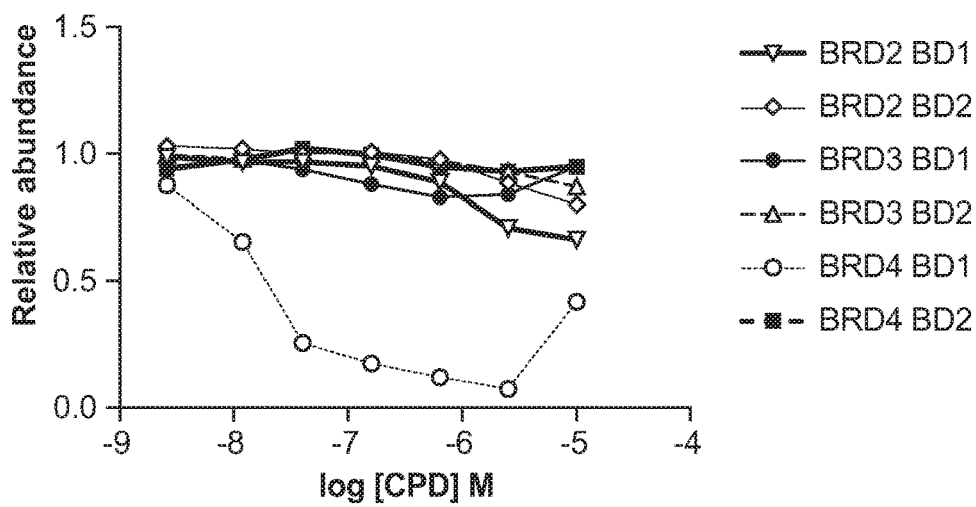
FIG. 19B  BJG-02-119
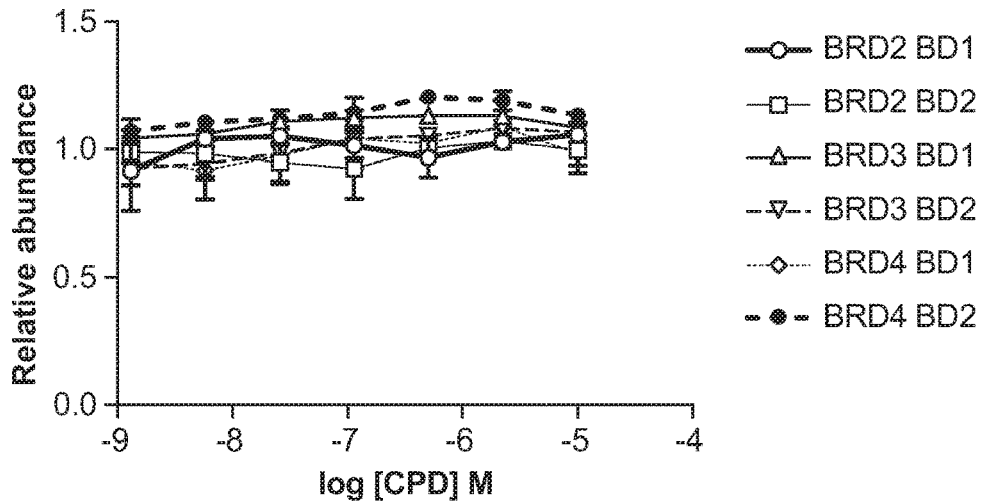
FIG. 19C  BSJ-02-174

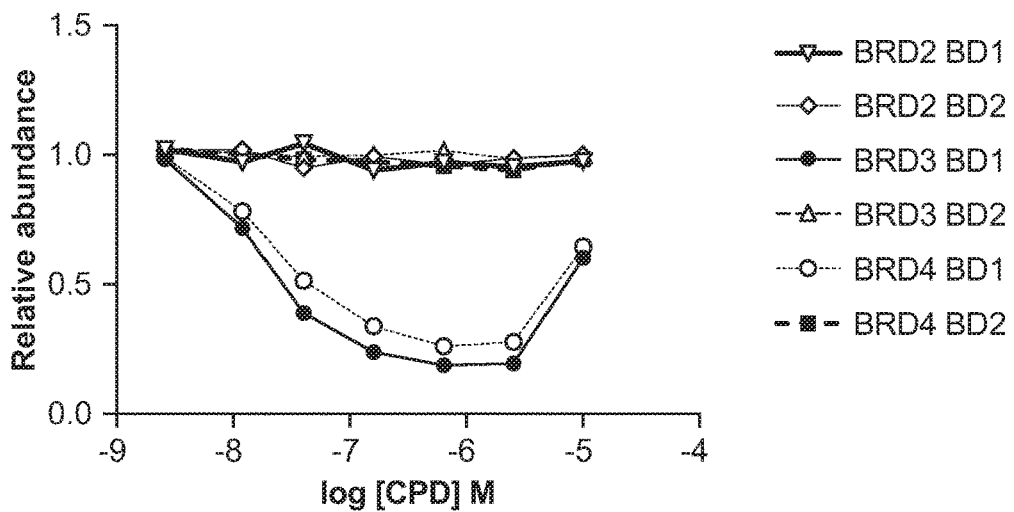
FIG. 19D  ZXH-3-52
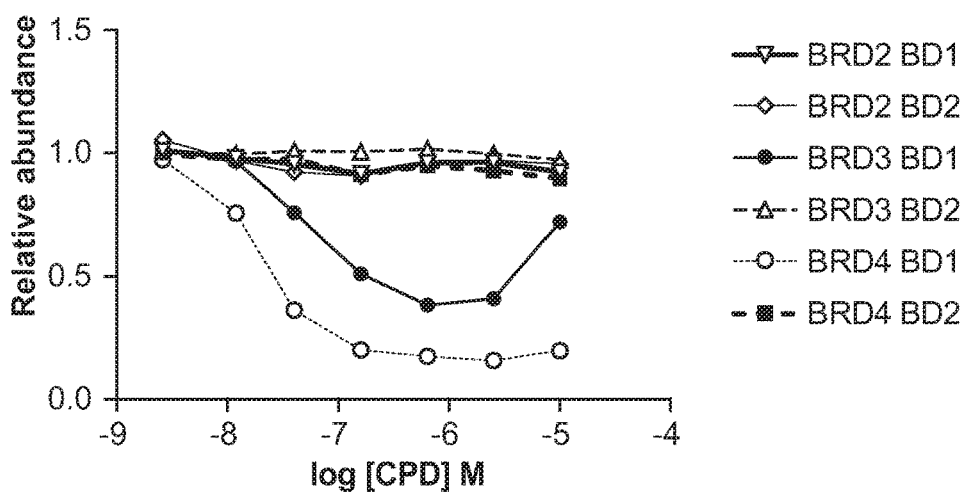
FIG. 19E  ZXH-3-195
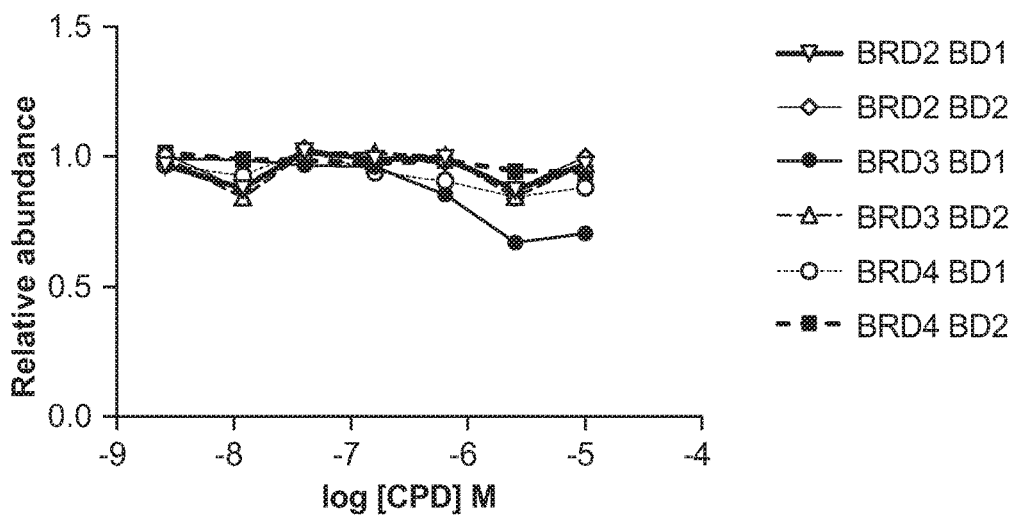
FIG. 19F  ZXH-3-28

HETEROBIFUNCTIONAL COMPOUNDS WITH IMPROVED SPECIFICITY

RELATED APPLICATIONS

This application is a national stage application, filed under 35 U.S.C. § 371, of International Application No. PCT/US2018/056680, filed Oct. 19, 2018, which claims the benefit of priority under 35 U.S.C. § 119(e) to U.S. Provisional Application No. 62/575,156, filed Oct. 20, 2017, each of which is incorporated herein by reference in its entirety.

GOVERNMENT LICENSE RIGHTS

This invention was made with government support under grant number R01 CA214608 awarded by the National Institutes of Health. The government has certain rights in the invention.

FIELD OF THE INVENTION

The present invention generally relates to heterobifunctional small molecule compounds (also known as PROTACs), and more specifically to heterobifunctional small molecule degraders that can degrade a target protein with high levels of specificity.

BACKGROUND OF THE INVENTION

While long sought after, rational design of synthetic chemical matter that is capable of inducing selective protein dimerization has remained challenging. Significant progress has recently been made towards chemically induced targeted protein degradation using heterobifunctional compounds also known as degraders or PROTACs (PROteolysis-TArgeting Chimeras) (Bondeson et al., 2015; Buckley et al., 2015; Gadd et al., 2017; Gustafson et al., 2015; Kenten & Roberts, 2001; J. Lu et al., 2015; Sakamoto et al., 2001; Winter et al., 2015). Targeted protein degradation refers to small molecule induced ubiquitination and degradation of disease targets, in which the small molecule simultaneously recruits both a ubiquitin E3 ligase and the target protein into close proximity of each other which leads to ubiquitination of the target protein. Clinical proof of concept for targeted protein degradation is provided by the recent discovery that the potent anti-cancer drugs thalidomide, lenalidomide and pomalidomide (collectively known as IMiDs) exert their thersapeutic effects through induced degradation of key efficacy targets, such as IKZF1, IKZF3, ZFP91, or casein kinase 1 alpha (Ck1α) (An et al., 2017; Kronke et al., 2015; G. Petzold, Fischer, & Thoma, 2016). IMiDs bind cereblon (CRBN), the substrate receptor of the E3 ubiquitin ligase, and act by redirecting the activity of the CRL4$^{CRBN}$ ligase to ubiquitinate the proteins targeted for degradation. (Chamberlain et al., 2014; Fischer et al., 2014; Ito et al., 2010); G. Petzold et al., 2016).

PROTACs (or degraders) typically contain an E3 ligase binding scaffold (E3-moiety), which is often an analogue of thalidomide (which bind to the E3 ubiquinase known as cereblon), or a ligand to the von Hippel-Lindau tumor suppressor (VHL) protein (Buckley et al., 2012), which is attached via a linker to another small molecule (target-moiety) that binds a target protein of interest (FIG. 1A and FIGS. 7A and B). Recruitment of the target protein to the E3 ubiquitin ligase facilitates ubiquitination and subsequent degradation of the target protein (Raina & Crews, 2017). This principle has been successfully applied to several targets including the Bromodomain and Extra Terminal (BET) family (BRD2, BRD3, BRD4), RIPK2, BCR-ABL, FKBP12, BRD9, and ERRa Thus, PROTACs constitute a promising new pharmacologic modality and is being widely explored in chemical biology and drug discovery. (Bondeson et al., 2015; Lai et al., 2016; J. Lu et al., 2015; Raina et al., 2016; Remillard et al., 2017; Toure & Crews, 2016; Winter et al., 2015).

However, among other issues, the selectivity of degraders for target proteins can be unpredictable. For example, MZ1 which is a PROTAC that contains a VHL-ligand linked to the BRD4 ligand JQ1, showed complexation not only with the second bromodomain of BRD4 (BRD4$_{BD2}$) but also with the second bromodomains of the homologous BET proteins BRD2 and BRD3. It remains to be seen if PROTACs that target BRD4 for degradation via recruitment of cereblon exhibit similar binding profiles. Based upon these current limitations, there remains a need for heterobifunctional compounds (PROTACs) that can selectively degrade a target protein to the substantial exclusion of other homologous proteins.

SUMMARY OF THE INVENTION

A first aspect of the present invention provides a heterobifunctional compound that selectively degrades a target protein. The heterobifunctional compounds of the present invention are represented by Formula (I):

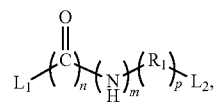

wherein n is 0 or 1; m is 0 or 1; p is 0 or 1; and R$_1$ is an ether, an alkyl ether, an alkyl amine, C$_1$ alkyl, C$_2$ alkyl, C$_3$ alkyl, C$_4$ alkyl, C$_5$ alkyl, C$_6$ alkyl, or a 5- or 6-member cyclic group; wherein L$_1$ binds a target protein and at least one other protein; and wherein L$_2$ binds an E3 ubiquitin ligase, or a pharmaceutically acceptable salt, ester or stereoisomer thereof. In some embodiments, the at least one other protein to which L$_1$ binds has a high sequence identity with the target protein. In some embodiments, the at least one other protein to which L$_1$ binds is homologous to the target protein.

The heterobifunctional compounds enable selective ubiquitin-mediated degradation of the target protein relative to the at least one other protein to which L$_1$ binds, regardless of whether L$_1$ binds to the at least one other protein with equal, greater or lesser affinity. Thus, the inventive heterobifunctional compounds may be useful in selectively degrading a specific protein that is implicated in a disease or condition. In some embodiments, the at least one other protein to which L$_1$ binds is left substantially non-degraded.

In some embodiments, the heterobifunctional compound includes a targeting ligand L$_1$ that binds bromodomain protein BRD4 (e.g., to the first and/or second bromodomains of BRD4) and to at least one other protein which is BRD3 and/or BDR2 with similar affinity, but enables the selective degradation of BRD4. In some embodiments, the targeting ligand binds the bromodomain proteins BRD2, BRD3, and BRD4 with substantially equal affinity, yet the heterobifunctional compound selectively degrades BRD4. In some embodiments, the targeting ligand is JQ1 or an analog thereof.

A second aspect of the invention provides a pharmaceutical composition comprising an effective amount of the heterobifunctional compound, or a pharmaceutically acceptable salt, ester or stereoisomer thereof.

In various aspects, the invention provides a method of treating a subject having a disease or disorder mediated by dysfunctional or dysregulated protein function, comprising administering to a subject in need thereof the heterobifunctional compound which targets the dysfunctional or dysregulated protein.

In various aspects, the invention provides a method of selectively degrading a target protein by contacting a cell with the heterobifunctional compound under conditions and for a period of time sufficient to result in selective degradation of the target protein.

BRIEF DESCRIPTION OF THE DRAWINGS

FIG. 2A-FIG. 2F show data demonstrating that dBET mediated BRD4 recruitment is governed by negative cooperativity. All data in FIG. 2A, FIG. 2C, and FIG. 2D represent biological replicates presented as means±s.d. (n=3).

FIG. 2A is a bar graph that shows TR-FRET data where dBET23 is titrated to DDB1ΔB-CRBN$_{SPY-BODIPY}$, Terbium-Streptavidin and various BRD4$_{BD1-biotin}$ wild type and mutant proteins. The mean peak heights for dose response curves of three independent replicates are shown as bar charts.

FIG. 2B is an image that shows surface representation of CRBN highlighting the residues involved in dBET23 mediated BRD4$_{BD1}$ binding in orange.

FIG. 2C is a graph that shows competitive binding assay for dBET1 binding to DDB1ΔB-CRBN. Increasing concentrations of dBET1 titrated to preformed DDB1ΔB-CRBN-lenalidomide$_{Atto565}$ complex in presence or absence of BRD4$_{BD1}$ or BRD4$_{BD2}$ are shown.

FIG. 2D-FIG. 2F are graphs that show similar competitive assays for dBET6, dBET23 and dBET57, respectively.

FIG. 3A-FIG. 3F are graphs that show quantitative assessment of cellular degradation for BRD4$_{BD1}$ and BRD4$_{BD2}$. Data in FIG. 3A-FIG. 3F represent four biological replicates analyzed in technical duplicates with 5000 cells each, and presented as the means±s.d.

FIG. 3A-FIG. 3C are graphs that show quantitative assessment of cellular degradation using a BRD4$_{BD1}$-EGFP reporter assay. Cells stably expressing BRD4$_{BD1}$-EGFP and mCherry were treated with increasing concentrations of lenalidomide, dBET1, dBET6, dBET23, dBET55, dBET57, dBET70, and MZ1 and the EGFP and mCherry signals followed using flow cytometry analysis.

FIG. 3D-FIG. 3F are graphs that show quantitative assessment of cellular degradation using a BRD4$_{BD2}$-EGFP reporter assay. Cells stably expressing BRD4$_{BD2}$-EGFP and mCherry were treated with increasing concentrations of dBET1, dBET6, dBET23, dBET55, dBET57, dBET70, MZ1 and lenalidomide. EGFP and mCherry signals were measured using flow cytometry analysis.

FIG. 4A is a bar graph that shows TR-FRET data where dBET23 is titrated to BRD4$_{BD1}$-SPYCATCHER-BODIPY, Terbium-antiHis antibody and various His6-DDB1ΔB-CRBN wild type and His6-DDB1-CRBN mutant proteins. The mean peak heights for dose response curves of three independent replicates are shown as bar charts.

FIG. 4B is a bar graph that shows TR-FRET data where dBET23 is titrated to DDB1ΔB-CRBN$_{SPYCATCHER-BODIPY}$, Terbium-Streptavidin and various BRD4$_{BD1-biotin}$ wild type and mutant proteins. The mean peak heights for dose response curves of three independent replicates are shown as bar charts.

FIG. 4C is a bar graph that shows TR-FRET data where dBET57 is titrated to BRD4$_{BD1}$-SPYCATCHER-BODIPY, Terbium-antiHis antibody and various His6-DDB1ΔB-CRBN wild type and His6-DDB1-CRBN mutant proteins.

FIG. 4D is a bar graph that shows TR-FRET data where dBET57 is titrated to DDB1ΔB-CRBN$_{SPYCATCHER-BODIPY}$, Terbium-Streptavidin and various BRD4$_{BD1-biotin}$ wild type and mutant proteins. Data in FIG. 4A-FIG. 4D represent biological replicates presented as means±s.d. (n=3).

FIG. 4E is an image that shows the chemical structure of dBET57 with the target-moiety in red, the linker in black and green, and the E3-moiety in blue.

FIG. 4F is an image that shows a cartoon representation of DDB1ΔB-CRBN-dBET57-BRD4$_{BD1}$: DDB1 highlighting domains BPA (red), BPC (orange) and DDB1-CTD (grey); CRBN with domains NTD (blue), HBD (cyan) and CTD (green); BRD4$_{BD1}$ (magenta). The Zn$^{2+}$-ion is drawn as a grey sphere. dBET57 was not modelled in this structure but instead superpositions of lenalidomide (from pdb: 5fqd) and JQ1 (from pdb: 3mxf) are shown in yellow sticks.

FIG. 4G is an image that shows superposition of CRBN and BRD4$_{BD1}$ for the dBET23 and dBET57 containing complexes. Superposition was carried out over the CRBN-CTD (residues 320-400).

FIG. 4H is an image that shows surface representation of CRBN highlighting the BRD4$_{BD1}$ interacting residues for the dBET57 mediated recruitment in orange.

FIG. 5A is an image of an interface RMSD that shows symmetric docking energy landscape for the binding of BRD4$_{BD1}$ to a CRBN-lenalidomide complex. The two low energy decoys that exhibit a conformation compatible with dBET binding are indicated by bold numbers. The symmetric docking energy landscape for local perturbation docking experiments on decoy 12662 compatible with dBET mediated binding is shown as insert.

FIG. 5B is an image that shows superposition of the DDB1ΔB-CRBN-dBET23-BRD4$_{BD1}$ structure and the top solution from local perturbation of decoy 12662.

FIG. 5C is an image that shows cartoon representations of three representative clusters from the global docking run.

FIG. 6A is an image that shows a cartoon representation of structures from cluster 19, and close-up view highlighting the proximity of the JQ1 analog and lenalidomide that provided the rationale for synthesizing the heterobifunctional small molecule degrader ZXH-03-26, which is shown in FIG. 6B.

FIG. 6C is a graph that shows quantitative assessment of cellular degradation using a EGFP/mCherry reporter assay. Cells stably expressing BRD4$_{BD1}$-EGFP (or constructs harbouring BRD2$_{BD1}$, BRD2$_{BD2}$, BRD3$_{BD1}$, BRD3$_{BD2}$, BRD4$_{BD2}$) and mCherry were treated with increasing concentrations of ZXH-03-26 and the EGFP and mCherry signals followed using flow cytometry analysis.

FIG. 6D-FIG. 6F are graphs that show quantitative assessment of cellular degradation using a EGFP/mCherry reporter assay. Cells stably expressing BRD4$_{BD1}$-EGFP (or constructs harbouring BRD2$_{BD1}$, BRD2$_{BD2}$, BRD3$_{BD1}$, BRD3$_{BD2}$, BRD4$_{BD2}$) and mCherry were treated with increasing concentrations dBET6 (FIG. 6D), MZ1 (FIG. 6E), and dBET57 (FIG. 6F).

FIG. 6G are immunoblots that demonstrate cellular degradation of endogenous BRD4 in HEK293T cells that were treated with increasing concentrations of ZXH-03-26 or dBET6 for 5 hours.

FIG. 6H s are immunoblots that show degradation of BRD2 and BRD3 by compounds dDEBT6 and ZXH-03-26.

In FIGS. 8A-C, DDB1 is shown in grey, CRBN in blue, and BRD4$_{BD1}$ (wildtype and mutant) in magenta.

FIG. 9A-FIG. 9H show data demonstrating negative cooperativity governing CRBN-dBET-BRD4 interactions.

FIG. 9A is an image that shows a schematic of fluorescence polarization based CRBN binding assay. Atto565-Lenalidomide fluorophore is displaced by PROTAC bound BRD4$_{BD1/2}$.

FIG. 9B is a graph that shows fluorescence polarization competitive binding assay for dBET55 binding to DDB1ΔB-CRBN. Increasing concentrations of dBET55 titrated to preformed DDB1ΔB-CRBN-lenalidomide$_{Atto565}$ complex in presence or absence of BRD4$_{BD1}$ or BRD4$_{BD2}$.

FIG. 9C-FIG. 9G are graphs that show fluorescence polarization competitive binding assay for dBET1, dBET6, dBET23, dBET55, and dBET57, respectively, to DDB1ΔB-CRBN with increasing concentrations of dBETs titrated to preformed DDB1ΔB-CRBN-lenalidomide$_{Atto565}$ complex in presence or absence of BRD4$_{BD1}$ or BRD4$_{BD2}$ at concentrations of 1 µM, 5 µM, and 20 µM. The data at 5 µM BRD4$_{BD1/2}$ was replotted for FIGS. 2C-F and FIG. 9B.

FIG. 9H is a table that shows summary of apparent cooperativity factors $α_{app}$.

FIG. 11A is an image that shows the different surfaces CRBN utilizes to interact with a variety with neo-substrates as illustrated by the superposition of DDB1ΔB-CRBN-dBET23-BRD4$_{BD1}$, DDB1ΔB-CRBN-lenalidomide-Ck1α (PDB entry 5fqd), and DDB1-CRBN-CC885-GSPT1 (PDB entry 5hxb). A close-up of the common hydrophobic interface between GSPT1-CRBN-NTD and BRD4$_{BD1}$-CRBN-NTD is shown in the top right box.

FIG. 11B is a graph that shows a competitive binding assay where titrating BRD4$_{BD1}$ or BRD4$_{BD2}$ into a preformed complex of DDB1-CRBN-dBET57-IKZF1Δ demonstrated mutually exclusive binding of BRD4 with neosubstrates such as Ck1α or IKZF1/3.

FIG. 11C is an image that shows a surface representation of CRBN and BRD4$_{BD1}$ of DDB1-CRBN-dBET23-BRD4$_{BD1}$ crystal structure, showing dBET23 as stick representation. The hypothetical linker path from the acid position on JQ1 is shown with red spheres indicating the distance of a carbon-carbon bond and illustrating that the 2-carbon linker of dBET57 would be insufficient to bridge the gap.

FIG. 11D is a graph that shows TR-FRET data where dBET6 degrader was titrated to BRD4$_{BD1,SPYCATCHER-BODIPY}$ Terbium-antiHis antibody, and wild type or various mutants of His6-DDB1-His6-CRBN complex. The peak height of the dose response curve for three independent replicates was quantified and is depicted as bar charts. The TR-FRET data in this figure are biological replicates presented as means±s.d. (n=3).

FIG. 11E shows TR-FRET data where dBET6 degrader was titrated to DDB1ΔB-CRBN$_{SPYCATCHER-BODIPY}$, Terbium-Streptavidin and wild type or mutants of BRD4$_{BD1-biotin}$. The peak height of the dose response curve for three independent replicates was quantified and is depicted as bar charts. The TR-FRET data in this figure are biological replicates presented as means±s.d. (n=3).

FIG. 11F and FIG. H are graphs that show TR-FRET data where dBET1 and dBET55, respectively, were titrated to $BRD4_{BD1SPYCATCHER-BODIPY}$ Terbium-antiHis antibody, and wild type or various mutants of His6-DDB1-His6-CRBN complex. The peak height of the dose response curve for three independent replicates was quantified and is depicted as bar charts. The TR-FRET data in this figure are biological replicates presented as means±s.d. (n=3).

FIG. 11G and FIG. 11I are graphs that show TR-FRET data where dBET1 and dBET55, respectively, were titrated to $BRD4_{BD1SPYCATCHER-BODIPY}$ Terbium-antiHis antibody, and wild type or various mutants of His6-DDB1-His6-CRBN complex. The peak height of the dose response curve for three independent replicates was quantified and is depicted as bar charts. The TR-FRET data in this figure are biological replicates presented as means±s.d. (n=3).

FIG. 12A is an image that shows a cartoon representation of DDB1-CRBN-dBET57-$BRD4_{BD1}$ complex with the $2F_O$-$F_C$ map contoured at 1.5σ. Domains are coloured as DDB1-BPA (red), DDB1-BPC (orange), DDB1-CTD (grey), CRBN-NTD (blue), CRBN-HBD (cyan), CRBN-CTD (green), and $BRD4_{BD1}$ (magenta).

FIG. 12B is an image that shows anomalous difference map contoured at 4σ shown in green for data collected at the Zn peak showing the position of the Zn in the final model. 2 $F_O$-$F_C$ map is shown as blue mesh.

FIG. 12C is an image that shows $F_O$-$F_C$ map contoured at 3.5σ and shown in green and red, together with 2 $F_O$-$F_C$ map contoured at 1.5σ and shown in blue. Positive difference density is observed for the Thalidomide (Thal) and JQ1 binding sites.

FIG. 13A is an image of an interface RMSD shows symmetric docking energy landscape for the binding of Ck1α to a CRBN-lenalidomide complex. Symmetric docking energy landscape for local perturbation docking experiments on a lowest energy decoy 00689 is shown as an insert.

FIG. 13B is an image that shows superposition of the DDB1ΔB-CRBN-lenalidomide-Ck1α structure (PDB: 5fqd) and the top solution, decoy 0173, from FIG. 13A.

FIG. 13C is an image of an interface RMSD shows symmetric energy docking landscape for the binding of Ck1α to a CRBN-lenalidomide complex. The conformer parameter file for lenalidomide was restricted to a conformer not favorable of Ck1α binding.

FIG. 13D is an image that shows superposition of the DDB1ΔB-CRBN-lenalidomide-Ck1α structure (PDB: 5fqd) and the top solution from FIG. 13C.

FIG. 14A-FIG. 14E show co-degradation of IMiD neo-substrates such as IKZF1/3.

FIG. 14A is a graph that shows TR-FRET data where titration of the indicated molecules to DDB1ΔB-$CRBN_{SPYCATCHER-BODIPY}$, Terbium-streptavidin and $IKZF1\Delta_{biotin}$. Data in this figure are presented as means±s.d. (n=3).

FIG. 14B is a graph that shows quantitative assessment of cellular degradation of an IKZF1-EGFP reporter using flow cytometry analysis. Cells stably expressing IKZF1Δ-EGFP and mCherry were treated with increasing concentrations of the indicated molecules and the EGFP and mCherry signals followed using flow cytometry analysis. Data in this figure are presented as means±s.d. (n=4).

FIG. 14C is an image that shows a model of a CRBN-IKZF1ZnF2 complex (adapted from Petzold et al., 2016) bound to lenalidomide. Potential hydrogen bonds are indicated as dashed lines.

FIG. 14D is a scatter plot that shows the fold changes in relative abundance comparing dBET23 to DMSO control treatment (MM.1s) determined using quantitative proteomics. Negative false discovery rate adjusted P Values are shown on the x-axis and log 2 fold changes on the y-axis. Data shown are three biological replicates measured in a single 10-plex TMT experiment.

FIG. 14E is a scatter plot that shows a similar experiment as FIG. 14D but for dBET70 to DMSO control.

FIG. 15A is a graph that shows selective degradation of BRD4 by ZXH-2-147 using quantitative assessment of cellular degradation using EGFP/mCherry reporter assay. Cells stably expressing $BRD4_{BD1}$-EGFP (or constructs harbouring $BRD2_{BD1}$, $BRD2_{BD2}$, $BRD3_{BD1}$, $BRD3_{BD2}$, $BRD4_{BD2}$) and mCherry were treated with increasing concentrations of ZXH-02-147 and the EGFP and mCherry signals followed using flow cytometry analysis.

FIG. 15B is a graph that shows selective degradation of BRD4 by ZXH-2-184 using the same quantitative assessment as FIG. 15A.

FIG. 15C is a graph that shows a lack of selective degradation of BRD4 by ZXH-3-27 using the same quantitative assessment as FIG. 15A.

FIG. 16A-FIG. 16L shows selective degradation of BRD4 by certain heterobifunctional small molecule degraders.

FIG. 16A, FIG. 16C, FIG. 16E, FIG. 16G, FIG. 16I, and FIG. 16K show chemical structures of ZXH-3-79, ZXH-3-27, ZXH-2-147, ZXH-2-184, ZXH-3-26, and ZXH-3-82.

FIG. 16B, FIG. 16D, FIG. 16F, FIG. 16H, FIG. 16J, and FIG. 16L show degradation of BRD4 by ZXH-3-79, ZXH-3-27, ZXH-2-147, ZXH-2-184, ZXH-3-26, and ZXH-3-82, respectively, via quantitative assessment of cellular degradation using EGFP/mCherry reporter assay. Cells stably expressing $BRD4_{BD1}$-EGFP (or constructs harbouring $BRD2_{BD1}$, $BRD2_{BD2}$, $BRD3_{BD1}$, $BRD3_{BD2}$, $BRD4_{BD1}$, $BRD4_{BD2}$) and mCherry were treated with increasing concentrations of ZXH-03-79 and the EGFP and mCherry signals followed using flow cytometry analysis.

FIG. 17A-FIG. 17I are bar graphs that show TR-FRET data illustrating mutational profiles of various heterobifunctional compounds. TR-FRET data for dBET1 (FIG. 17A), dBET6 (FIG. 17B), dBET23 (FIG. 17.C), dBET55 (FIG. 17D), dBET57 (FIG. 17E), ZXH-3-26 (FIGS. 17F and H) and dBET70 (FIGS. 17G and I) titrated to DDB1ΔB-$CRBN_{SPYCATCHER-BODIPY}$, Terbium-Streptavidin and various $BRD4_{BD1}$-biotin wild type and mutant proteins are shown. The mean peak heights for dose response curves of three independent replicates are shown as bar charts. The TR-FRET data in FIGS. 17A-I represent biological replicates presented as means±s.d. (n=3).

FIG. 19A-FIG. 19G are graphs that show selective degradation of bromodomains by BJG-02-119, BSJ-02-174BJG-02-030, ZXH-3-52, ZXH-3-195, ZXH-3-28, and ZXH-4-28, respectively, via quantitative assessment of cellular degradation using EGFP/mCherry reporter assay. Cells stably expressing $BRD4_{BD1}$-EGFP (or constructs harbouring $BRD2_{BD1}$, $BRD2_{BD2}$, $BRD3_{BD1}$, $BRD3_{BD2}$, $BRD4_{BD1}$, $BRD4_{BD2}$) and mCherry were treated with increasing concentrations of degrader, incubated for 5 h, and the EGFP and mCherry signals followed using cellular imaging-based degradation assay. BSJ-02-119 and BSJ-02-174 n=2, others n=1.

DETAILED DESCRIPTION OF THE INVENTION

Figure 1A:
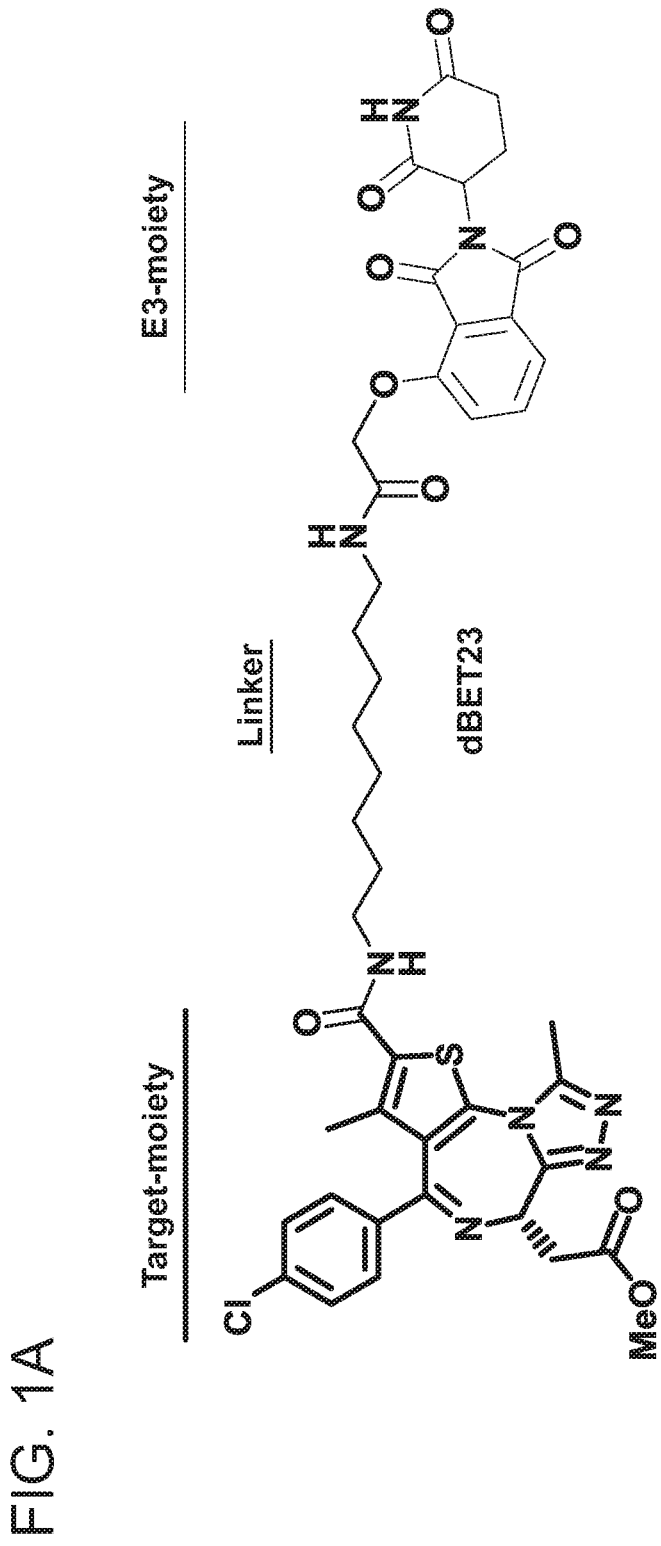
FIG. 1A is an image that shows the chemical structure of dBET23 with the target-moiety in red, the linker in black and green, and the E3-moiety in blue.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to compounds of the present invention, and to the extent the following terms are used herein to further describe them, the following definitions apply.

As used herein, the term "alkyl" refers to a saturated linear or branched-chain monovalent hydrocarbon radical. In one embodiment, the alkyl radical is a C1-C6 group. In other embodiments, the alkyl radical is a C0-C6, C1-C6, C1-C5, C1-C4 or C1-C3 group (wherein C0 alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl. In some embodiments, an alkyl group is a C1-C3 alkyl group. In some embodiments, an alkyl group is a C1-C2 alkyl group.

As used herein, the term "alkylene" refers to a straight or branched divalent hydrocarbon chain linking the rest of the molecule to a radical group, consisting solely of carbon and hydrogen, containing no unsaturation and having from one to 8 carbon atoms, for example, methylene, ethylene, propylene, n-butylene, and the like. The alkylene chain may be attached to the rest of the molecule through a single bond and to the radical group through a single bond. In some embodiments, the alkylene group contains one to 6 carbon atoms (C1-C6 alkylene). In other embodiments, an alkylene group contains one to 5 carbon atoms (C1-C5 alkylene). In other embodiments, an alkylene group contains one to 4 carbon atoms (C1-C4 alkylene). In other embodiments, an alkylene contains one to three carbon atoms (C1-C3 alkylene). In other embodiments, an alkylene group contains one to two carbon atoms (C1-C2 alkylene). In other embodiments, an alkylene group contains one carbon atom (C1 alkylene).

As used herein, the term "ester" is represented by the formula —OC(O)Z1 or —C(O)OZ1, where Z1 may be an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "ether" is represented by the formula Z1OZ2, where Z1 and Z2 can be, independently, an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "carbocyclic" (also "carbocyclyl") refers to a group that used alone or as part of a larger moiety, contains a saturated, partially unsaturated, or aromatic ring system having 5 to 6 carbon atoms, that is alone or part of a larger moiety (e.g., an alkcarbocyclic group). In one embodiment, carbocyclyl includes 5 to 6 carbon atoms (C5-C6). Representative examples of monocyclic carbocyclyls include cyclopentyl and cyclohexyl, 1-cyclohex-1-enyl, 1-cyclohex-2-enyl, 1-cyclohex-3-enyl, cyclohexadienyl and phenyl. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula -Rc-carbocyclyl where Rc is an alkylene chain. The term carbocyclic also embraces carbocyclylalkoxy groups which as used herein refer to a group bonded through an oxygen atom of the formula —O-Rc-carbocyclyl where Rc is an alkylene chain.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or S(O)2). The term heterocyclyl includes mono-, bi-, tri-, fused, bridged, and spiro-ring systems, and combinations thereof. In some embodiments, a heterocyclyl refers to a 5 to 6 membered heterocyclyl ring system. In some embodiments, a heterocyclyl refers to a saturated ring system, such as a 5 to 6 membered saturated heterocyclyl ring system. In some embodiments, a heterocyclyl refers to a heteroaryl ring system, such as a 5 to 6 membered heteroaryl ring system. The term heterocyclyl also includes C5-C6 heterocycloalkyl, which is a saturated or partially unsaturated ring system containing one or more heteroatoms.

In some embodiments, heterocyclyl includes 5-6 membered monocycles. In some embodiments, the heterocyclyl group includes 0 to 3 double bonds. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups.

The term "selective degradation" refers to ubiquitin-mediated degradation of a target protein, where the target protein is degraded to a higher level relative to the at least one other protein to which $L_1$ binds. In some embodiments, the heterobifunctional compound achieves degradation of the target protein with substantially no degradation of the at least one other protein.

The term "binding" as it relates to interaction between the targeting ligand and the target protein, typically refers to an inter-molecular interaction that is substantially specific in that binding of the targeting ligand with other proteins that lack high sequence identity to (e.g., are non-homologous with) the target protein present in the cell is functionally insignificant. The term "high sequence identity" as used herein refers to proteins that share at least about 30%, about 35%, about 40%, about 50%, about 60%, about 70%, about 80%, about 90%, about 95%, or up to less than 100% sequence identity with the target protein. The term "homologous" as used herein refers to a plurality of proteins having a common lineage and which share, at least in a targeting ligand binding portion thereof, a high sequence identity.

The term "binding" as it relates to interaction between the degron and the E3 ubiquitin ligase, typically refers to an inter-molecular interaction that may or may not exhibit an affinity level that equals or exceeds that affinity between the targeting ligand and the target protein, but nonetheless wherein the affinity is sufficient to achieve recruitment of the ligase to the targeted degradation and the selective degradation of the targeted protein.

The term "binding conformation" refers to the spatial relationship between proteins that are bound to each other, and may be represented in terms of shortest path distance between the bound proteins, orientation of one protein with respect to the other protein, inter-molecular interactions (e.g., binding affinity or energy level) between the proteins, identification of amino acid residues that form the inter-molecular bonds between the two proteins, and/or any other information that can represent the spatial relationship between the two proteins in empirical terms.

The term "ligand-induced dimerization" refers to bringing together of two proteins within close proximity to one-another by means of binding each of the two proteins to a ligand, where the two ligands may be part of the same compound (e.g., heterobifunctional compound). The proximity between the two proteins may be sufficient to enable one of the two proteins to functionally act on the other protein (e.g., one protein enzymatically modifying the other protein or degrading the other protein).

The term "homologous proteins" refers to a plurality of proteins that due to their common lineage, share similar amino acid sequences, of at least portions (e.g., functional domains or epitopes) of proteins, where the extent of similarity between the amino acid sequences of the proteins is significantly higher than that the similarity that is expected from two completely unrelated proteins.

The heterobifunctional compounds of the present invention are represented by Formula (I):

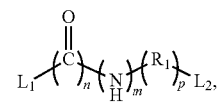

wherein n is 0 or 1; m is 0 or 1; p is 0 or 1; and $R_1$ is an ether, an alkyl ether, an alkyl amine, $C_1$ alkyl, $C_2$ alkyl, $C_3$ alkyl, $C_4$ alkyl, $C_5$ alkyl, $C_6$ alkyl, or a 5- or 6-member cyclic group; wherein $L_1$ binds a target protein and at least one other protein; and wherein $L_2$ binds an E3 ubiquitin ligase or a component of an E3 ubiquitin ligase, or a pharmaceutically acceptable salt, ester or stereoisomer thereof. In some embodiments, the at least one other protein to which $L_1$ binds has a high sequence identity with the target protein. In some embodiments, the at least one other protein to which $L_1$ binds is homologous to the target protein.

The linker has a structure represented by formula (II):

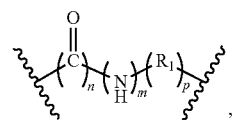

wherein n is 0 or 1; m is 0 or 1; p is 0 or 1; and $R_1$ is an ether (e.g., a polyethylene glycol chain ranging from 1 to 2 ethylene glycol units), an alkyl ether, an alkyl amine, C1-6 alkylene or a 5- to 6-membered carbocyclic or heterocyclic group.

In various embodiments, the linker of formula (II) is represented by any of the following structures:

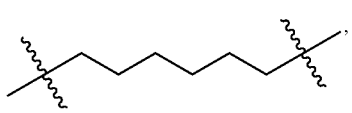

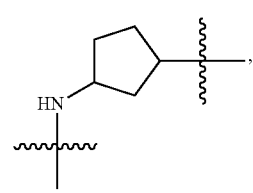

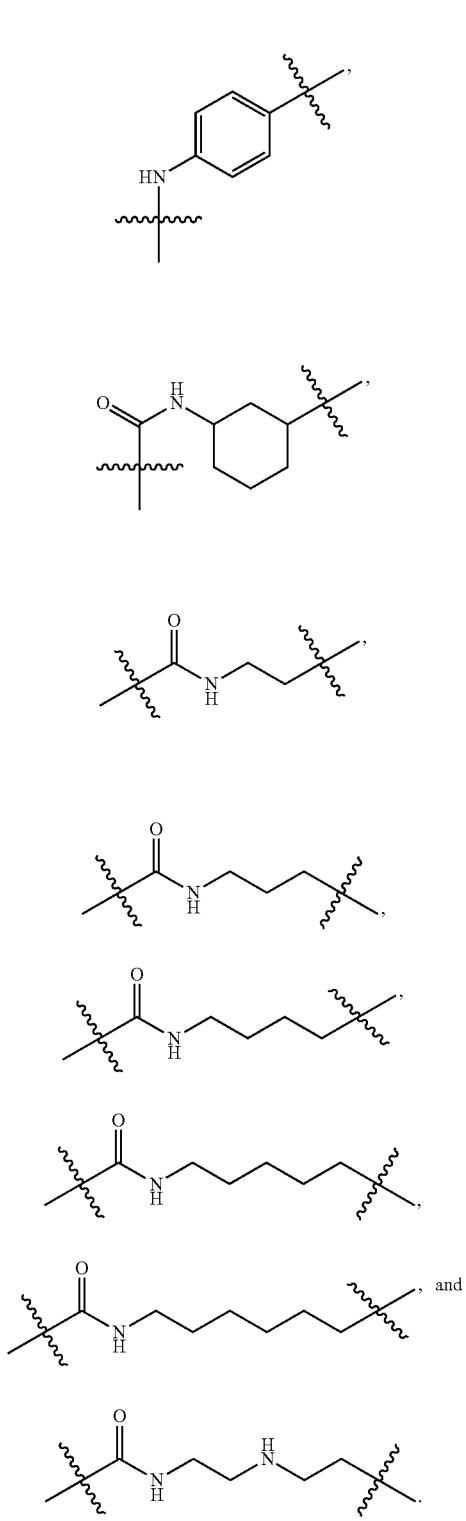
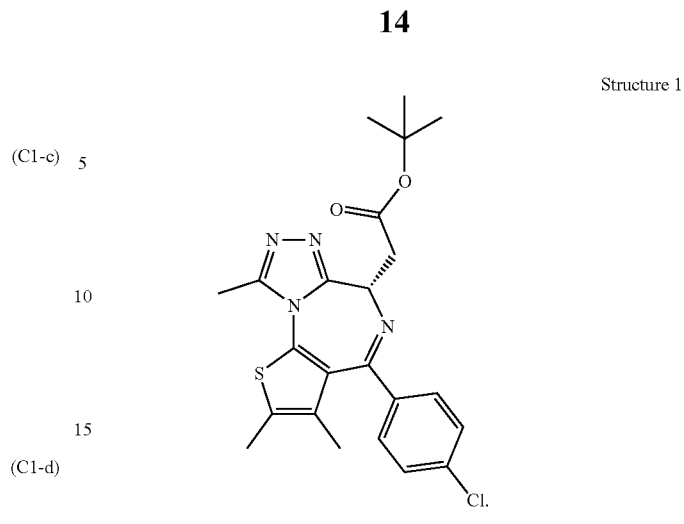
Representative examples of $L_1$ which are analogs of JQ1 have the following structures:
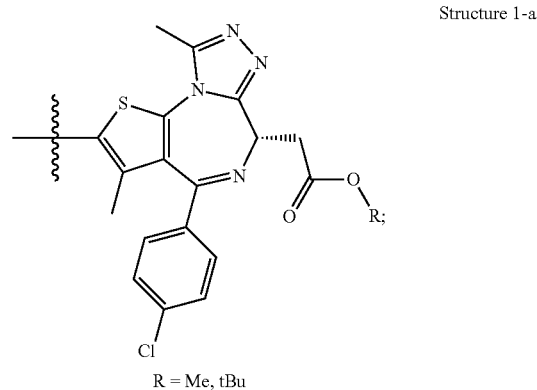
R = Me, tBu
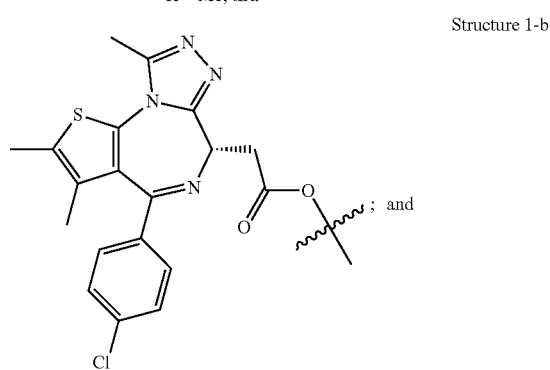
; and
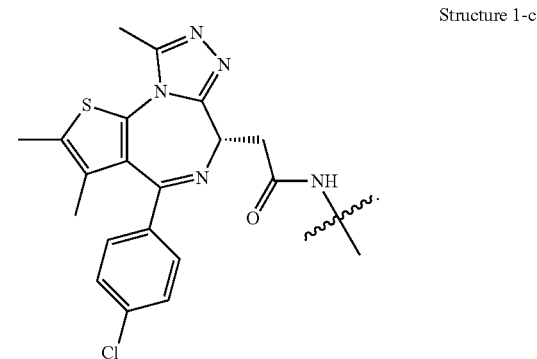
In various embodiments, the target protein is a member of BET family bromodomain-containing proteins. In various embodiments, the target protein is BRD4. A representative example of a targeting ligand ($L_1$) that binds BRD4 is JQ1 (Structure 1) or an analog thereof.

In various embodiments, $L_1$ is a thiophene analog of JQ1. represented by structure 2:

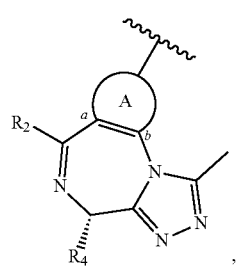

Structure 2 wherein

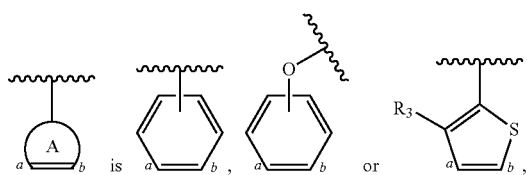

wherein $R_3$ is methyl or

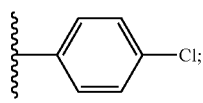

$R_2$ is

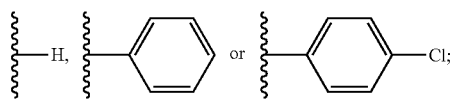

and $R_4$ is

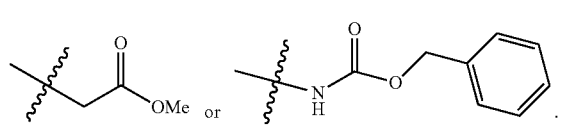 [SMILES: *CC(=O)OC ; *NC(=O)OCc1ccccc1]

Accordingly, in various embodiments the compound of formula (I) includes a ligand $L_1$ that is represented by any of the following structures:

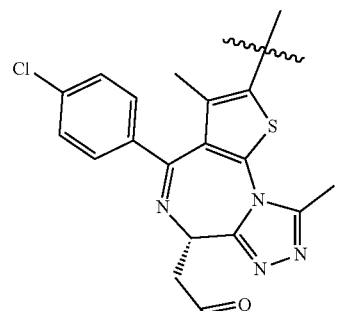

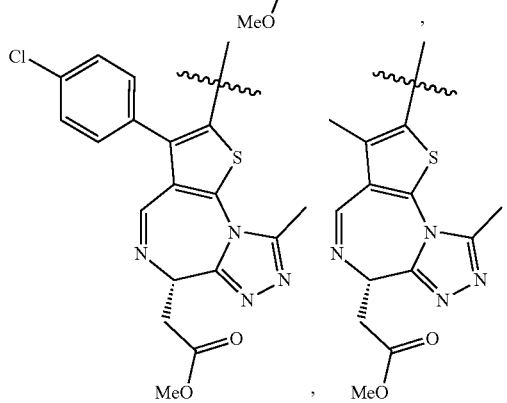

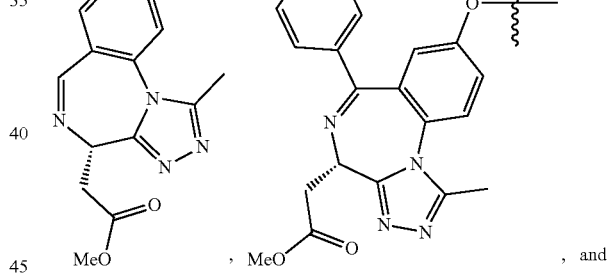

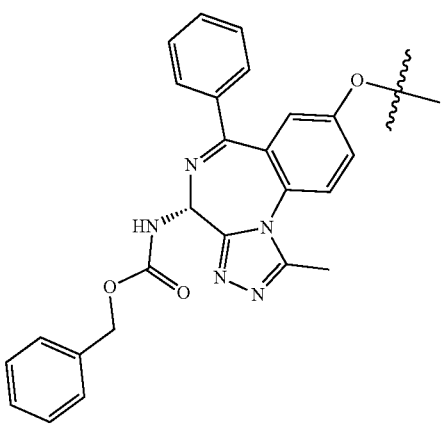

In various embodiments, $L_2$ is an IMiD (e.g., thalidomide, lenalidomide or pomalidomide or an analog thereof).

In various embodiments, $L_2$ is represented by any of the following structures:

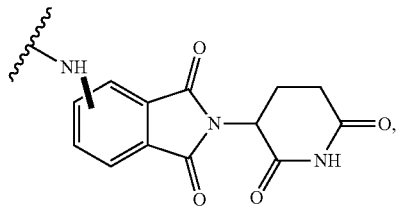
L2-a

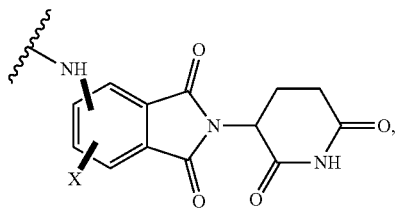
L2-b

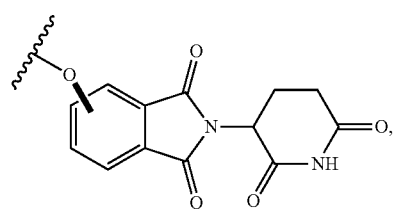
L2-c

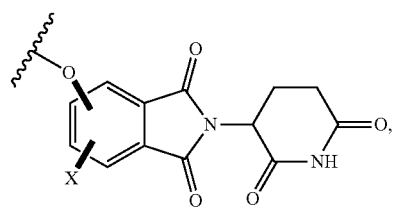
L2-d

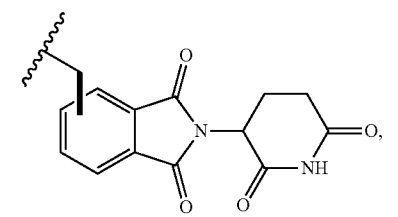
L2-e

-continued

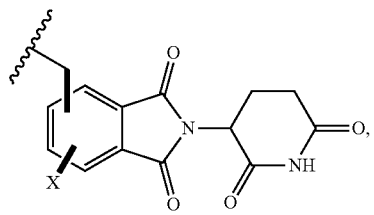
L2-f

L2-g

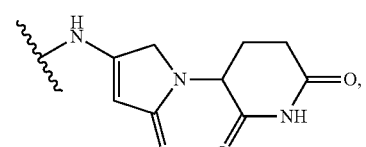

L2-h

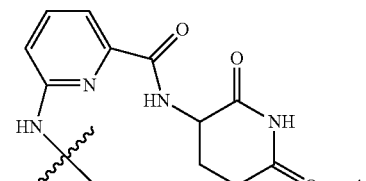

, and

L2-i

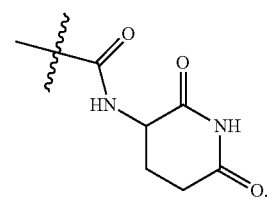

Thus, in some embodiments, the compounds of the present invention are represented by any structures of formula I, wherein $L_1$ is represented by any structures $L_1$ described herein, structure 1, structure 1-a to Structure 1-c and structure 2, the linker is represented by any of the structures C1-a to C1-J, and $L_2$ is represented by any of the structures L2-a to L2-I, or a pharmaceutically acceptable salt or stereoisomer thereof.

In various embodiments, the bifunctional compound of formula (I) is represented by any of the following structures:

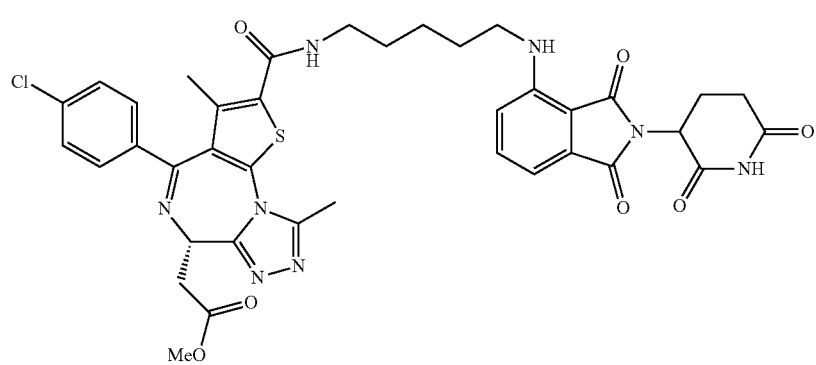

ZXH-3-26

-continued
ZXH-2-147
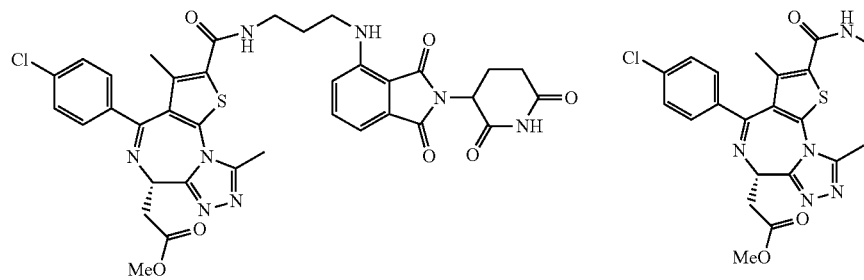
ZXH-2-184
ZXH-3-82
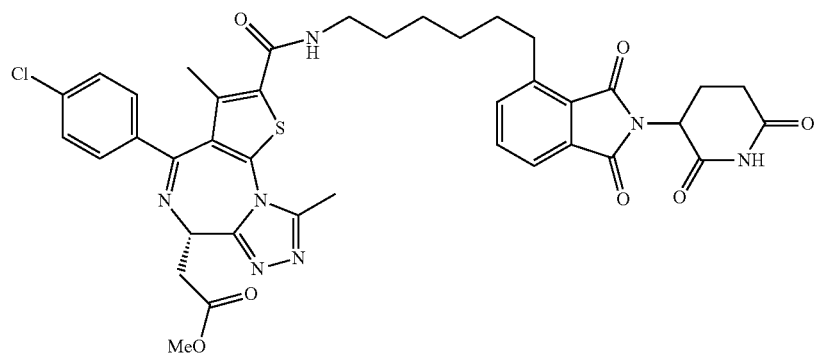
ZXH-3-028
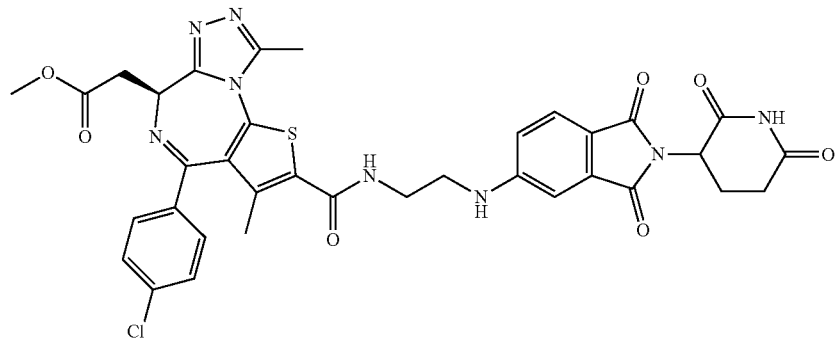
ZXH-3-195
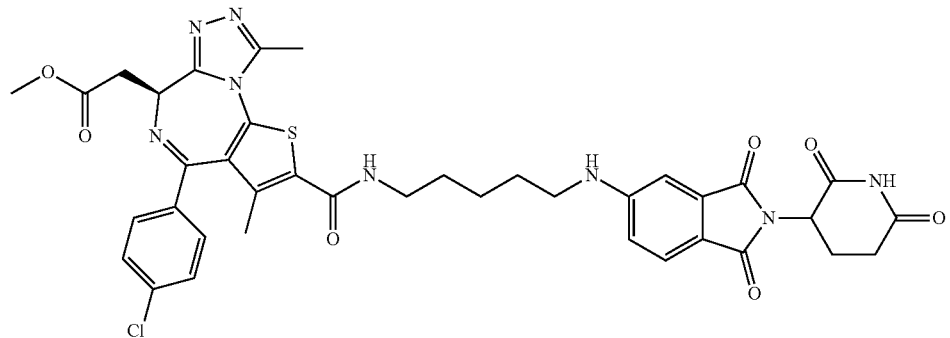
ZXH-3-142
ZXH-3-052
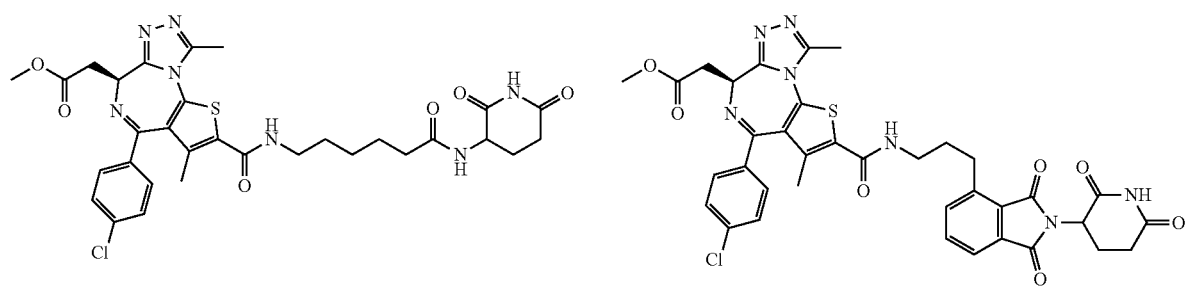

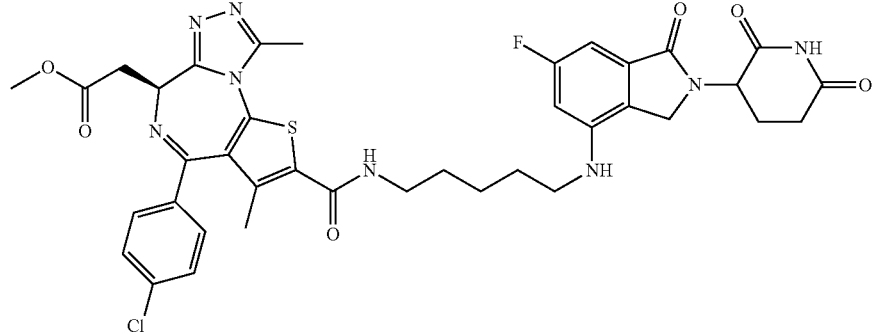
BJG-01-174
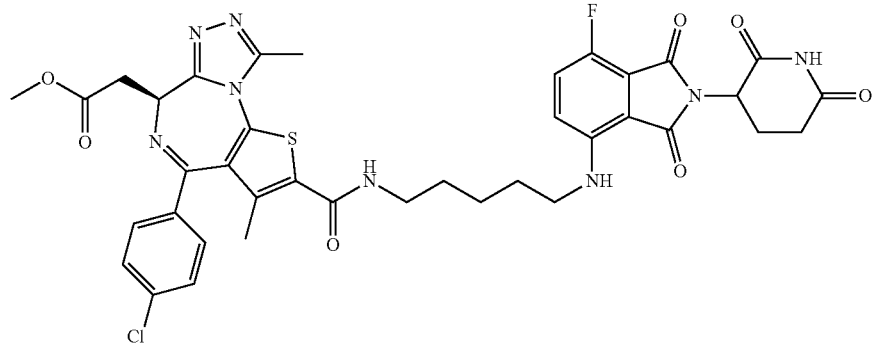
BJG-02-119
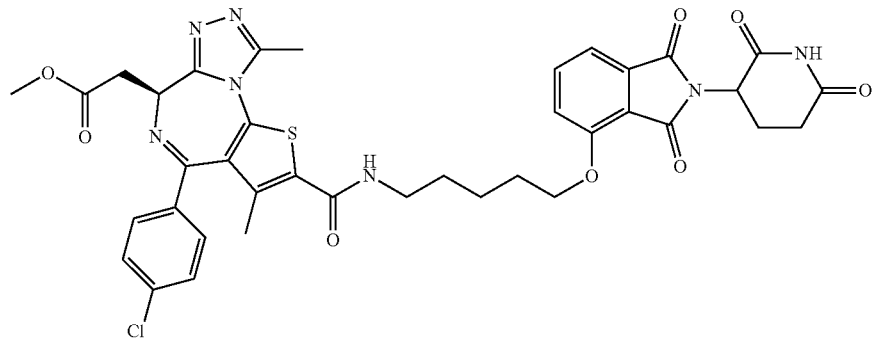
BJG-02-030
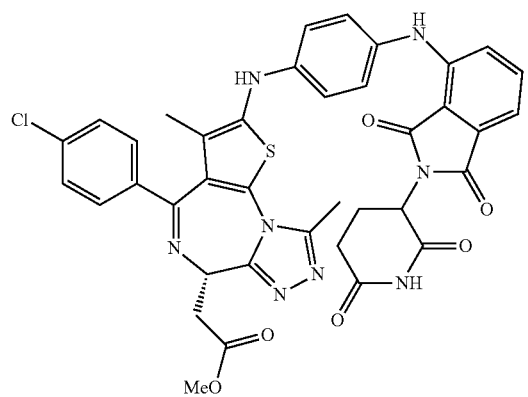
BRD4-D1
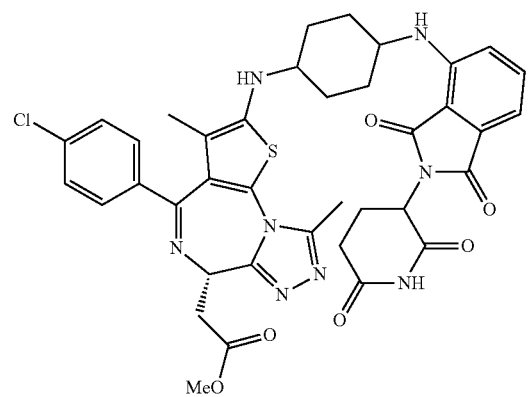
BRD4-D2

-continued
BRD4-D3
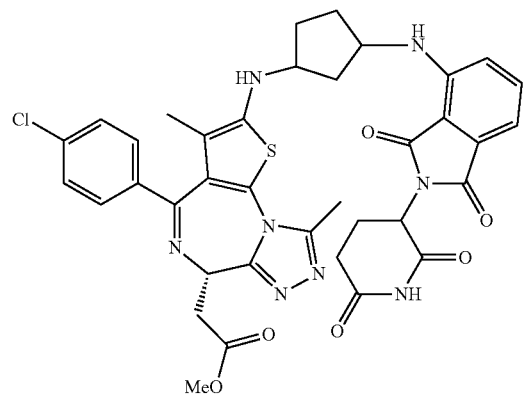
BRD4-D4
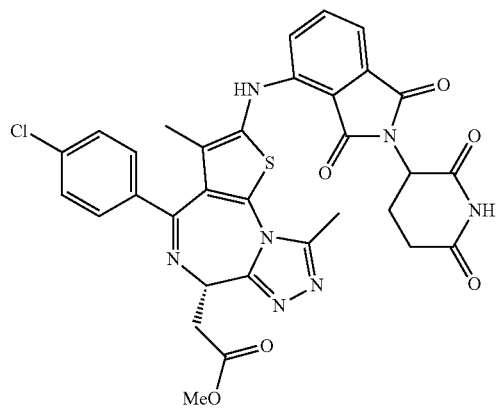
BRD4-D5
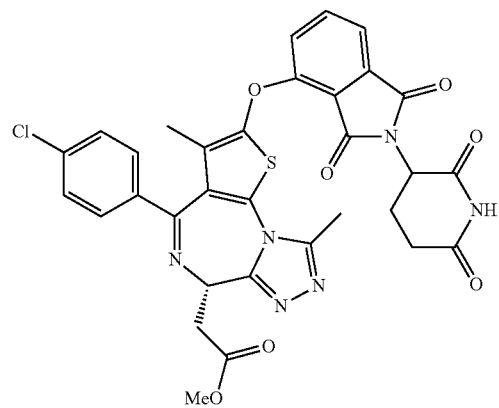
BRD4-D6
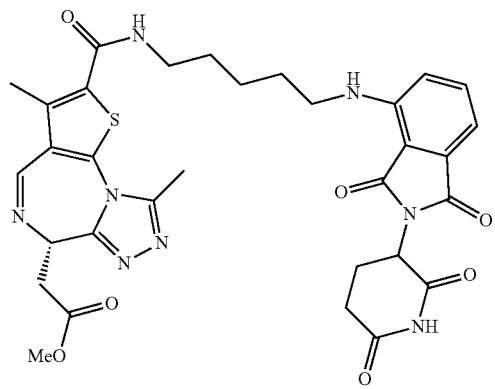
BRD4-D7
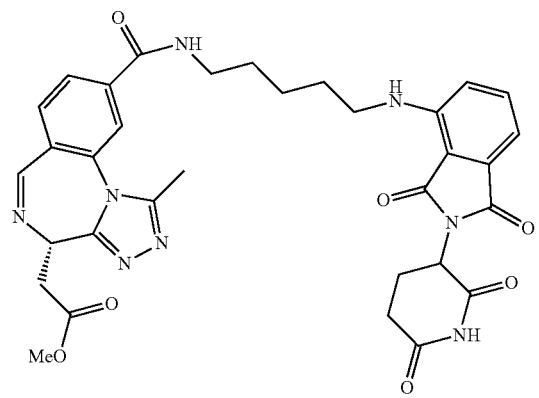
BRD4-D8
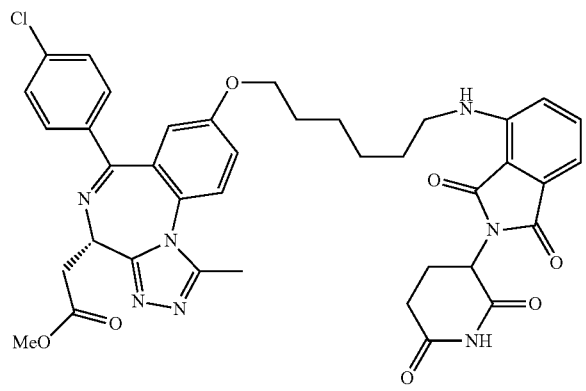
BRD4-D9
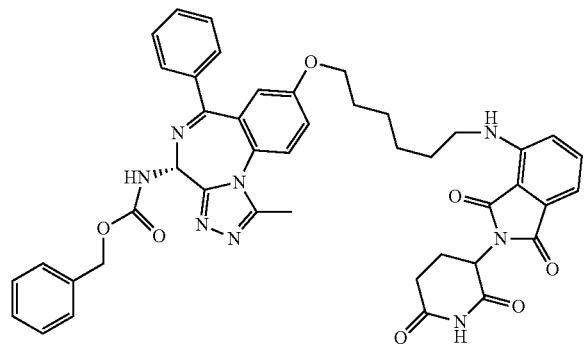
BRD4-D10
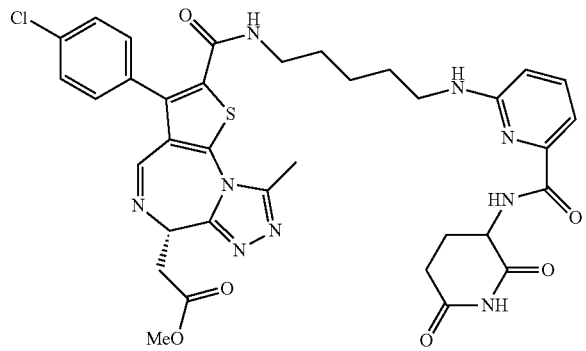

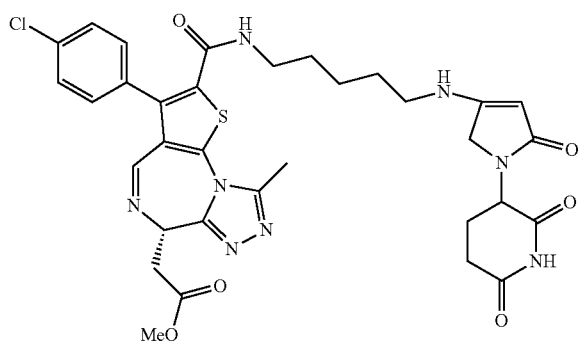

BRD4-D11

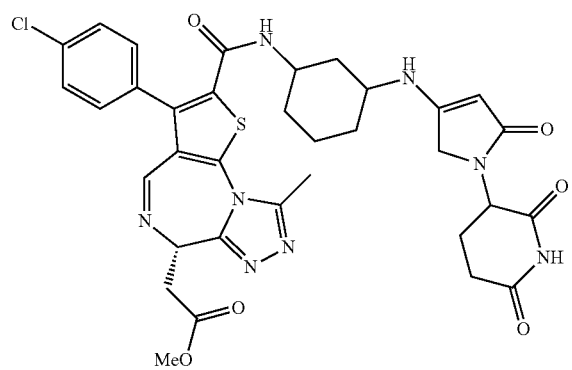

BRD4-D12

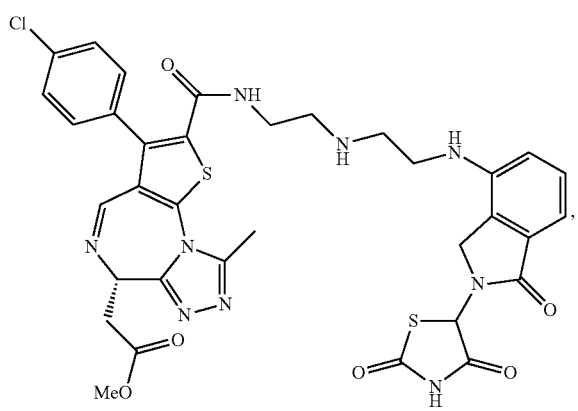

BRD4-D13 and pharmaceutically acceptable salts, esters and stereoisomers thereof.

Compounds of the present invention (which as used hereinafter, refer to both immunomodulatory compounds of formula (I) and the degraders of formula (I)) may be in the form of a free acid or free base, or a pharmaceutically acceptable salt or ester. As used herein, the term "pharmaceutically acceptable" in the context of a salt or ester refers to a salt or ester of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt or ester" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin. Suitable base salts include aluminum, calcium, lithium, magnesium, potassium, sodium, or zinc, salts. Representative examples of pharmaceutically acceptable esters include (e.g., methyl, ethyl, isopropyl and tert-butyl esters).

In some embodiments, the compounds of the present invention is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2H$, may afford certain therapeutic advantages resulting from greater metabolic stability, for example, increased in vivo half-life or reduced dosage requirements, and thus may be advantageous in some circumstances. For example, in compounds of formula (I) that target BRD4, a JQ1 moiety may be deuterated in order to increase half-life.

Compounds of the present invention may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present invention may be made and used in the form of individual isomers and substantially free of other isomers, or in the form of a mixture of various isomers, e.g., racemic mixtures of stereoisomers.

In addition, the compounds of the present invention embrace the use of N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the conjugates presented herein are also considered to be disclosed herein.

Without intending to be bound by any particular theory of operation, it is believed that the heterobifunctional compound mediates the ligand-induced dimerization of the target protein and the E3 ubiquitin ligase or the component of the E3 ubiquitin ligase, such that the binding conformation between the target protein and the E3 ubiquitin ligase or the component of the E3 ubiquitin ligase result distinct mutational signature of binding, and that, the binding affinity of the heterobifunctional compound to the E3 ubiquitin ligase or the component of E3 ubiquitin ligase is reduced when the heterobifunctional compound is bound to the target protein (e.g., the $DC_{50/5h}$ is about 500 nM or less, about 50 nM or less, about 10 nM or less, about 5 nM or less, or about 1 nM or less).

Methods of Synthesis

Broadly, the inventive compounds or pharmaceutically-acceptable salts, esters or stereoisomers thereof, may be prepared by any process known to be applicable to the preparation of chemically related compounds. The compounds of the present invention will be better understood in connection with the synthetic schemes that are described in various working examples and which illustrate non-limiting methods by which the compounds of the invention may be prepared.

Pharmaceutical Compositions

The compounds of the present invention may be formulated into several different types of pharmaceutical compositions that contain a therapeutically effective amount of the compound, and a pharmaceutically acceptable carrier. Generally, the inventive compounds may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Accordingly, compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds of the present invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

To the extent that compounds of the present invention are water-soluble, they may be formulated as solutions for parenteral and oral delivery forms. Parenteral administration may also be advantageous in that the compound may be administered relatively quickly such as in the case of a single-dose treatment and/or an acute condition.

Injectable preparations for parenteral administration may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, compounds of the present invention may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Other routes of administration that may be suitable for the compounds of the present invention include buccal, inhalation, topical, transdermal, transmucosal, ophthalmic, rectal and vaginal.

The compositions may be formulated for buccal or sublingual administration, examples of which include tablets, lozenges and gels.

The compositions may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Compounds may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, and cetyl or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerine, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a compound of the application or a pharmaceutically acceptable salt or a stereoisomer thereof; or a composition including the compound of the application or a pharmaceutically acceptable salt or a stereoisomer thereof, effective in producing the desired therapeutic response in a particular patient suffering from a disease or disorder mediated by the dysfunctional or dysregulated target protein. The term "therapeutically effective amount" includes the amount of the compound of the application or a pharmaceutically acceptable salt or a stereoisomer thereof, when administered, may induce a positive modification in the disease or disorder to be treated (e.g., remission), or is sufficient to prevent development or progression of the disease or disorder, or alleviate to some extent, one or more of the symptoms of the disease or disorder being treated in a subject. In respect of the therapeutic amount of the compound, the amount of the compound used for the treatment of a subject is low enough to avoid undue or severe side effects, within the scope of sound medical Judgment can also be considered. The therapeutically effective amount of the compound or composition will be varied with the particular condition being treated, the severity of the condition being treated or prevented, the duration of the treatment, the nature of concurrent therapy, the age and physical condition of the end user, the specific compound or composition employed and the particular pharmaceutically acceptable carrier utilized.

The total daily dosage of the compounds and usage thereof may be decided in accordance with standard medical practice, e.g., by the attending physician using sound medical judgment. The specific therapeutically effective dose for any particular patient will depend upon a variety of factors including the disease or disorder being treated and the severity thereof (e.g., its present status); the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", 10th Edition, A. Gilman, J. Hardman and L. Limbird, eds., McGraw-Hill Press, 155-173, 2001).

In some embodiments, the therapeutic regimens include titrating the dosages administered to the patient so as to achieve a specified measure of therapeutic efficacy. Such measures include a reduction in the cancer cell population in the patient. In treating certain human patients having solid tumors, for example, extracting multiple tissue specimens from a suspected tumor site may prove impracticable. In these cases, the dosage of the compound for a human patient may be extrapolated from doses in animal models that are effective to reduce the cancer population in those animal models. In the animal models, the treatment may be adjusted so as to achieve a reduction in the number or amount of cancer cells found in a test specimen extracted from an animal after undergoing the treatment, as compared with a reference sample. The reference sample can be a specimen extracted from the same animal, prior to receiving the treatment. In specific embodiments, the number or amount of cancer cells in the test specimen is at least 2%, 5%, 10%, 15%, 20%, 30%, 40%, 50% or 60% lower than in the reference sample. The doses effective in reducing the number or amount of cancer cells in the animals can be normalized to body surface area (e.g., $mg/m^2$) to provide an equivalent human dose.

Compounds of the present invention may be effective over a wide dosage range. In some embodiments, the total daily dosage (e.g., for adult humans) may range from about 0.001 to about 1000 mg, from 0.01 to about 1000 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. Individual dosage may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mgs).

Methods of Use

The compounds of the present invention may be useful in the treatment of diseases and disorders wherein a dysfunctional or dysregulated protein (that can be targeted for degradation by cereblon, participates in the inception, manifestation of one or more symptoms or markers, severity or progression of the disease or disorder), and where the degradation of the targeted protein may confer a therapeutic benefit. The diseases or disorders may be said to be characterized or mediated by dysfunctional or dysregulated protein activity (e.g., elevated protein levels compared to a non-pathological state). A "disease" is generally regarded as a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health. In some embodiments, compounds of the application may be useful in the treatment of proliferative diseases and disorders (e.g., cancer or benign neoplasms). As used herein, the term "cell proliferative disease or disorder" refers to the conditions characterized by unregulated or abnormal cell growth, or both. Cell proliferative disorders include noncancerous conditions, precancerous conditions, and cancer.

The present methods thus include administering a therapeutically effective amount of a compound to a subject in need thereof. The term "subject" as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "suffering from or suspected of suffering from" a specific disease or disorder may have a sufficient number of risk factors or presents with a sufficient number or combination of signs or symptoms such that a medical professional could diagnose or suspect that the subject was suffering from the disease or disorder. Methods for identification of subjects suffering from or suspected of suffering from conditions associated with cancer is within the ability of those in the art. Subjects suffering from, and suspected of suffering from, a specific disease, condition, or syndrome are not necessarily two distinct groups. For purposes of the present application, "subjects" and "patients" are used interchangeably.

In general, methods of using the compounds of the present invention include administering to a subject in need thereof a therapeutically effective amount of a compound of the present invention.

Exemplary types of non-cancerous diseases or disorders that may be amenable to treatment with the compounds of the present invention include inflammatory diseases and conditions, autoimmune diseases, heart diseases, viral diseases, chronic and acute kidney diseases or injuries, obesity, metabolic diseases, allergic and genetic diseases.

Representative examples of specific non-cancerous diseases and disorders include rheumatoid arthritis, inflammation, lymphoproliferative conditions, acromegaly, rheumatoid spondylitis, osteoarthritis, gout, sepsis, septic shock, endotoxic shock, gram-negative sepsis, toxic shock syndrome, asthma, adult respiratory distress syndrome, chronic obstructive pulmonary disease, chronic pulmonary inflammation, inflammatory bowel disease, Crohn's disease, systemic lupus erythematosus, multiple sclerosis, juvenile-onset diabetes, systemic lupus erythematosus, autoimmune uveoretinitis, autoimmune vasculitis, bullous pemphigus, myasthenia gravis, autoimmune thyroditis or Hashimoto's disease, Sjogren's syndrome, granulomatous orchitis, autoimmune oophoritis, sarcoidosis, rheumatic carditis, ankylosing spondylitis, Grave's disease, autoimmune thrombocytopenic purpura, psoriasis, eczema, ulcerative colitis, pancreatic fibrosis, hepatic fibrosis, acute and chronic renal disease, irritable bowel syndrome, pyresis, restenosis, cerebral malaria, stroke and ischemic injury, neural trauma, Alzheimer's disease, Huntington's disease, Parkinson's disease, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptures, or prolapsed intervertebral disk syndrome, osteopetrosis, thrombosis, restenosis, silicosis, pulmonary sarcosis, bone resorption diseases, such as osteoporosis, graft-versus-host reaction, Multiple Sclerosis, lupus, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, down syndrome, cystic fibrosis, Duchenne muscular dystrophy, haemophilia, Klinefelter's syndrome, neurofibromatosis, phenylketonuria, Prader-Willi syndrome, sickle cell disease, Tay-Sachs disease, Turner syndrome, urea cycle disorders, thalassemia, cystic fibrosis, rheumatoid arthritis, Sjogren's syndrome, uveitis, polymyositis, and dermatomyositis, arteriosclerosis, amyotrophic lateral sclerosis, asociality, affective disorders, systemic lupus erythematosus, immune response, varicosis, vaginitis, including chronic recurrent yeast vaginitis, depression, Sudden Infant Death Syndrome, and varicosis.

In other embodiments, the methods are directed to treating subjects having cancer. Broadly, the compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) including leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, cone and joint cancer, brain cancer (e.g., brain stem glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, rectal cancer, cutaneous T-cell lymphoma, lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin's lymphoma, hypopharyngeal cancer, intraocular melanoma, ocular cancer, islet cell tumors (endocrine pancreas), Kaposi Sarcoma, renal cancer, kidney cancer, clear cell renal cell carcinoma, laryngeal cancer, acute lymphoblastic leukemia, acute myeloid leukemia, chronic lymphocytic leukemia, chronic myelogenous leukemia, hair cell leukemia, lip and oral cavity cancer, liver cancer, lung cancer, non-small cell lung cancer, small cell lung cancer, AIDS-related lymphoma, non-Hodgkin's lymphoma, primary central nervous system lymphoma, Waldenstrom's macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoids, myelodysplastic syndromes, myelodysplastic/myeloproliferative diseases, acute myeloid leukemia, multiple myeloma, chromic myeloproliferative disorders, nasopharyngeal cancer, neuroblastoma, oral cancer, oral cavity cancer, oropharyngeal cancer, ovarian cancer (e.g., ovarian epithelial cancer, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma rhabdomyosarcoma, salivary gland cancer, Ewing family of sarcoma tumors, Kaposi Sarcoma, soft tissue sarcoma, uterine cancer, merkel cell skin carcinoma, small intestine cancer, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilms' Tumor.

Sarcomas that may be treatable with compounds of the present invention include both soft tissue and bone cancers alike, representative examples of which include osteosarcoma or osteogenic sarcoma (bone), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue) and mesenchymous or mixed mesodermal tumor (mixed connective tissue types).

In some embodiments, methods of the present invention entail treatment of subjects having cell proliferative diseases or disorders of the hematological system, liver (hepatocellular), brain, lung, colorectal (e.g., colon), pancreas, prostate, skin, ovary, breast, skin (e.g., melanoma), and endometrium.

As used herein, "cell proliferative diseases or disorders of the hematologic system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), acute myeloid leukemia (AML), mantle cell lymphoma (MCL) and ALK+ anaplastic large cell lymphoma) (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, refractory B-cell non-Hodgkin's lymphoma, and relapsed B-cell non-Hodgkin's lymphoma), childhood lymphomas, and lymphomas of lymphocytic and cutaneous origin, e.g., small lymphocytic lymphoma), leukemia (including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia), myeloid neoplasms and mast cell neoplasms.

As used herein, "cell proliferative diseases or disorders of the lung" include all forms of cell proliferative disorders affecting lung cells. Cell proliferative disorders of the lung include lung cancer, a precancer or precancerous condition of the lung, benign growths or lesions of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma", bronchioloalveolar carcinoma, giant cell carcinoma, spindle cell carcinoma, and large cell neuroendocrine carcinoma. Lung cancer includes lung neoplasms having histologic and ultrastructural heterogeneity (e.g., mixed cell types).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer. Colon cancer includes malignant colon neoplasms, carcinoma in situ, typical carcinoid tumors, and atypical carcinoid tumors. Colon cancer includes adenocarcinoma, squamous cell carcinoma, and squamous cell carcinoma. Colon cancer can be associated with a hereditary syndrome such as hereditary nonpolyposis colorectal cancer, familiar adenomatous polyposis, MYH-associated polyposis, Gardner's syndrome, Peutz-Jeghers syndrome, Turcot's syndrome and juvenile polyposis. Cell proliferative disorders of the colon can be characterized by hyperplasia, metaplasia, and dysplasia of the colon.

As used herein, "cell proliferative diseases or disorders of the pancreas" include all forms of cell proliferative disorders affecting pancreatic cells. Cell proliferative disorders of the pancreas may include pancreatic cancer, an precancer or precancerous condition of the pancreas, hyperplasia of the pancreas, and dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast.

In some embodiments, wherein the method entails use of a bifunctional compound that targets a BRD protein, the subject may have a cancer e.g., NUT midline carcinoma, treatment-refractory acute myeloid leukemia, myelodysplastic syndrome, multiple myeloma, triple negative- and estrogen receptor-positive breast cancers, small cell and non-small cell lung cancers, castration resistant prostate cancer, pancreatic ductal adenocarcinoma, colorectal cancer, neuroblastoma and N-Myc Proto-Oncogene Protein (MYCN)-driven solid tumors.

The compounds of the present application may be administered to a patient, e.g., a cancer patient, as a monotherapy or by way of combination therapy, and as a front-line therapy or a follow-on therapy for patients who are unresponsive to front line therapy. Therapy may be "first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but are intolerant to the particular treatment. Therapy may also be given as an adjuvant treatment, i.e., to prevent reoccurrence of cancer in patients with no currently detectable disease or after surgical removal of a tumor. Thus, in some embodiments, the compound may be administered to a patient who has received another therapy, such as chemotherapy, radioimmunotherapy, surgical therapy, immunotherapy, radiation therapy, targeted therapy or any combination thereof.

The methods of the present application may entail administration of compounds of the invention or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5 or 6 weeks, and in other embodiments entails a 28-day cycle which includes daily administration for 3 weeks (21 days).

Combination Therapy

The compounds of the present invention may be used in combination with at least one other active agent, e.g., anti-cancer agent or regimen, in treating diseases and disorders. The term "in combination" in this context means that the agents are co-administered, which includes substantially contemporaneous administration, by the same or separate dosage forms, or sequentially, e.g., as part of the same treatment regimen or by way of successive treatment regimens. Thus, if given sequentially, at the onset of administration of the second compound, the first of the two compounds is in some cases still detectable at effective concentrations at the site of treatment.

In some embodiments, the treatment regimen may include administration of a compound of the invention in combination with one or more additional anticancer therapeutics. The dosage of the additional anticancer therapeutic may be the same or even lower than known or recommended doses. See, Hardman et al., eds., Goodman & Gilman's *The Pharmacological Basis Of Basis Of Therapeutics,* 10th ed., McGraw-Hill, New York, 2001; Physician's Desk Reference 60th ed., 2006. Anti-cancer agents that may be used in combination with the inventive compounds are known in the art. See, e.g., U.S. Pat. No. 9,101,622 (Section 5.2 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, the compound of the invention and the additional anticancer therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more anticancer therapeutics may be administered within the same patient visit.

The active agents are administered concurrently to a subject in the same or separate compositions. The combination therapeutics of the invention may be administered to a subject by the same or different routes of administration. The term "concurrently" is not limited to the administration of the anticancer therapeutics at exactly the same time. Rather, it is meant that they are administered to a subject in a sequence and within a time interval such that they can act together (e.g., synergistically to provide an increased benefit than if they were administered otherwise). For example, the therapeutics may be administered at the same time or sequentially in any order at different points in time; however, if not administered at the same time, they should be administered sufficiently close in time so as to provide the desired therapeutic effect, which may be in a synergistic fashion.

When the active components of the combination are not administered in the same pharmaceutical composition, it is understood that they can be administered in any order to a subject in need thereof. For example, a compound of the present application can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional anticancer therapeutic, to a subject in need thereof. In various aspects, the anticancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one example, the anticancer therapeutics are administered within the same office visit. In another example, the combination anticancer therapeutics may be administered at 1 minute to 24 hours apart.

In some embodiments, the compound of the present invention and the additional agent or therapeutic (e.g., an anti-cancer therapeutic) are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anti-cancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain the compound of the present application or a pharmaceutical composition. The kits or pharmaceutical systems of the invention may also include printed instructions for using the compounds and compositions.

These and other aspects of the present application will be further appreciated upon consideration of the following non-limiting working examples.

EXAMPLES

Figure 6A:
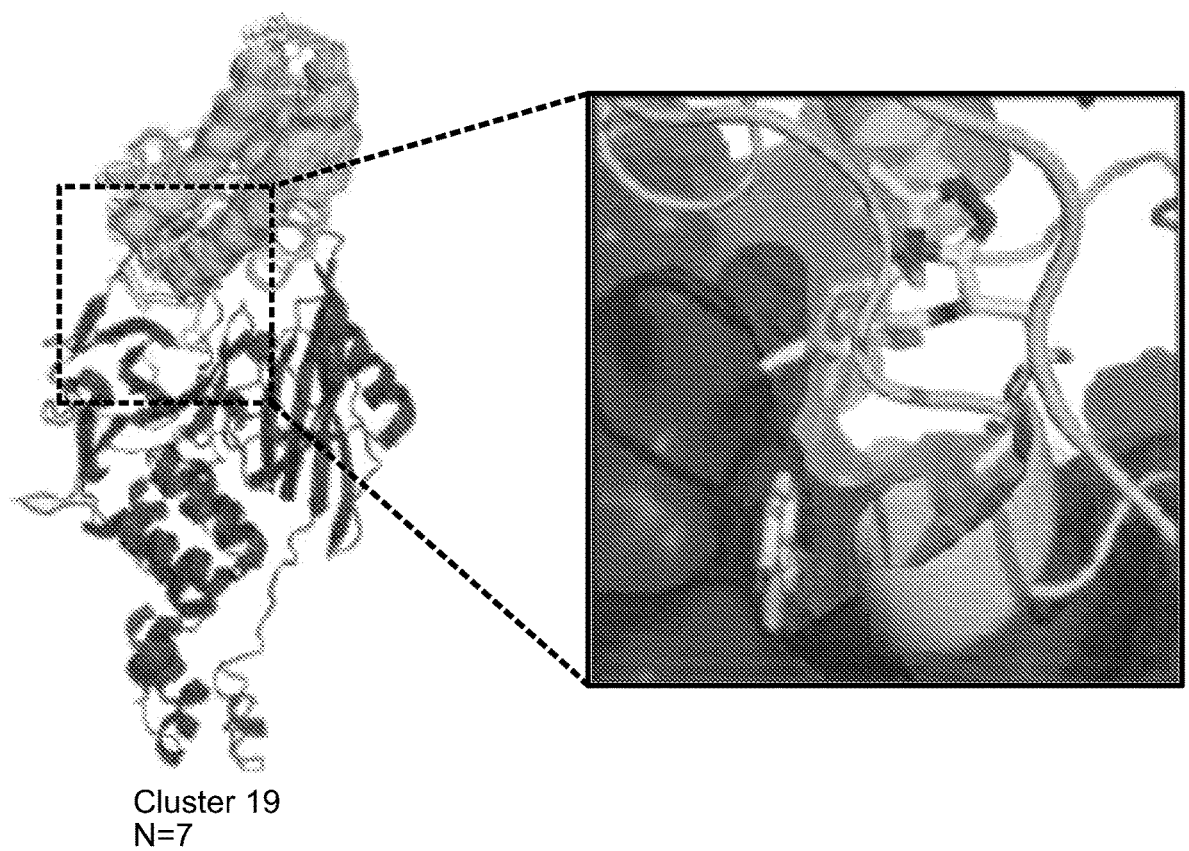
FIG. 6A-FIG. 6H show data demonstrating degradation of BET family proteins by certain heterobifunctional small molecule degraders.
Figure 6B:
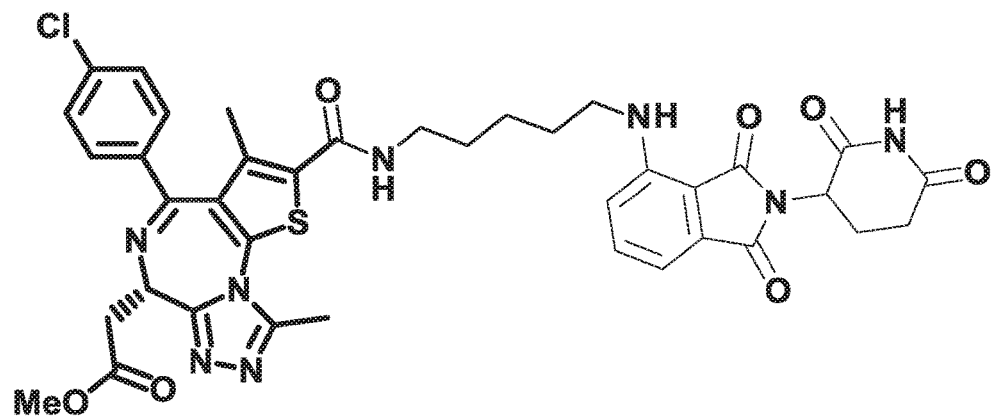
Figure 6C:
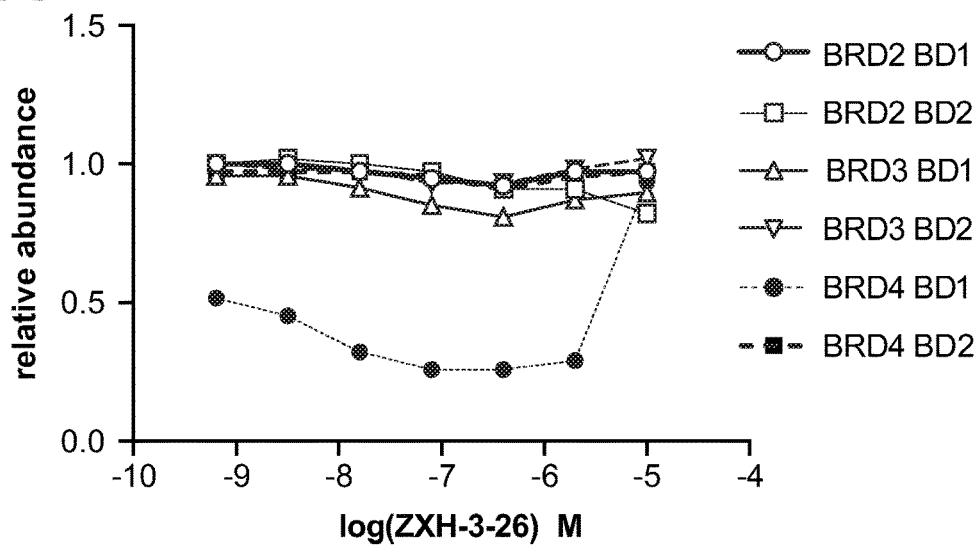
Figure 6D:
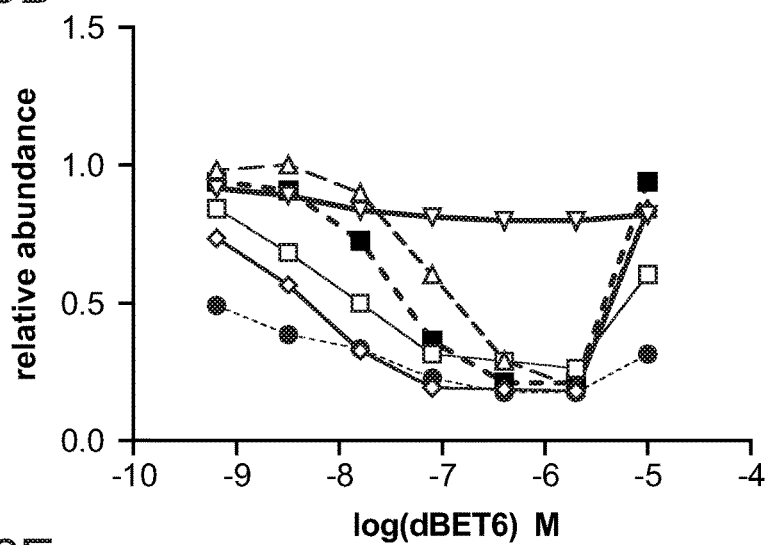
Figure 6E:
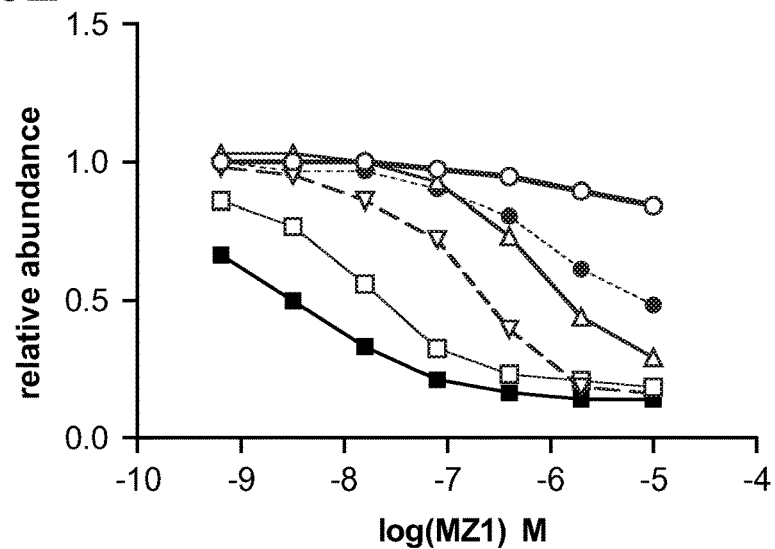
Figure 6F:
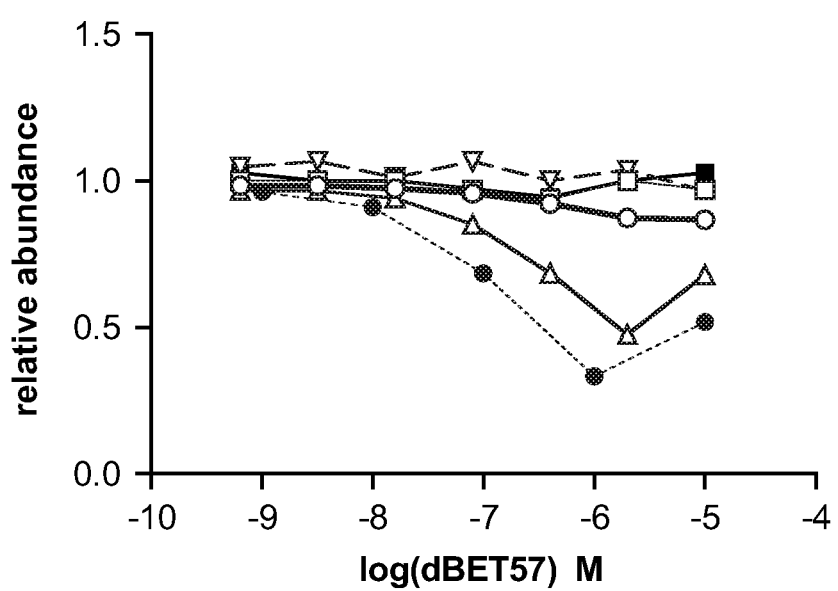
Figure 6G:
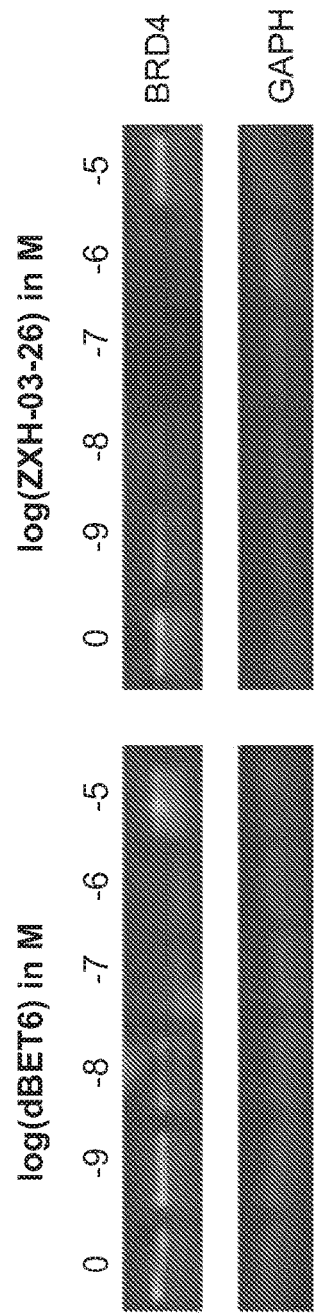
Figure 6H:
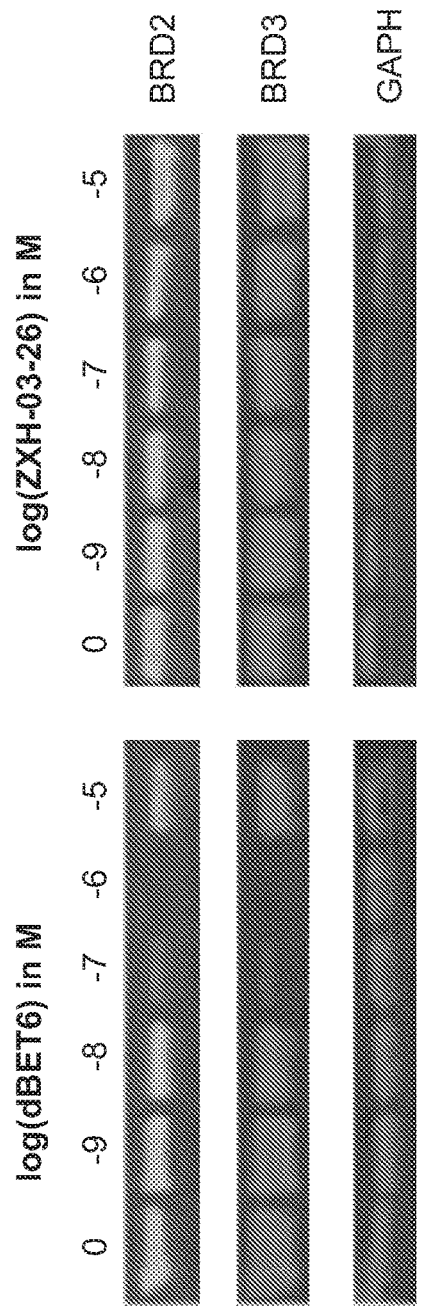

By way of introduction, the Examples show that an inventive compound ZXH-03-26 shows activity exclusively on the first bromodomain of BRD4, and spares degradation of BRD2 or 3 at concentrations >10 μM (FIG. 6C), while non-inventive bifunctional compounds dBET6 and MZ1 (used as controls) show activity on most bromodomains (FIG. 6D). The examples also describe experiments wherein bromodomain degradation for non-inventive degrader dBET57 was assessed to test whether any short linker would result in selectivity for $BRD4_{BD1}$. In contrast to ZXH-03-26, dBET57 is nearly equipotent on $BRD3_{BD1}$ and $BRD4_{BD1}$ (FIG. 6E). The examples describe further experiments designed to test whether the selective ZXH-03-26 retains activity on endogenous full length BRD4. HEK293T cells were treated with increasing concentrations of ZXH-03-26. Immunoblot analysis confirms that ZXH-03-26 degrades endogenous BRD4 with comparable efficacy compared to the best pan-BET degrader dBET6 (FIG. 6G), while being inactive on BRD2 and BRD3 (FIG. 6H).

Thus, the examples demonstrate that binding to a distinct conformation can yield a highly selective degrader molecule and that selectivity can be achieved across highly homologous domains such as the bromodomains of BET proteins.

More specifically, the following Examples present a comprehensive structural, biochemical and cellular analysis of heterobifunctional compound (PROTAC)-mediated degradation of BET family proteins, including specific degradation of BRD4 over other BET family proteins. The Examples demonstrate that the ligase-PROTAC-substrate binding mode is unexpectedly plastic, and that this plasticity results in multiple low energy binding conformations that can be exploited to achieve favourable binding modes and help to rationalize heterobifunctional compound specificity. Based on this new finding, heterobifunctional compounds that are specific for BRD4 over other homologous BET family proteins are synthesized, and specific degradation of BRD4 by these working examples of the invention are shown.

Through multiple X-ray crystal structures of PROTAC bound CRL4$^{CRBN}$-BRD4 complexes, the Examples below demonstrate that plastic inter-protein contacts result in multiple distinct binding conformations depending on the bound PROTAC. The Examples also demonstrate that effective degradation does not require tight cooperative binding; however, distinct binding conformations are unique to ligase-substrate pairs and define selectivity. The Examples further demonstrate a computational approach to protein-protein docking and demonstrate the versatility of this approach through rational design of the first PROTAC that can discriminate between the highly homologous BET bromodomains of BRD2/3/4, leading to synthesis of a highly effective and selective BRD4 degrader.

The Examples provide a detailed understanding of the molecular basis for target recruitment and selectivity, which is critically required to enable rational design of degraders. The Examples utilize comprehensive characterization of the ligand dependent CRBN/BRD4 interaction to demonstrate that binding between proteins that have not evolved to interact is unexpectedly plastic. Multiple X-ray crystal structures show that plasticity results in several distinct low energy binding conformations, which are selectively bound by ligands. The Examples demonstrate that computational protein-protein docking can reveal the underlying inter-protein contacts and inform the design of BRD4 selective degraders that can discriminate between highly homologous BET bromodomains. The Examples demonstrating that plastic inter-protein contacts confer selectivity for ligand-induced protein dimerization provide a conceptual framework for the development of high specificity heterobifunctional compounds. The Examples further provide exemplary heterobifunctional compounds that are specific for BRD4 over other BET family proteins.

Figure 7A:
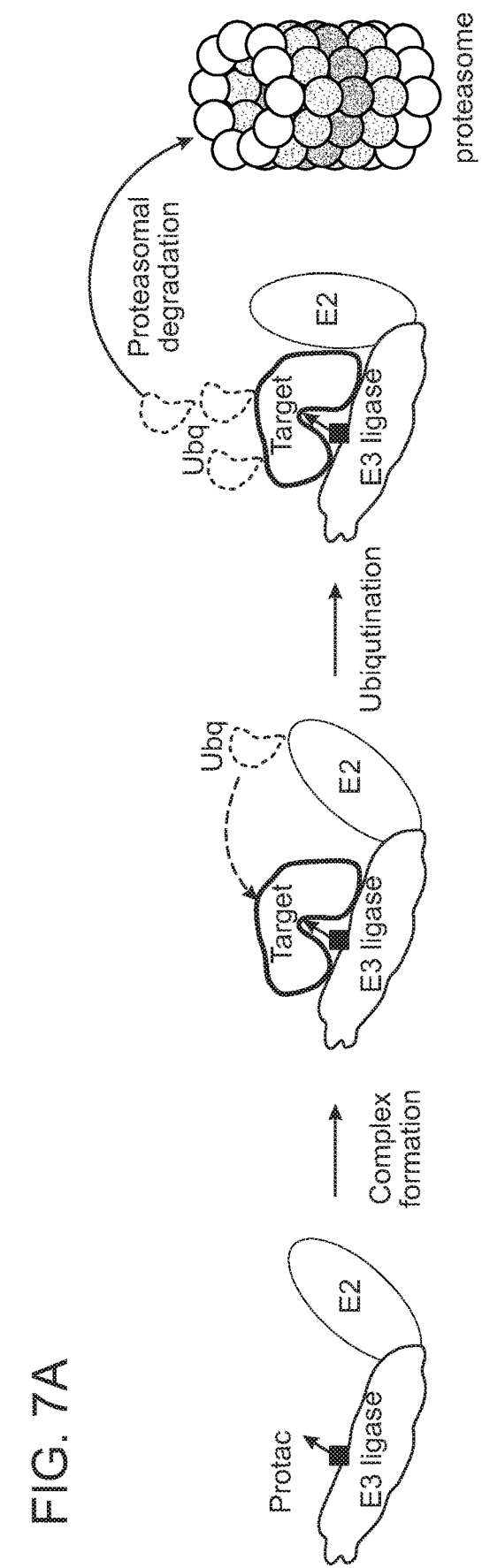
FIG. 7A is an image that shows a schematic representation of the heterobifunctional ligand (PROTAC/degrader) mediated degradation.
Figure 7B:
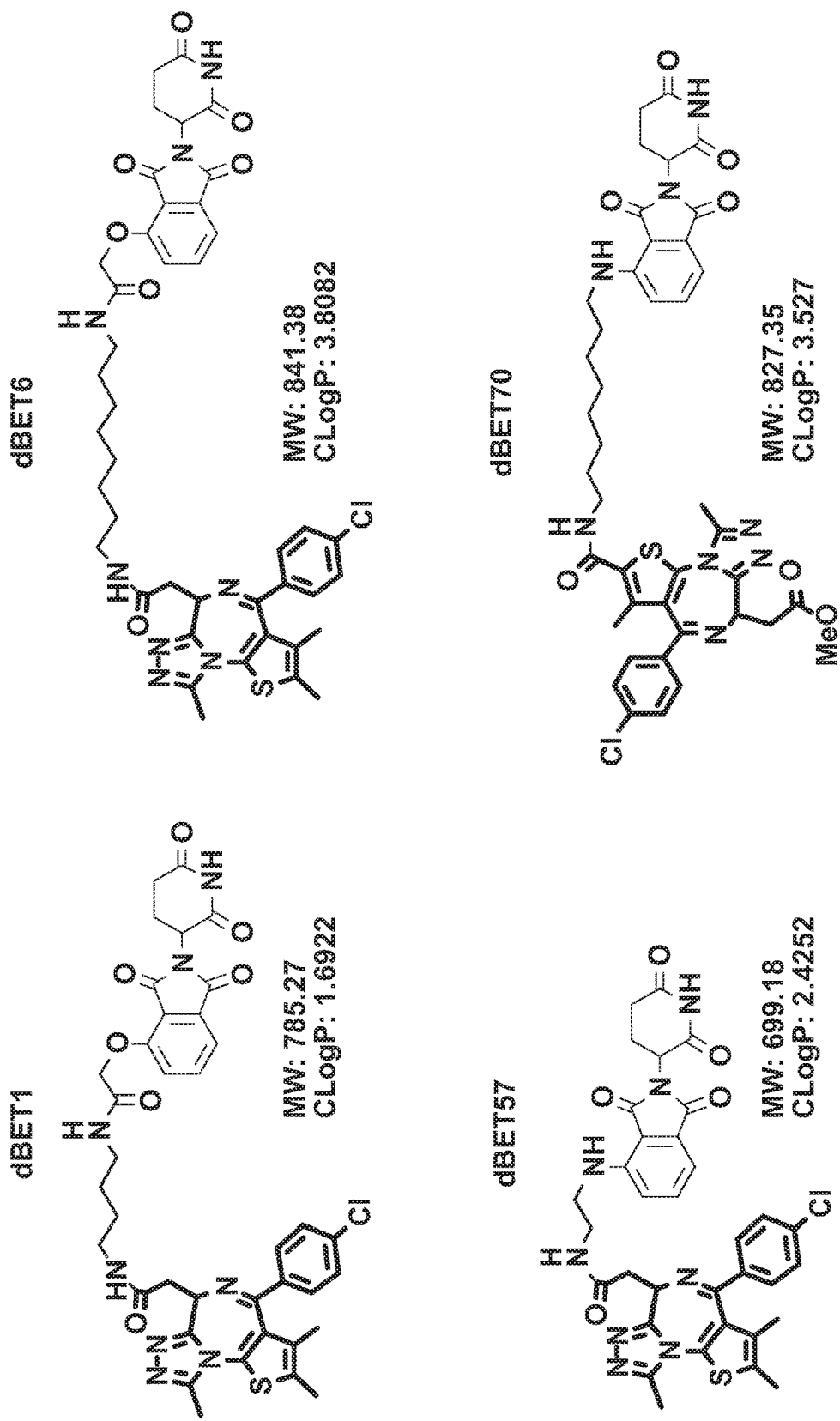
FIG. 7B is an image that shows chemical structures, molecular weight and C Log P for the heterobifunctional small molecule degraders (BET inhibitor JQ1-(S) coloured in red, thalidomide moiety coloured in blue and the linker in black and green).
Figure 7B:
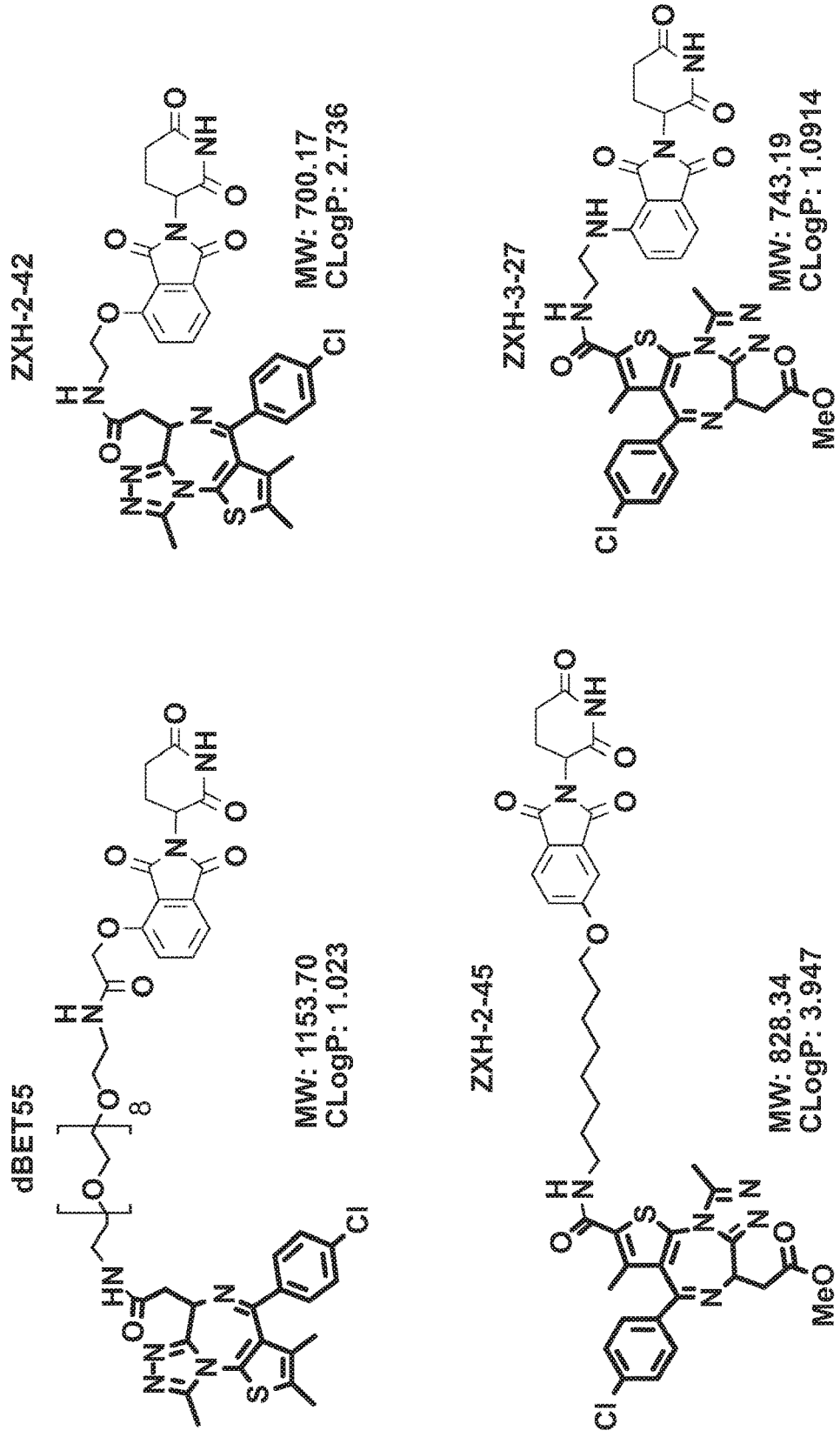
Figure 7B:
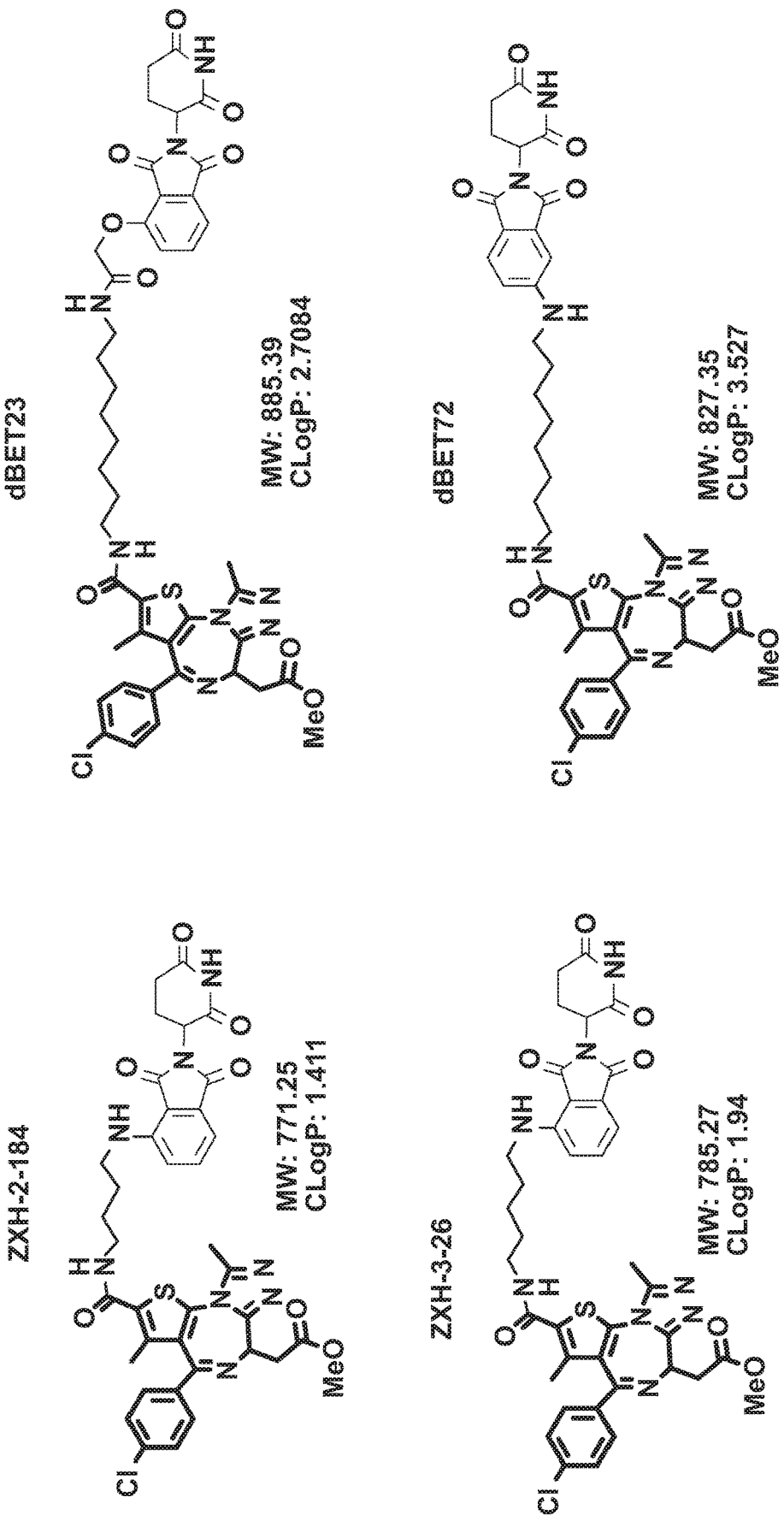
Figure 7B:
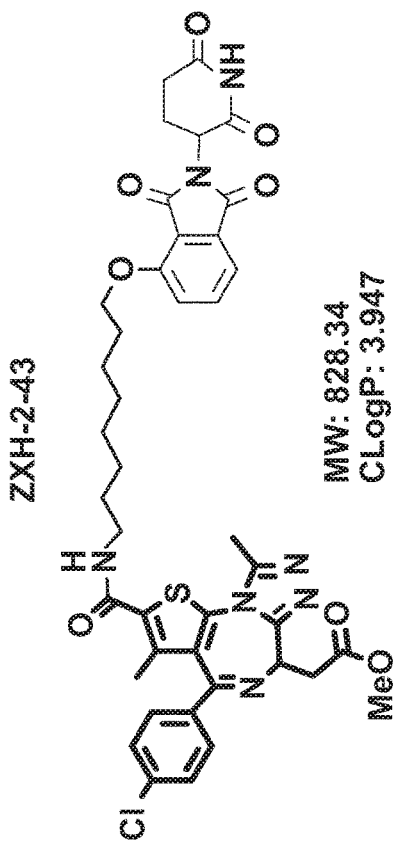
Figure 7B:
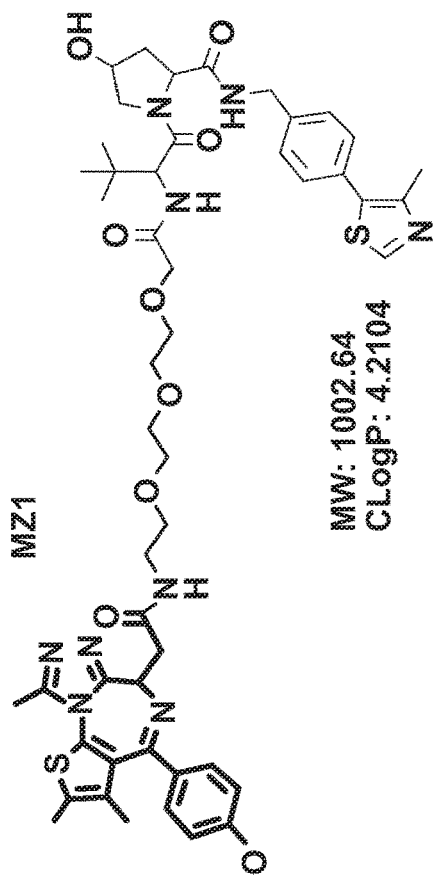
Figure 7B:
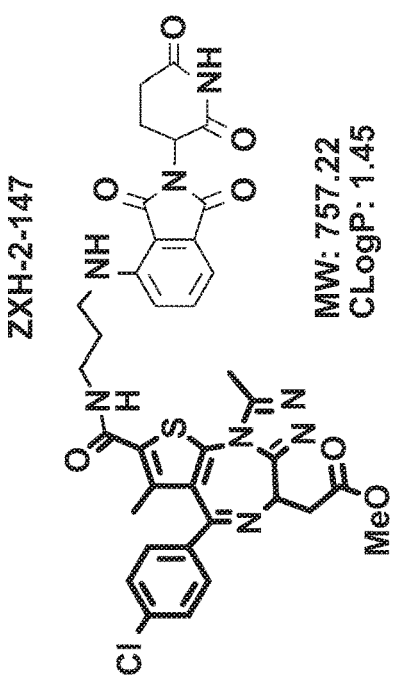
Figures 7C, 7D, 7E:
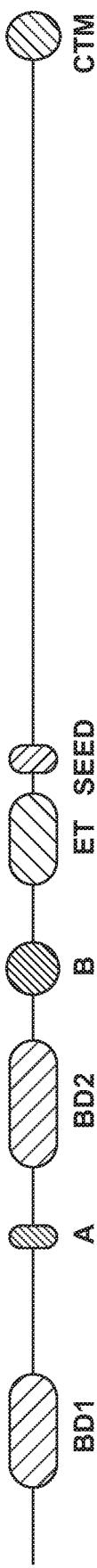
FIG. 7C is an image that shows multiple sequence alignment of BD1 and BD2 from different BET bromodomain paralogs.
FIG. 7D is an image that shows multiple sequence alignment of BD1 and BD2 from human BRD4.
FIG. 7E is an image that shows domain architecture of BDR4 (A and B-DNA binding motifs; ET—external domain; SEED—Ser/Glu/Asp-rich region; CTM—C-terminal domain).

Since small changes to the PROTAC can result in dramatically altered cell permeability or solubility, the Examples below devised a synthetic system based on the recruitment of isolated BRD4 bromodomains to CRL4$^{CRBN}$. Like other members of the BET family, BRD4 contains two bromodomains: bromodomain 1 (aa 75-147 and referred to as BRD4$_{BD1}$) and BRD4$_{BD2}$ (aa 368-440), and sequence conservation between the two is limited (FIG. 7C-FIG. 7E). These distinct domains bind the JQ1 based target-moiety with equal affinities (Filippakopoulos, Qi et al. 2010), hence establish a model system to understand how amino acid sequence and thereby protein surface properties influence protein dimerization. The Examples below utilized a series of compounds synthesized to bind CRBN and the bromodomains of BRD4 (referred to as dBETs, see FIG. 7B) (Winter, Buckley et al. 2015). dBET molecules comprise the E3-moiety thalidomide to bind to CRL4$^{cRBN}$, a flexible linker of variable length and composition, and a target-moiety, JQ1, that binds to BRD4$_{BD1}$ and BRD4$_{BD2}$ with equal affinities (Filippakopoulos, Qi et al. 2010).

Example 1: Crystal Structure of a DDB1ΔB-CRBN-dBET23-BRD4$_{BD1}$ Complex

Figure 1B:
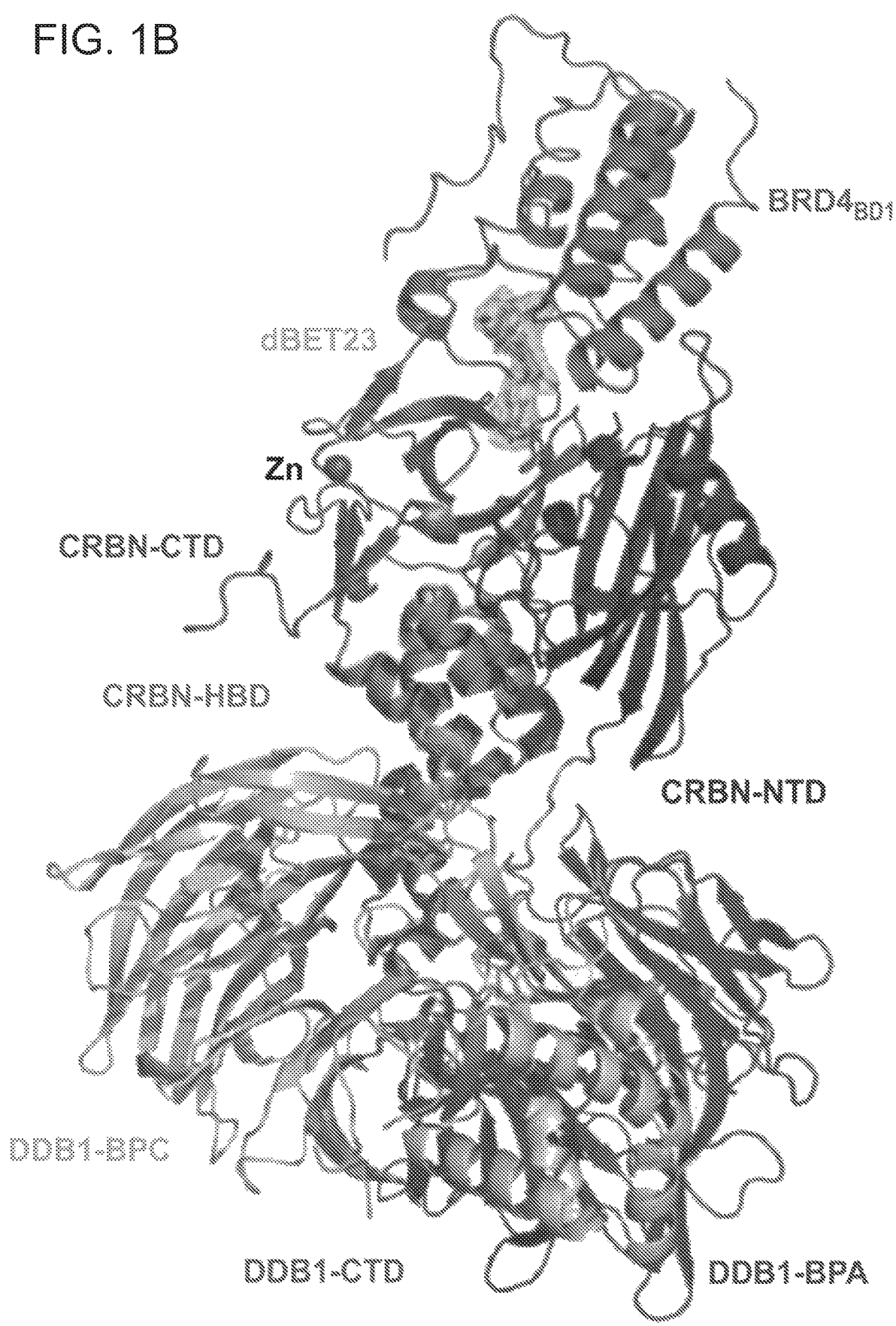
FIG. 1B is an image that shows a cartoon representation of DDB1ΔB-CRBN-dBET23-BRD4$_{BD1}$: DDB1 highlighting domains BPA (red), BPC (orange) and DDB1-CTD (grey); CRBN with domains NTD (blue), HBD (cyan) and CTD (green); and BRD4$_{BD1}$ (magenta). The Zn$^{2+}$-ion is shown as a grey sphere and dBET23 as sticks representation in yellow. The $F_O$-$F_C$ map is shown as green mesh for dBET23 contoured at 3.0σ.
Figure 1C:
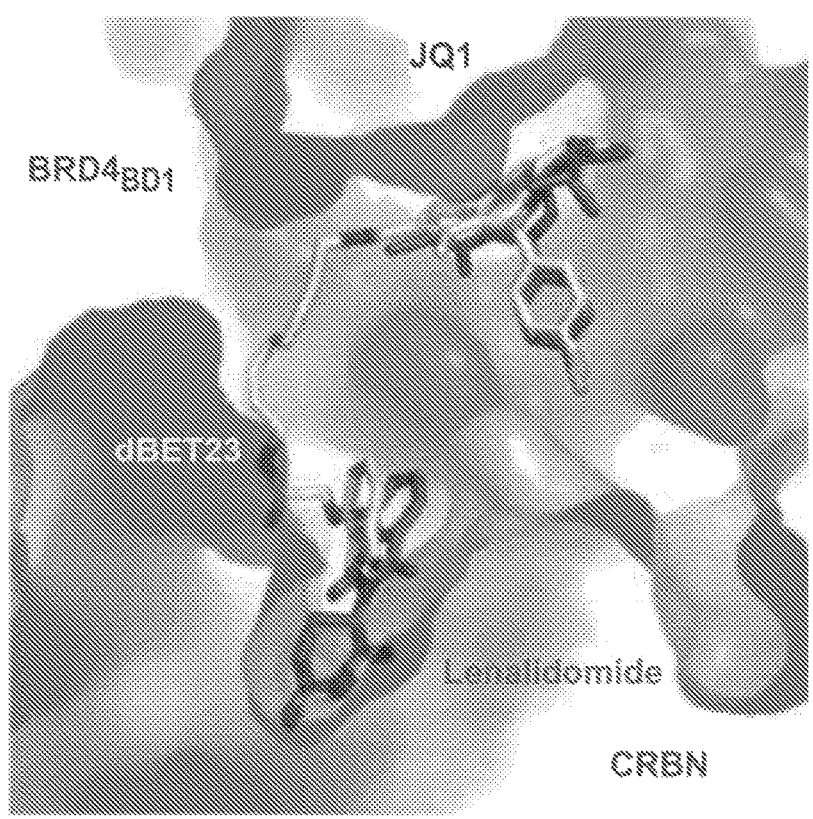
FIG. 1C is an image that shows superposition of DDB1ΔB-CRBN-dBET23-BRD4$_{BD1}$ with human CRBN bound to lenalidomide (PDB: 4tz4) and BRD4$_{BD1}$ bound to JQ1-(S) (PDB: 3mxf). Surface representation for CRBN and BRD4$_{BD1}$ are shown in grey and magenta, respectively. dBET23 is shown in yellow, JQ1 in green, and thalidomide in cyan.

To determine the structural basis of BRD4 recruitment to CRBN, DDB1ΔB-CRBN, and BRD4$_{BD1}$ complexes bound to different dBET molecules were reconstituted. Initial crystals were obtained for the ~165 kDa hsDDB1ΔB-hsCRBN-dBET23-hsBRD4$_{BD1}$ (dBET23 comprises an 8-carbon linker to bridge the oxy-acetamide of pomalidomide to the thiophene group of JQ1) complex and its structure was determined to 3.5 Å resolution (FIG. 1B) by molecular replacement using a DDB1ΔB-CRBN model (PDB: 5fqd, see Table 1). The DDB1 β-propeller domains A and C (BPA and BPC) bind CRBN but do not contribute contacts to BRD4$_{BD1}$. CRBN consists of three domains, the N-terminal domain (NTD), the helical-bundle domain (HBD) and the C-terminal domain (CTD), which harbours the thalidomide binding pocket (Fischer, Bohm et al. 2014). The small molecule degrader dBET23 occupies the canonical binding sites on CRBN and BRD4$_{BD1}$ for lenalidomide and JQ1, respectively (FIG. 1C).

Figure 1D:
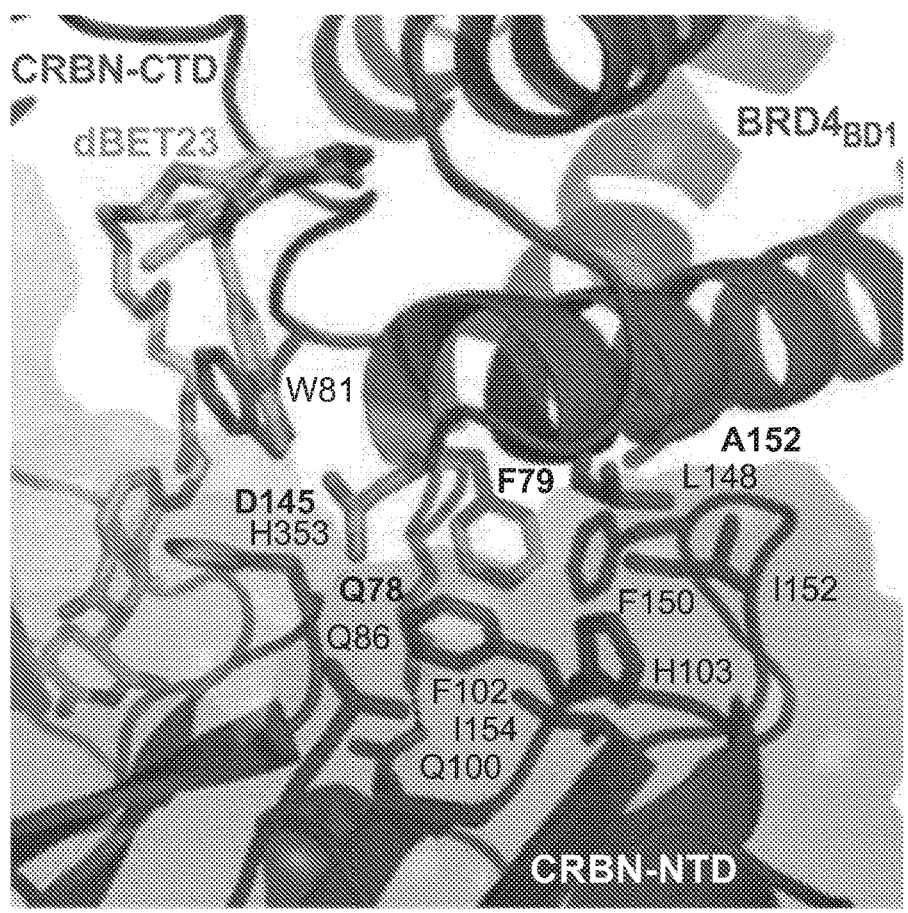
FIG. 1D is an image that shows side-chain interactions between BRD4$_{BD1}$, CRBN, and dBET23. Dashed lines indicate hydrogen bonds. Residues of BRD4$_{BD1}$ mutated in this study are highlighted in cyan.
Figure 2B:
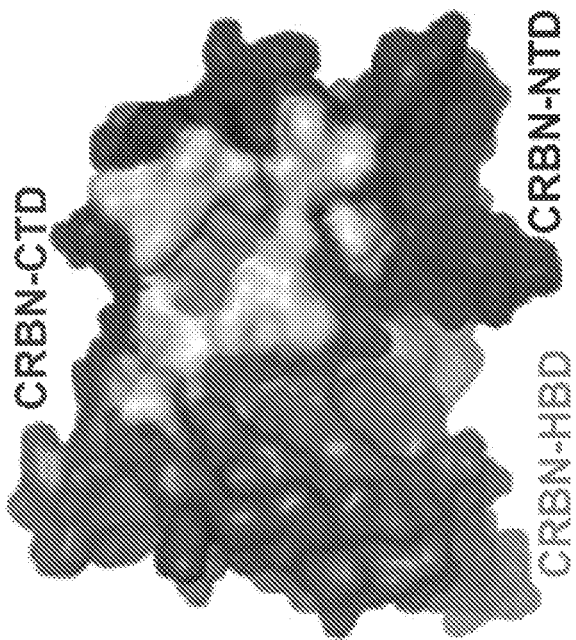
Figure 2A:
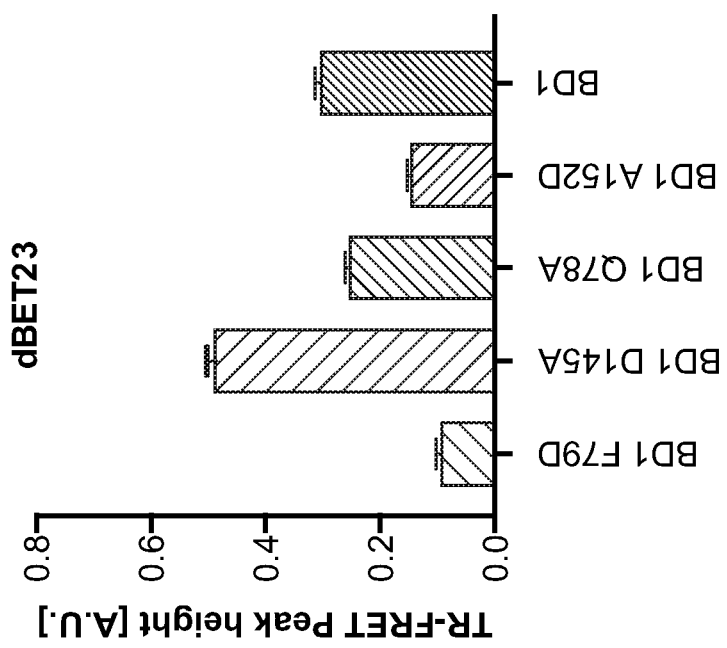
Figure 3F:
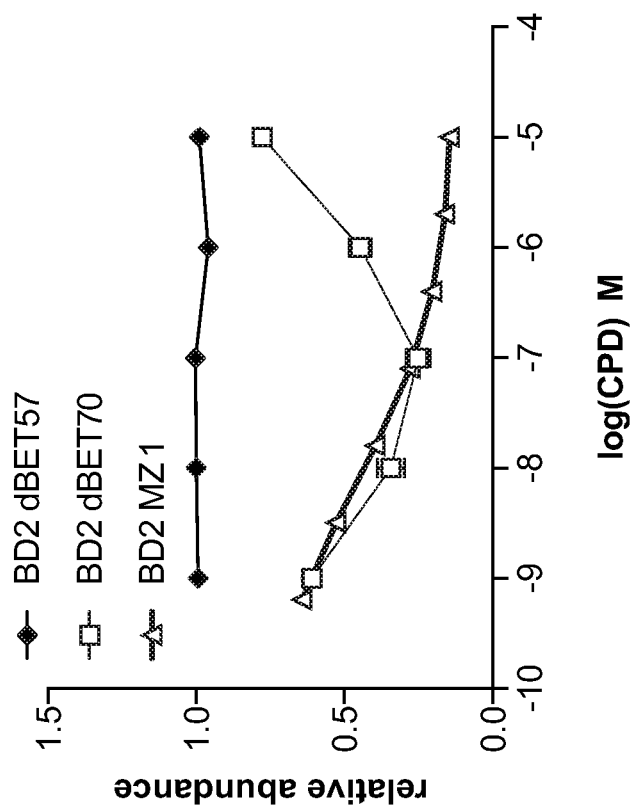
Figure 3E:
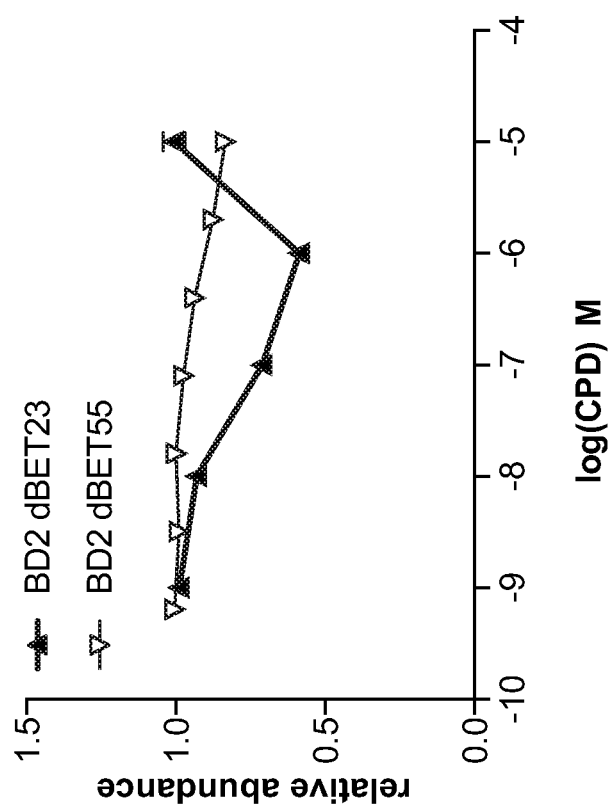

BRD4$_{BD1}$ interacts with CRBN through contacts with the NTD domain of CRBN and with CRBN residues in direct proximity to the thalidomide-binding pocket (FIG. 1D). CRBN binds the BRD4$_{BD1}$ αC helix (aa 145-161) and residues in the BRD4$_{BD1}$ ZA loop (aa 76-104) (Filippakopoulos, Picaud et al. 2012). The αC helix forms hydrophobic interactions with two loops in the CRBN-NTD (aa 101-104 and aa 147-154). Residues Leu148, Met149, Ala152, and Leu156 in the αC helix together with His77 and Phe79 in the ZA loop, form a hydrophobic patch that interacts with Phe102, His103, Phe150, Gly151, Ile152, and Ile154 in the CRBN-NTD. BRD4$_{BD1}$ Gln78 forms a hydrogen bond with Gln100 in the CRBN-NTD (FIG. 1D). Consequently, mutations of the BRD4$_{BD1}$ residues Phe79Asp, Ala152Asp, and Gln78Ala all reduce tertiary complex formation as monitored by measuring the peak-height in a TR-FRET dimerization assay (FIG. 2A). The Examples further showed that Asp145 is buried in a hydrophobic environment, and accordingly, introducing an Asp145Ala mutation strengthens the binding of BRD4$_{BD1}$ to CRBN (FIG. 2A). The interaction between CRBN and BRD4$_{BD1}$ consists of a total buried surface area of ~550 Å$^2$ (FIG. 2B) (Krissinel and Henrick 2007), comparable to that observed for CRBN-Ck1α (~600 Å$^2$) and GSPT1 (~600 Å$^2$) (Matyskiela, Lu et al. 2016, Petzold, Fischer et al. 2016).

Figure 8A:
FIG. 8A is an image that shows a cartoon representation of DDB1ΔB-CRBN-dBET6-BRD4$_{BD1}$. The $F_O$-$F_C$ map is shown as green mesh for dBET6 contoured at 4.0σ.
Figure 8B:
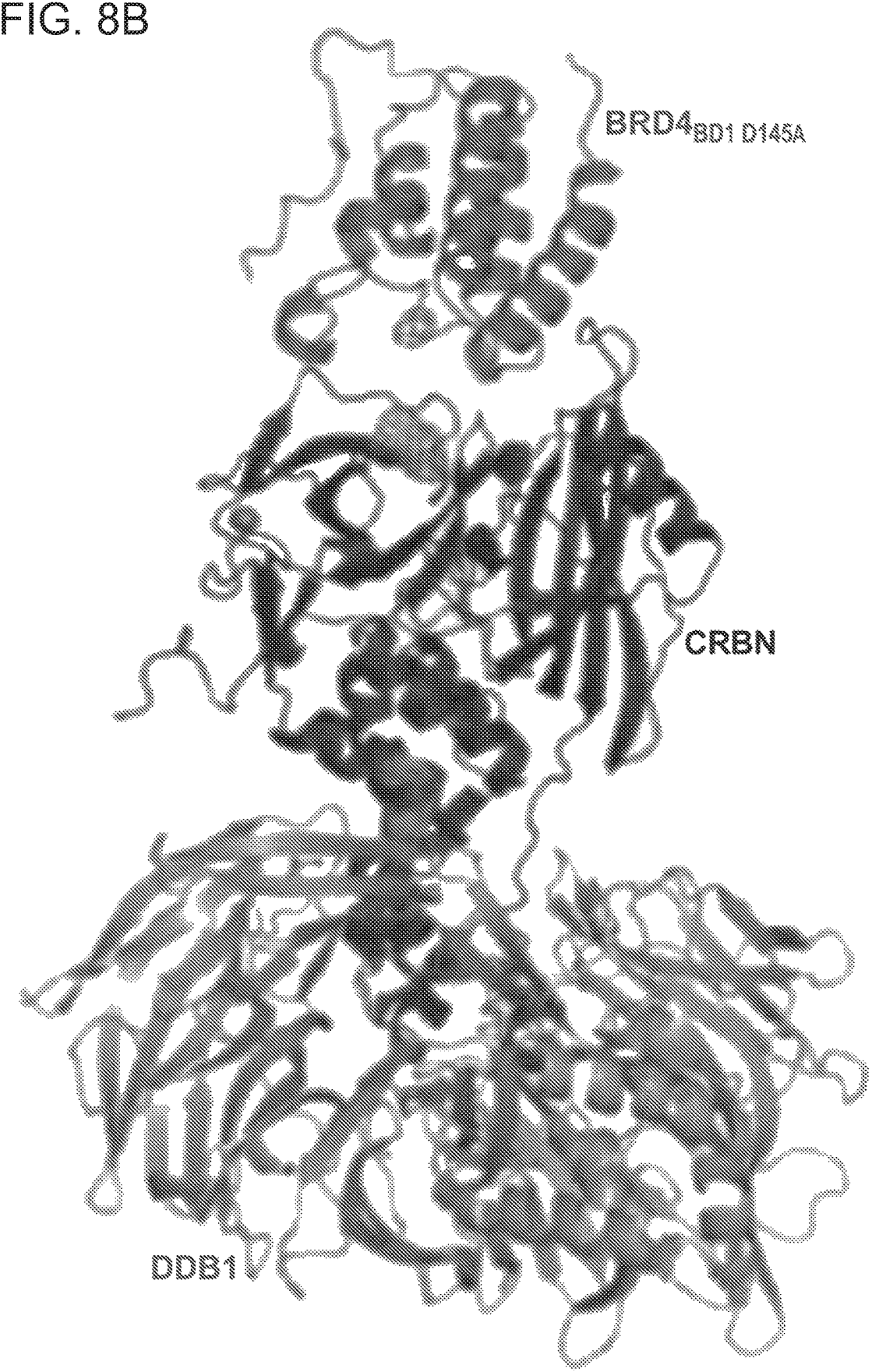
FIG. 8B is an image that shows a cartoon representation of DDB1ΔB-CRBN-dBET70-BRD4$_{BD1}$. The $F_O$-$F_C$ map is shown as green mesh for dBET70 contoured at 4.0σ.
Figure 8C:
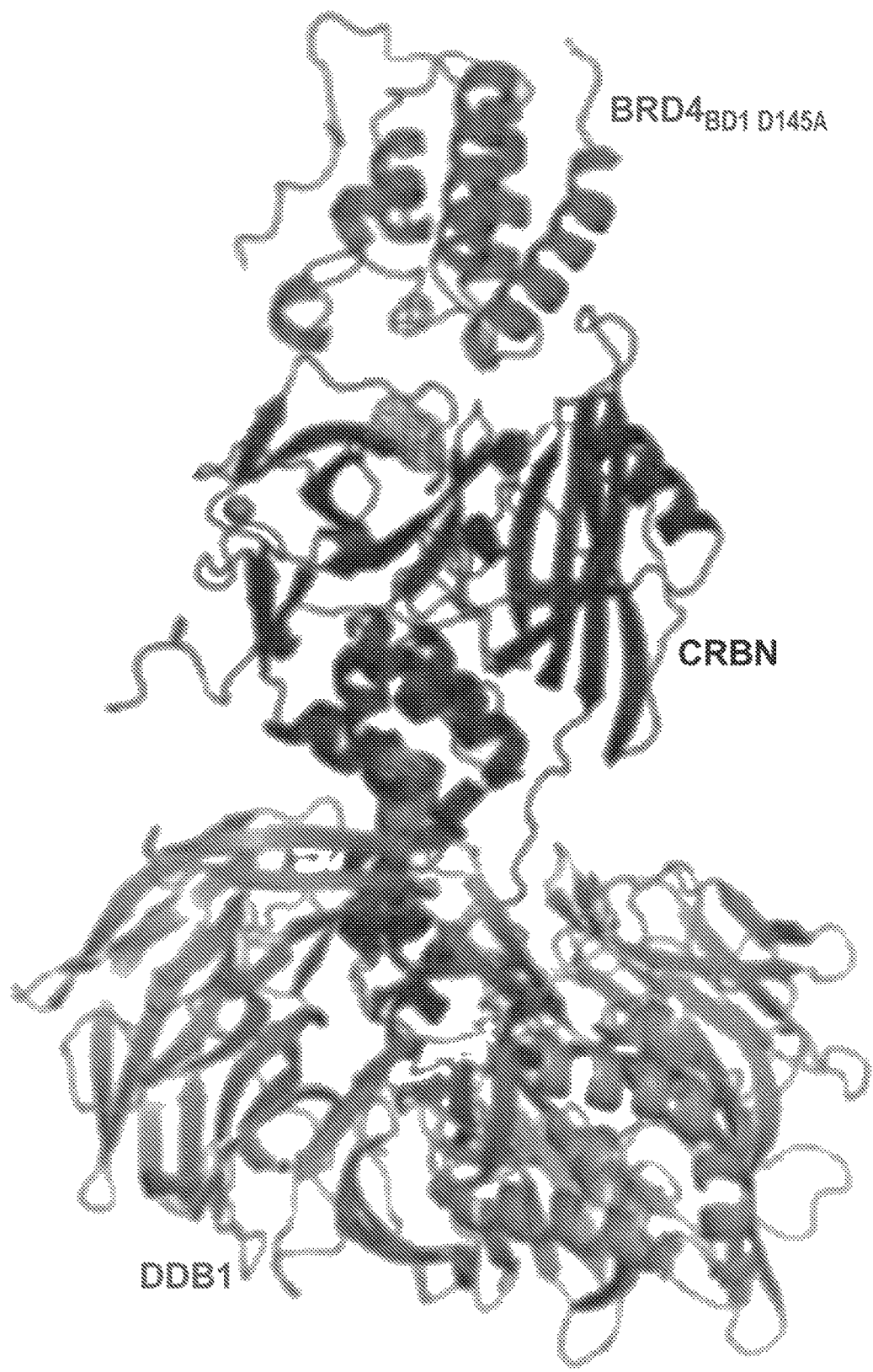
FIG. 8C is an image that shows a cartoon representation of DDB1ΔB-CRBN-dBET55-BRD4$_{BD1/D145A}$. The $F_O$-$F_C$ map is shown as green mesh contoured at 3.0σ.
Figure 8D:
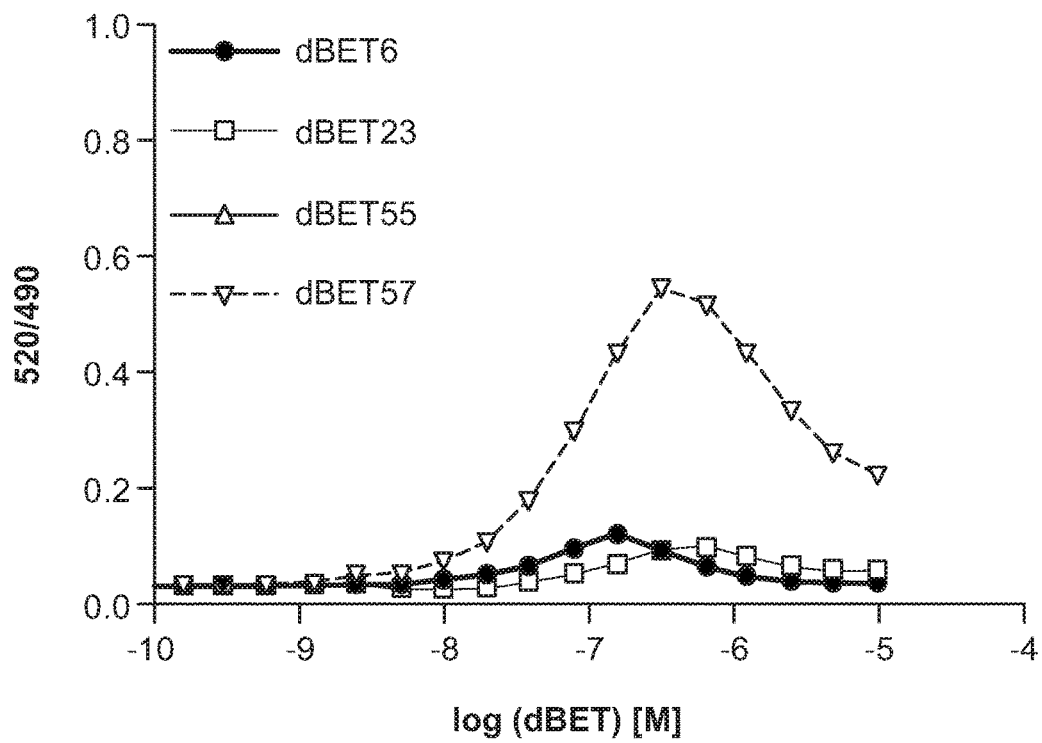
FIG. 8D-FIG. 8J are tables that show TR-FRET data underlying bar charts shown in FIG. 2A, FIG. 4A-FIGS. 4D and 11D-L. The TR-FRET data in FIG. 8D-FIG. 8J represent biological replicates presented as means±s.d. (n=3).
Figure 8E:
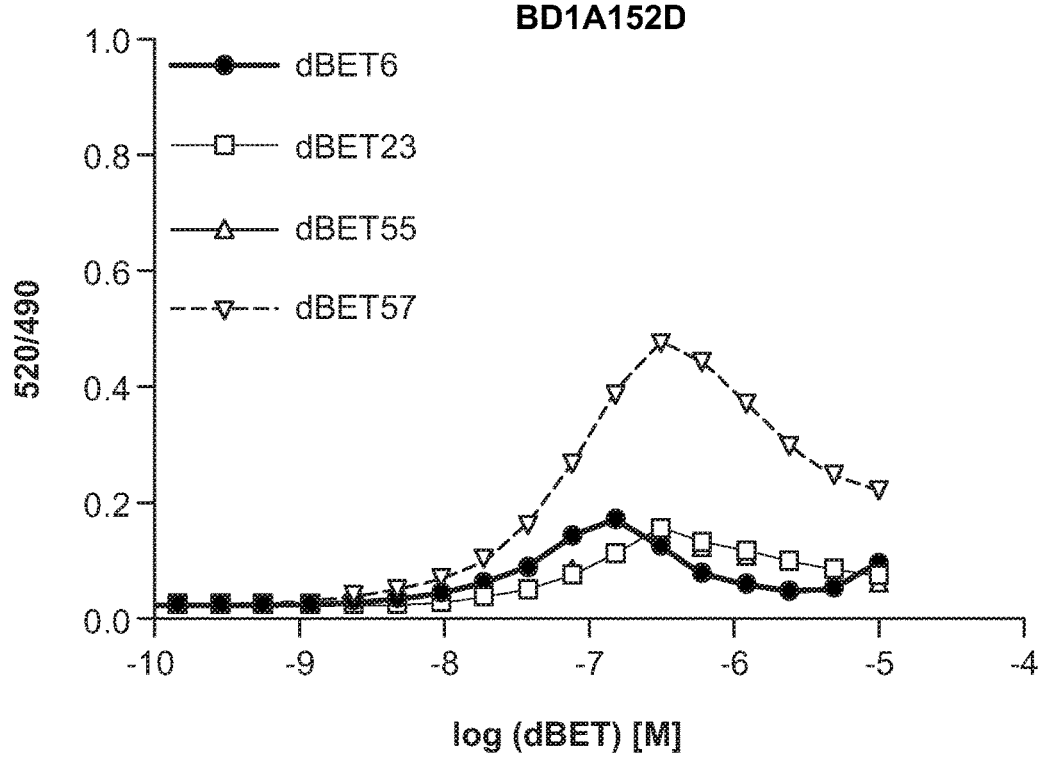
Figure 8F:
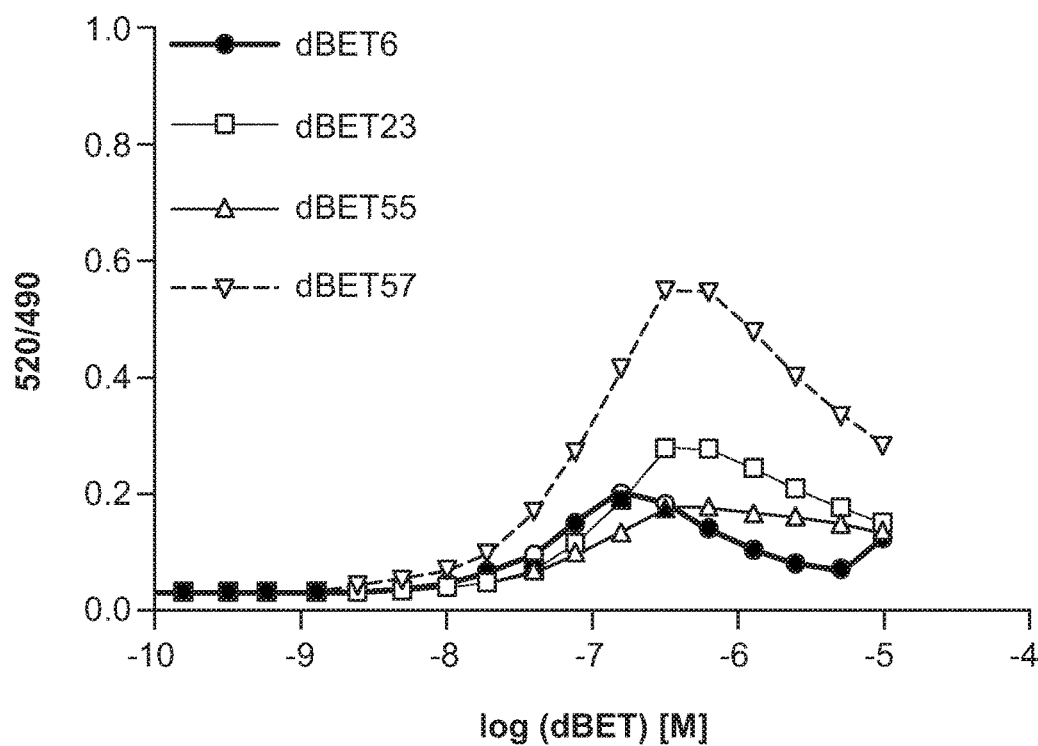
Figure 8G:
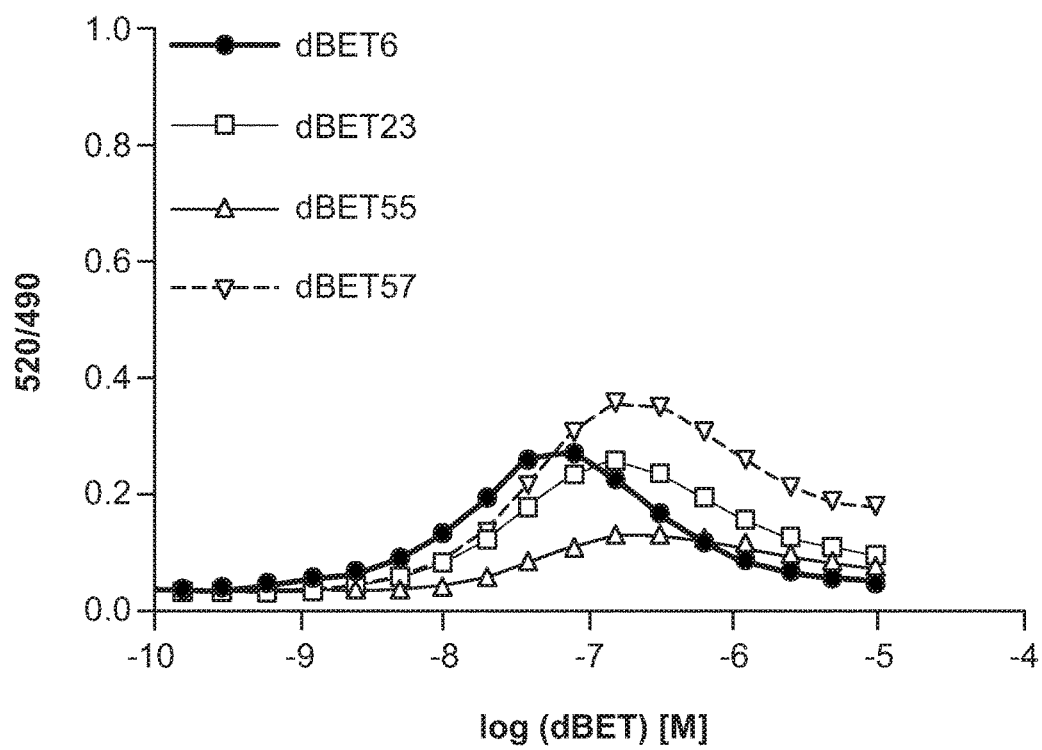
Figure 8H:
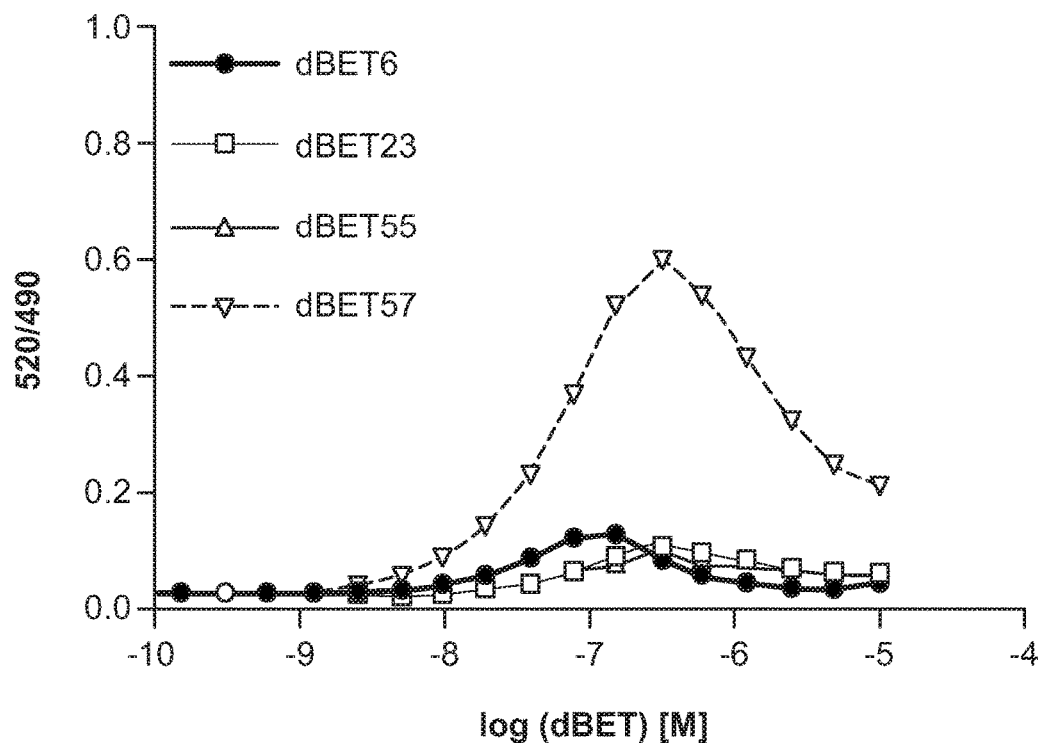
Figure 8I:
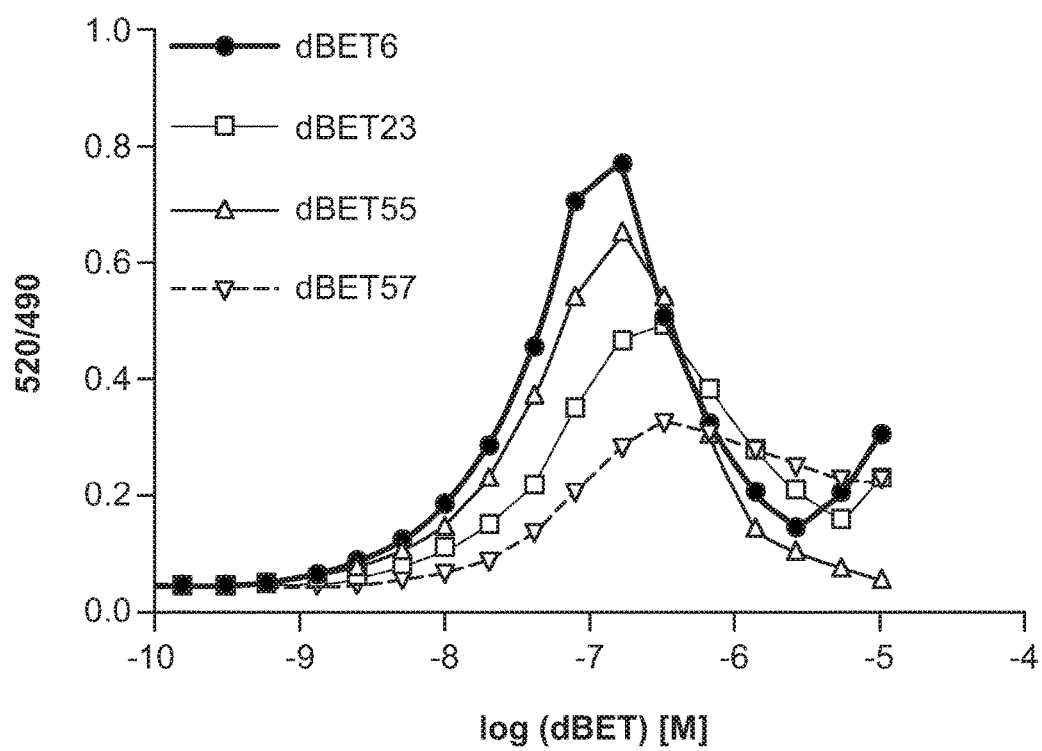
Figure 8J:
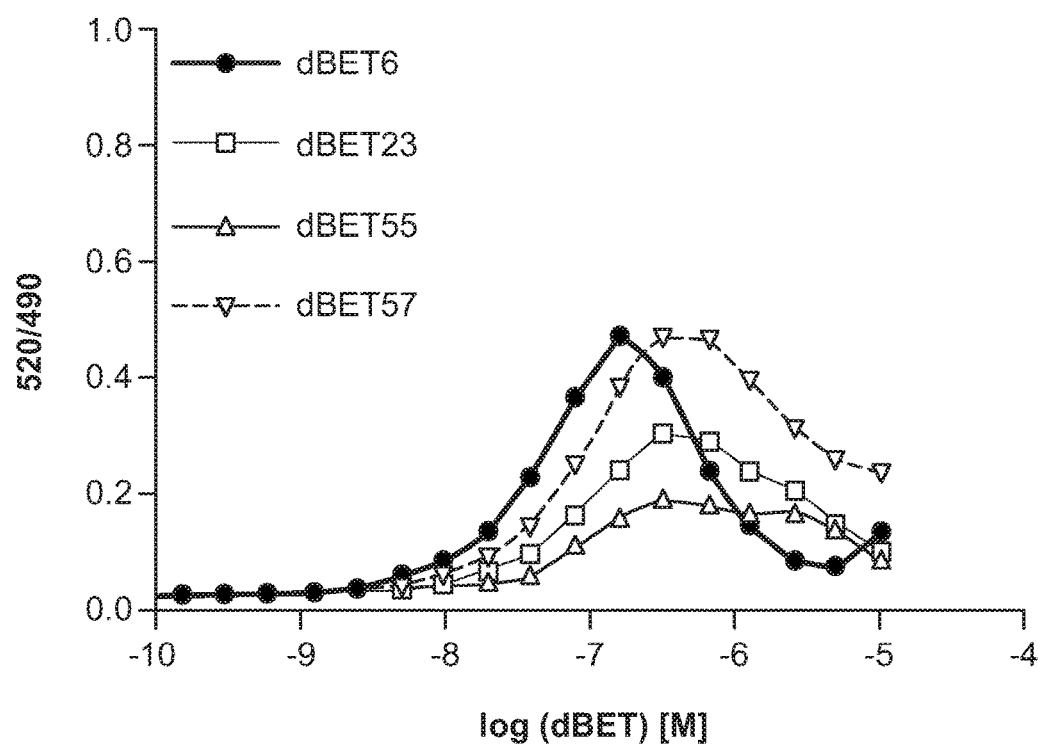
Figure 9A:
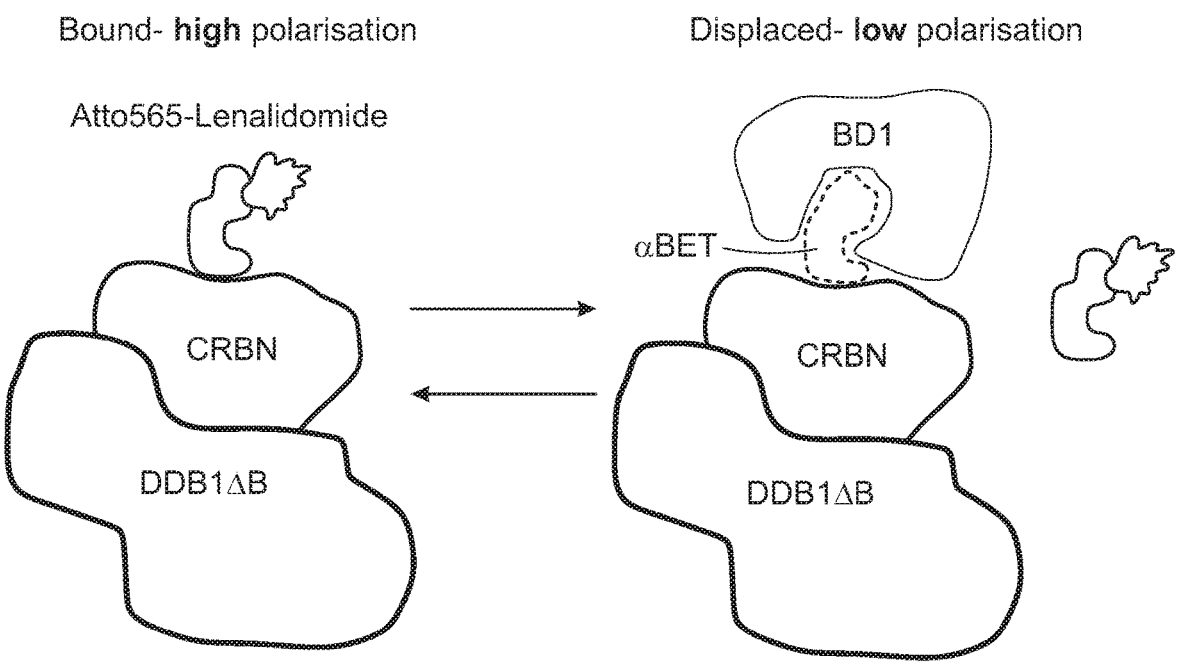
Figure 9B:
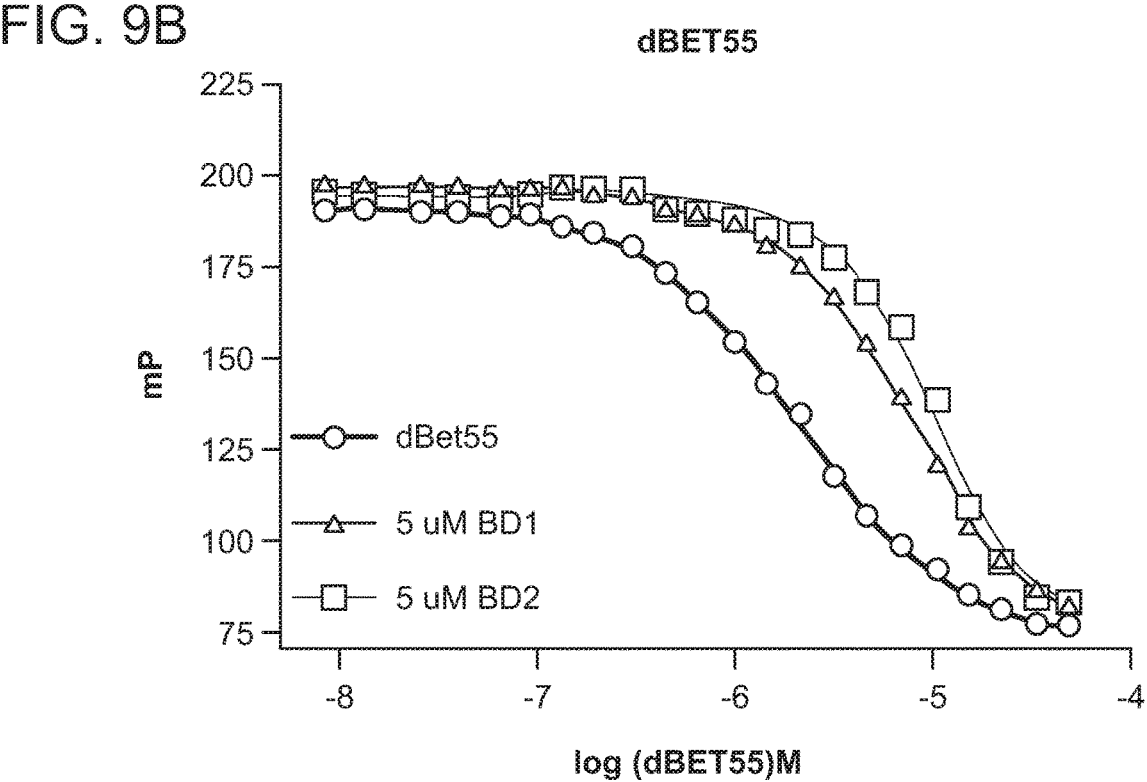
Figure 9C:
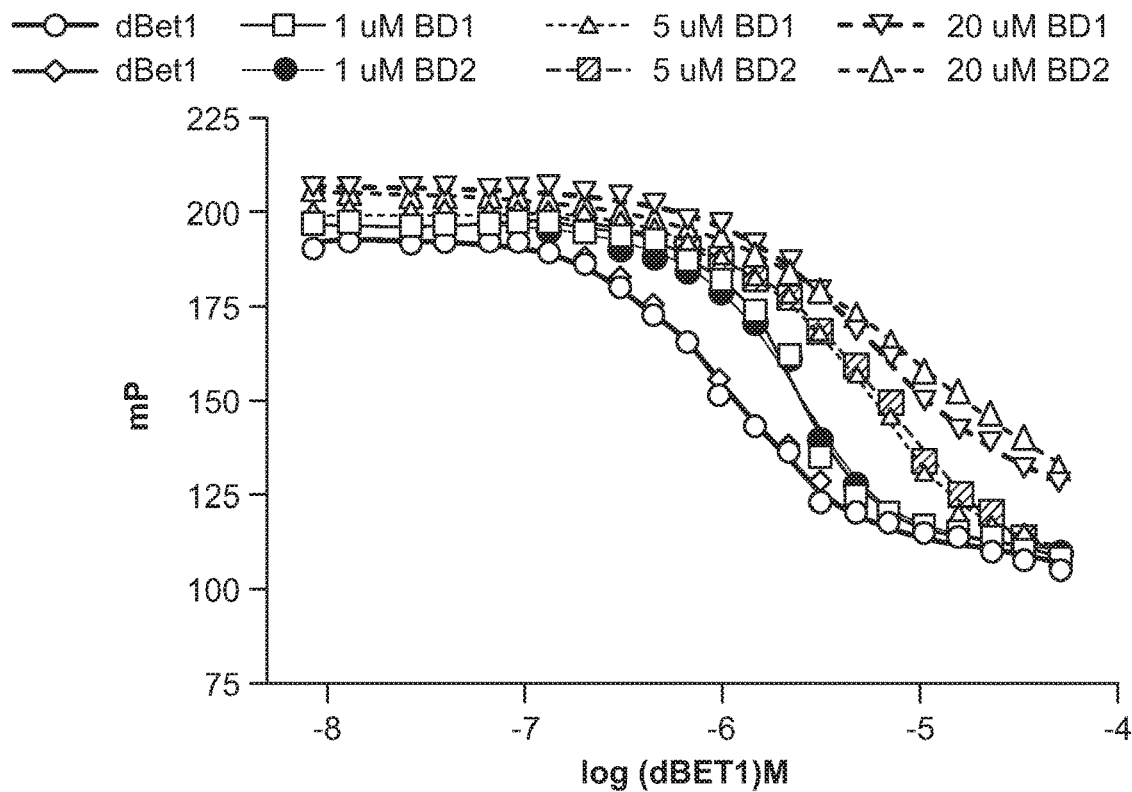
Figure 9D:
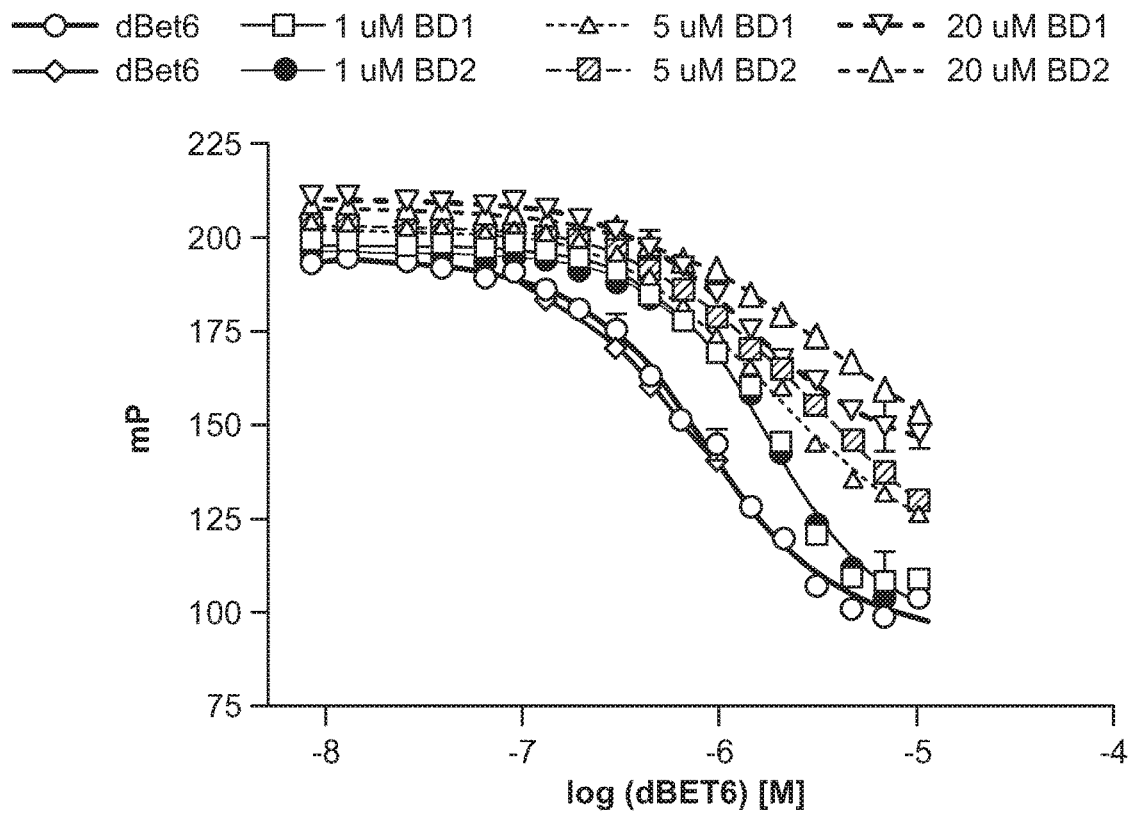
Figures 9G, 9H:
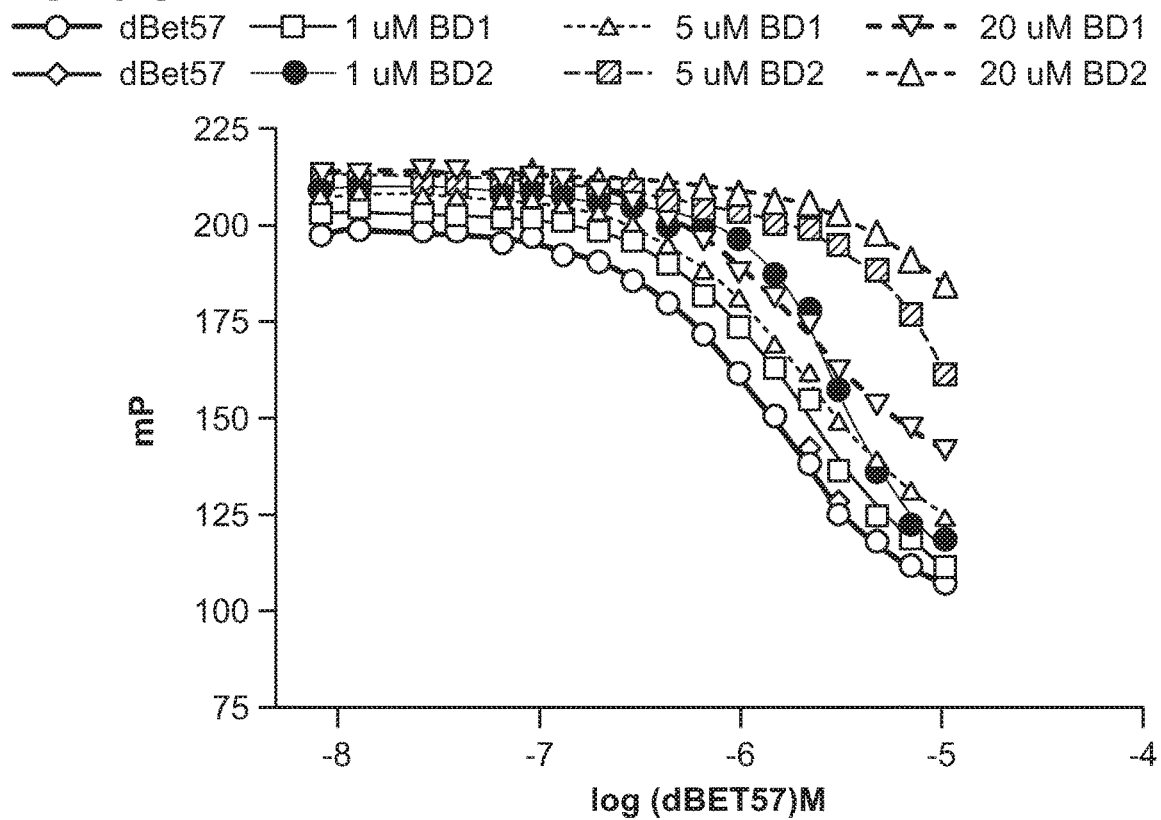
Figure 10A:
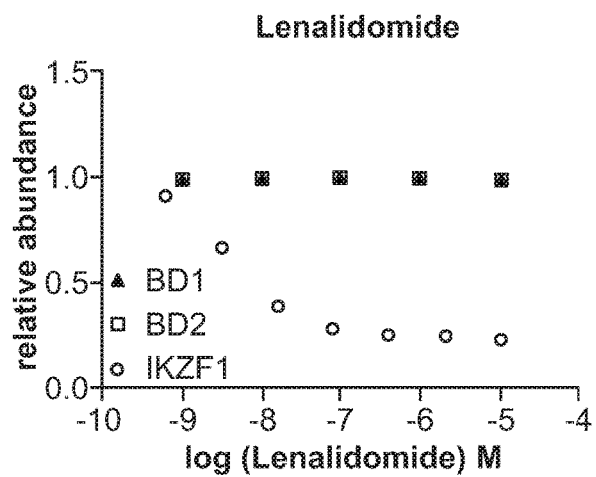
FIG. 10A-FIG. 10L are graphs that show quantitative assessment of cellular degradation of BRD4$_{BD1}$-EGFP/BRD4$_{BD2}$-EGFP and IKZF1Δ-EGFP by lenalidomide, dBET1, dBET6, dBET23, dBET55, dBET57, dBET70, dBET72, MZ1, ZXH-2-42, ZXH-2-43, and ZXH-2-45, respectively, using flow cytometry analysis. Cells stably expressing BRD4$_{BD1}$-EGFP/BRD4$_{BD2}$-EGFP or IKZF1Δ-EGFP with a mCherry reporter were treated with increasing concentrations of the heterobifunctional small molecule degraders with the EGFP and mCherry signals quantified using flow cytometry analysis.
Figure 10B:
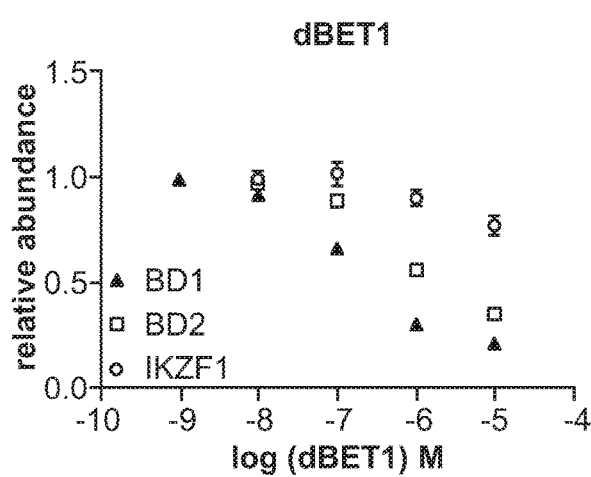
Figure 10C:
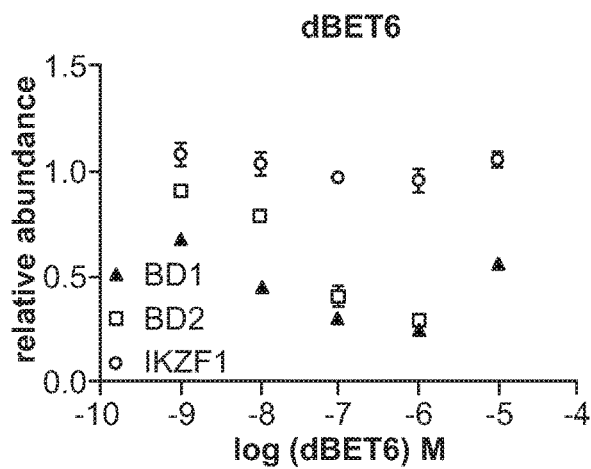
Figure 10D:
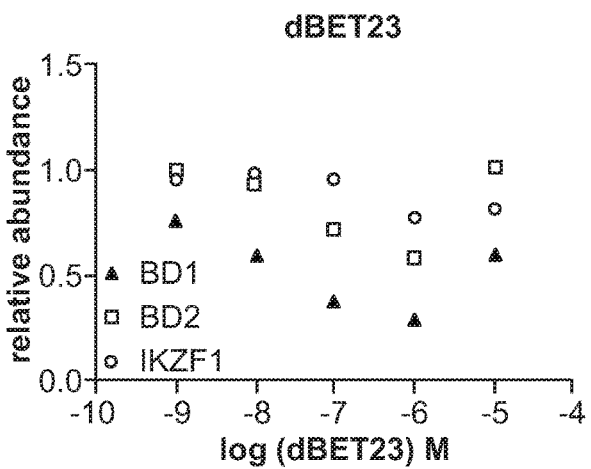
Figure 10E:
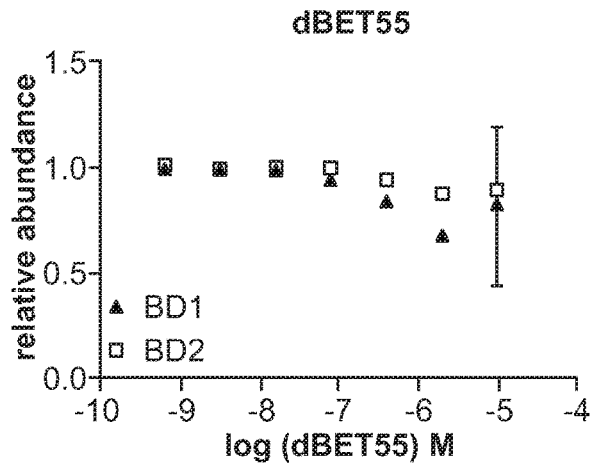
Figure 10F:
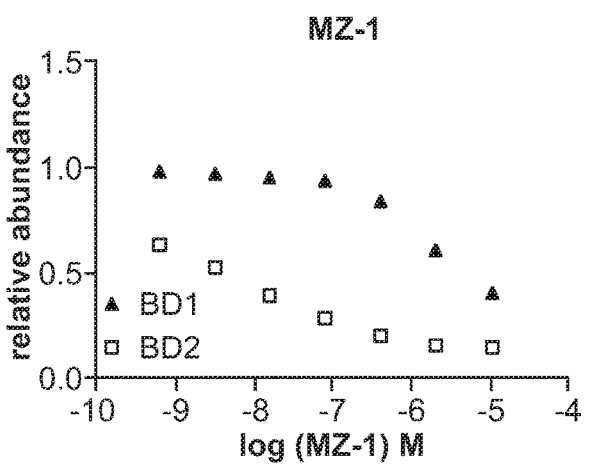
Figure 10G:
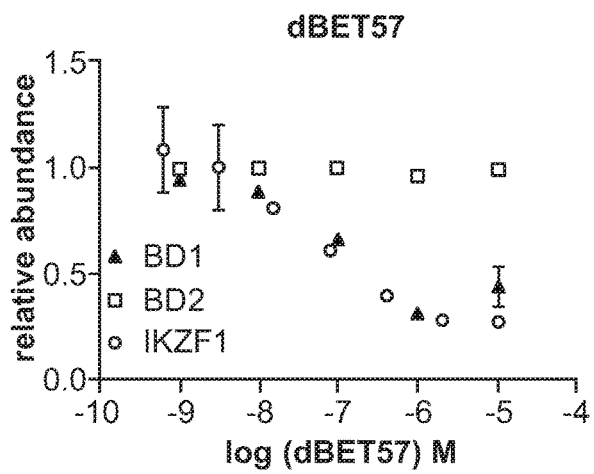
Figure 10H:
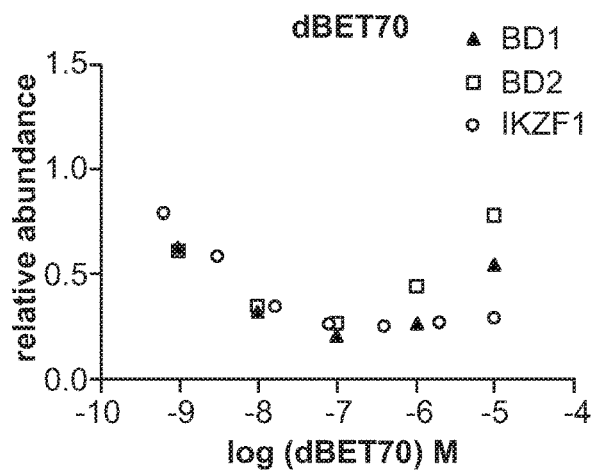
Figure 10I:
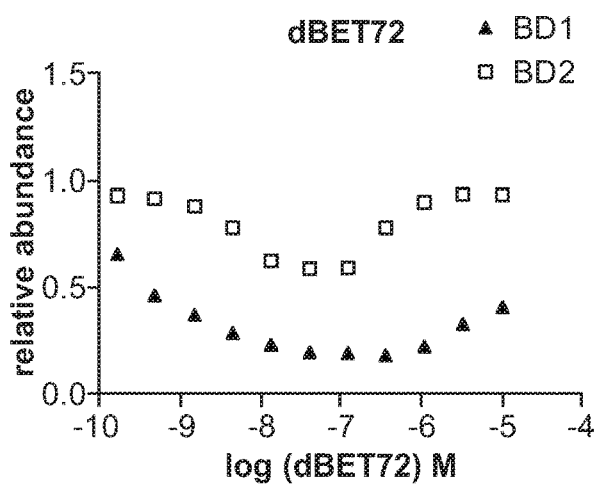
Figure 10J:
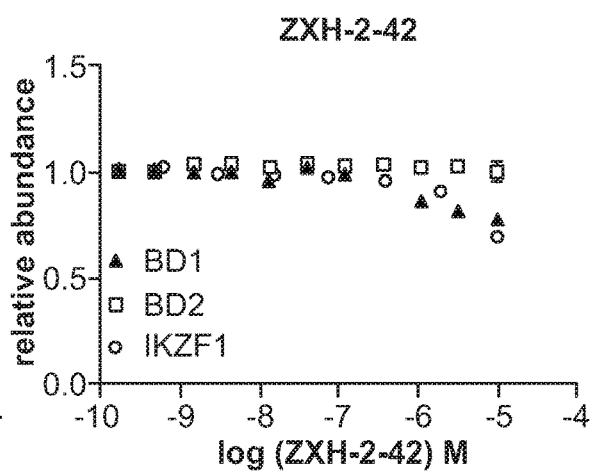
Figure 10K:
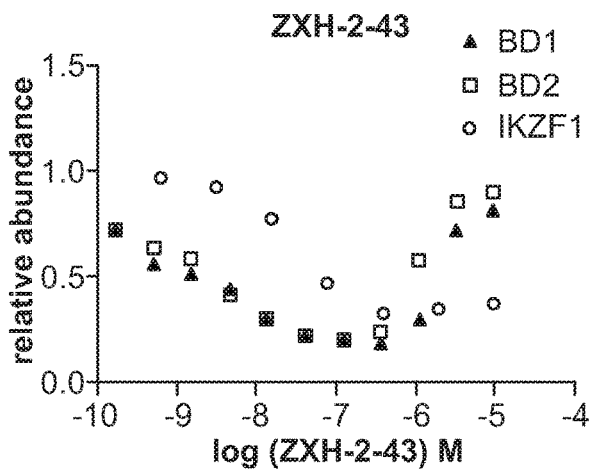
Figure 10L:
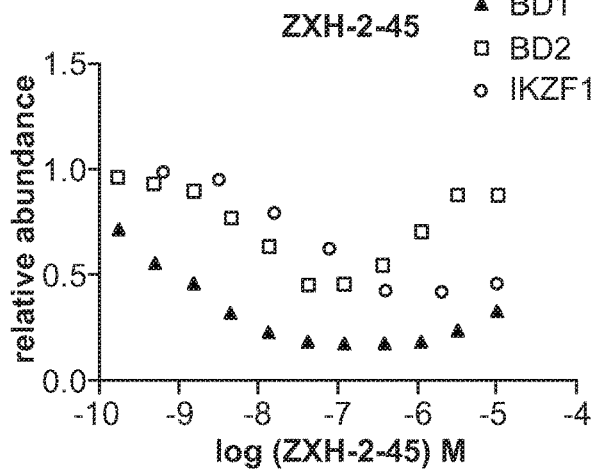

In addition to dBET23, the Examples determined crystal structure with the related molecules dBET6 (3.3 Å resolution), dBET70 (4.3 Å resolution)—both have linkers of similar length—and significantly longer dBET55 (4.0 Å resolution and crystallized with BRD4$_{BD1\ (D145A)}$). The overall structures of these complexes are comparable to the structure obtained with dBET23 (FIGS. 8A and B) and the involvement of near identical inter-protein contacts is further confirmed by similar effects of BRD4$_{BD1}$ interface mutations on complex formation (FIG. 8C).

Example 2: Inter-Protein Contacts are Unique to BRD4$_{BD1}$

The amino acid sequences of BRD4$_{BD1}$ to BRD4B$_{D2}$ are 49% similar (FIG. 7D), yet none of the key residues in the αC helix or the ZA loop involved in contacts with CRBN are identical. The Examples addressed whether affinity of BRD4$_{BD2}$ for CRBN is reduced in the presence of dBET6 or dBET23. While the determination of absolute binding affinities is difficult for a three body binding problem (Douglass, Miller et al. 2013), a qualitative measure of the relative affinities (or cooperativity of binding) can be indirectly obtained through CRBN-dBET binding assays in presence or absence of purified BRD4$_{BD1}$ or BRD4$_{BD2}$ protein. Using a lenalidomide-Atto565 fluorescent probe, binding of dBETs to CRBN was measured by competitive titration (FIGS. 2C-F). Next, the Examples show similar binding experiments in presence of increasing concentrations of either BRD4$_{BD1}$ or BRD4$_{BD2}$ to assess the cooperativity of ternary complex formation. An apparent cooperativity factor alpha was defined as $\alpha_{app}$=IC$_{50}$[binary]/IC$_{50}$[ternary], with positive cooperativity resulting in $\alpha_{app}$>1, and negative cooperativity in $\alpha_{app}$<1 (see FIG. 2C-FIG. 2F and FIG. 9A-FIG. 9G). dBET6, exhibited an IC$_{50}$ of ~0.8 μM in the absence of BRD4, which increases to an IC$_{50}$ of 1.8 μM ($\alpha_{app}$=0.6) in the presence of BRD4$_{BD1}$, and an IC$_{50}$ of ~4.1 μM ($\alpha_{app}$=0.2) in the presence of BRD4$_{BD2}$ (FIG. 2D and FIG. 9A-FIG. 9C), indicative of negative cooperativity for both BRD4$_{BD1}$ and BRD4$_{BD2}$. For dBET23 and dBET57 the difference between BRD4$_{BD1}$ and BRD4$_{BD2}$ is more pronounced, with $\alpha_{app}$=0.4 (dBET23) and $\alpha_{app}$=0.8 (dBET57) for BRD4$_{BD1}$ and $\alpha_{app}$<0.1 for BRD4$_{BD2}$ (the binding in presence of BRD4$_{BD2}$ is too weak to quantify), indicating negative cooperativity and a preference for binding to BRD4$_{BD1}$ (FIG. 2E and FIG. 2F and FIG. 9A-FIG. 9G).

To better understand the drivers of selectivity and to test whether the observed differences in cooperativity would result in differential degradation of isolated BRD4 bromodomains, a system was developed that allowed us to directly quantify cellular degradation of either BRD4$_{BD1}$ or BRD4$_{BD2}$. Reporter cells that stably express BRD4$_{BD1}$-EGFP followed by a P2A splice site separated mCherry, were treated with increasing concentrations of dBET molecules (FIG. 3A-FIG. 3F). This assay format enables quantitative readout of BRD4$_{BD1}$ degradation with the GFP/mCherry ratio using flow cytometry (similar reporter cells were used for BRD4$_{BD2}$, or an IKZF protein that has internal deletions 41-82, 4197-239, and 4256-519 hereafter referred to as IKZFΔ). The Examples demonstrate that dBET6

($DC_{50/5h}$~10 nM, with $DC_{50/5h}$ referring to half-maximal degradation after 5 hours of treatment), dBET23 ($DC_{50/5h}$~50 nM) and dBET70 ($DC_{50/5h}$~5 nM) exhibit the most potent effects on $BRD4_{BD1}$ protein levels, followed by dBET1 ($DC_{50/5h}$~500 nM) and dBET57 ($DC_{50/5h}$~500 nM) (FIGS. 3A-C and FIGS. 10A-L). For $BRD4_{BD2}$, dBET70 ($DC_{50/5h}$~5 nM) has the most pronounced effects, followed by dBET6 ($DC_{50/5h}$~50 nM), dBET23 ($DC_{50/5h}$>1 µM) and dBET1 ($DC_{50/5h}$ dBET57, which exhibits significant degradation of $BRD4_{BD1}$, is inactive on $BRD4_{BD2}$ (FIGS. 3D-F and FIGS. 10A-L). The cellular activity is thus directly proportional to the observed cooperativity factors (FIGS. 9A-B), and dBET57 was found remarkably selective for $BRD4_{BD1}$ in biochemical and cellular assays (FIG. 2F and FIGS. 3A-F).

Example 3: Plastic Binding Confers Selectivity to dBETs

Figure 11A:
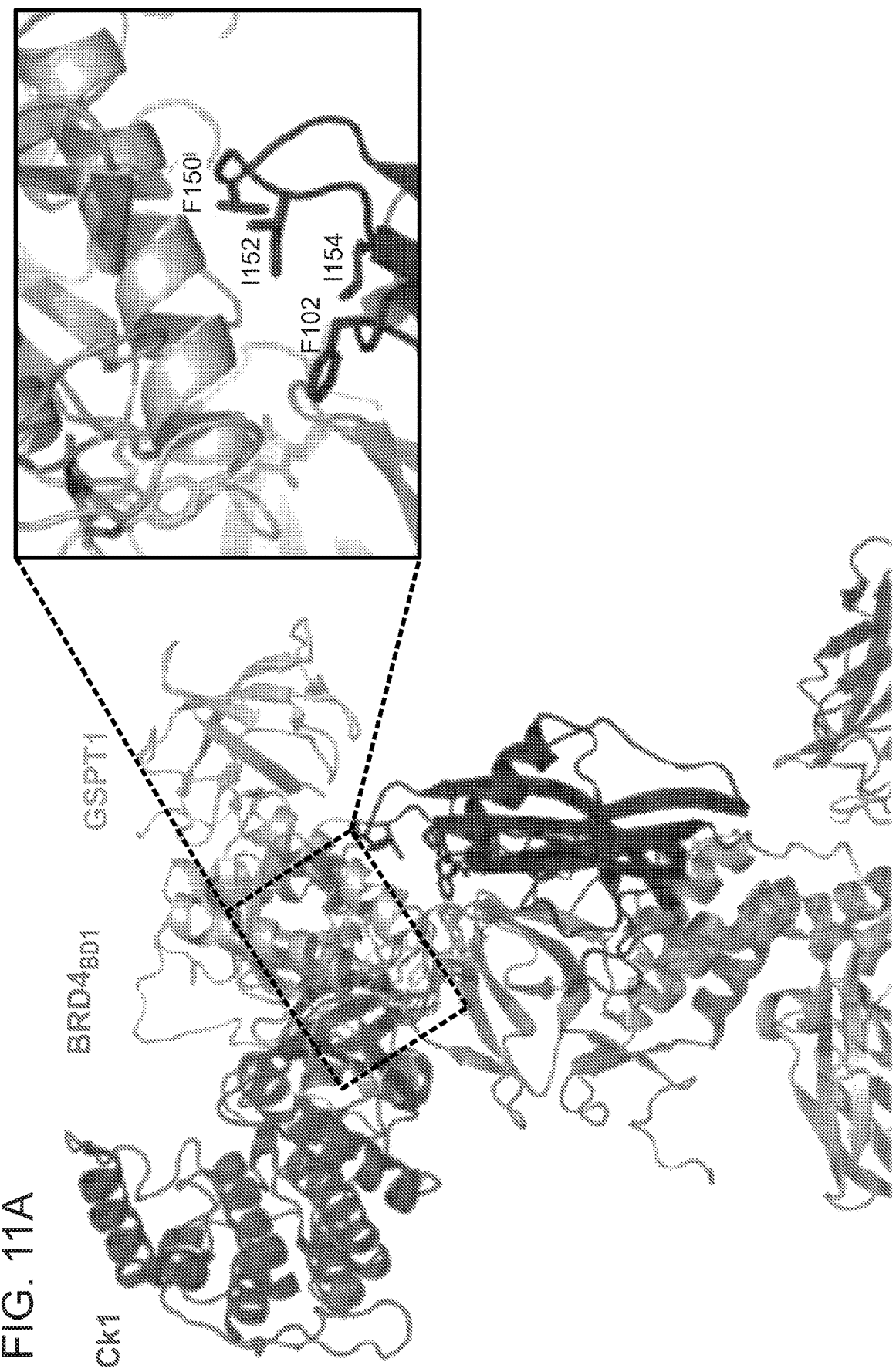
FIG. 11A-FIG. 11I show plasticity of CRBN-substrate interactions.
Figure 11B:
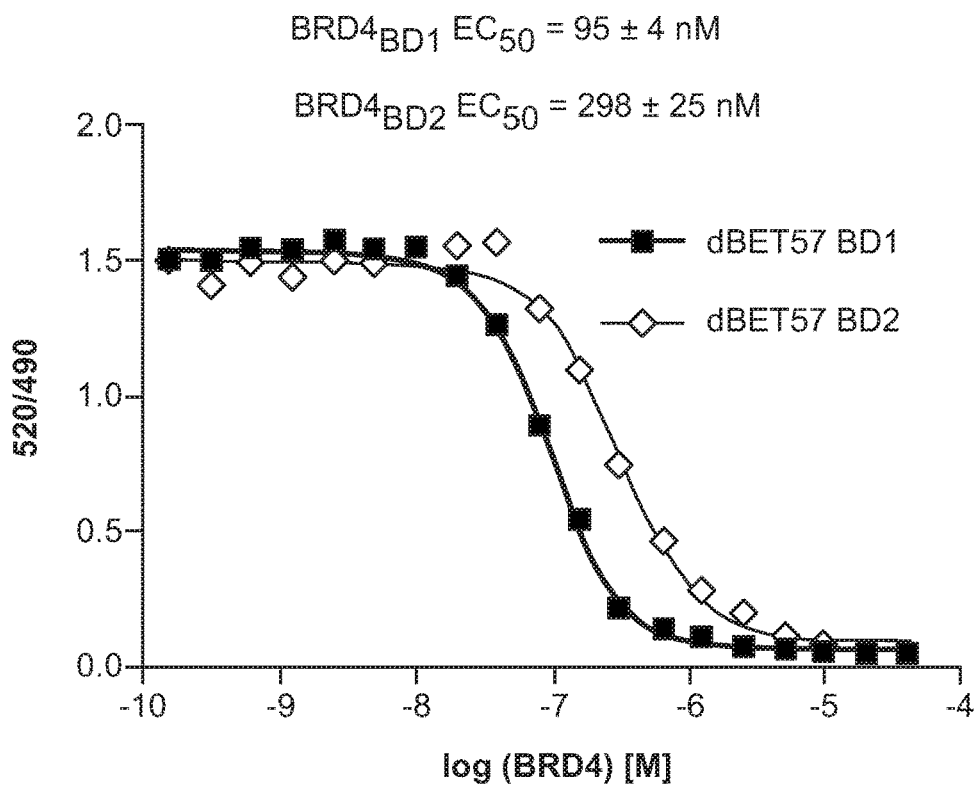
Figure 11C:
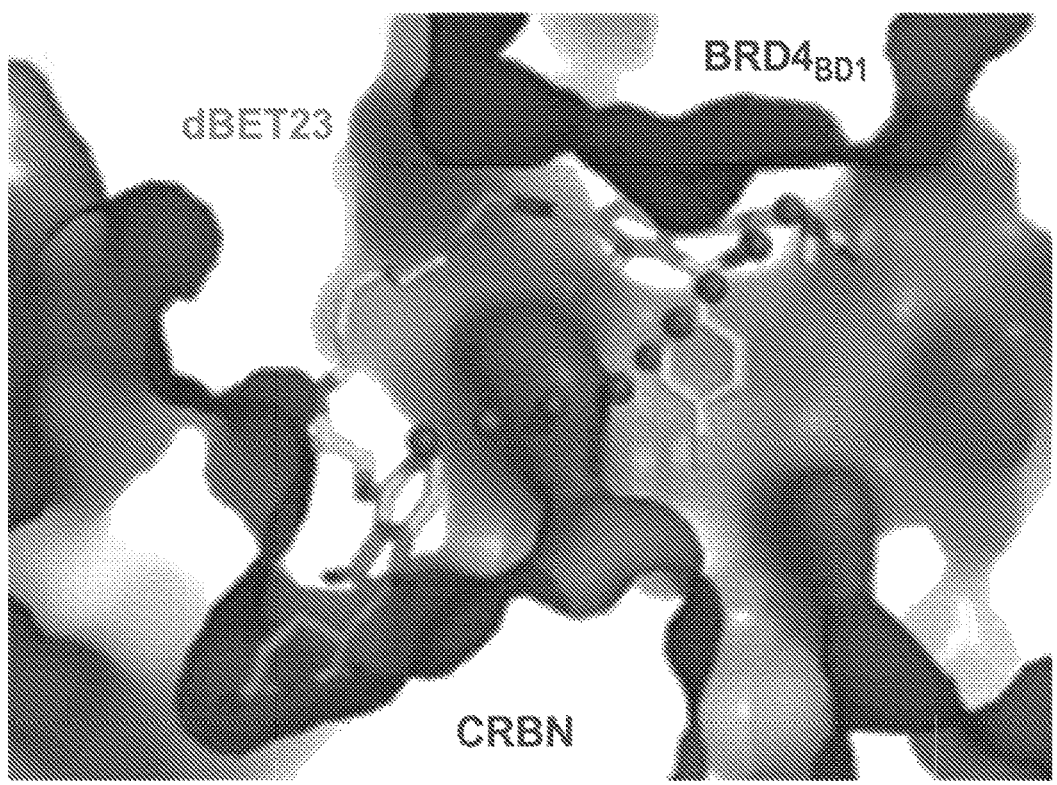
Figure 11D:
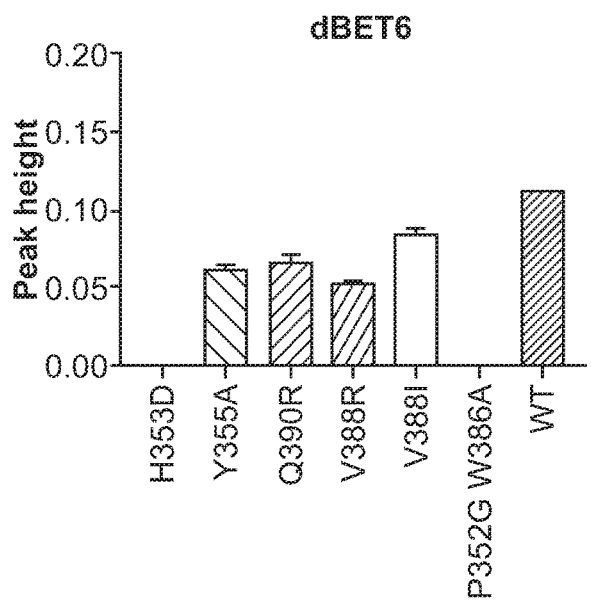
Figure 11E:
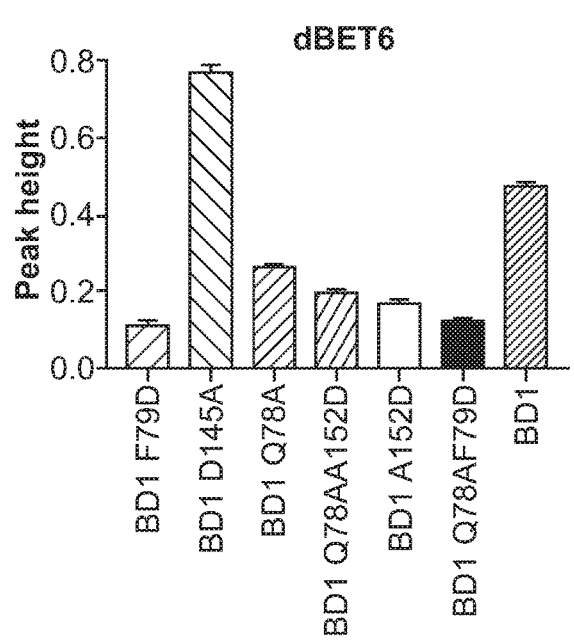
Figure 11F:
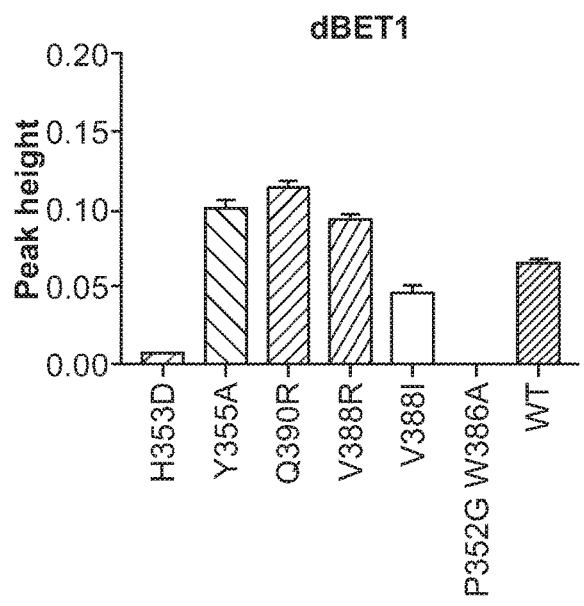
Figure 11G:
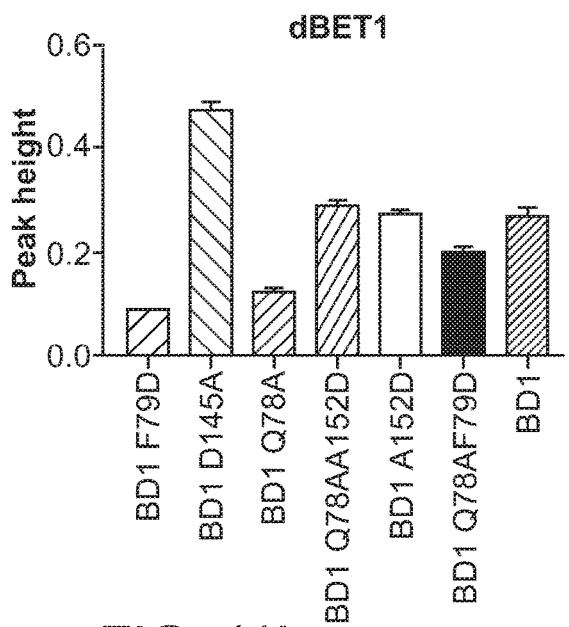
Figure 11H:
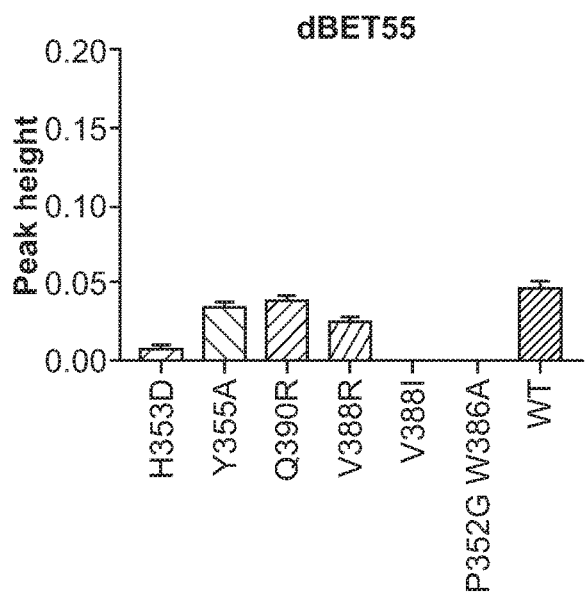
Figure 11I:
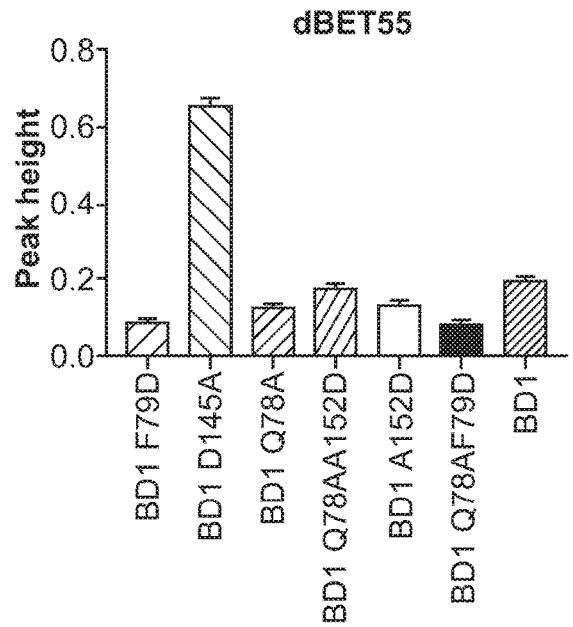

When comparing the CRBN-dBET23-$BRD4_{BD1}$ structure to the previously determined structures of CRBN-Ck1α (Petzold, Fischer et al. 2016), and CRBN-GSPT1 (Matyskiela, Lu et al. 2016), the Examples show that these neo-substrates use different surfaces on CRBN to stabilize tertiary complex formation (FIG. 11A). The Examples also show that molecules with short linkers, such as dBET57, would not be able to dimerize CRBN and BRD4 in the conformation observed in the CRBN-dBET23-$BRD4_{BD1}$ structure since a minimum of 8 carbons would be required to bridge the E3-moeity with the target-moiety and dBET57 comprises a 2-carbon linker (FIG. 11C). Additional Examples address whether dBET molecules incompatible with the observed binding mode, such as dBET57 or dBET1, would bind in a different overall conformation.

To explore potential differences in binding, mutational analysis was performed. A set of single amino acid point mutations was introduced in CRBN and $BRD4_{BD1}$ to obtain a mutational signature of binding. When comparing the mutational signatures of different dBETs, the Examples show that while dBET6 and 23 share similar profiles (FIGS. 4A and B, and 11D and E), the mutational signatures of dBET1 and dBET57 are distinct (FIG. 4A-FIG. 4D and FIG. 11D-FIG. 11I). This suggests that different dBET molecules—depending on linker length and linkage position—result in distinct binding conformations of CRBN-BRD4 complex formation.

Figure 4B:
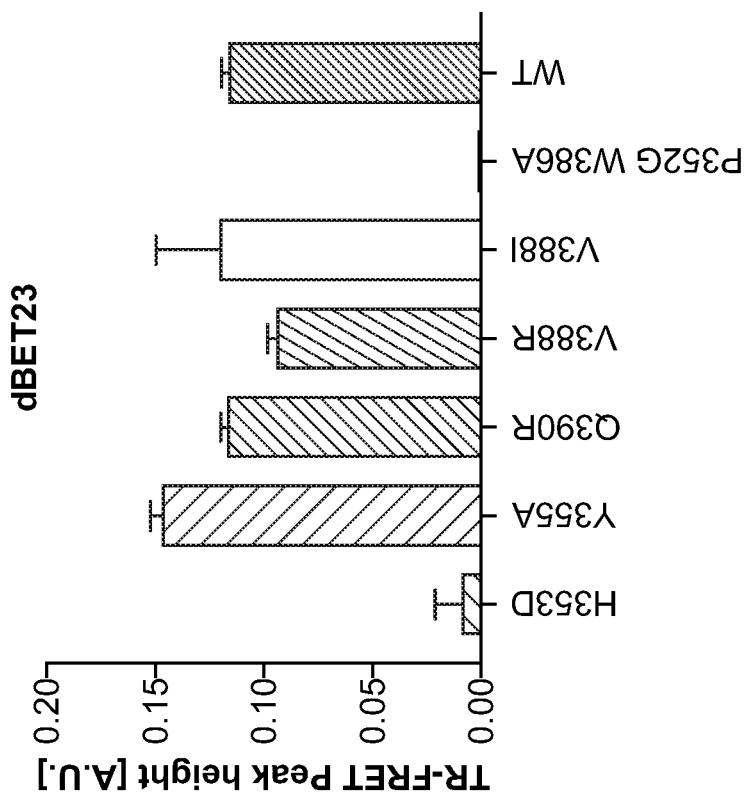
FIG. 4A-FIG. 4H show data demonstrating plasticity of CRBN-substrate interactions.
Figure 4A:
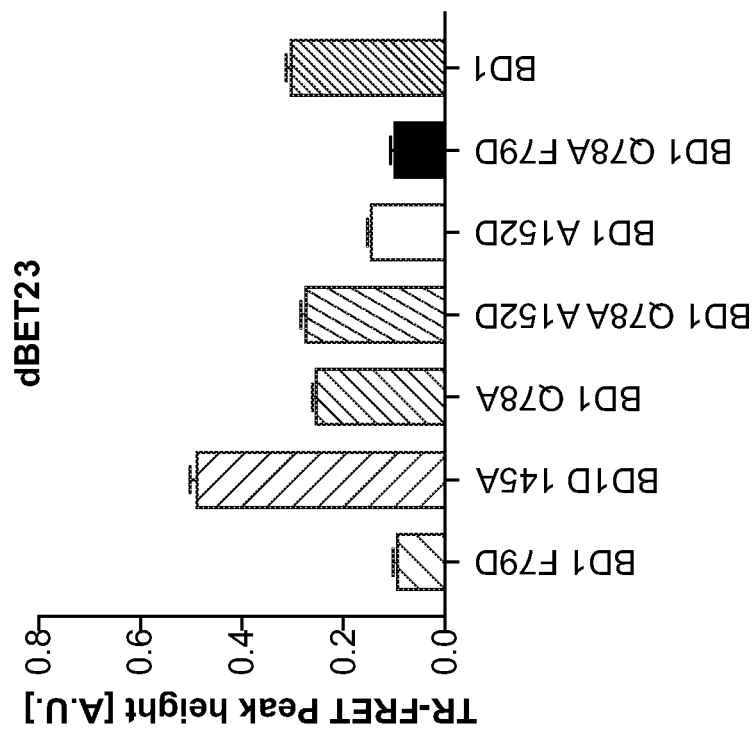
Figure 4D:
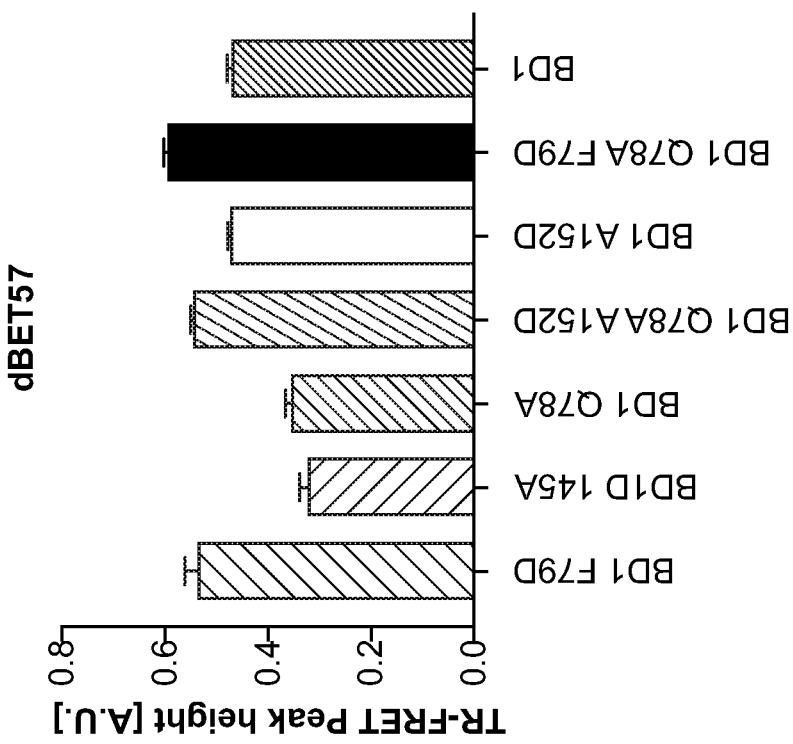
Figure 4C:
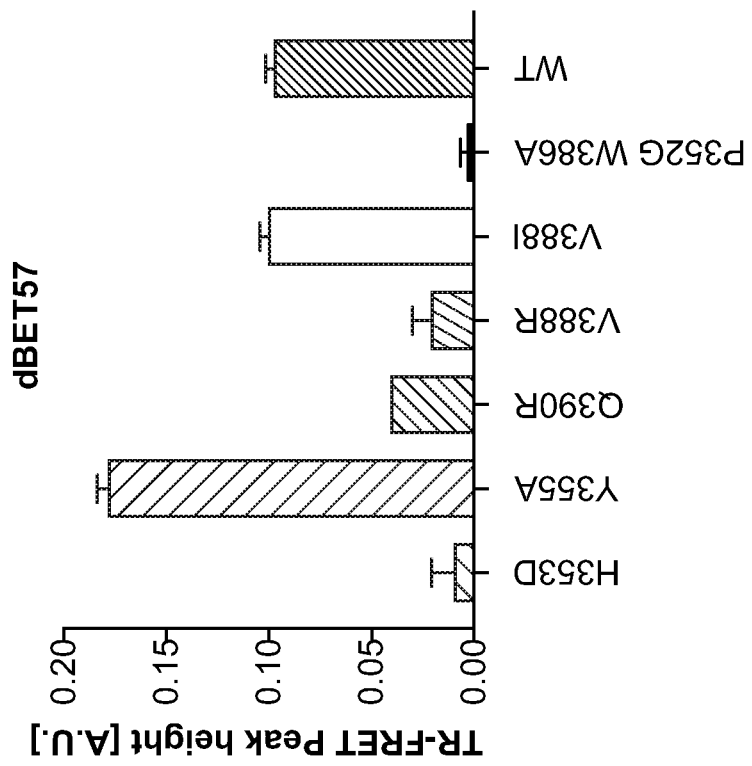
Figure 4E:
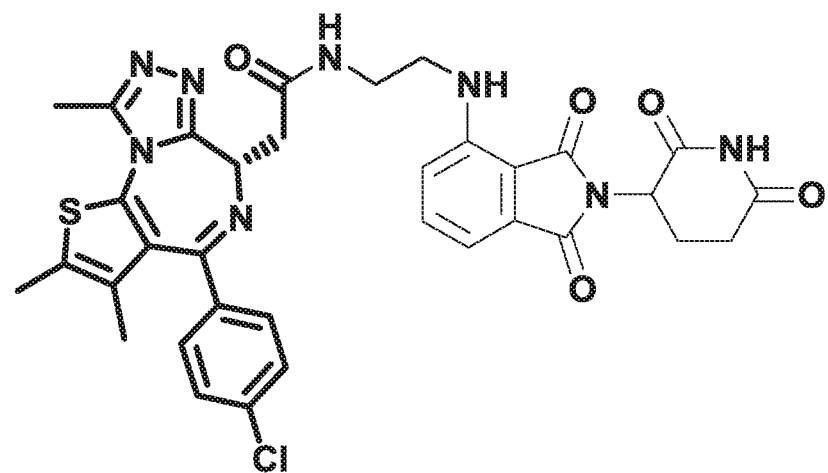
Figure 4F:
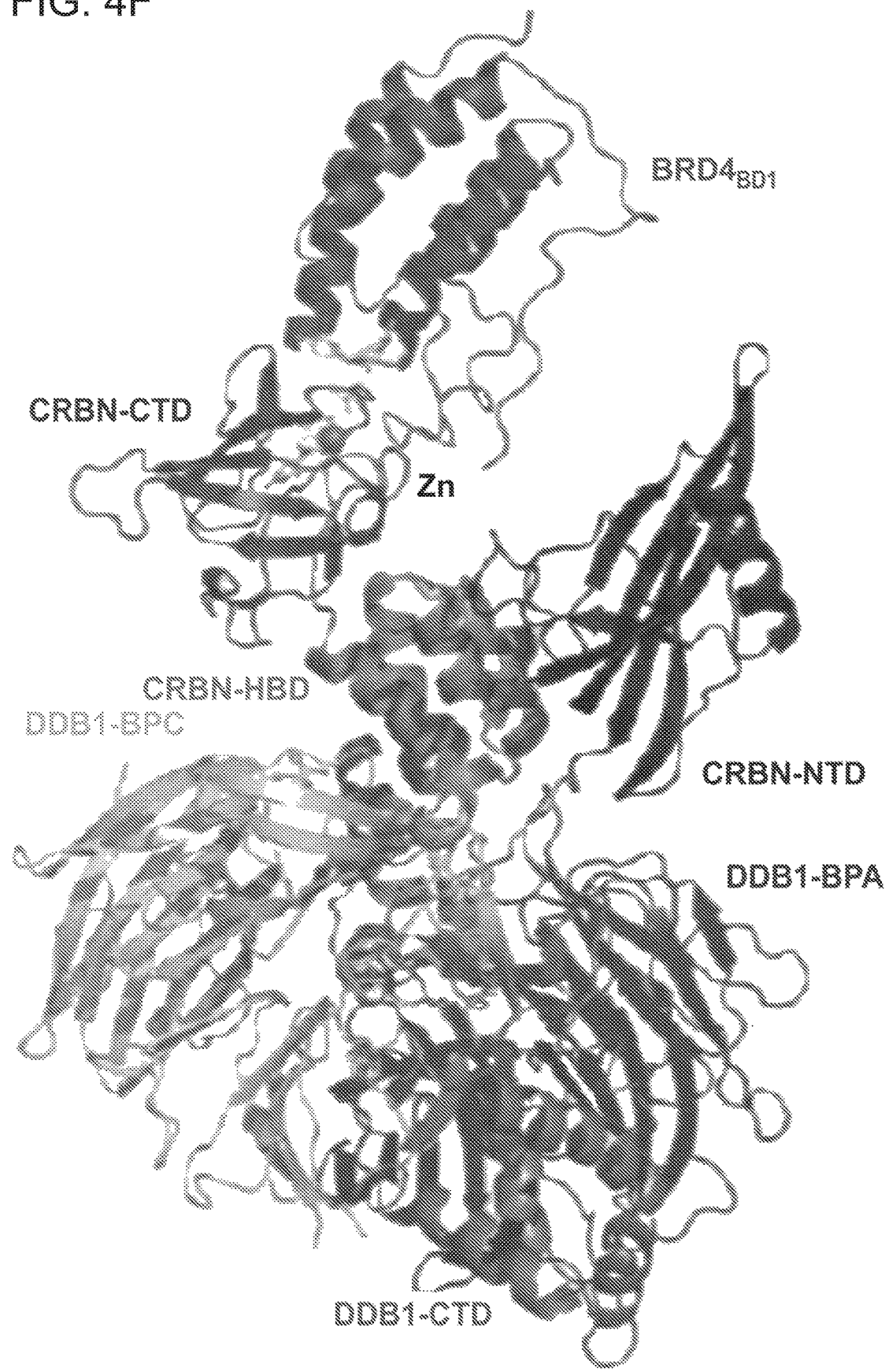
Figure 4G:
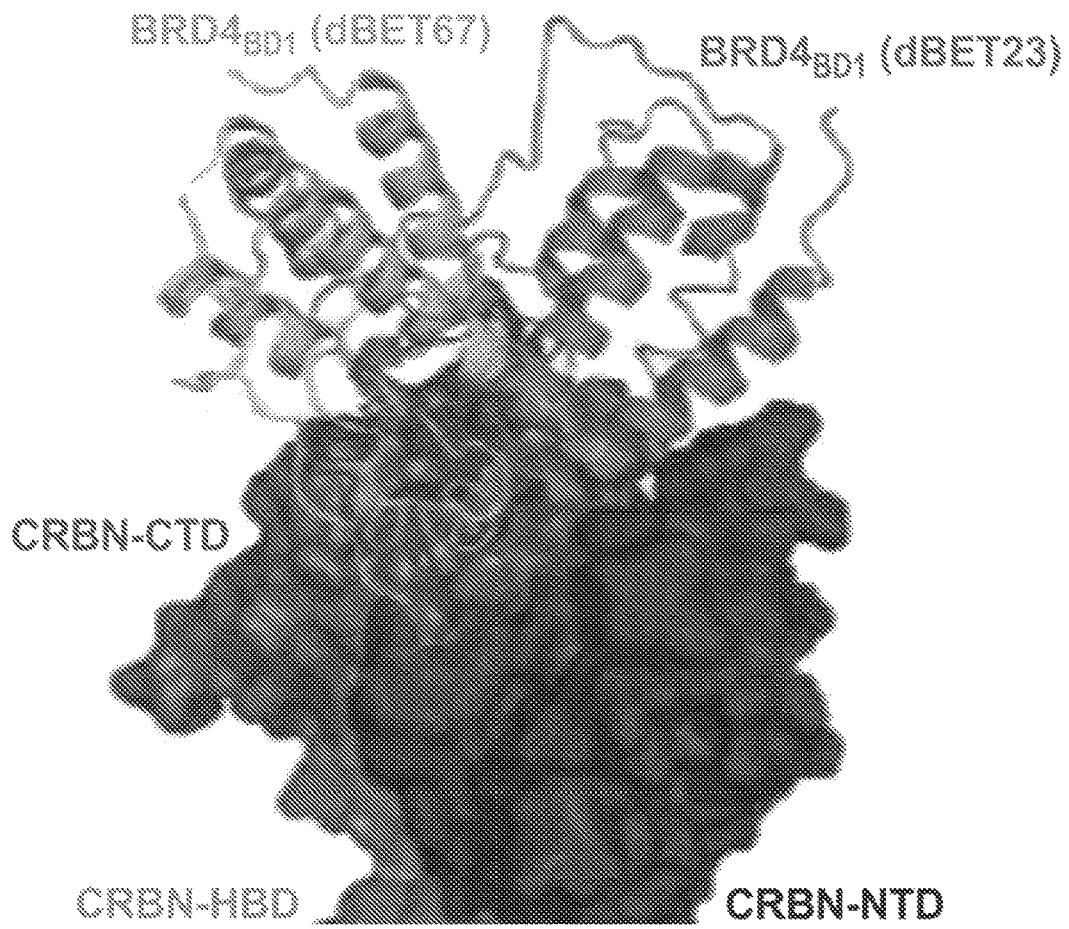
Figure 4H:
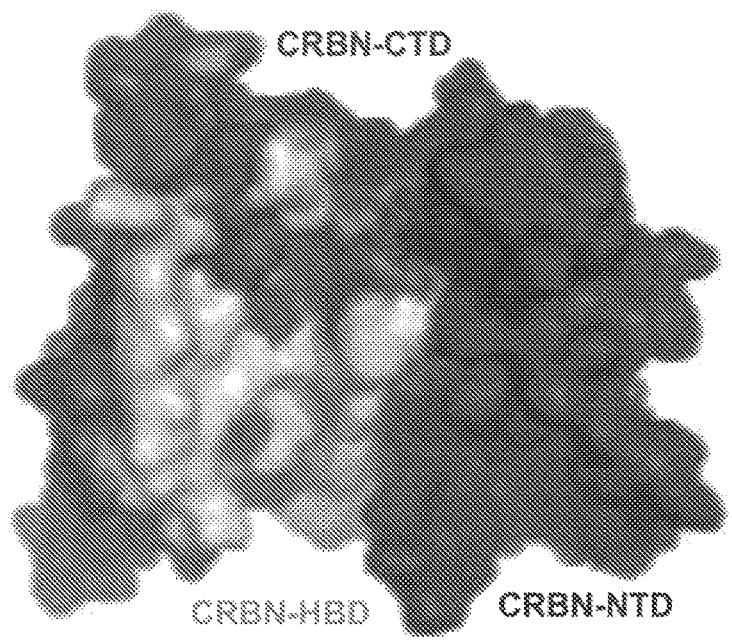
Figure 12A:
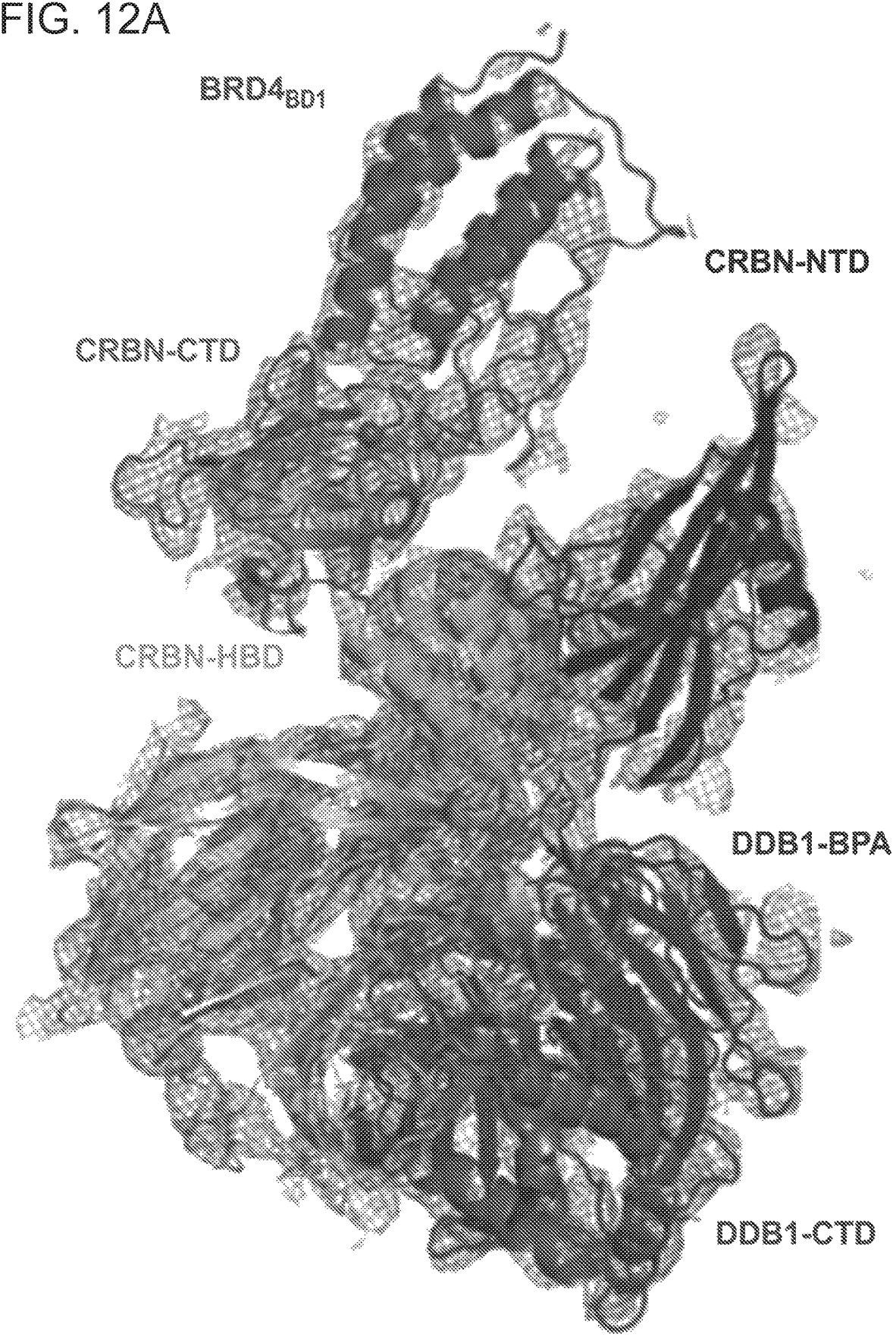
FIG. 12A-FIG. 12C show experimental validation of DDB1-CRBN-dBET57-$BRD4_{BD1}$ structure.
Figure 12B:
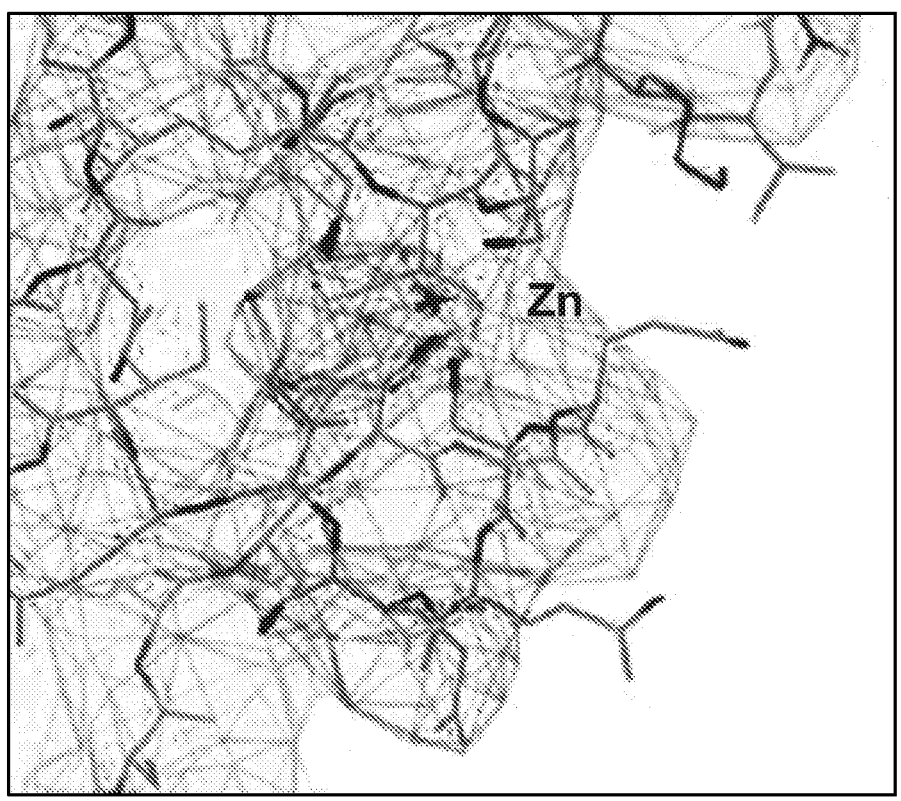
Figure 12C:
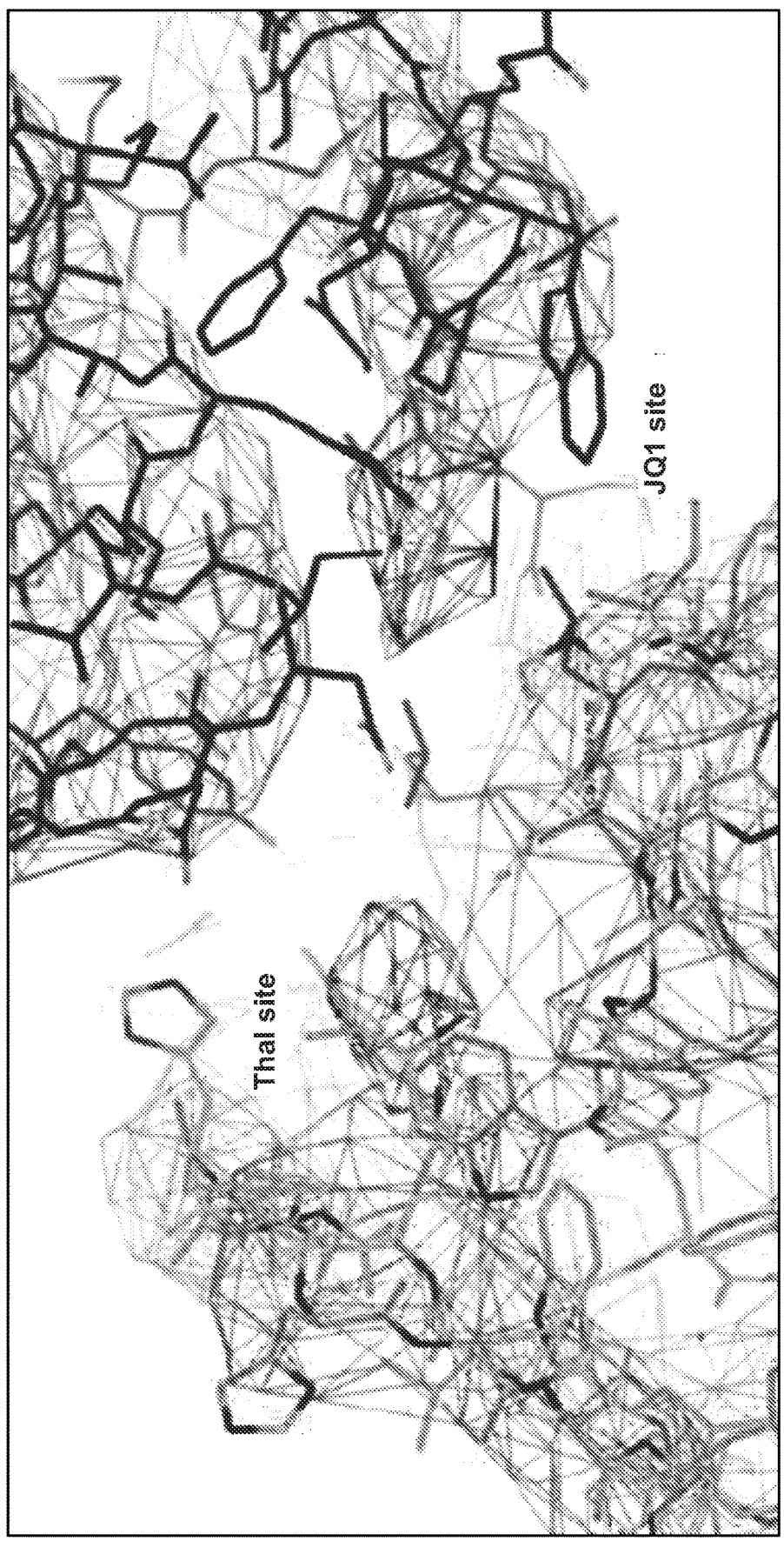
Figure 13A:
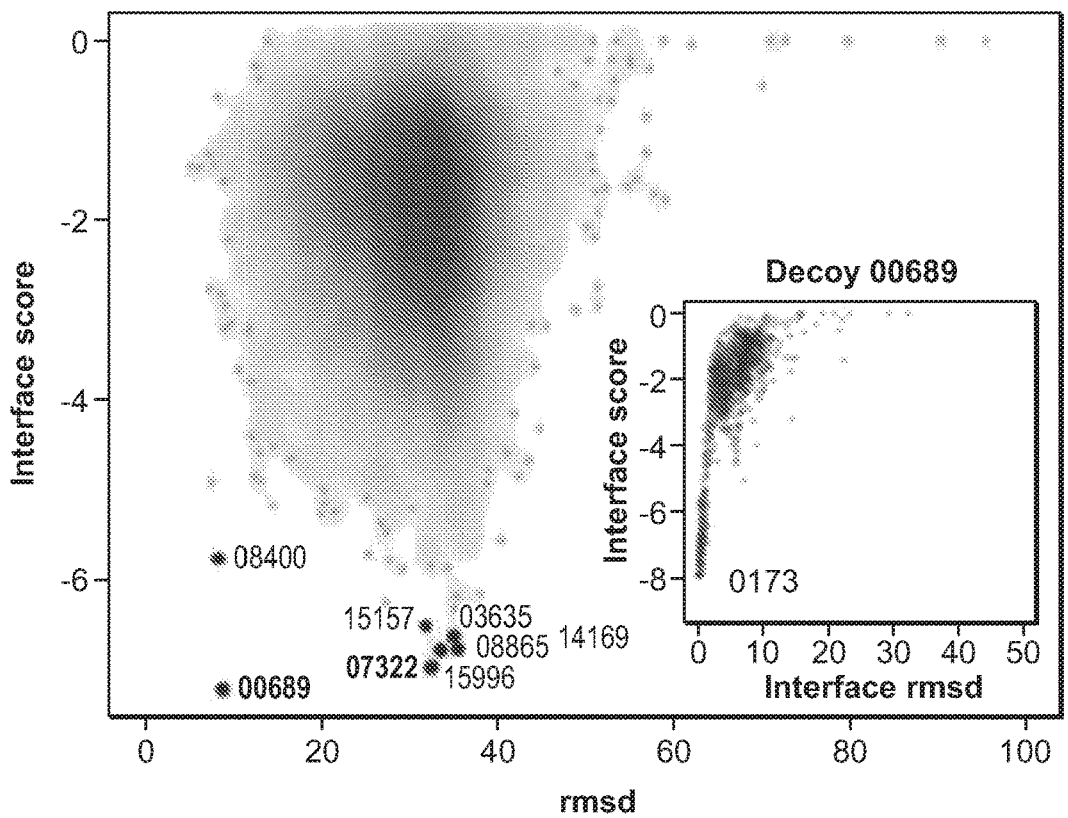
FIG. 13A-FIG. 13D show in silico docking of CRBN-lenalidomide-Ck1 complex.
Figure 13B:
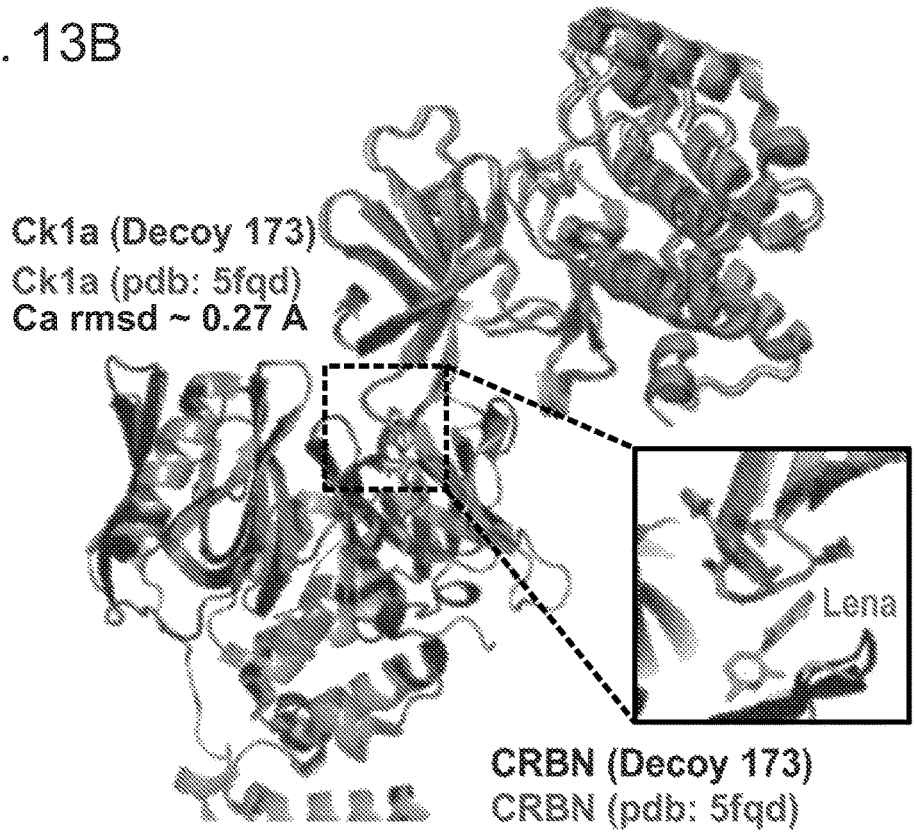
Figure 13C:
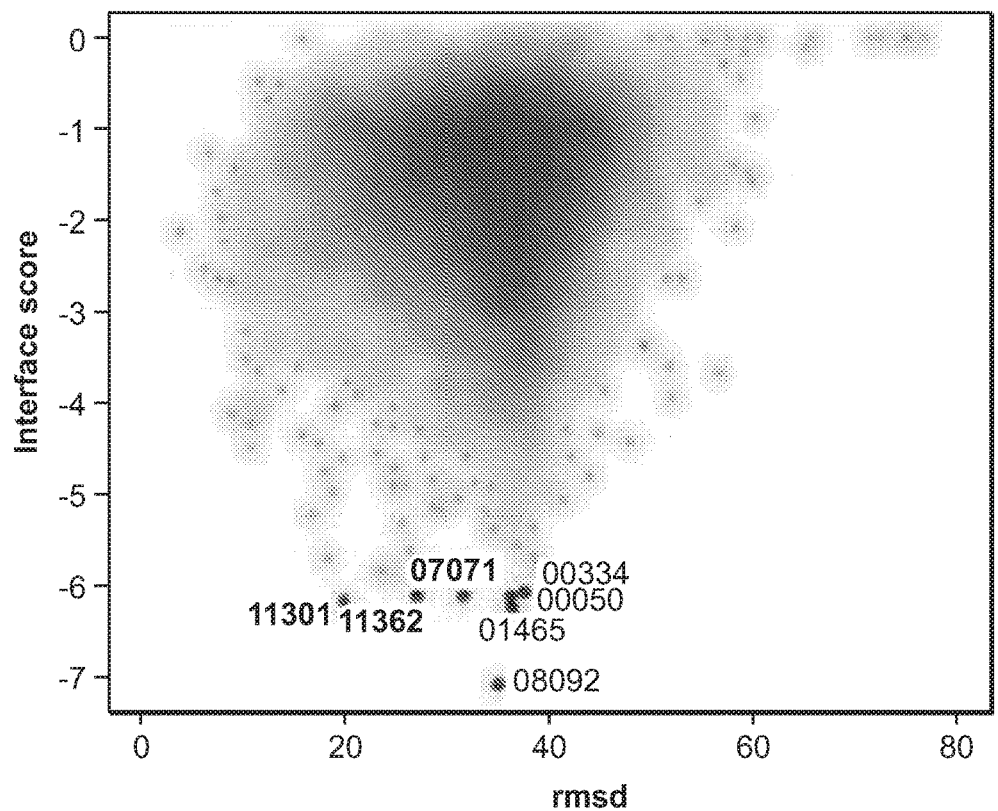
Figure 13D:
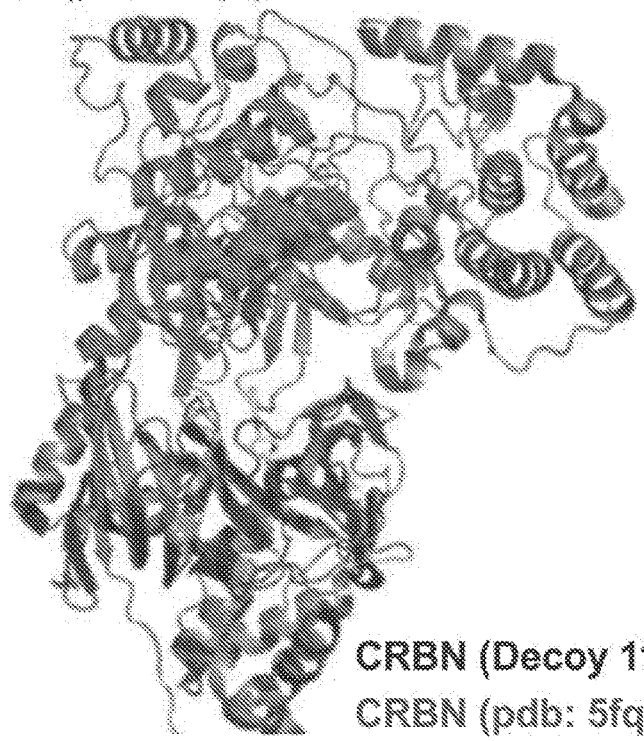

To obtain insights into the molecular basis of this plastic CRBN/$BRD4_{BD1}$ interactions, dBET57 (the molecule with the most pronounced selectivity for $BRD4_{BD1}$ over $BRD4_{BD2}$.) was crystallized. Crystals were obtained for a reconstituted DDB1ΔB-CRBN-dBET57-$BRD4_{BD1}$ complex and determined the structure to 6.8 Å resolution (see FIG. 12A-FIG. 12C for experimental validation of the structure). While the limited resolution prevents detailed interpretation of the molecular interactions that govern the CRBN-BRD4 interface, the overall binding mode is clearly resolved (FIG. 4F and FIG. 12A). In this complex, $BRD4_{BD1}$ interacts with the CTD of CRBN, instead of the NTD as observed with dBET6/23 (FIG. 4E-FIG. 4H), which results in BRD4 now utilizing an entirely different set of residues for inter-protein contexts (compare FIG. 2B and FIG. 4H). In the dBET57 bound structure, the Examples show that CRBN unfolds and the CRBN-NTD and CRBN-CTD domains no longer interact (FIG. 4E-FIG. 4F). This unexpected behaviour could be due to the high salt crystallization condition (1.6 M Phosphate) or part of the intrinsic CRBN plasticity. The binding mode observed with dBET57, however, is fully compatible with a regular CRBN conformation (FIG. 4G) and dBET57 mediated binding thus expected to occur with both CRBN conformations (see FIG. 12A-FIG. 12C). The unexpected plasticity in dBET dependent binding of CRBN to the exact same protein, $BRD4_{BD1}$, provides a rationale how PROTACs that share the same E3- and target-moieties can still exhibit different selectivity profiles. Depending on the linker, different surface residues in the target protein may be involved in complex formation.

FIG. 12A shows that CRBN was found in a not previously observed conformation, in which the thalidomide binding CRBN-CTD domain translates and rotates away from the CRBN-HBD and CRBN-NTD domains. This results in an open conformation that exposes large areas of CRBN that are typically buried. The high salt crystallization condition could be a driver of this structural rearrangement, and together with crystal contacts induce this conformation. It is possible that that this conformational dynamic is an intrinsic feature of CRBN to accommodate a variety of substrates and future studies are necessary to address this. Based on the compatibility of the observed $BRD4_{BD1}$ binding conformation with the open and closed CRBN conformations, it can be concluded that for the interpretation of the data, the conformational change is negligible.

Example 4: Protein Docking Reveals Binding Energy Landscape

The mutational signatures obtained for different dBET molecules, the structural arrangements for dBET6/23/70 and dBET57 complexes, together with the absence of any coevolution between CRBN and BRD4 let us hypothesize that BRD4 bromodomains can bind to CRBN in multiple different orientations depending on the ligand. Assessing such potential binding conformations to reduce chemical search space would be highly desirable. In silico protein-protein docking provides an attractive surrogate to in vitro experiments. The Examples addressed whether the Rosetta protein docking framework (Sircar, Chaudhury et al. 2010) would allow modelling of such possible binding modes. One of the characteristics of Monte-Carlo docking algorithms is the stochastic sampling of low energy conformations, which frequently results in multiple solutions. While this often complicates the identification of evolved interactions between proteins, sampling of possible conformations provides an advantage in the study of degrader-induced binding modes since it enables exploration of the repertoire of low energy conformations.

The Examples confirmed that computational methods can predict ligand mediated protein-protein interactions by docking Ck1α to the CRBN-lenalidomide complex (FIG. 13A-FIG. 13D). The Examples further addressed whether computational docking would be able to provide models for possible PROTAC-induced binding modes by docking CRBN and the target $BRD4_{BD1}$ in absence of dBET. One obvious complication is that a dominant component of the binding energy between ligase and substrate is provided by the degrader itself, which is absent in docking simulations, and the scoring of solely neomorphic interactions will likely result in many low energy conformations to be generated.

Figure 5A:
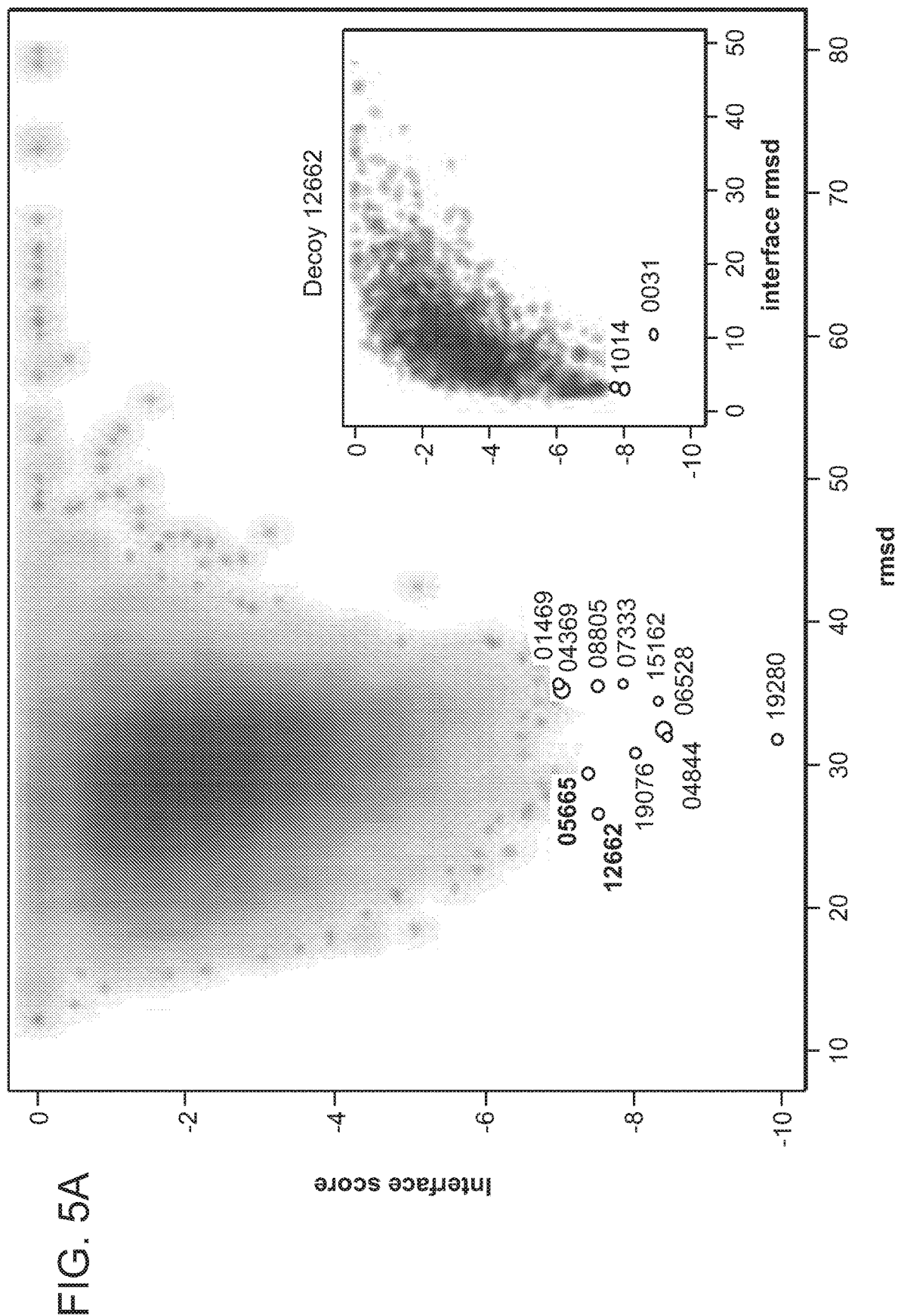
FIG. 5A-FIG. 5C show in silico docking to predict binding modes.
Figure 5B:
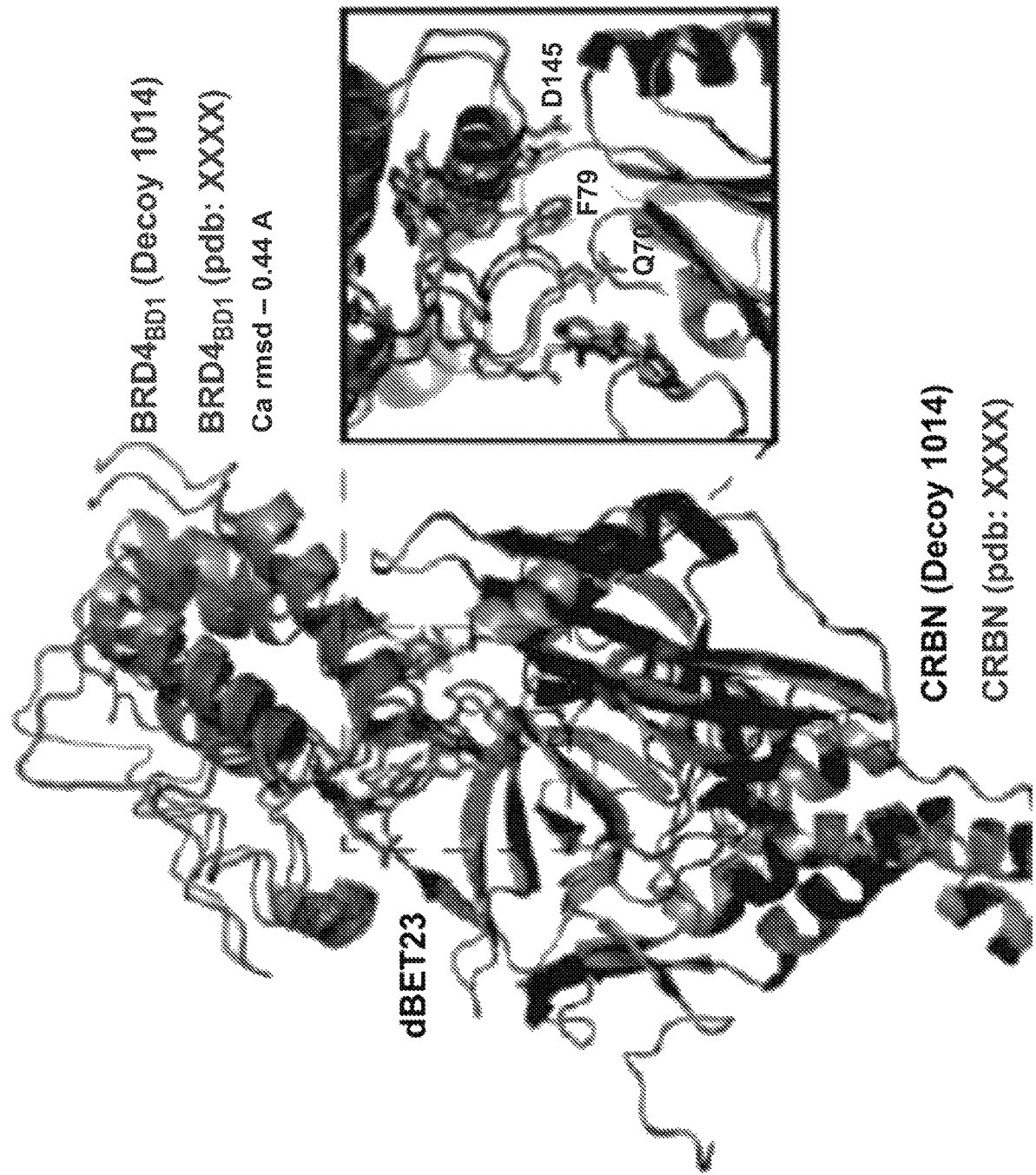

Using the crystal structure of lenalidomide bound CRBN (pdb: 4tz4) and JQ1 bound $BRD4_{BD1}$ (pdb: 3mxf), a global docking experiment (20,000 models) was performed using Rosetta docking (FIG. 5A). Clustering the top 200 lowest scoring docking conformations, a conformation was identified that closely resembles the conformation observed in the dBET23 crystals. This model was further confirmed by local docking (2,000 models) of the low energy model (FIG. 5A and FIG. 5B).

Figure 5C:
Figure 5C:
Figure 5C:

As predicted for a much weaker interaction between CRBN and BRD4$_{BD1}$ in absence of a degrader, multiple low energy minima are found. Based on the hypothesis that the docking experiment will sample the repertoire of low energy binding conformations, clustering of the top 200 conformations provides a set of feasible binding modes (see, FIG. 5C) for representative clusters). While it remains to be shown whether docking can predict binding modes accurately, the overall conformational landscape provides a rationale for the design of required minimal linker lengths and suggest suitable linkage positions. In theory, the shortest possible linker for a ligase-target pair should provide the most selective compound since it will restrict the number of possible binding conformations. To test whether the docking information could be used to inform the design of PROTACs, poses were sorted by minimal required linker length between the JQ1 thiophene and lenalidomide, and found a linker of 2-3 atoms sufficient to bridge the two moieties (FIG. 6A). The according molecules (ZXH-02-147 and ZXH-03-26) were synthesized (FIGS. 6B and 7B).

Figure 14A:
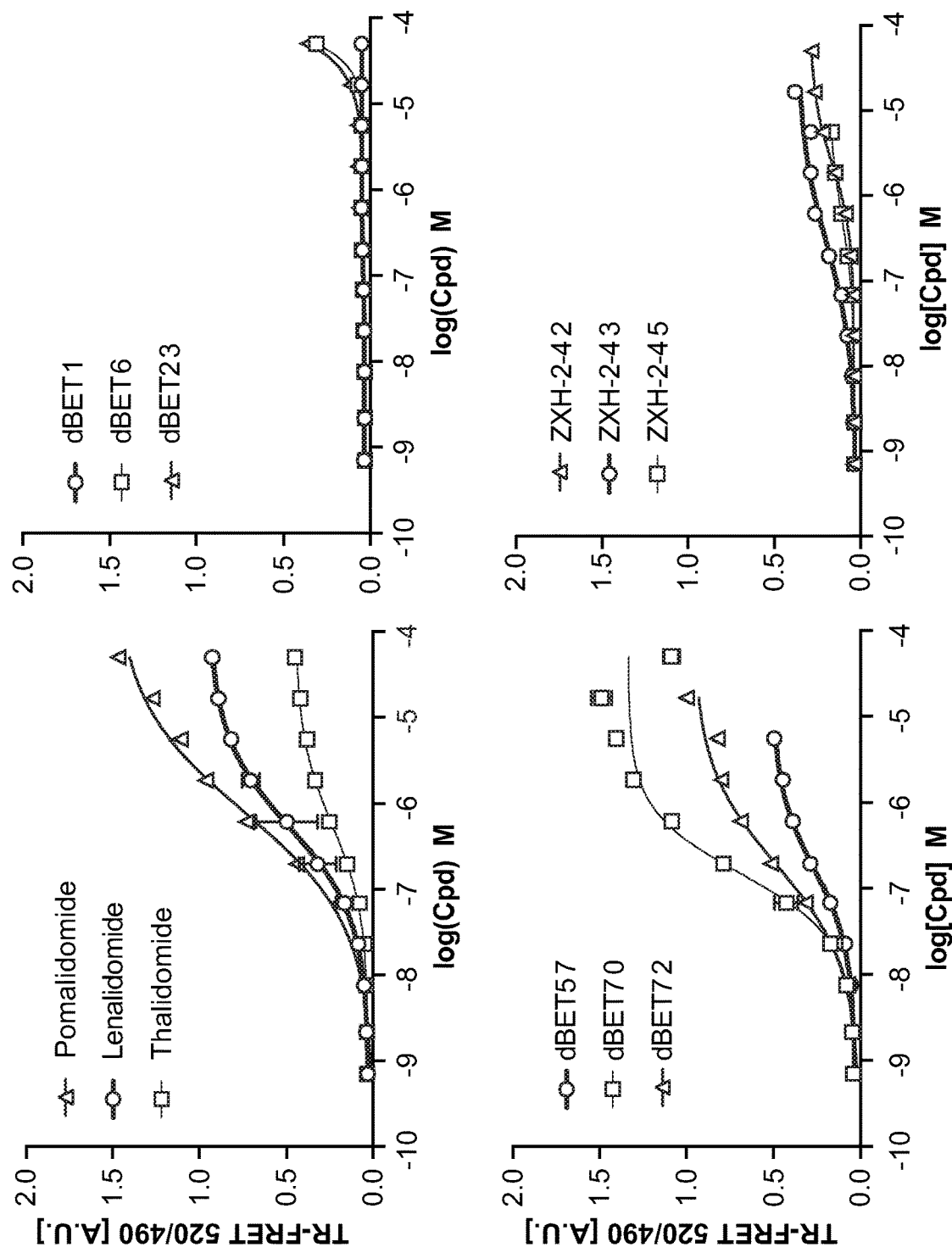

The Examples addressed whether certain degraders (PROTACs) would be capable of directly inducing binding of IKZF1 (and other IMiD targets) to CRBN. A CRBN-IKZF1Δ binding assay was used to measure binding of IKZF1Δ, to CRBN in presence of dBET1, dBET6, dBET23, dBET57, dBET70, and dBET72, as well as lenalidomide as control (FIG. 14A). The Examples show that dBET1/6/23 do not induce IKZF1-CRBN complex formation, while dBET57, dBET70 and dBET72 show pronounced complex formation. Both, dBET57 and dBET70 share the aniline of lenalidomide, while dBET1/6/23 all have an oxy-acetamide linkage. Based on the previously described model of IKZF1-CRBN binding (FIG. 14C) the phthalimide aniline nitrogen may be involved in a hydrogen bond with IKZF1 Q146. A straight linker out of this phthalimide position could be tolerated, while an adjacent amide bond (as in the oxy-acetamide linkage) may cause a steric clash with IKZF1. Alternatively, the secondary amine nitrogen could be a hydrogen bond donor and, with the ether oxygen being a hydrogen bond acceptor, this donor/acceptor substitution could explain the difference in strength of the IKZF1 interaction. The nitrogen linkage of dBET57, dBET70 and dBET72 were replaced with an oxygen-ether linkage resulting in compounds ZXH-2-42, ZXH-2-43, and ZXH-2-45, respectively. The ability of the oxygen-ether compounds to induce binding of IKZF1 was greatly reduced compared to their nitrogen analogs; however, it was not eliminated, as seen in the case of the oxy-acetamide substitution.

Example 5: Dose Dependent Degradation of an IKZF1Δ-EGFP Fusion Protein

Dose dependent degradation of an IKZF1Δ-EGFP fusion protein was assessed in HEK293T cells (see methods), and used the in vitro structure activity relationship (SAR) to develop a model of cellular IKZF1 degradation (FIG. 14B). dBET1/6/23 are relatively ineffective at promoting IKZF1 degradation, dBET70/72 are equipotent to lenalidomide, and dBET57 is comparable to thalidomide, in accordance with the biochemical data. The Examples show that by modifying the substitution at the IMiD moiety, the co-degradation of other substrates—such as IKZF1—can be controlled or modulated. To test whether this would be effective in a cellular multiple myeloma model, MM.1s cells were treated for five hours with either 1 μM dBET23, 1 μM dBET70 or DMSO as a control. Using a quantitative proteomics approach (see methods), the Examples demonstrate that dBET70 but not dBET23 exhibits pronounced co-degradation of CRBN-lenalidomide neo-substrates IKZF1, IKZF3 and ZFP91 (FIGS. 14D and E).

Figure 15A:
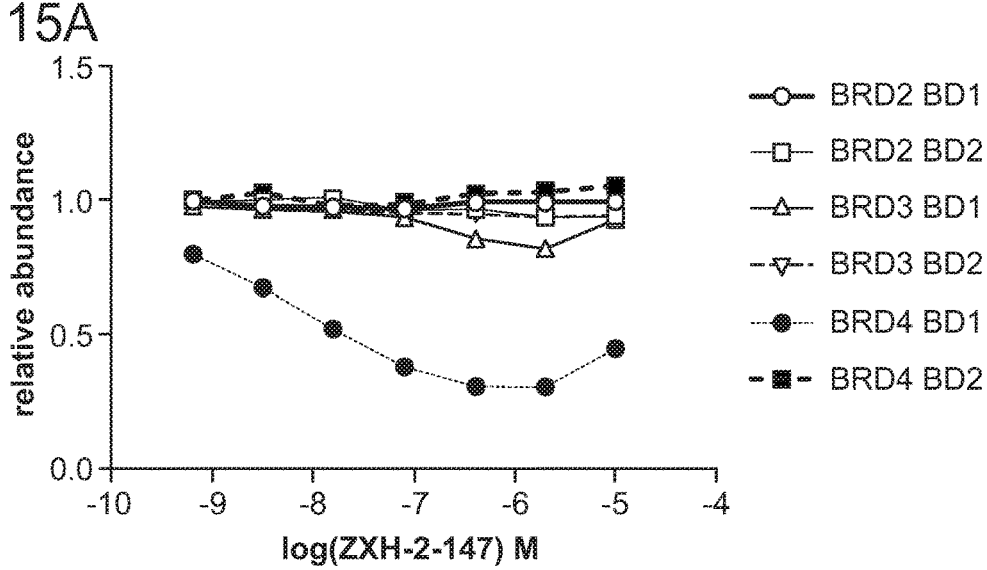
FIG. 15A-FIG. 15C show selective degradation of BRD4 by certain heterobifunctional small molecule degraders ZXH-3-147 and 184, as compared to non-selective degradation of BET family proteins by ZXH-3-27.
Figure 15B:
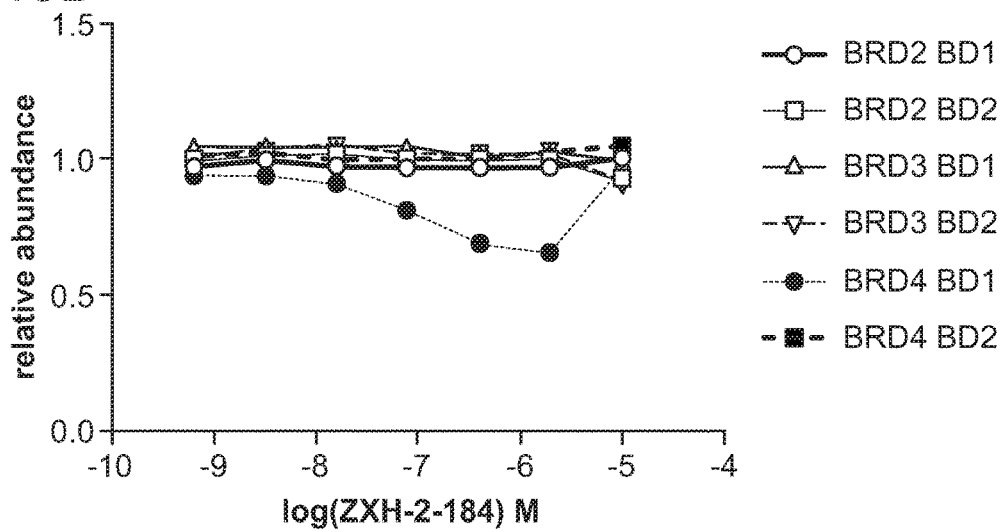
Figure 15C:
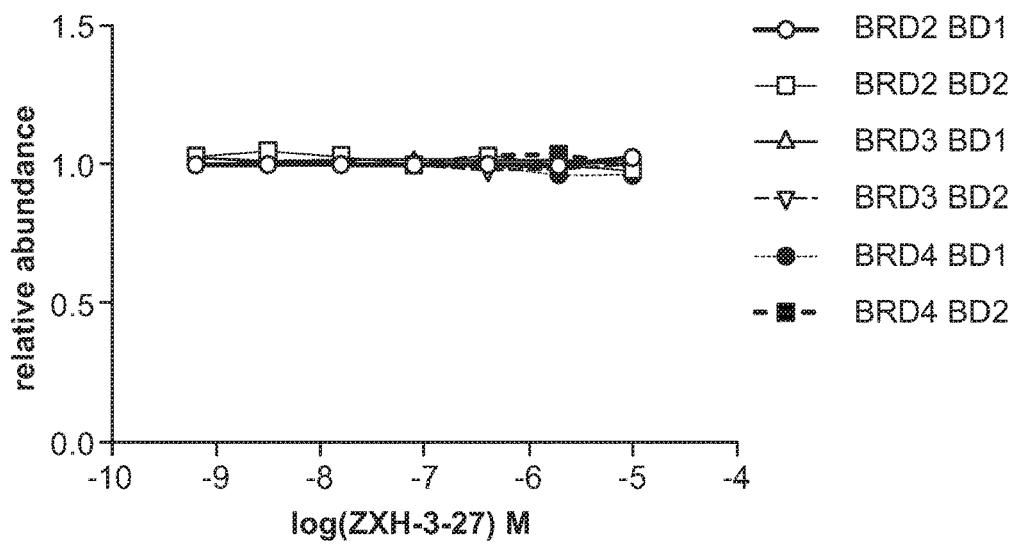
Figure 16A:
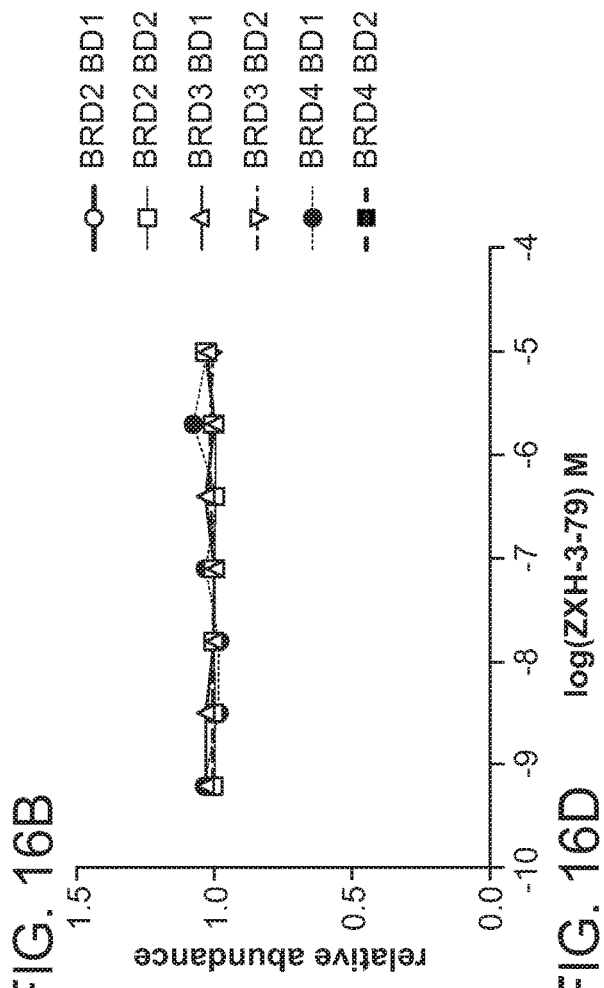
Figure 16B:
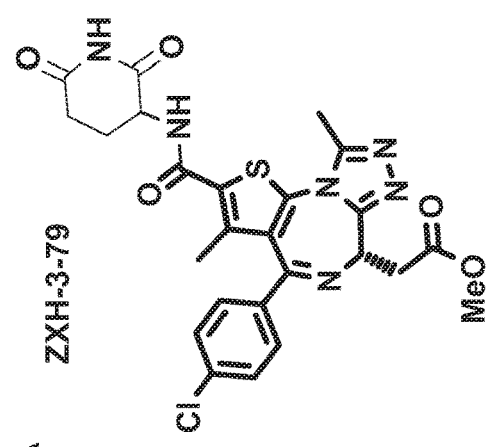
Figure 16C:
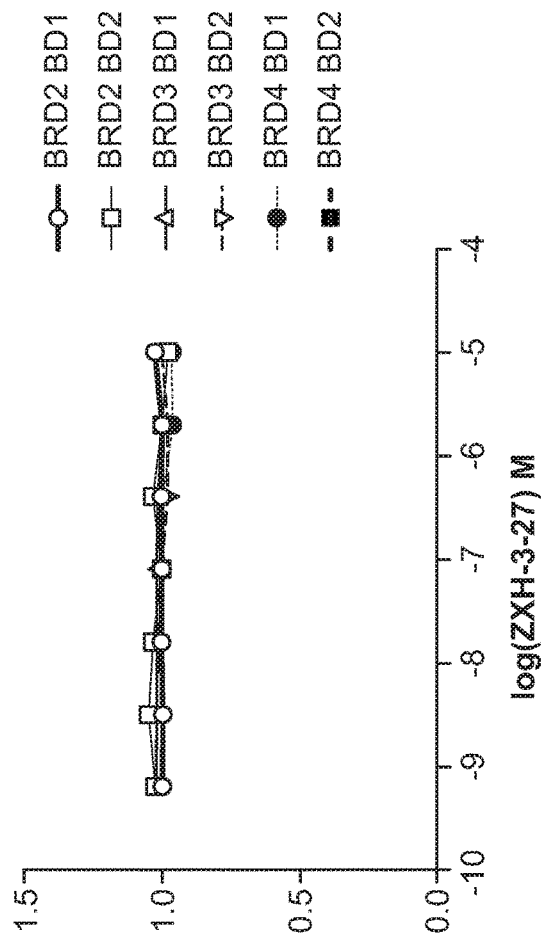
Figure 16D:
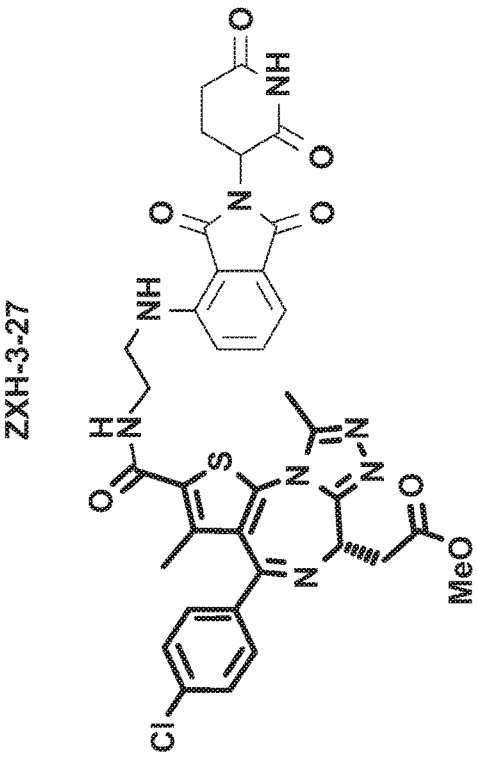
Figure 16E:
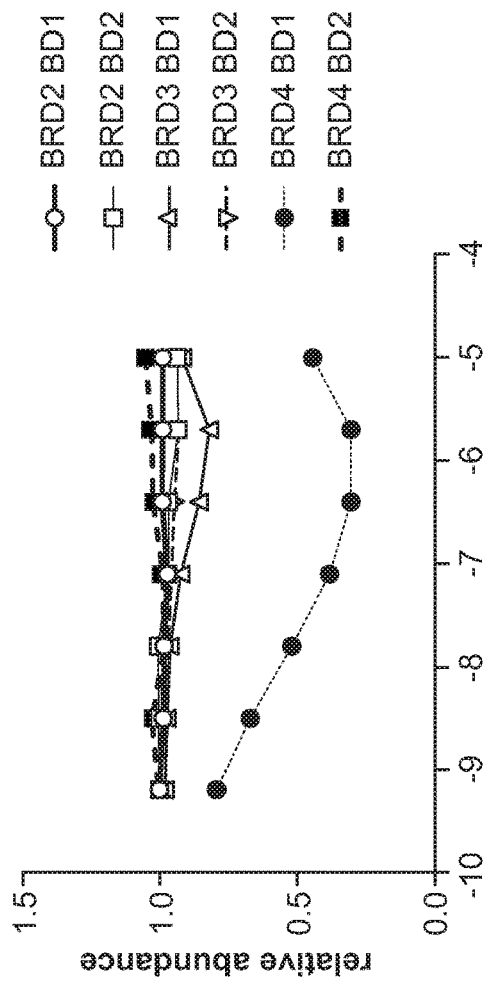
Figure 16F:
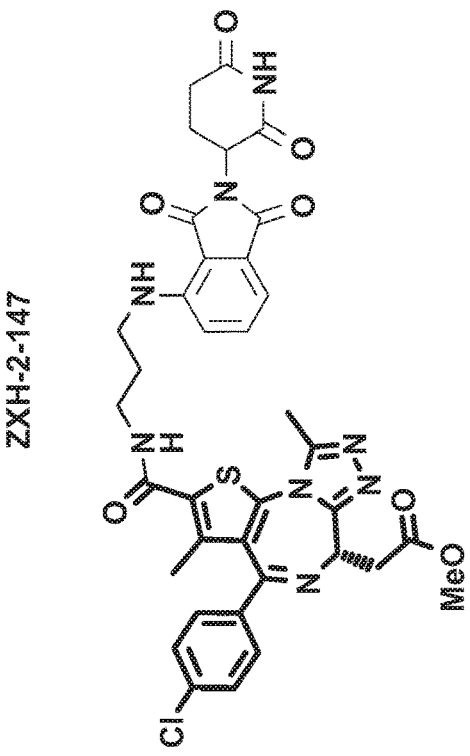
Figure 16G:
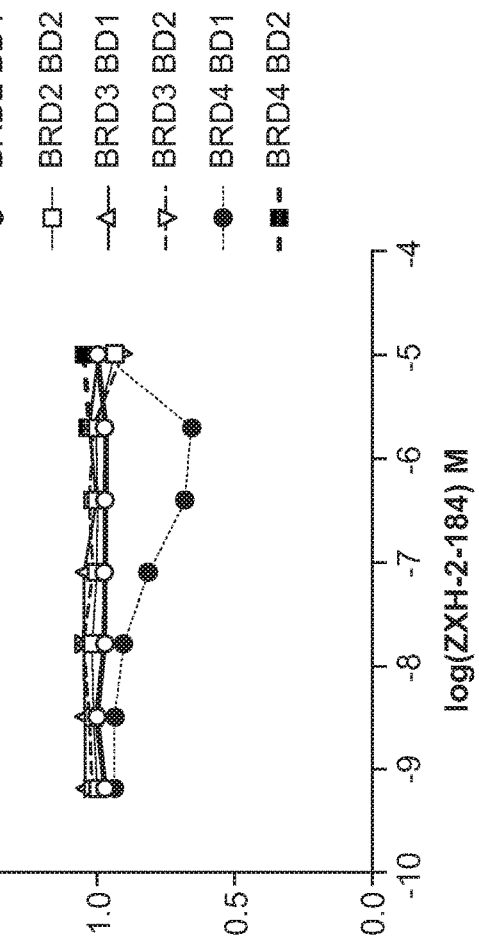
Figure 16H:
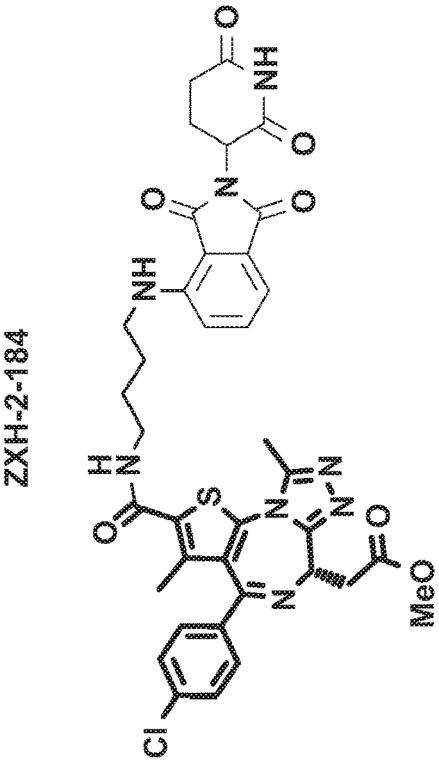
Figure 16J:
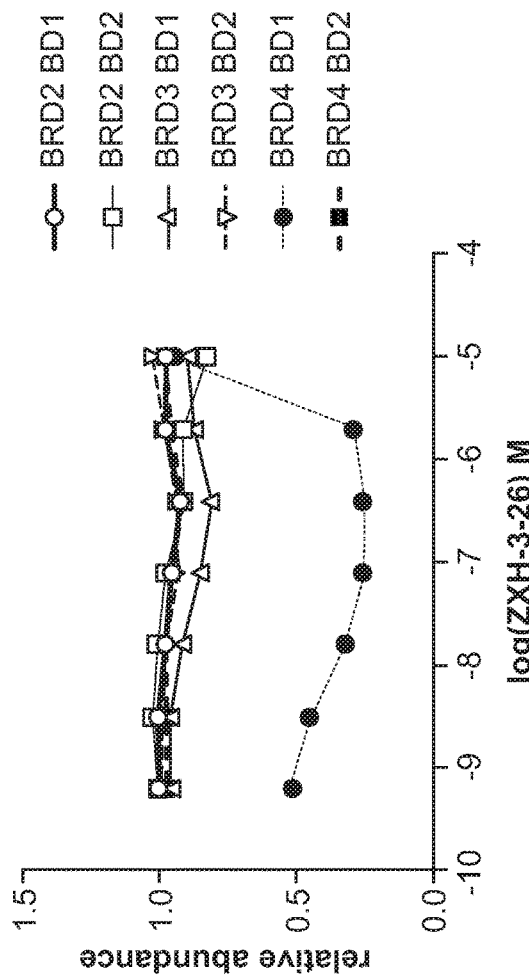
Figure 16J:
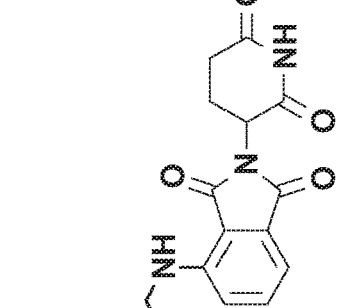
Figure 16L:
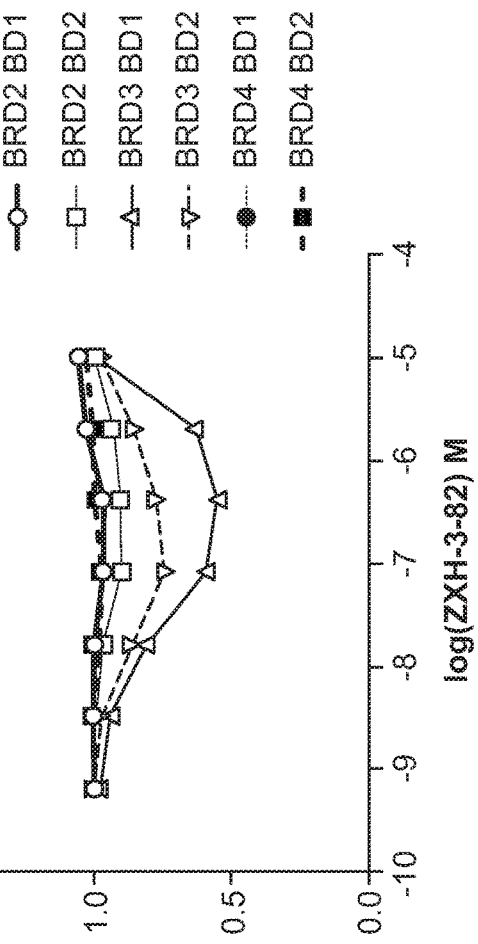
Figure 16L:
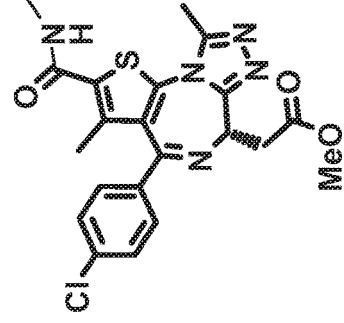
Figure 17A:
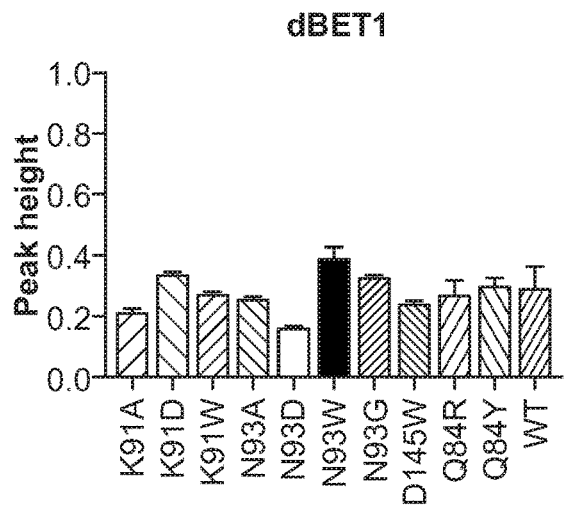
Figure 17B:
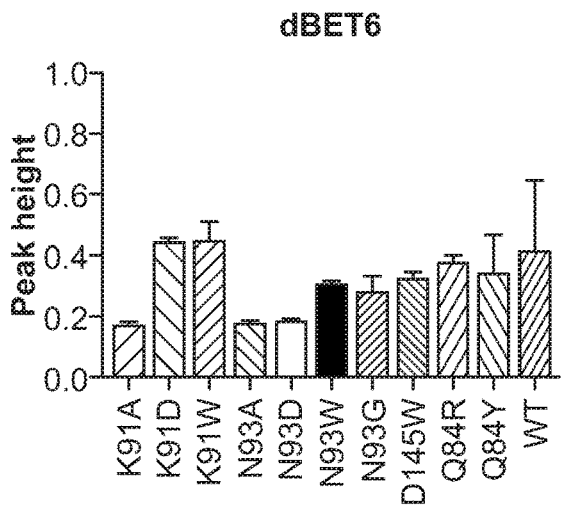
Figure 17C:
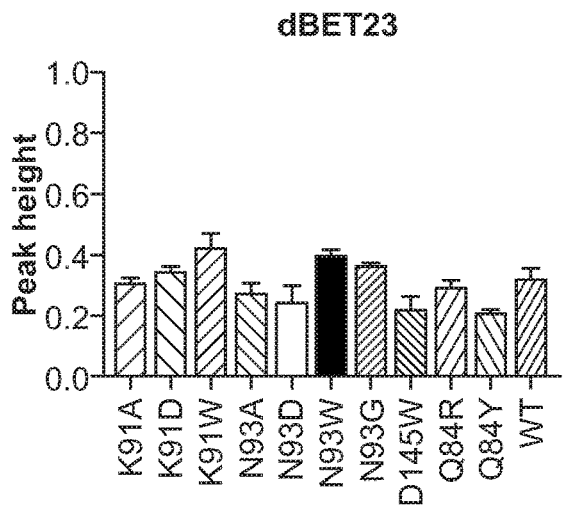
Figure 17D:
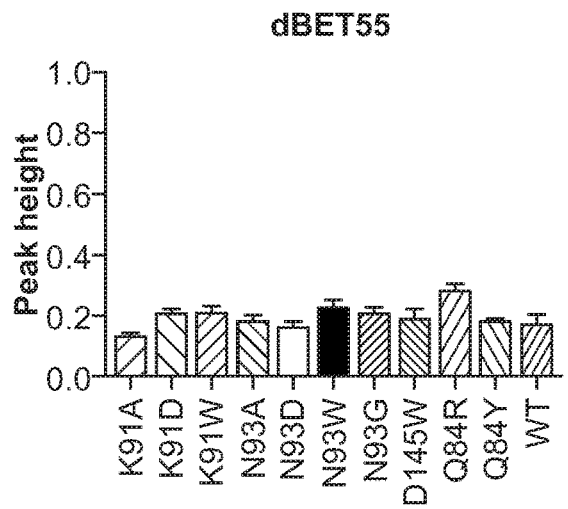
Figure 17E:
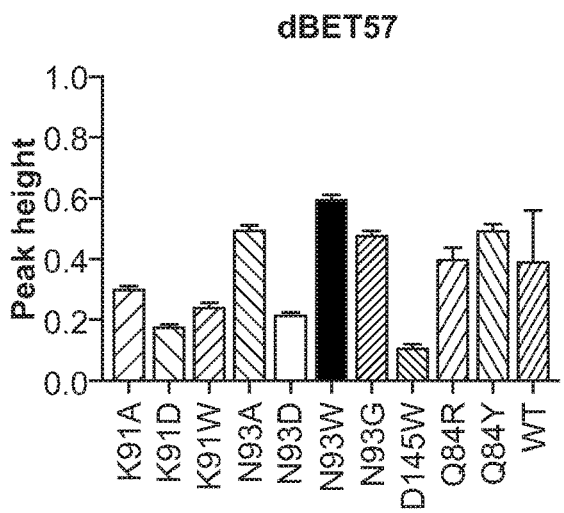
Figure 17F:
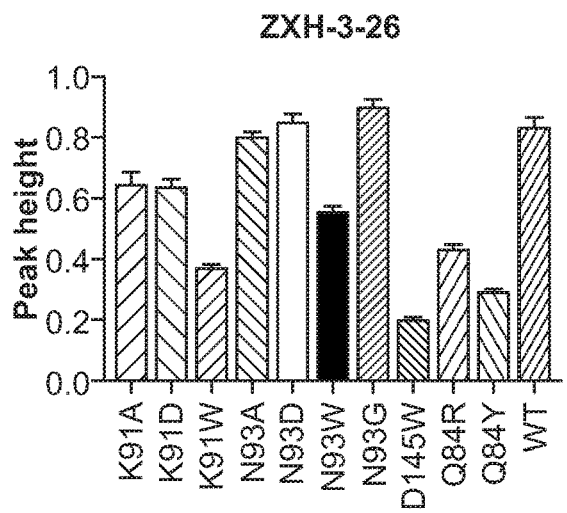

Cellular degradation assays show that ZXH-02-147 and ZXH-03-26 are active on BRD4$_{BD1}$, in accordance with the docking results (FIGS. 6C and 15A), and that ZXH-03-26 exhibits a DC$_{50/5h}$~5 nM comparable to the best pan-BRD degrader dBET6. To test whether these molecules exhibit isoform selectivity, the cellular reporter system was expanded to include the individual bromodomains of BRD2 and BRD3 and tested cellular degradation along with BRD4.

Discussion of Examples 1-5

An integrated approach combining structural, biochemical, and cellular data was used to establish the molecular basis of PROTAC-mediated neo-substrate recruitment to the CRL4$^{CRBN}$ E3 ubiquitin ligase. The Examples above show that inter-protein contacts, while contributing relatively little binding affinity to the interaction, can be drivers of selectivity, and that highly effective degraders (e.g. the low nanomolar (nM) cellular activity of dBET6 or dBET70) can be achieved in absence of tight binding or positive cooperativity. Through multiple X-ray crystal structures together with comprehensive biochemical, cellular, and computational characterization, the Examples demonstrate that binding between ligase and substrate is surprisingly plastic and thus adapt distinct conformations depending on linker length and position. The Examples also demonstrate that exploiting such 'local' energy/entropy minima underlies selectivity as seen for dBET57. The Examples further demonstrate that in silico protein docking can be used to reveal low energy binding modes and can guide development of heterobifunctional degraders that can discriminate between the highly homologous BET bromodomains, such as ZXH-03-26. The Examples above further demonstrate that biochemical properties translate to cellular activity with respect to BRD4 on-target and IKZF1 off-target degradation and that the IKZF1 degradation can be tuned by IMiD linker composition (FIG. 14A-FIG. 14E).

The Examples above demonstrate that the same two proteins can bind in different overall conformations, which results in distinct surface patches on the ligase and target to interact. This plasticity underlies the principle of selectivity. PROTACs therefore appear to exploit natural and widely occurring non-specific interactions by increasing the local concentration of the two protein binding partners. Non-specific interactions are widespread and thought to occur between any two proteins with affinities >10 mM (Kuriyan and Eisenberg 2007). However, these interaction surfaces are not random as they require a certain degree of surface complementarity to avoid unfavourable contacts such as opposing charged surfaces. The constraints of relatively short linkers result in only few accessible inter-protein contact conformations. In theory, rationally designed linkers restricted to a specific binding mode unique to a ligase/substrate pair should be sufficient to drive selectivity since such a restricted conformation is unlikely to occur in a close orthologue. The Examples above show that such can be achieved in practice with the compound ZXH-03-26.

The absence of positive cooperativity and the existence of multiple distinct binding conformations carries further important implications. The unnecessity for high affinity ligase-substrate interactions implies that a wide variety of E3 ligases can be explored to achieve desirable properties such as tissue specificity. The Examples above demonstrate with dBET57 and ZXH-03-26 that effective PROTACs can be designed to harbour relatively short linkers, which results in favourable and more 'drug-like' overall properties (FIG. 7B). The Examples above demonstrate that such short linker compounds exhibit high selectivity since the number of accessible binding conformations is reduced. Selectivity can also be further explored using different E3-moeities, as seen for CRBN- and VHL-targeting PROTACs (FIGS. 3A-C). The Examples above demonstrate that computational modelling can provide an elegant surrogate, which depends only on a known structure for the individual components (ligase and target), and has the potential to enable initial predictions of possible linker length and trajectory to guide medicinal chemistry.

With ZXH-03-26, ZXH-2-184, ZXH-2-147, and ZXH-3-82, the Examples above provides working examples of heterobifunctional compounds that selectively targets BRD4 for degradation and spares BRD2 and BRD3, which also represents the first small molecule to allow pharmacologic targeting of BRD4 without significant inhibition/degradation of BRD2/3. This has implications for future developments since efficacy of BRD4 inhibition has been established for a variety of malignancies (Zuber, Shi et al. 2011, Chau, Hurwitz et al. 2016), while on-target toxicity has been observed in pre-clinical and clinical studies (Stathis, Zucca et al. 2016). It is conceivable that selective degradation of BRD4 will retain efficacy, while significantly reducing on-target toxicity in NUT midline carcinomas, which depend on the BRD4-NUT fusion protein. Such selective targeting of an oncogenic fusion protein has been shown as effective treatment strategy in the case of BCR-ABL and Gleevec (Buchdunger, Cioffi et al. 2000). ZXH-03-26, ZXH-2-184, ZXH-2-147, and ZXH-3-82 present examples of heterobifunctional compounds that can selectively degrade the BRD4-NUT oncogenic fusion protein.

Example 6: Cellular Imaging-Based Degradation Assay

Figure 19G:
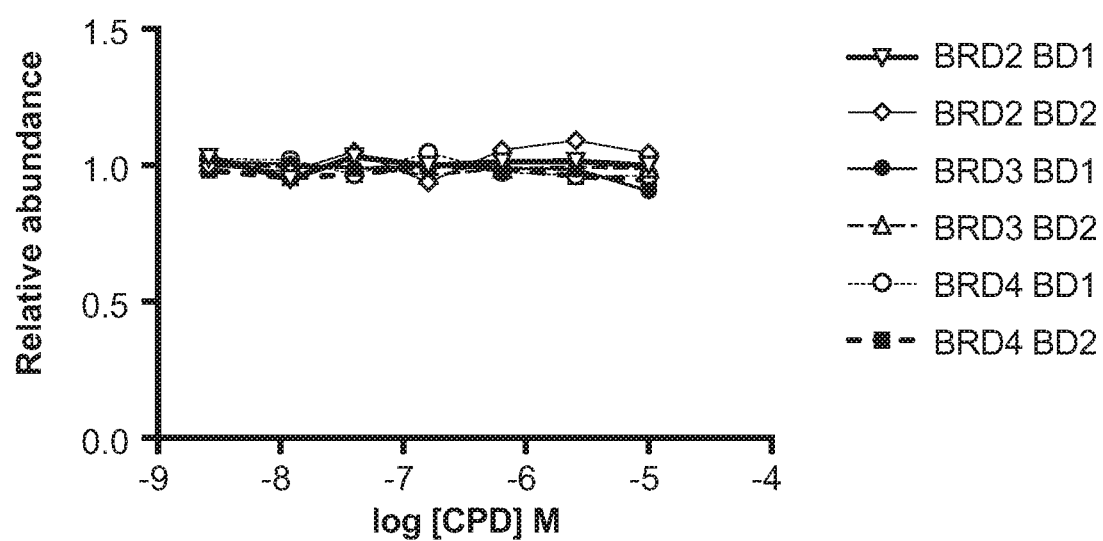
Figure 20A:
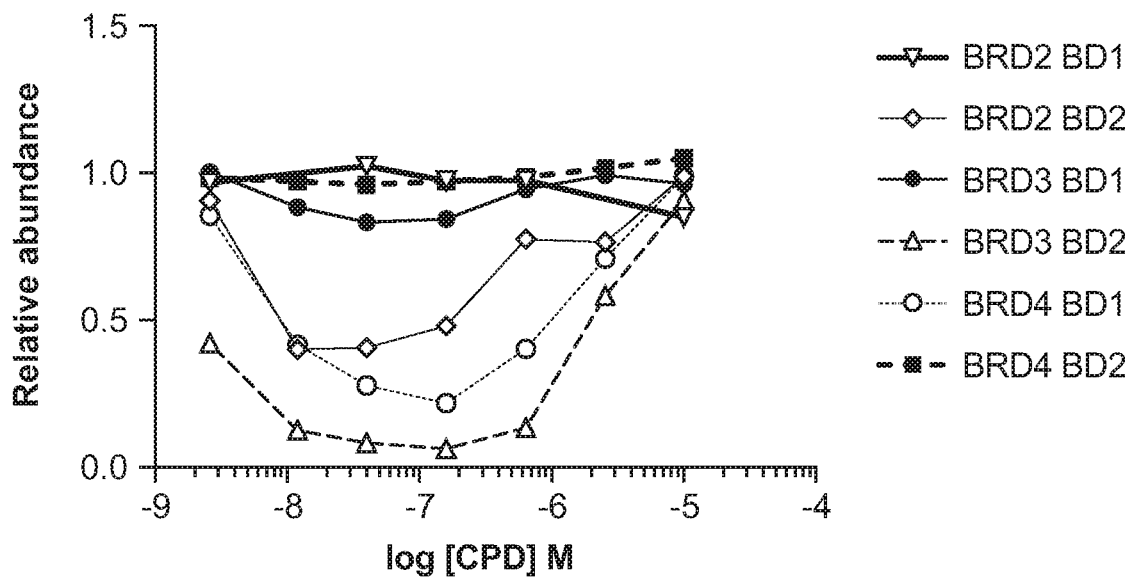
FIG. 20A-FIG. 20D are graphs that show degradation of bromodomains by ZXH-3-117, ZXH-2-42, ZXH-2-43, ZXH-2-45. Cells stably expressing $BRD4_{BD1}$-EGFP (or constructs harbouring $BRD2_{BD1}$, $BRD2_{BD2}$, $BRD3_{BD1}$, $BRD3_{BD2}$, $BRD4_{BD1}$, $BRD4_{BD2}$) and mCherry were treated with increasing concentrations of degrader, incubated for 5 h, and the EGFP and mCherry signals followed using cellular imaging-based degradation assay, n=1.
Figure 20B:
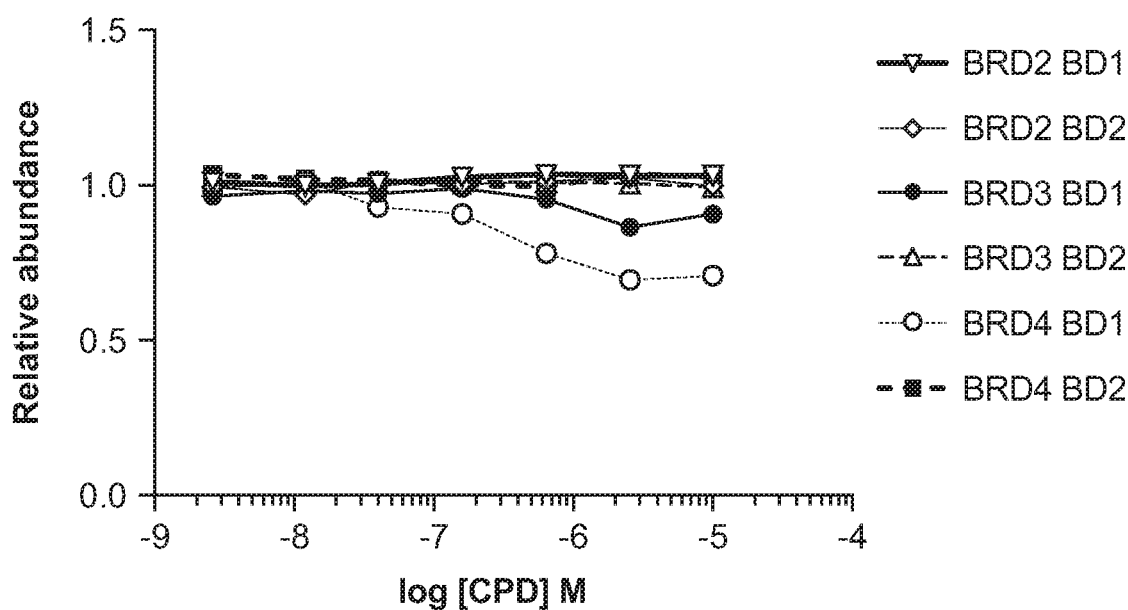
Figure 20C:
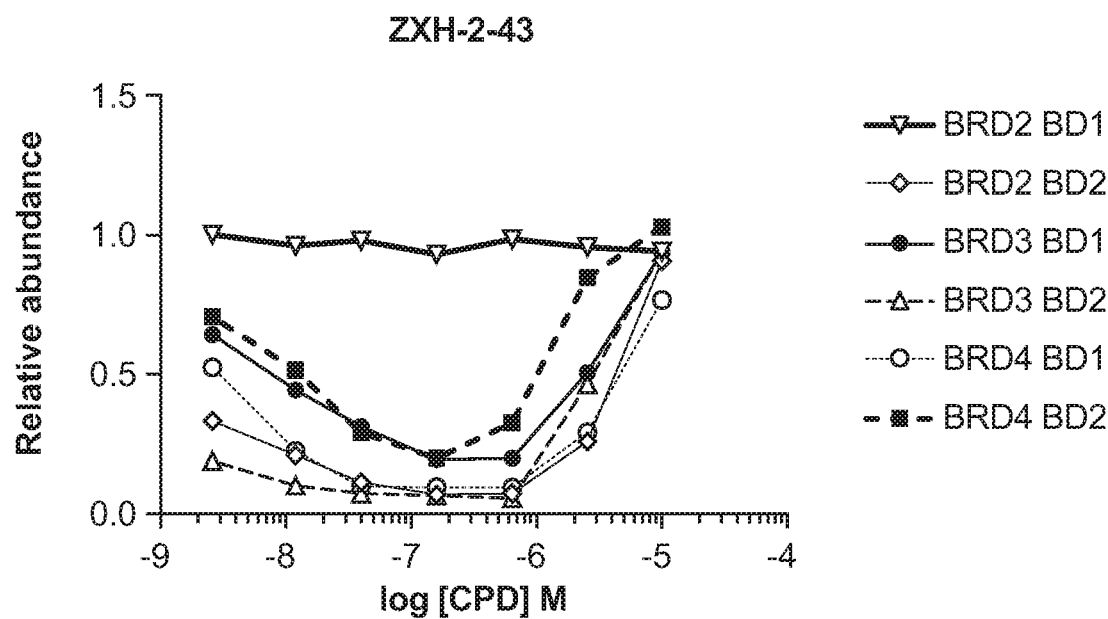
Figure 20D:
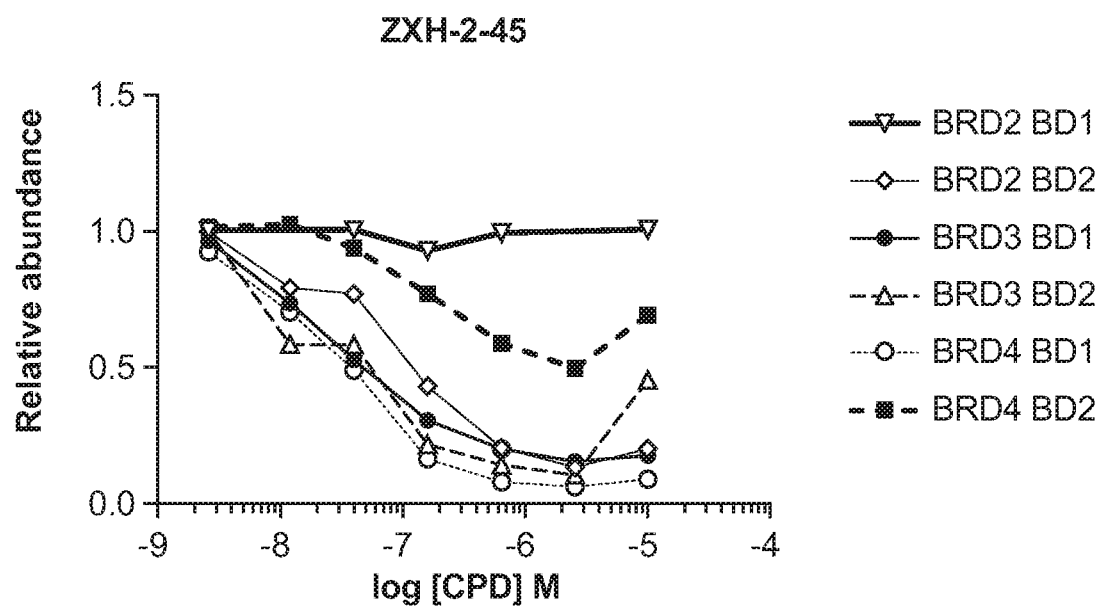

Close analogs of ZXH-03-26 were further explored using cellular imaging-based assay (FIG. 19-FIG. 20) Substitution in linker composition from secondary amine nitrogen (as in ZXH-3-26) to oxygen (as in BJG-02-030) maintained BRD4$_{BD1}$ degradation selectivity, with reduced activity (FIG. 19A). In addition, location of fluorine substitution in pthalimide ring of IMiD, has shown to be critical with BJG-02-119 maintaining selectivity, with reduced activity as compared to ZXH-3-26, and BJG-01-174 resulting in inactive degrader (FIG. 19A-FIG. 19G). Furthermore, more rigid oxoacetamide linker analog of ZXH-3-26, results in inactive degrader ZXH-4-28, changing the linker exit position on IMiD as in ZXH-3-28, also results in inactive molecule, suggesting that both the linker attachment chemistry and the attachment location are crucial in maintaining active degradation. BRD3/BRD4 selective degraders were also observed as exemplified by ZXH-3-52 (FIG. 19 D) and to lesser extend ZXH-3-195 (FIG. 19 E).

Further increasing ZXH-3-26 linker length by one atom results in loss of selectivity as observed for ZXH-3-117 (FIG. 20A-FIG. 20D). Short ether linker analog ZXH-2-42 showed significantly reduced activity.

Figure 14B:
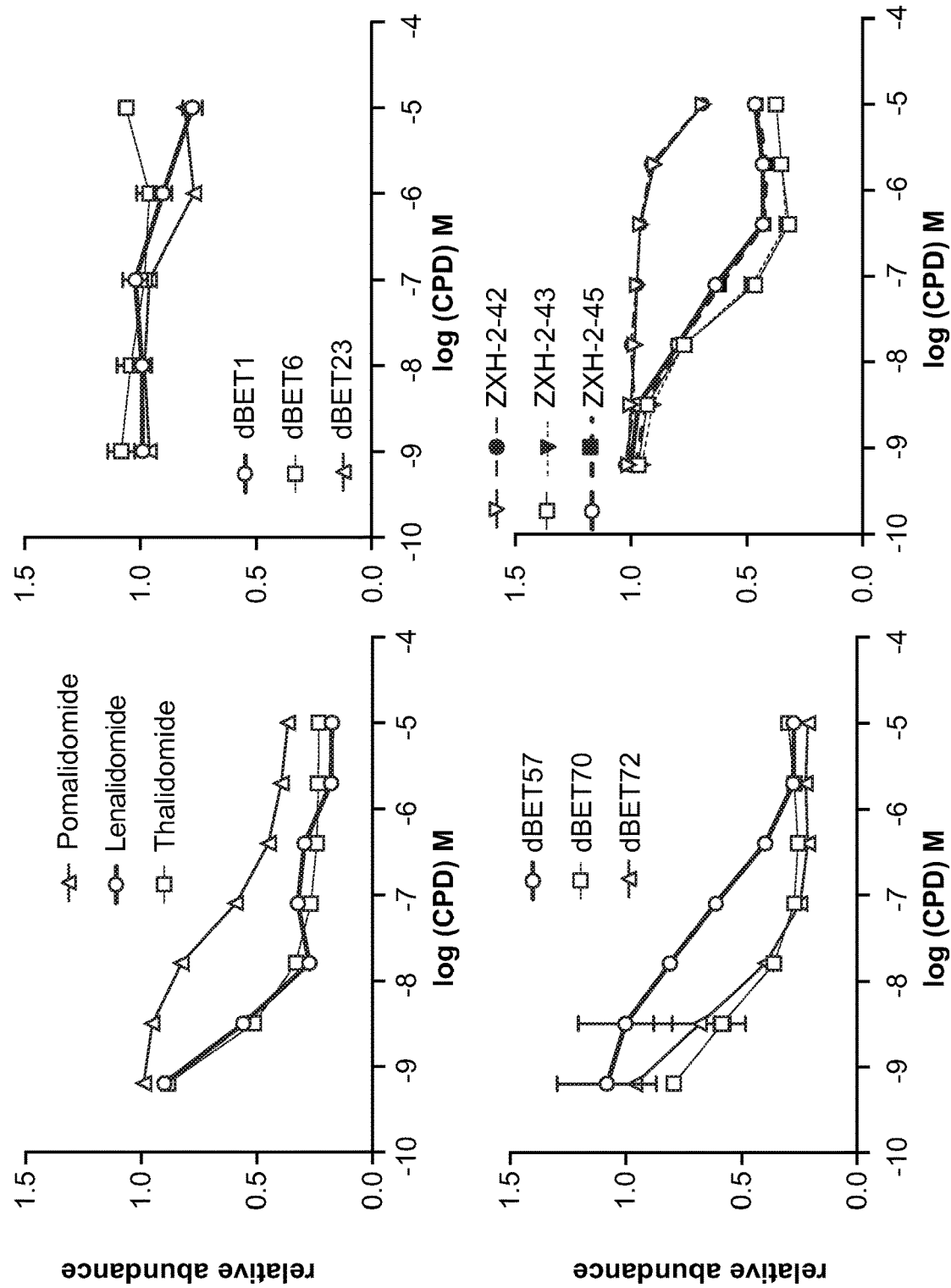
Figure 14C:
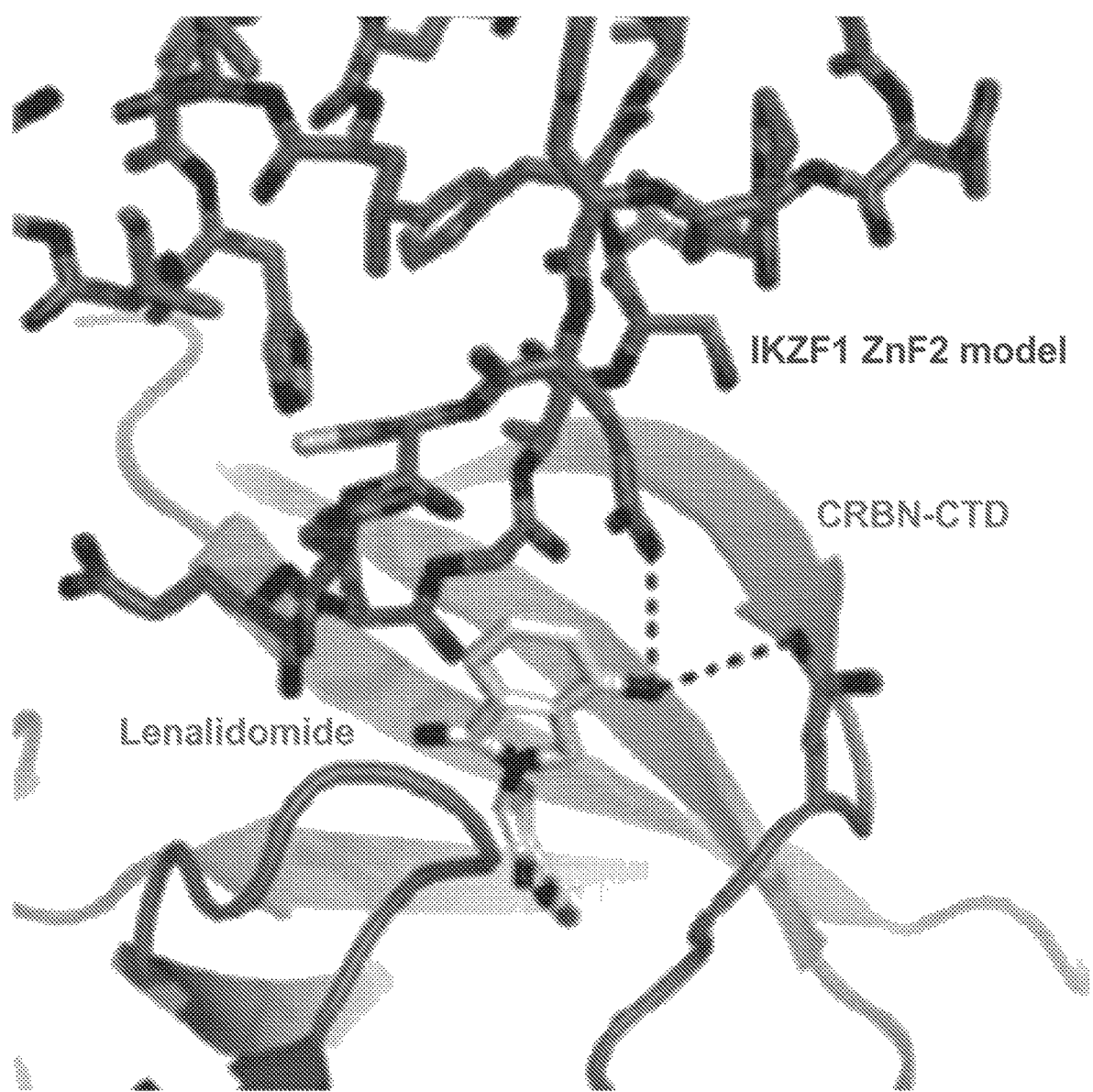

Finally, as shown on FIGS. 14A and 14B, compounds ZXH-2-43 and ZXH-2-45 that showed reduced IKZF1 binding and IKZF1 degradation were able to induce potent degradation of bromodomains. Compound ZXH-2-43 showed significant degradation of BRD2/3/4 even at 2.6 nM concentration (FIG. 20 C).

Cells stably expressing bromodomain-GFP with mCherry reporter were seeded at 30-50% confluency in 384 well plates (3764, Corning) with 50 µL FluoroBrite DMEM media (Gibco, A18967) containing 10% FBS per well a day before compound treatment. Compounds (see Figure legends) were dispensed using D300e Digital Dispenser (HP) normalized to 0.5% DMSO and incubated with cells for 5 h. The assay plate was imaged immediately using Acumen eX3/HCI (TTPLabtech) High Content Imager with 488 nm and 561 nm lasers in 2 µm×1 µm grid per well format. The resulting images were analyzed using CellProfiler™ (Carpenter, et al., GenomeBiology 7:r100 (2006)). A series of image analysis steps ('image analysis pipeline') was constructed.

The CellProfiler™ pipeline steps are briefly outlined here. First, the red and green channels were aligned and cropped to target the middle of each well (to avoid analysis of heavily clumped cells at the edges), and a background illumination function was calculated for both red and green channels of each well individually and subtracted to correct for illumination variations across the 384-well plate from various sources of error. An additional step was then applied to the green channel to suppress the analysis of large auto fluorescent artifacts and enhance the analysis of cell specific fluorescence by way of selecting for objects under a given size, 30 A.U., and with a given shape, speckles. mCherry-positive cells were then identified in the red channel filtering for objects between 8-60 pixels in diameter and using intensity to distinguish between clumped objects. The green channel was then segmented into GFP positive and negative areas and objects were labeled as GFP positive if at least 40% of it overlapped with a GFP positive area. The fraction of GFP-positive cells/mCherry-positive cells (GFP/mCherry ratio) in each well was then calculated, and the green and red images were rescaled for visualization. The GFP/mCherry ratio was normalized to DMSO and analyzed in GraphPad Prism 7.

Example 7: Constructs and Protein Purification

Wild-type and mutant versions of human DDB1, human CRBN, and human IKZF1Δ were cloned in pAC-derived vectors (Abdulrahman, Uhring et al. 2009) and recombinant proteins were expressed as N-terminal His$_6$ (DDB1ΔB, CRBN), StrepII-Avi (IKZF1A) or his$_6$-3C-Spy (CRBN) (Zakeri, Fierer et al. 2012) fusions in *Trichoplusia ni* High-Five insect cells using the baculovirus expression system (Invitrogen). Wild-type and mutant BRD4$_{BD1}$ and BRD4$_{BD2}$ subcloned into *E. coli* pET100/D-TOPO vector with N-terminal His$_6$-Avi fusions were obtained from Invitrogen, BRD4$_{BD1/2}$ were subcloned into N-terminal his$_6$-MBP-TEV-Spy pETDuet vector and all expressed in BL21-DE3 or BL21-DE3 Rosetta cells using standard protocols. For purification of His$_6$ and GST tagged proteins, cells were resuspended in buffer containing 50 mM tris (hydroxymethyl) aminomethane hydrochloride (Tris-HCl) pH 8.0, 200 mM NaCl, 1 mM tris (2-carboxyethyl)phosphine (TCEP), 1 mM phenylmethylsulfonyl fluoride (PMSF), 1× protease inhibitor cocktail (Sigma) and lysed by sonication. Cells expressing StrepII-Avi-IKZF1A were lysed in the presence of 50 mM Tris-HCl pH 8.0, 500 mM NaCl, 1 mM TCEP, 1 mM PMSF and 1× protease inhibitor cocktail (Sigma). Following ultracentrifugation, the soluble fraction was passed over appropriate affinity resin Strep-Tactin Sepharose (IBA) or Ni Sepharose 6 Fast Flow affinity resin (GE Healthcare) or Glutathione Sepharose 4B (GE Healthcare) and eluted with wash buffer (50 mM Tris-HCl pH 8.0, 200 mM NaCl, 1 mM TCEP) supplemented with 2.5 mM D-Desthiobiotin (IBA) or 100 mM imidazole (Fischer Chemical) or 10 mM glutathione (Fischer BioReagents) respectively. The affinity-purified protein was either further purified (CRBN-DDB1ΔB, IKZF1Δ, Spy-BRD4$_{BD1}$) via ion exchange chromatography (Poros 50HQ) and subjected to size exclusion chromatography or concentrated and directly loaded on the size exclusion chromatography in 50 mM HEPES pH 7.4, 200 mM NaCl and 1 mM TCEP. Biotinylation of IKZF1Δ and BRD4$_{BD1}$, BRD4$_{BD2}$ variants was performed as previously described (Petzold, Fischer et al. 2016).

The protein-containing fractions were concentrated using ultrafiltration (Millipore) and flash frozen in liquid nitrogen (DDB1ΔB-CRBN constructs at 40-120 μM, biotinylated His$_6$-Avi-BRD4 mutants and WT, and not biotinylated WT at ~25-100 μM, biotinylated StrepII-Avi-IKZF1 at ~20 μM concentration) and stored at –80° C. or directly covalently labelled with BODIPY-FL-SpyCatchers$_{50C}$ (His$_6$-3C-Spy-CRBN-His$_6$-DDB1ΔB, Spy-BRD4$_{BD1}$) as described below.

Example 8: Labelling of Spycatcher with BODIPY-FL-Maleimide

Spycatcher containing a Ser50Cys mutation was obtained as synthetic dsDNA fragment from IDT (Integrated DNA technologies) and subcloned as GST-TEV fusion protein in a pET-Duet derived vector. Spycatcher S50C was expressed in BL21 DE3 and cells were lysed in the presence of 50 mM Tris-HCl pH 8.0, 200 mM NaCl, 1 mM TCEP and 1 mM PMSF. Following ultracentrifugation, the soluble fraction was passed over Glutathione Sepharose 4B (GE Healthcare) and eluted with wash buffer (50 mM Tris-HCl pH 8.0, 200 mM NaCl, 1 mM TCEP) supplemented with 10 mM glutathione (Fischer BioReagents). The affinity-purified protein was subjected to size exclusion chromatography, concentrated and flash frozen in liquid nitrogen.

Purified Spycatchers$_{50C}$ protein was incubated with DTT (8 mM) at 4° C. for 1 h. DTT was removed using a ENRich SEC650 10/300 (Bio-rad) size exclusion column in a buffer containing 50 mM Tris pH 7.5 and 150 mM NaCl, 0.1 mM TCEP. BODIPY-FL-maleimide (Thermo Fisher) was dissolved in 100% DMSO and mixed with Spycatchers$_{50C}$ to achieve 2.5 molar excess of BODIPY-FL-maleimide. SpyCatchers$_{50C}$ labelling was carried out at room temperature (RT) for 3 h and stored overnight at 4° C. Labelled Spycatchers$_{50C}$ was purified on a ENRich SEC650 10/300 (Bio-rad) size exclusion column in 50 mM Tris pH 7.5, 150 mM NaCl, 0.25 mM TCEP and 10% (v/v) glycerol, concentrated by ultrafiltration (Millipore), flash frozen (~40 μM) in liquid nitrogen and stored at –80° C.

Example 9: BODIPY-FL-Spycatcher Labelling of CRBN-DDB1ΔB and BRD4$_{BD1}$

Purified His$_6$-DDB1ΔB-His$_6$-3C-Spy-CRBN or His$_6$-Spy-BRD4$_{BD1}$ was incubated overnight at 4° C. with BODIPY-FL labelled SpyCatchers$_{50C}$ protein at stoichiometric ratio. Protein was concentrated and loaded on the ENrich SEC 650 10/300 (Bio-rad) size exclusion column and the fluorescence monitored with absorption at 280 nm and 490 nm. Protein peak corresponding to the labeled protein was pooled, concentrated by ultrafiltration (Millipore), flash frozen (~9.6 μM for His$_6$-DDB1ΔB-His$_6$-3C-Spy-CRBN$_{BODIPY\ SpyCatcher}$ or ~22 uM for His$_6$-Spy-BRD4$_{BD1}$) in liquid nitrogen and stored at –80° C.

Example 10: Crystallization and Data Collection

Previously developed DDB1 construct was used that lack WD40 propeller B (BPB, residues 396-705) domain (Petzold, Fischer et al. 2016) (referred to as DDB1ΔB) successful in crystallization of lenalidomide-CK1α complex. For crystallization of His$_6$-DDB1ΔB-His$_6$-CRBN-dBET6/23/70-his$_6$-BRD4$_{BD1}$ and His$_6$-DDB1ΔB-His$_6$-CRBN-dBET55-His$_{6-Avi}$-BRD4$_{BD1\ D145A}$ complexes 145 μM of dBET was mixed with 70 μM BRD4$_{BD1}$ or BRD4$_{BD1\ D145A}$ and 80 μM His$_6$-DDB1ΔB-His$_6$-CRBN and incubated for 15 min either on ice or at RT. Crystallisation plates were set up in 3 sub-well plates (Intelli, Art Robbins) by vapour diffusion using NT8 (Formulatrix) at 20° C. and images acquired using Rocklmager® 1000 (Formulatrix®). Crystals appeared in wells B9-F9 and H9 of Morpheus® HT Screen (Molecular Dimensions) within few hours and were fully grown after 3 days. Single uniform crystals (length 80-100 μm) were present in condition C9 (10% (w/v) PEG20k, 20% (w/v) PEG550 MME, 0.1 M BICINE pH 8.5) in 2:1 or 1:1 protein to precipitant ratio in 150 or 225 nL drops. Further optimisation of condition in Morpheus® HT Screen C$_9$ by Silver Bullets (Hampton Research) additive screening in 1:10 additive to reservoir ratio resulted in optimal crystals for dBET6, dBET23, dBET55 and dBET70 in Silver Bullet wells D7, B5, G4 and F6 respectively, in 2:1 protein to precipitant ratio of 225 or 400 nL drops. Crystals were cryo-protected in reservoir solution supplemented with 25-30% PEG 400 containing 150-300 μM respective dBET and flash-cooled in liquid nitrogen. The Examples show that crystals harvested after 2-3 days resulted in optimal diffraction. Diffraction data were collected at the APS Chicago (beamline 24-ID-C) with a Pilatus 6M-F detector at a temperature of 100 K, or for dBET6 co-crystal structure at beamline 24-ID-E with a Eiger 16M detector at a temperature of 100 K. Data were indexed and integrated using XDS (Kabsch 2010) and scaled using AIMLESS supported by other programs of the CCP4 suite (Winn, Ballard et al. 2011) or RAPD pipeline (APS Chicago). Data processing statistics, refinement statistics and model quality parameters are provided in Table 1.

dBET57 containing crystals were obtained by mixing His$_6$-DDB1ΔB-His$_6$-CRBN at 75 μM, with dBET57 at 140 μM and BRD4$_{BD1}$ at 140 μM in condition B5 of the Hampton Index HT screen (1.26 M NaH$_2$PO$_4$, 0.14 M K$_2$HPO$_4$). Single crystals were harvested, stabilized by addition of 25% ethylene glycol containing dBET57 at 50 μM. Diffraction data were collected at the APS Chicago (beamline 24-ID-C) with a Pilatus 6M-F detector at a temperature of 100° K, at wavelengths of 0.9962 Å for native, 1.2828 Å for Zn peak, and 1.7712 for S peak. Data were indexed and integrated using XDS (Kabsch 2010) and scaled using AIMLESS supported by other programs of the CCP4 suite (Winn, Ballard et al. 2011). Data processing statistics, refinement statistics and model quality parameters are provided in Table 2.

Example 11: Structure Determination and Model Building

The DDB1ΔB-CRBN-dBET6/23/70-BRD4$_{BD1}$ and DDB1ΔB-CRBN-dBET55-BRD4$_{BD1/D145A}$ quaternary complexes crystallized in space group P6$_5$22 with single complex in the unit cell. PHASER (McCoy, Grosse-Kunstleve et al. 2007) was used to determine the structures by molecular replacement using a crystallographic model of DDB1ΔB-CRBN omitting Ck1α based on a crystal structure PDB 5fqd. The initial model was iteratively improved with COOT and refined using PHENIX.REFINE (Afonine, Grosse-Kunstleve et al. 2012) and autoBUSTER (Bricogne G, Blanc E et al. 2011) with ligand restraints generated by Grade server (Global Phasing) or phenix.elbow (Moriarty, Grosse-Kunstleve et al. 2009). Protein geometry analysis revealed 0.63%, 0.55%, 0.94%, 0.72%, 1.02% Ramachandran outliers, with 95.43%, 95.27%, 94.68%, 93.99, 92.18% residues in favoured regions and 3.94%, 4.18%, 4.38%, 5.29%, 6.80% residues in allowed regions for the complexes with dBET6, 23, 55, 57 and 70 respectively.

The DDB1ΔB-CRBN-dBET57-BRD4$_{BD1}$ complex crystallized in space group I422 with a single complex in the unit cell. PHASER (McCoy, Grosse-Kunstleve et al. 2007) was used for molecular replacement using models of hsDDB1ΔB-hsCRBN-HBD derived from pdb: 5fqd, hsCRBN-NTD derived from pdb: 5fqd, and BRD4$_{BD1}$ (pdb: 3mxf). The model was rigid body refined using PHENIX.REFINE (Afonine, Grosse-Kunstleve et al. 2012) and the hsCRBN-CTD was subsequently placed using Coot Jiggle-Fit (part of Coot EM scripts from Alan Brown and Paul Emsley). The final model was rigid body refined using PHENIX.REFINE and autoBUSTER (Bricogne G, Blanc E et al. 2011). Anomalous maps were calculated with PHENIX.MAPS (Afonine, Grosse-Kunstleve et al. 2012).

Figures were generated with PyMOL (The PyMOL Molecular Graphics System, Version 1.8.6.0 Schrödinger, LLC) and model quality was assessed with MOLPROBITY (Chen, Arendall et al. 2010). Interaction surfaces were determined with PISA (Krissinel and Henrick 2007). The IKZF1 homology model was taken from (Petzold, Fischer et al. 2016).

Example 12: Time-Resolved Fluorescence Resonance Energy Transfer (TR-FRET)

Compounds in dimerization assays were dispensed in a 384-well microplate (Corning, 4514) using D300e Digital Dispenser (HP) normalized to 2% DMSO into 200 nM biotinylated His$_6$-avi-bromodomain (WT or mutant) or 80 nM biotinylated StrepII-avi-IKZF1A, 100 nM His$_6$-DDB1ΔB-His$_6$-CRBN$_{BODIPYY\text{-}Spycatcher}$ and 2 nM terbium-coupled streptavidin (Invitrogen) in a buffer containing 50 mM Tris pH 7.5, 100 mM NaCl, 0.1% Pluronic® F-68 solution (Sigma) and 2% DMSO (4% DMSO final). Compounds in CRBN mutants dimerization assay were dispensed as described above into 200 nM His$_6$-DDB1-His$_6$-CRBN$_{mutants}$ or 200 nM His$_6$-DDB1ΔB-His$_6$-CRBN$_{WT}$, 100 nM BRD4$_{BD1\text{-}BODIPY\text{-}SpyCatcher}$ and 2 nM terbium-anti-HIS Ab (Invitrogen) in a buffer containing 50 mM Tris pH 7.5, 100 mM NaCl, 0.1% Pluronic F-68 solution (Sigma) and 2% DMSO (4% DMSO final). Before TR-FRET measurements were conducted, the reactions were incubated for 15 min at RT. After excitation of terbium fluorescence at 337 nm, emission at 490 nm (terbium) and 520 nm (BODIPY) were recorded with a 70 μs delay over 600 μs to reduce background fluorescence and the reaction was followed over 30 200 second cycles of each data point using a PHERAstar® FS microplate reader (BMG Labtech). The TR-FRET signal of each data point was extracted by calculating the 520/490 nm ratio. The heterobifunctional nature of small molecule degraders results in a three-body binding equilibrium complicated by potential cooperativity or avidity effects arising from protein-protein interactions (Douglass, Miller et al. 2013), all of which precludes direct interpretation of the binding data. However, assuming constant concentrations of BRD4$_{BD1}$, DDB1ΔB-CRBN, and fluorescent labels, as well as similar binding conformations, the peak height of the TR-FRET can be used as an indication for the amount of tertiary complex formation (containing BRD4$_{BD1/BD2}$, dBET, and CRBN) (Douglass, Miller et al. 2013). The peak height of TR-FRET dBET dose response data was calculated in GraphPad Prism 7 using Area Under Curve analysis for three independent replicates (n=3) and the mean peak height and standard deviation calculated.

Counter titrations with unlabelled proteins were carried out by addition of solution of 200 nM His$_6$-DDB1ΔB-His$_6$-CRBN$_{BODIPY\text{-}Spycatcher}$, 160 nM biotinylated His$_6$-Avi-IKZF1Δ, 4 nM terbium-coupled streptavidin and 2 μM of dBET57, incubated for 15 min on ice, to equal volume of titrated unlabelled His$_6$-Avi-BRD4$_{BD1}$ or His$_6$-Avi-BRD4$_{BD2}$ to the final assay concentrations.

The 520/490 nm ratios in IKZF1A TR-FRET assays were plotted to calculate the half maximal effective concentrations (EC$_{50}$—for unlabelled protein titrations) or IC$_{50}$ (for compound titrations) assuming a single binding site using GraphPad Prism 7 variable slope equation. The standard deviation in IKZF1A TR-FRET compound titrations was calculated from three biological replicates (n=3) as an average of 5 technical replicates per well per experiment, or as an average of 5 technical replicates of single experiment for unlabelled protein titrations.

Example 13: Fluorescence Polarization

Atto565-conjugated lenalidomide (10 nM) was mixed with increasing concentration of purified his$_6$-DDB1ΔB-his$_6$-CRBN (10 μM final top concentration, 2-fold, 23 point dilution and DMSO control) in 384-well microplates (Corning, 4514) and incubated for 15 min at RT. The change in fluorescence polarization was monitored using a PHERAstar® FS microplate reader (BMG Labtech) for 20 min in 120 s cycles. The Atto565-lenalidomide bound fraction was calculated as described (Marks, Qadir et al. 2005) and the K$_d$ was obtained from a fit in GraphPad Prism 7 from four independent replicates (n=4).

Compounds in Atto565-Lenalidomide displacement assay were dispensed in a 384-well microplate (Corning, 4514) using D300e Digital Dispenser (HP) normalized to 2% DMSO into 10 nM Atto565-Leanlidomide, 100 nM DDB1ΔB-CRBN, 50 mM Tris pH 7.5, 100 mM NaCl, 0.1% Pluronic F-68 solution (Sigma), 0.5 mg/ml BSA (Sigma) containing 2% DMSO (4% DMSO final). Compound titrations were performed in presence of 0, 1, 5, 20 μM of unbiotinylated his$_6$-avi-BRD4$_{BD1}$ or his$_6$-avi-BRD4$_{BD2}$ and incubated for 60 min at RT. The change in fluorescence polarization was monitored using a PHERAstar® FS microplate reader (BMG Labtech) for 20 min in 200 s cycles. Data from two independent measurements (n=2) was plotted and IC$_{50}$ values estimated using variable slope equation in GraphPad Prism 7.

Example 14: Cellular Degradation Assays

IKZF1A, BRD2$_{BD1}$, BRD2$_{BD2}$, BRD3$_{BD1}$, BRD3$_{BD2}$, BRD4$_{BD1}$, and BRD4$_{BD2}$ were subcloned into mammalian pcDNA5/FRT Vector (Ampicillin and Hygromycin B resistant) modified to contain MCS-eGFP-P2A-mCherry. Stable cell lines expressing eGFP-protein fusion and mCherry reporter were generated using Flip-In 293 system. Plasmid (0.3 μg) and pOG44 (4.7 μg) DNA were preincubated in 100

μL of Opti-MEM™ I (Gibco®, Life Technologies) media containing 0.05 mg/ml Lipofectamine® 2000 (Invitrogen) for 20 min and added to Flip-In 293 cells containing 1.9 ml of DMEM media (Gibco®, Life Technologies) per well in a 6-well plate format (Falcon, 353046). Cells were propagated after 48 h and transferred into a 10 cm$^2$ plate (Corning, 430165) in DMEM media containing 50 μg/ml of Hygromycin B (REF 10687010, Invitrogen) as a selection marker. Following 2-3 passage cycle FACS (FACSAria II, BD) was used to enrich for cells expressing eGFP and mCherry.

Cells were seeded at 30-50% confluency in either 24, 48 or 96 well plates (3524, 3548, 3596 respectively, Costar) a day before compound treatment. Titrated compounds were incubated with cells for 5 h following trypsinisation and resuspention in DMEM media, transferred into 96-well plates (353910, Falcon) and analyzed by flow cytometer (guava easyCyte™ HT, Millipore). Signal from 5000 cells per well was acquired in singlicate or duplicate and the eGFP and mCherry florescence monitored. Data was analyzed using FlowJo (FlowJo, LCC). Forward and side scatter outliers, frequently associated with cell debris, were removed leaving >90% of total cells, followed by removal of eGFP and mCherry signal outliers, leaving 88-90% of total cells creating the set used for quantification. The eGFP protein abundance relative to mCherry was then quantified as a ten-fold amplified ratio for each individual cell using the formula: 10×eGFP/mCherry. The median of the ratio was then calculated per set, normalized to the median of the DMSO ratio, and is denoted as relative abundance. Standard deviation is calculated from four replicates (n=4) unless described otherwise.

Example 15: Western Blot for Cellular BRD2/3/4 Degradation

HEK293T cells were seeded at 90% confluency in 12 well plates (353043, Falcon), left to attach for 1.5 h, followed by the compound treatment for 5 h. Primary and secondary antibodies used included anti-BRD4 at 1:1000 dilution (A301-985A-M, Bethyl Laboratories), anti-BRD2 at 1:2,000 dilution (A302-582A, Bethyl Laboratories), anti-BRD3 at 1:500 dilution (ab56342, Abcam®), anti-GAPDH at 1:10,000 dilution (G8795, Sigma), IRDye® 680 Donkey anti-mouse at 1:10,000 dilution (926-68072, LiCor®) and IRDye800 Goat anti-rabbit at 1:10,000 dilution (926-32211, LiCor®).

Example 16: Sample Preparation and TMT LC-MS3 Mass Spectrometry Analysis

MM.1s cell were treated with DMSO, 1 μM dBET23, or dBET70 in biological triplicates for 5 hours and cells harvested by centrifugation. Lysis buffer (8 M Urea, 1% SDS, 50 mM Tris pH 8.5, Protease and Phosphatase inhibitors from Roche) was added to the cell pellets to achieve a cell lysate with a protein concentration between 2-8 mg mL$^{-1}$. A micro-BCA assay (Pierce) was used to determine the final protein concentration in the cell lysate. 200 μg proteins for each sample were reduced and alkylated as previously described. Proteins were precipitated using methanol/chloroform. In brief, four volumes of methanol were added to the cell lysate, followed by one volume of chloroform, and finally three volumes of water. The mixture was vortexed and centrifuged to separate the chloroform phase from the aqueous phase. The precipitated protein was washed with one volume of ice-cold methanol. The washed precipitated protein was allowed to air dry. Precipitated protein was resuspended in 4 M Urea, 50 mM Tris pH 8.5. Proteins were first digested with LysC (1:50; enzyme:protein) for 12 hours at 25° C. The LysC digestion was diluted down in 1 M Urea, 50 mM Tris pH 8.5 and then digested with trypsin (1:100; enzyme:protein) for another 8 hours at 25° C. Peptides were desalted using a $C_{18}$ solid phase extraction cartridges (Waters). Dried peptides were resuspended in 200 mM EPPS, pH 8.0. Peptide quantification was performed using the micro-BCA assay (Pierce). The same amount of peptide from each condition was labelled with tandem mass tag (TMT) reagent (1:4; peptide:TMT label) (Pierce). The 10-plex labelling reactions were performed for 2 hours at 25° C. Modification of tyrosine residue with TMT was reversed by the addition of 5% hydroxyl amine for 15 minutes at 25° C. The reaction was quenched with 0.5% TFA and samples were combined at a 1:1:1:1:1:1:1:1:1:1 ratio. Combined samples were desalted and offline fractionated into 96 fractions using an aeris peptide xb-c18 column (phenomenex) at pH 8.0. Fractions were recombined in a non-continuous manner into 24 fractions and every second fraction was used for subsequent mass spectrometry analysis.

Data were collected using an Orbitrap Fusion Lumos mass spectrometer (Thermo Fisher Scientific, San Jose, Calif., USA) coupled with a Proxeon EASY-nLC™ 1200 LC pump (Thermo Fisher Scientific). Peptides were separated on a 75 μm inner diameter microcapillary column packed with 35 cm of Accucore C18 resin (2.6 μm, 100 Å, Thermo Fisher Scientific). Peptides were separated using a 3 hr gradient of 6-27% acetonitrile in 0.125% formic acid with a flow rate of 400 nL/min.

Each analysis used an MS$^3$-based TMT method as described previously (McAlister, Nusinow et al. 2014). The data were acquired using a mass range of m/z 350-1350, resolution 120,000, AGC target 1×10$^6$, maximum injection time 100 ms, dynamic exclusion of 120 seconds for the peptide measurements in the Orbitrap. Data dependent MS$^2$ spectra were acquired in the ion trap with a normalized collision energy (NCE) set at 35%, AGC target set to 1.8×10$^4$ and a maximum injection time of 120 ms. MS$^3$ scans were acquired in the Orbitrap with a HCD collision energy set to 55%, AGC target set to 1.5×10$^5$, maximum injection time of 150 ms, resolution at 50,000 and with a maximum synchronous precursor selection (SPS) precursors set to 10.

Proteome Discoverer™ 2.1 (Thermo Fisher) was used to for .RAW file processing and controlling peptide and protein level false discovery rates, assembling proteins from peptides, and protein quantification from peptides. MS/MS spectra were searched against a Uniprot human database (September 2016) with both the forward and reverse sequences. Database search criteria are as follows: tryptic with two missed cleavages, a precursor mass tolerance of 50 ppm, fragment ion mass tolerance of 1.0 Da, static alkylation of cysteine (57.02146 Da), static TMT labelling of lysine residues and N-termini of peptides (229.16293 Da), and variable oxidation of methionine (15.99491 Da). TMT reporter ion intensities were measured using a 0.003 Da window around the theoretical m/z for each reporter ion in the MS$^3$ scan. Peptide spectral matches with poor quality MS$^3$ spectra were excluded from quantitation (<summed signal-to-noise across 10 channels and <0.5 precursor isolation specificity).

Reporter ion intensities were normalised and scaled in the R framework (Team 2013). Statistical analysis was carried out using the limma package within the R framework (Ritchie, Phipson et al. 2015).

Example 17: Protein Docking

All protein docking was carried out using Rosetta 3.7 provided through SBGrid (Morin, Eisenbraun et al. 2013). Input models were downloaded from the PDB (hsCRBN pdb: 4tz4; BRD4$_{BD1}$ pdb: 3mxf, BRD4$_{BD2}$ pdb: 2ouo, and hsCSNK1A1 pdb: 5fqd). Ligand conformers were generated using OpenEye Omega (OpenEye scientific) and parameter files generated using Rosetta 'molfile_to_params.py'. Relevant PDB's were combined into a single file and prepared for docking using the Rosetta dockingprepackprotoca program. Initial global docking was performed using Rosetta dockingprotocol mpi' with the following command line options:
partners A_B—dock_pert 5 25—randomize2—ex1 ex2aro-nstruct 20000 providing the combined pdb and ligand specific parameter files as input.

For Ck1α, and the initial analysis of BRD4$_{BD1}$, the two lowest scoring solutions were used for local perturbation docking with Rosetta dockingprotocol mpi' with the following command line options:
partners A_B—dock_pert 8 18—ex1 ex2aro-nstruct 2000

To assess the landscape of possible binding modes for BRD4$_{BD1}$ and BRD4$_{BD2}$, the top 200 lowest scoring docking decoys were selected and hierarchical clustered according to the compound centroids and orientations. The lowest scoring model of each cluster was loaded into pymol and decoys that would position the thalidomide and JQ1 binding sites on CRBN and BRD4$_{BD1/2}$, respectively, more than 30 Å apart. The remaining decoys were considered.

Methods were developed for the design of heterobifunctional compounds based on computational protein-protein docking, including methods for analysis of the docking results and the inference of design information for chemical synthesis. These methods were applied to the BET family protein BRD4 to synthesize working examples.

Figure 18:
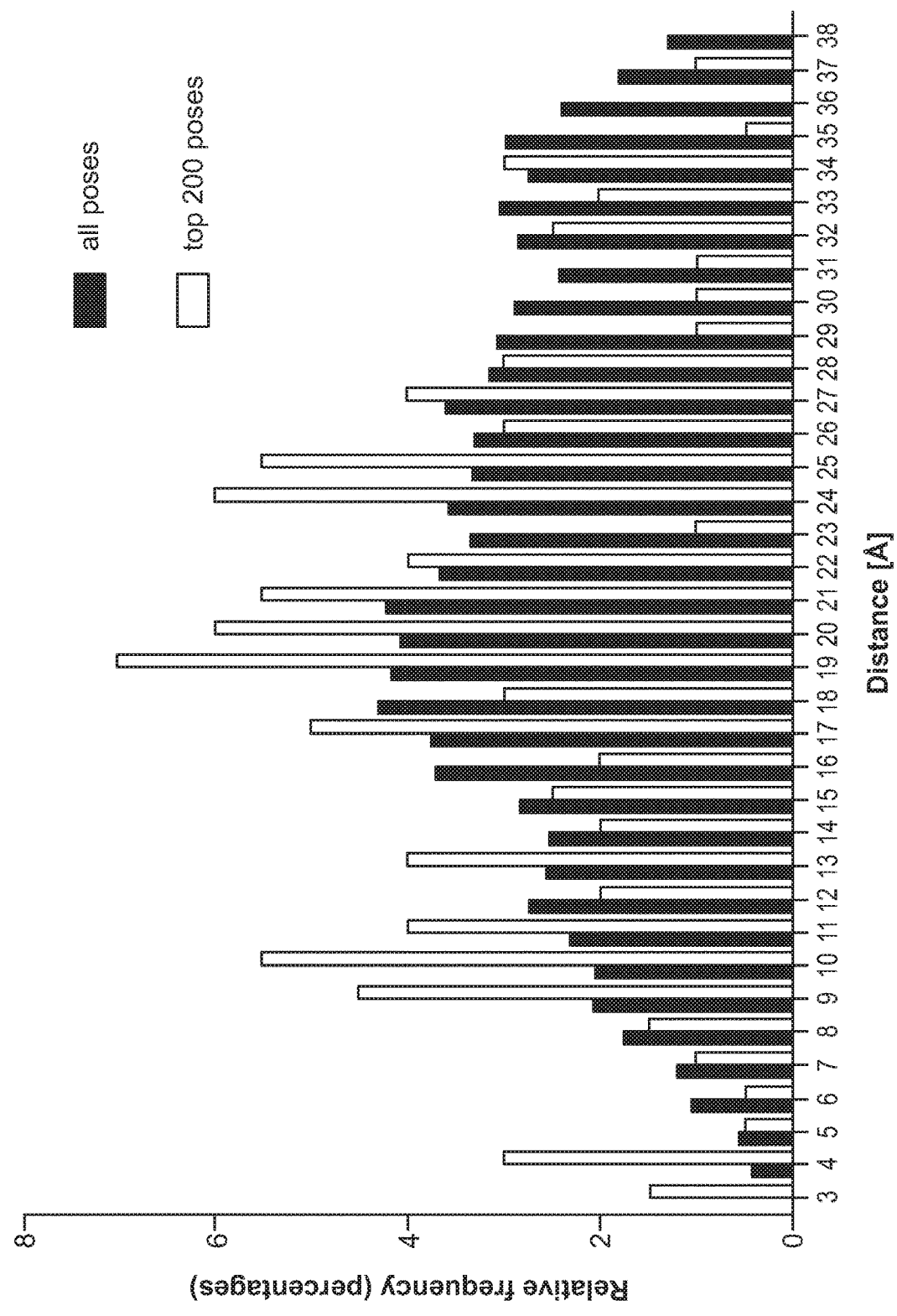
FIG. 18 is bar graph that shows histogram of shortest pairwise distances found in docking poses between solvent exposed atoms of JQ1 bound to $BRD4_{BD1}$ and Lenalidomide bound to CRBN. Distances from 10,000 docking poses are shown in black and top 200 poses based on the docking score in gray.

Protein-protein docking programs such as Rosetta output docked poses of the two proteins. In one embodiment, BRD4$_{BD1}$ was docked with CRBN in the presence of the ligands, JQ1 and lenalidomide respectively, resulting in 10,000 scored poses. Then, the shortest distance paths between a set of solvent exposed atoms on both ligands was calculated and plotted those as a histogram of the distances (FIG. 18). Histogram of 10,000 distances and the distances from top 200 scoring poses present clearly distinct profiles. The profile of all poses approximates a normal distribution, whereas the profile of the top 200 poses has clear regions (i.e., clusters) of distances that occurred with higher frequency (FIG. 18). These clusters indicate a preference for the complex formation in these particular distance constraints.

Data analysis and statistics for all steps were performed using the R framework (Team 2013) or Matlab.

Example 18: Synthesis of dBET6

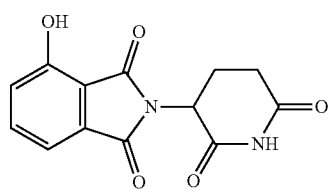 [SMILES: O=C1CCC(N2C(=O)c3cccc(O)c3C2=O)C(=O)N1]

2-(2,6-dioxopiperidin-3-yl)-4-hydroxyisoindoline-1,3-dione

3-Hydroxyphthalic anhydride (1.641 g, 10 mmol, 1 eq.) and 3-aminopiperidine-2,6-dione hydrochloride (1.646 g, 10 mmol, 1 eq.) were dissolved in pyridine (40 mL, 0.25 M) and heated to 110° C. After 14 hours, the mixture was cooled to room temperature and concentrated under reduced pressure. Purification by column chromatography (ISCO, 24 g silica column, 0-10% MeOH/DCM) gave the desired product as a tan solid (2.424 g, 8.84 mmol, 88%).

$^1$H NMR (400 MHz, DMSO-d$_6$) δ 11.08 (s, 2H), 7.65 (dd, J=8.4, 7.2 Hz, 1H), 7.36-7.28 (m, 1H), 7.25 (dd, J=8.4, 0.6 Hz, 1H), 5.07 (dd, J=12.8, 5.4 Hz, 1H), 2.88 (ddd, J=17.3, 14.0, 5.4 Hz, 1H), 2.63-2.50 (m, 2H), 2.08-1.95 (m, 1H).

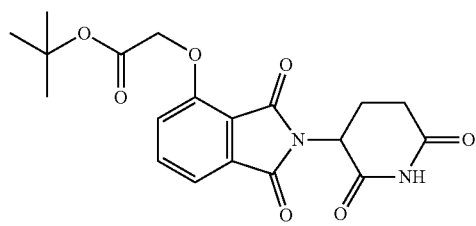 [SMILES: CC(C)(C)OC(=O)COc1cccc2c1C(=O)N(C1CCC(=O)NC1=O)C2=O]

tert-Butyl 2-((2-(2,6-dioxopiperidin-3-yl)-1,3-dioxoisoindolin-4-yl)oxy)acetate 2-(2,6-dioxopiperidin-3-yl)-4-hydroxyisoindoline-1,3-dione (1.568 g, 5.71 mmol, 1 eq.) was dissolved in DMF (57 mL, 0.1 M) at room temperature. Potassium carbonate (1.19 g, 8.58 mmol, 1.5 eq.) and tert-butyl bromoacetate (0.843 mL, 5.71 mmol, 1 eq.) were then added. After 2 hours, the mixture was diluted with EtOAc and washed once with water, then twice with brine. The organic layer was dried over sodium sulfate, filtered and concentrated under reduced pressure. Purification by column chromatography (ISCO, 24 g silica column, 0-100% EtOAc/hexanes, 21 minute gradient) gave the desired product as a cream colored solid (2.06 g, 5.30 mmol, 93%).

$^1$H NMR (500 MHz, C$_D$Cl3) δ 7.94 (s, 1H), 7.67 (dd, J=8.4, 7.3 Hz, 1H), 7.52 (d, J=6.8 Hz, 1H), 7.11 (d, J=8.3 Hz, 1H), 4.97 (dd, J=12.3, 5.3 Hz, 1H), 4.79 (s, 2H), 2.95-2.89 (m, 1H), 2.85-2.71 (m, 2H), 2.14 (dtd, J=10.2, 5.0, 2.7 Hz, 1H), 1.48 (s, 9H).

LCMS 389.33 (M+H)$^+$.

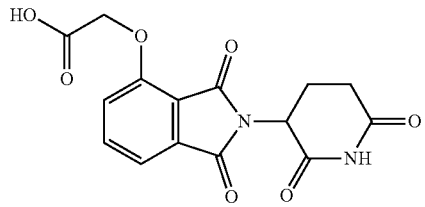 [SMILES: O=C(O)COc1cccc2c1C(=O)N(C1CCC(=O)NC1=O)C2=O]

2-((2-(2,6-Dioxopiperidin-3-yl)-1,3-dioxoisoindolin-4-yl)oxy)acetic acid tert-Butyl 2-((2-(2,6-dioxopiperidin-3-yl)-1,3-dioxoisoindolin-4-yl)oxy)acetate (2.06 g, 5.30 mmol, 1 eq.) was dissolved in trifluoroacetic acid (TFA) (53 mL, 0.1M) at room temperature. After 4 hours, the solution was diluted with DCM and concentrated under reduced pressure. The resultant cream colored solid (1.484 g, 4.47 mmol, 84%) was deemed sufficiently pure and carried onto the next step without further purification.

$^1$H NMR (500 MHz, DMSO-d$_6$) δ 11.11 (s, 1H), 7.79 (dd, J=8.4, 7.4 Hz, 1H), 7.48 (d, J=7.2 Hz, 1H), 7.39 (d, J=8.6 Hz, 1H), 5.10 (dd, J=12.8, 5.4 Hz, 1H), 4.99 (s, 2H), 2.93-2.89 (m, 1H), 2.63-2.51 (m, 2H), 2.04 (ddd, J=10.5, 5.4, 3.1 Hz, 1H).

LCMS 333.25 (M+H)$^+$.

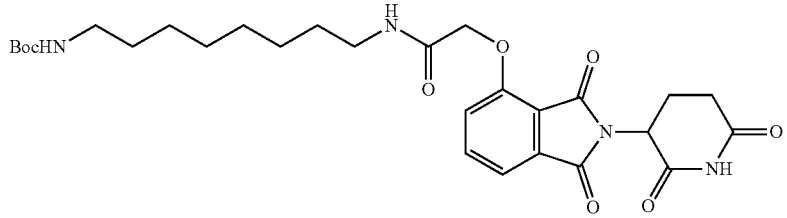 [SMILES: CC(C)(C)OC(=O)NCCCCCCCCNC(=O)COc1cccc2c1C(=O)N(C1CCC(=O)NC1=O)C2=O]

tert-Butyl (8-(2-(2-(2,6-dioxopiperidin-3-yl)-1,3-dioxoisoindolin-4-yl)oxy)acetamido)octyl)carbamate Boc-1,8-diaminooctane (2.10 g, 8.59 mmol, 1.1 eq.) was dissolved in DMF (86 mL). In a separate flask, 2-((2-(2,6-dioxopiperidin-3-yl)-1,3-dioxoisoindolin-4-yl)oxy)acetic acid (2.60 g, 7.81 mmol, 1 eq.) was dissolved in DMF (78 mL). The solution of Boc-1,8-diaminooctane in DMF was then added, followed by N,N-diisopropylethylamine (DIPEA) (4.08 mL, 23.4 mmol. 3 eq.) and 1-[bis(dimethylamino)methylene]-1H-1,2,3-triazolo[4,5-b]pyridinium 3-oxid hexafluorophosphate 0 (2.97 g, 7.81 mmol, 1 eq.). The mixture was stirred for 19 hours at room temperature, then diluted with EtOAc (600 mL). The organic layer was washed sequentially with 200 mL of half saturated sodium chloride, 200 mL 10% citric acid (aq.), 200 mL of half saturated sodium chloride, 200 mL of saturated sodium bicarbonate (aq.), 200 mL water and twice with 200 mL brine. The organic layer was dried over sodium sulfate, filtered and concentrated under reduced pressure. Purification by column chromatography (ISCO, 40 g column, 0-5% MeOH/DCM, 35 minute gradient) gave the desired product as a white solid (3.53 g, 6.32 mmol, 81%).

$^1$H NMR (500 MHz, CDCl$_3$) δ 8.49 (s, 1H), 7.74 (dd, J=8.3, 7.4 Hz, 1H), 7.55 (d, J=7.2 Hz, 1H), 7.39 (t, J=5.3 Hz, 1H), 7.19 (d, J=8.4 Hz, 1H), 4.97 (dd, J=12.4, 5.3 Hz, 1H), 4.63 (d, J=2.2 Hz, 2H), 4.59 (d, J=10.0 Hz, 1H), 3.36 (q, J=6.9 Hz, 2H), 3.12-3.03 (m, 2H), 2.95-2.72 (m, 3H), 2.16 (ddt, J=10.3, 5.2, 2.7 Hz, 1H), 1.59 (p, J=7.1 Hz, 2H), 1.37 (d, J=67.6 Hz, 19H).

LCMS 559.47 (M+H)$^+$.

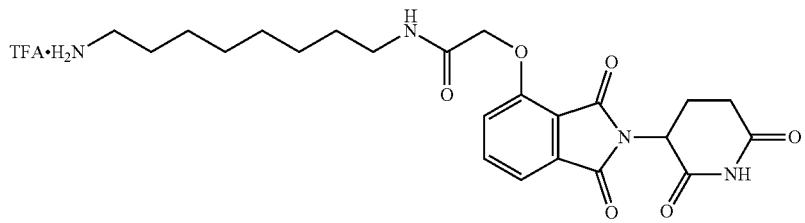

N-(8-Aminooctyl)-2-((2-(2,6-dioxopiperidin-3-yl)-1,3-dioxoisoindolin-4-yl)oxy)acetamide trifluoroacetate tert-Butyl (8-(2-((2-(2,6-dioxopiperidin-3-yl)-1,3-dioxoisoindolin-4-yl)oxy)acetamido)octyl)carbamate (3.53 g, 6.32 mmol, 1 eq.) was dissolved in TFA (63 mL, 0.1M) and heated to 50° C. After 1 hour, the mixture was cooled to room temperature, diluted with MeOH and concentrated under reduced pressure. The crude material was triturated with diethyl ether and dried under vacuum to give a white solid (2.93 g, 5.12 mmol, 81%).

$^1$H NMR (500 MHz, MeOD) δ 7.82 (dd, J=8.4, 7.4 Hz, 1H), 7.55 (d, J=7.2 Hz, 1H), 7.44 (d, J=8.4 Hz, 1H), 5.14 (dd, J=12.5, 5.5 Hz, 1H), 4.76 (s, 2H), 3.33 (dd, J=6.8, 1.8 Hz, 1H), 3.30 (s, 1H), 2.94-2.85 (m, 3H), 2.80-2.69 (m, 2H), 2.19-2.11 (m, 1H), 1.60 (dq, J=24.8, 7.0 Hz, 4H), 1.37 (s, 8H).

LCMS 459.45 (M+H)$^+$.

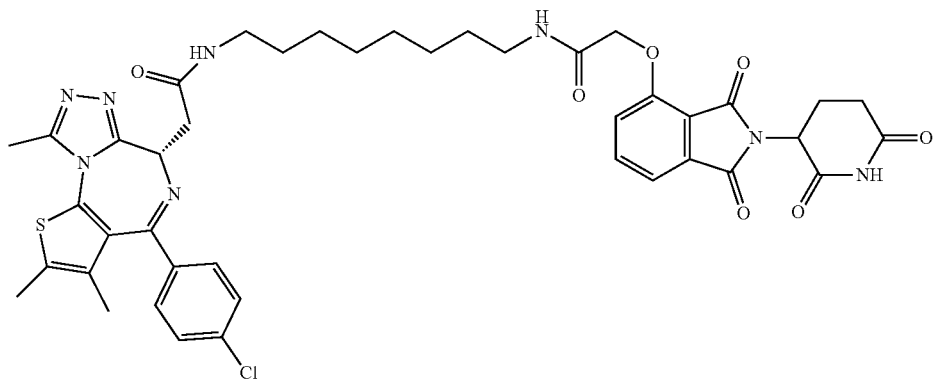 [SMILES: Cc1sc2c(c1C)C(c1ccc(Cl)cc1)=N[C@@H](CC(=O)NCCCCCCCCNC(=O)COc1cccc3c1C(=O)N(C1CCC(=O)NC1=O)C3=O)c1nnc(C)n1-2]

dBET6

(S)-2-(4-(4-chlorophenyl)-2,3,9-trimethyl-6H-thieno[3,2-f][1,2,4]triazolo[4,3-a][1,4]diazepin-6-yl)acetic acid (JQ-acid) (0.894 g, 2.23 mmol, 1 eq.) and N-(8-aminooctyl)-2-((2-((2,6-dioxopiperidin-3-yl)-1,3-dioxoisoindolin-4-yl)oxy)acetamide trifluoroacetate (1.277 g) were dissolved in DMF (22.3 mL, 0.1M) at room temperature. DIPEA (1.17 mL, 6.69 mmol, 3 eq.) was added, followed by HATU (0.848 g, 2.23 mmol, 1 eq.). The mixture was stirred for 23 hours, and then diluted with EtOAc. The organic layer was washed with saturated sodium bicarbonate, water and three times with brine. The organic layer was then dried under sodium sulfate, filtered and concentrated under reduced pressure. Purification by column chromatography (ISCO, 40 g column, 4-10% MeOH/DCM, 35 minute gradient) gave dBET6 as a cream colored solid (1.573 g, 1.87 mmol, 84%).

$^1$H NMR (500 MHz, MeOD) δ 7.80 (dd, J=8.3, 7.5 Hz, 1H), 7.53 (d, J=7.3 Hz, 1H), 7.46-7.37 (m, 5H), 5.11 (ddd, J=12.6, 8.2, 5.5 Hz, 1H), 4.75 (s, 2H), 4.63 (dd, J=9.0, 5.2 Hz, 1H), 3.41 (ddd, J=14.9, 9.0, 2.2 Hz, 1H), 3.30-3.14 (m, 5H), 2.86 (ddt, J=19.8, 14.6, 5.2 Hz, 1H), 2.78-2.66 (m, 5H), 2.44 (s, 3H), 2.13 (ddq, J=15.3, 7.7, 4.8, 3.8 Hz, 1H), 1.69 (s, 3H), 1.61-1.51 (m, 4H), 1.35 (s, 8H).

$^{13}$C NMR (126 MHz, MeOD) δ 174.49, 172.65, 171.30, 169.80, 168.28, 167.74, 166.18, 157.03, 156.24, 152.18, 138.19, 138.08, 137.97, 134.92, 133.52, 133.23, 132.02, 131.99, 131.33, 129.76, 121.65, 119.30, 117.94, 69.36, 55.27, 50.57, 40.49, 40.13, 38.84, 32.19, 30.49, 30.34, 30.31, 30.22, 27.92, 27.82, 23.64, 14.42, 12.92, 11.60.

LCMS 841.48 (M+H)$^+$.

Example 19: Synthesis of dBET23 dBET23

A 0.1 M solution of N-(8-aminooctyl)-2-((2-(2,6-dioxopiperidin-3-yl)-1,3-dioxoisoindolin-4-yl)oxy)acetamide trifluoroacetate in DMF (220 microliters, 0.0220 mmol, 1 eq.) was added to (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (9.87 mg, 0.0220 mmol, 1 eq.) at room temperature. DIPEA (11.5 microliters, 0.0660 mmol, 3 eq.) and HATU (8.4 mg, 0.0220 mmol, 1 eq.) were added. The mixture was then stirred for 21 hours, then diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as a white solid (8.84 mg, 0.00998 mmol, 45%).

$^1$H NMR (400 MHz, MeOD) δ 7.81 (dd, J=8.4, 7.4 Hz, 1H), 7.53 (d, J=7.3 Hz, 1H), 7.50-7.39 (m, 5H), 5.12 (dd, J=12.6, 5.4 Hz, 1H), 4.75 (s, 2H), 4.68 (t, J=7.2 Hz, 1H), 3.76 (s, 3H), 3.54 (d, J=7.2 Hz, 2H), 3.39-3.32 (m, 3H), 3.29 (s, 1H), 2.90-2.83 (m, 1H), 2.79-2.68 (m, 5H), 2.14 (dd, J=8.9, 3.7 Hz, 1H), 1.99 (s, 3H), 1.65-1.53 (m, 4H), 1.36 (d, J=6.5 Hz, 8H).

LCMS 885.47 (M+H)$^+$.

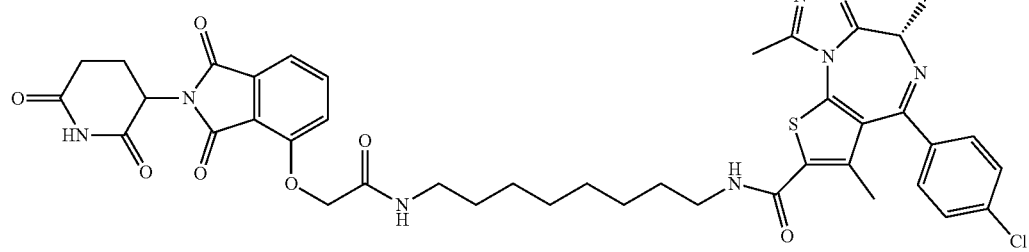

Example 20: Synthesis of dBET55

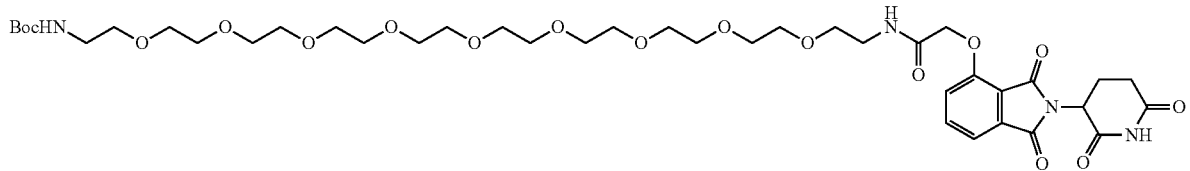 [SMILES: CC(C)(C)OC(=O)NCCOCCOCCOCCOCCOCCOCCOCCOCCOCCNC(=O)COc1cccc2c1C(=O)N(C1CCC(=O)NC1=O)C2=O]

tert-Butyl (1-((2-(2,6-dioxopiperidin-3-yl)-1,3-di-oxoisoindolin-4-yl)oxy)-2-oxo-6,9,12,15,18,21,24,27,30-nonaoxa-3-azatriacontan-32-yl)carbamate tert-Butyl (29-amino-3,6,9,12,15,18,21,24,27-nonaoxanonacosyl) carbamate (422.53 mg, 0.759 mmol, 1 eq.) as a solution in 15.18 ml DMF (0.1 M) was added to 2-((2-(2,6-dioxopiperidin-3-yl)-1,3-dioxoisoindolin-4-yl)oxy) acetic acid (252.26 mg, 0.759, 1 eq.). DIPEA (376.45 µl, 2.277 mmol, 3 eq.) was added, followed by HATU (288.6 mg, 0.759 mmol, 1 eq.). The mixture was stirred for 17 hours at room temperature. The mixture was then diluted with EtOAc and washed with saturated sodium bicarbonate, water then brine. The organic layer was dried over sodium sulfate, filtered and condensed to give a white solid (255.8 mg, 39% yield). The crude material was purified by column chromatography (ISCO, 12 g silica column, 0 to 10% MeOH/DCM 25 minute gradient) to give a white solid (105.3 mg, 16% yield).

$^1$H NMR (500 MHz, MeOD) δ 7.80 (dd, J=8.4, 7.3 Hz, 1H), 7.50 (dd, J=7.3 Hz, 1H), 7.43 (dd, J=8.5 Hz, 1H), 5.12 (dd, J=12.8, 5.5 Hz, 1H), 3.61 (m, J=8.2, 5.6, 2.6 Hz, 36H), 3.50 (dd, J=5.6, 1.9 Hz, 4H), 3.22 (q, J=5.5 Hz, 2H), 2.90 (ddd, J=17.5, 13.9, 5.3 Hz, 1H), 2.80-2.70 (m, 2H), 2.17 (m, J=13.1, 5.8, 2.8 Hz, 1H), 1.43 (s, 9H).

LCMS 871.35 (M+H)$^+$.

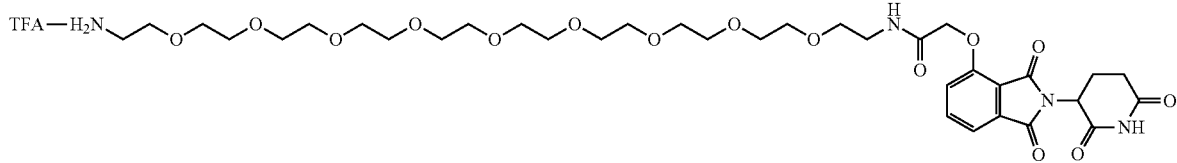

N-(29-Amino-3,6,9,12,15,18,21,24,27-nonaoxanonacosyl)-2-((2-(2,6-dioxopiperidin-3-yl)-1,3-dioxoisoindolin-4-yl)oxy)acetamide trifluoroacetate salt tert-Butyl (1-((2-(2,6-dioxopiperidin-3-yl)-1,3-dioxoisoindolin-4-yl)oxy)-2-oxo-6,9,12,15,18,21,24,27,30-nonaoxa-3-azatriacontan-32-yl)carbamate (105.3 mg, 0.121 mmol, 1 eq.) was added to 1.21 ml TFA (0.1M) and was stirred for 2 hours at 50° C. The mixture was diluted with methanol and condensed to give a white solid (104.28, 97% yield) with no further purification.

$^1$H NMR (500 MHz, DMSO-d$_6$) δ 11.11 (s, 1H), 8.00 (s, J=5.8 Hz, 1H), 7.82 (dd, J=7.9 Hz, 1H), 7.75-7.71 (s, 2H), 7.50 (dd, J=7.3 Hz, 1H), 7.40 (dd, J=8.6 Hz, 1H), 5.11 (dd, J=12.8, 5.4 Hz, 1H), 4.79 (s, 2H), 3.91-3.41 (m, 36H), 3.32 (t, J=5.7 Hz, 2H), 2.98 (m, J=5.5 Hz, 2H), 2.90 (ddd, J=18.1, 14.0, 5.3 Hz, 1H), 2.63-2.54 (m, 2H), 2.05 (dd, J=12.3, 6.1 Hz, 1H).

LCMS 771.80 (M+H)$^+$.

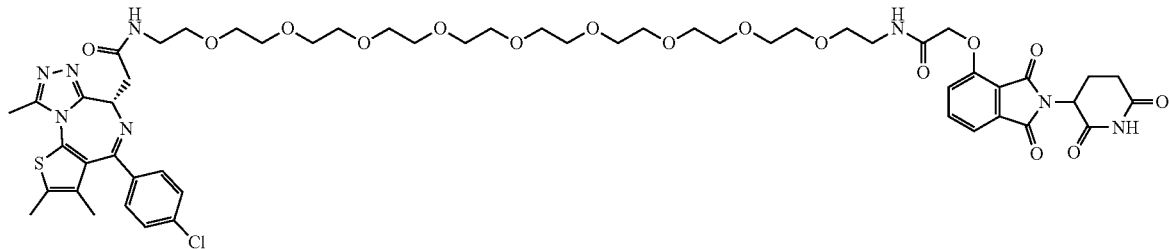 [SMILES: Cc1sc2c(c1C)C(c1ccc(Cl)cc1)=N[C@@H](CC(=O)NCCOCCOCCOCCOCCOCCOCCOCCOCCOCCNC(=O)COc1cccc3c1C(=O)N(C1CCC(=O)NC1=O)C3=O)c1nnc(C)n1-2]

dBET55

A 0.1 M solution of N-(29-amino-3,6,9,12,15,18,21,24,27-nonaoxanonacosyl)-2-((2-(2,6-dioxopiperidin-3-yl)-1,3-dioxoisoindolin-4-yl)oxy)acetamide trifluoroacetate in DMF (200 microliters, 0.020 mmol, 1 eq.) was added to JQ-acid (8.0 mg, 0.020 mmol, 1 eq.) at room temperature. DIPEA (10.5 microliters, 0.060 mmol, 3 eq.) and HATU (7.6 mg, 0.020 mmol, 1 eq.) were added. After 18 hours the mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-10% MeOH/DCM, 25 minute gradient) gave the desired product (10.55 mg, 0.00914 mmol, 46%).

$^1$H NMR (500 MHz, MeOD) δ 7.82 (dd, J=8.4, 7.4 Hz, 1H), 7.55 (d, J=7.0 Hz, 1H), 7.49-7.41 (m, 5H), 5.13 (dd, J=12.6, 5.5 Hz, 1H), 4.80 (s, 2H), 4.65 (dd, J=9.1, 5.1 Hz, 1H), 3.68-3.58 (m, 36H), 3.53-3.44 (m, 5H), 2.94-2.86 (m, 1H), 2.81-2.70 (m, 5H), 2.46 (s, 3H), 2.19-2.13 (m, 1H), 1.74-1.69 (m, 3H).

LCMS 1153.59 (M+H)$^+$.

Example 21: Synthesis of dBET57

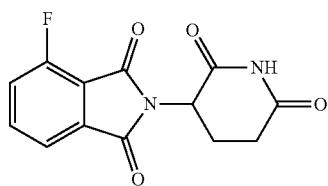 [SMILES: O=C1CCC(N2C(=O)c3cccc(F)c3C2=O)C(=O)N1]

2-(2,6-Dioxopiperidin-3-yl)-4-fluoroisoindoline-1,3-dione

3-Fluorophthalic anhydride (1.66 g, 10 mmol, 1 eq.) and 3-aminopiperidine-2,6-dione hydrochloride salt (1.81 g, 11 mmol, 1.1 eq.) were dissolved in AcOH (25 mL) followed by potassium acetate (3.04 g, 31 mmol, 3.1 eq.). The mixture was fitted with an air condenser and heated to 90° C. After 16 hours, the mixture was diluted with 100 mL water and cooled over ice. The slurry was then centrifuged (4000 rpm, 20 minutes, 4° C.) and decanted. The remaining solid was then resuspended in water, centrifuged and decanted again. The solid was then dissolved in MeOH and filtered through a silica plug (that had been pre-wetted with MeOH), washed with 50% MeOH/DCM and concentrated under reduced pressure to yield the desired product as a grey solid (2.12 g, 7.68 mmol, 77%).

$^1$H NMR (500 MHz, DMSO-$d_6$) δ 11.13 (s, 1H), 7.98-7.91 (m, 1H), 7.79 (d, J=7.3 Hz, 1H), 7.74 (t, J=8.8 Hz, 1H), 5.16 (dd, J=12.9, 5.4 Hz, 1H), 2.89 (ddd, J=17.2, 14.0, 5.5 Hz, 1H), 2.61 (ddd, J=17.1, 4.4, 2.4 Hz, 1H), 2.57-2.50 (m, 1H), 2.06 (dtd, J=13.0, 5.4, 2.3 Hz, 1H).

LCMS 277.21 (M+H)$^+$.

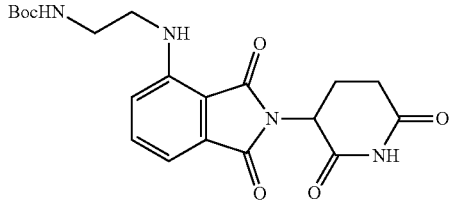 [SMILES: CC(C)(C)OC(=O)NCCNc1cccc2c1C(=O)N(C1CCC(=O)NC1=O)C2=O]

tert-Butyl (2-((2-(2,6-dioxopiperidin-3-yl)-1,3-dioxoisoindolin-4-yl)amino)ethyl) carbamate A stirred solution of 2-(2,6-dioxopiperidin-3-yl)-4-fluoroisoindoline-1,3-dione (174 mg, 0.630 mmol, 1 eq.) in DMF (6.3 mL, 0.1 M) was added DIPEA (220 µL, 1.26 mmol, 2 eq.) and 1-Boc-ethylendiamine (110 µL, 0.693 mmol, 1.1 eq.). The reaction mixture was heated to 90° C. overnight, whereupon it was cooled to room temperature and taken up in EtOAc (30 mL) and water (30 mL). The organic layer was washed with brine (3×20 mL), dried over Na$_2$SO$_4$ and concentrated in vacuo. The residue was purified by flash column chromatography on silica gel (0-10% MeOH in DCM) to give the title compound as a yellow solid (205 mg, 79%).

$^1$H NMR (500 MHz, CDCl$_3$) δ 8.08 (bs, 1H), 7.50 (dd, J=8.5, 7.1 Hz, 1H), 7.12 (d, J=7.1 Hz, 1H), 6.98 (d, J=8.5 Hz, 1H), 6.39 (t, J=6.1 Hz, 1H), 4.96-4.87 (m, 1H), 4.83 (bs, 1H), 3.50-3.41 (m, 2H), 3.41-3.35 (m, 2H), 2.92-2.66 (m, 3H), 2.16-2.09 (m, 1H), 1.45 (s, 9H).

LCMS 417.58 (M+H)$^+$.

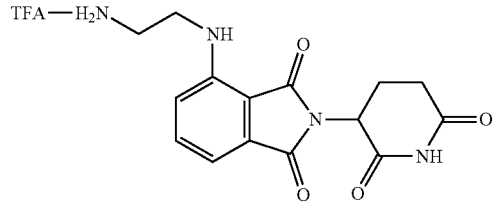

4-((2-Aminoethyl)amino)-2-(2,6-dioxopiperidin-3-yl)isoindoline-1,3-dione trifluoroacetate salt To a stirred solution of tert-butyl (2-((2-(2,6-dioxopiperidin-3-yl)-1,3-dioxoisoindolin-4-yl)amino)ethyl)carbamate (205 mg, 0.492 mmol, 1 eq.) in dichloromethane (2.25 mL) was added trifluoroacetic acid (0.250 mL). The reaction mixture was stirred at room temperature for 4 h, whereupon the volatiles were removed in vacuo. The title compound was obtained as a yellow solid (226 mg, >95%), that was used without further purification.

$^1$H NMR (500 MHz, MeOD) δ 7.64 (d, J=1.4 Hz, 1H), 7.27-7.05 (m, 2H), 5.10 (dd, J=12.5, 5.5 Hz, 1H), 3.70 (t,

J=6.0 Hz, 2H), 3.50-3.42 (m, 2H), 3.22 (t, J=6.0 Hz, 1H), 2.93-2.85 (m, 1H), 2.80-2.69 (m, 2H), 2.17-2.10 (m, 1H).

LCMS 317.53 (M+H)⁺.

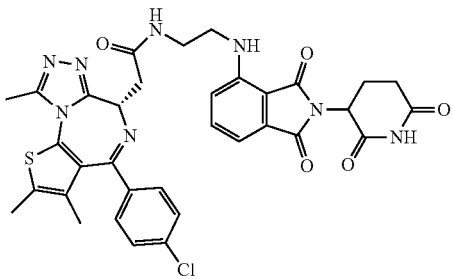 [SMILES: Cc1sc2c(c1C)C(c1ccc(Cl)cc1)=N[C@@H](CC(=O)NCCNc1cccc3c1C(=O)N(C1CCC(=O)NC1=O)C3=O)c1nnc(C)n1-2]

dBET57

JQ-acid (8.0 mg, 0.0200 mmol, 1 eq.) and 2-((2-(2,6-dioxopiperidin-3-yl)-1,3-dioxoisoindolin-4-yl)amino)ethan-1-aminium 2,2,2-trifluoroacetate (8.6 mg, 0.0200 mmol, 1 eq.) were dissolved in DMF (0.200 mL, 0.1 M) at room temperature. DIPEA (17.4 µL, 0.100 mmol, 5 eq.) and HATU (7.59 mg, 0.0200 mmol, 1 eq.) were then added and the mixture was stirred at room temperature overnight. The reaction mixture was taken up in EtOAc (15 mL), and washed with saturated (satd.) aqueous NaHCO₃ (aq.) (15 mL), water (15 mL) and brine (3×15 mL). The organic layer was dried over Na₂SO₄ and concentrated in vacuo. The residue was purified by flash column chromatography on silica gel (0-10% MeOH in DCM, Rf=0.3 (10% MeOH in DCM)) to give the title compound as a bright yellow solid (11.2 mg, 80%).

¹H NMR (400 MHz, CDCl₃) δ 8.49 (bs, 0.6H), 8.39 (bs, 0.4H), 7.51-7.43 (m, 1H), 7.38 (d, J=7.8 Hz, 2H), 7.29 (dd, J=8.8, 1.7 Hz, 2H), 7.07 (dd, J=7.1, 4.9 Hz, 1H), 6.97 (dd, J=8.6, 4.9 Hz, 1H), 6.48 (t, J=5.9 Hz, 1H), 6.40 (t, J=5.8 Hz, 0.6H), 4.91-4.82 (m, 0.4H), 4.65-4.60 (m, 1H), 3.62-3.38 (m, 6H), 2.87-2.64 (m, 3H), 2.63 (s, 3H), 2.40 (s, 6H), 2.12-2.04 (m, 1H), 1.67 (s, 3H), rotamers;

LCMS 700.34 (M+H)⁺.

Example 22: Synthesis of dBET70

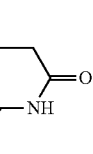

tert-Butyl (8-((2-(2,6-dioxopiperidin-3-yl)-1,3-dioxoisoindolin-4-yl)amino)octyl) carbamate 2-(2,6-Dioxopiperidin-3-yl)-4-fluoroisoindoline-1,3-dione (552.4 mg, 2.0 mmol, 1 eq.) and tert-butyl (8-aminooctyl)carbamate (537.6 mg, 2.2 mmol, 1.1 eq.) were dissolved in N-methylpyrrolidone (NMP) (10 mL). DIPEA (697 microliters, 4.0 mmol, 2 eq.) was added and the mixture was heated to 90° C. After 21 hours the mixture was cooled to room temperature and diluted with EtOAc. The organic layer was washed with 10% citric acid (aq), brine, saturated sodium bicarbonate (aq.), water, and three times with brine. The organic layer was then dried over sodium sulfate, filtered and concentrated under reduced pressure. The material was purified by column chromatography (ISCO, 12 g column, 0-5% MeOH/DCM, 25 minute gradient) to give the desired product as a yellow solid (0.62 g, 1.24 mmol, 62%).

¹H NMR (500 MHz, CDCl₃) δ 8.51 (s, 1H), 7.49-7.44 (m, 1H), 7.06 (d, J=7.1 Hz, 1H), 6.86 (d, J=8.6 Hz, 1H), 6.22 (t, J=5.4 Hz, 1H), 4.91 (dd, J=12.2, 5.3 Hz, 1H), 4.56 (s, 1H), 3.24 (q, J=6.7 Hz, 2H), 3.07 (t, J=12.7 Hz, 2H), 2.89-2.67 (m, 3H), 2.11 (dq, J=10.3, 3.6, 2.7 Hz, 1H), 1.64 (p, J=7.0 Hz, 2H), 1.36 (d, J=61.0 Hz, 19H).

¹³C NMR (126 MHz, CDCl₃) δ 171.47, 169.60, 168.68, 167.73, 156.06, 147.06, 136.15, 132.57, 116.71, 111.39, 109.91, 79.11, 48.95, 42.68, 40.66, 31.49, 30.09, 29.25, 29.20, 28.51, 26.89, 26.75, 22.89.

LCMS 501.39 (M+H)⁺.

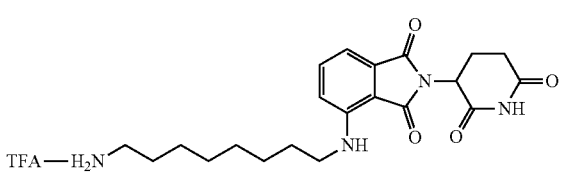

4-((8-Aminooctyl)amino)-2-(2,6-dioxopiperidin-3-yl)isoindoline-1,3-dione trifluoroacetate salt tert-Butyl (8-((2-(2,6-dioxopiperidin-3-yl)-1,3-dioxoisoindolin-4-yl)amino)octyl) carbamate (0.55 g, 1.099 mmol, 1 eq.) was dissolved in TFA (11 mL) and heated to 50° C. After 40 minutes, the mixture was concentrated under reduced pressure, triturated with Et₂O, and dried under high vacuum to yield a yellow residue (523 mg, 1.016 mmol, 93%) that was used without further purification.

¹H NMR (500 MHz, MeOD) δ 7.59-7.51 (m, 1H), 7.04 (dd, J=7.9, 1.7 Hz, 2H), 5.06 (dd, J=12.4, 5.5 Hz, 1H), 3.34 (d, J=7.0 Hz, 2H), 2.95-2.81 (m, 3H), 2.79-2.66 (m, 2H), 2.15-2.08 (m, 1H), 1.67 (tt, J=12.2, 7.2 Hz, 4H), 1.43 (d, J=22.2 Hz, 8H).

LCMS 401.39 (M+H)⁺.

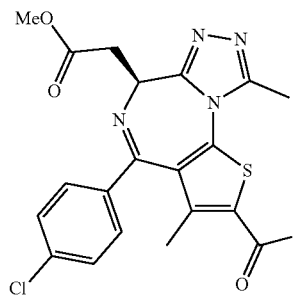

dBET70

(S)-4-(4-Chlorophenyl)-6-(2-methoxy-2-oxoethyl)-3,9-dimethyl-6H-thieno[3,2-f][1,2,4]triazolo[4,3-a][1,4]diazepine-2-carboxylic acid (201 mg, 0.452 mmol, 1 eq.) and 4-((8-aminooctyl)amino)-2-(2,6-dioxopiperidin-3-yl)isoindoline-1,3-dione trifluoroacetate salt (232.5 mg, 0.452 mmol, 1 eq.) were dissolved in DMF (4.5 mL). DIPEA (236 µL, 1.355 mmol, 3 eq.) and HATU (171.9 mg, 0.452 mmol, 1 eq.) were added and the mixture was stirred for 18 hours at room temperature. The mixture was then diluted with EtOAc, and washed three times with 1M HCl (aq), then once with brine, saturated sodium bicarbonate, water and brine. The organic layer was then dried over sodium sulfate, filtered and concentrated under reduced pressure. Purification by column chromatography (ISCO, 24 g silica column, 0-6% MeOH/DCM, 35 minute gradient) to give the desired product as a yellow solid (224.92 mg, 0.2719 mmol, 60%).

$^1$H NMR (500 MHz, MeOD) δ 7.54-7.50 (m, 1H), 7.45 (d, J=8.5 Hz, 2H), 7.42-7.38 (m, 2H), 7.00 (dd, J=7.8, 2.9 Hz, 2H), 5.00 (ddd, J=12.8, 5.4, 3.1 Hz, 1H), 4.66 (t, J=7.1 Hz, 1H), 3.75 (s, 3H), 3.53 (d, J=7.3 Hz, 2H), 3.37 (dq, J=15.7, 8.3, 7.7 Hz, 2H), 3.29 (d, J=6.9 Hz, 2H), 2.85 (ddd, J=18.3, 13.9, 5.1 Hz, 1H), 2.77-2.64 (m, 5H), 2.11-2.05 (m, 1H), 1.97 (s, 3H), 1.64 (dq, J=20.8, 6.8 Hz, 4H), 1.41 (d, J=21.1 Hz, 8H).

$^{13}$C NMR (126 MHz, MeOD) δ 174.60, 173.08, 171.59, 170.79, 169.25, 165.54, 163.65, 156.83, 152.44, 148.25, 138.20, 137.94, 137.86, 137.81, 137.22, 133.86, 132.42, 131.84, 131.26, 129.89, 117.96, 111.73, 110.94, 54.89, 52.47, 50.16, 43.37, 41.25, 37.13, 32.21, 30.29, 30.22, 30.17, 27.87, 27.78, 23.79, 16.57, 11.68.

LCMS 827.60 (M+H)$^+$.

Example 23: Synthesis of dBET72

2-(2,6-Dioxopiperidin-3-yl)-5-fluoroisoindoline-1,3-dione

4-Fluorophthalic anhydride (3.32 g, 20 mmol, 1 eq.) and 3-aminopiperidine-2,6-dione hydrochloride salt (3.620 g, 22 mmol, 1.1 eq.) were dissolved in AcOH (50 mL) followed by potassium acetate (6.08 g, 62 mmol, 3.1 eq.). The mixture was fitted with an air condenser and heated to 90° C. After 16 hours, the mixture was diluted with 200 mL water and cooled over ice. The slurry was then centrifuged (4000 rpm, 20 minutes, 4° C.) and decanted. The remaining solid was then resuspended in water, centrifuged and decanted again. The solid was then dissolved in MeOH and filtered through a silica plug (that had been pre-wetted with MeOH), washed with 50% MeOH/DCM and concentrated under reduced pressure to yield the desired product as a grey solid (2.1883 g, 7.92 mmol, 40%).

$^1$H NMR (500 MHz, DMSO-d$_6$) δ 11.13 (s, 1H), 8.01 (dd, J=8.3, 4.5 Hz, 1H), 7.85 (dd, J=7.4, 2.2 Hz, 1H), 7.72 (ddd, J=9.4, 8.4, 2.3 Hz, 1H), 5.16 (dd, J=12.9, 5.4 Hz, 1H), 2.89 (ddd, J=17.2, 13.9, 5.5 Hz, 1H), 2.65-2.51 (m, 2H), 2.07 (dtd, J=12.9, 5.3, 2.2 Hz, 1H).

LCMS 277.22 (M+H)$^+$.

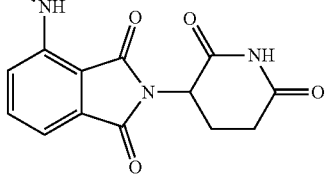

tert-Butyl (8-((2-(2,6-dioxopiperidin-3-yl)-1,3-dioxoisoindolin-5-yl)amino)octyl)carbamate 2-(2,6-Dioxopiperidin-3-yl)-5-fluoroisoindoline-1,3-dione (294 mg, 1.06 mmol, 1 eq.) and tert-butyl (8-aminooctyl)carbamate (286 mg, 1.17 mmol, 1.1 eq.) were dissolved in NMP (5.3 mL). DIPEA (369 microliters, 2.12 mmol, 2 eq.) was added and the mixture was heated to 90° C. After 19 hours the mixture was cooled to room temperature and diluted with EtOAc. The organic layer was washed with water and three times with brine. The organic layer was then dried over sodium sulfate, filtered and concentrated under reduced pressure. The material was purified by column chromatography (ISCO, 12 g column, 0-10% MeOH/DCM, 30 minute gradient) to give the desired product as a brown solid (0.3345 g, 0.6682 mmol, 63%).

¹H NMR (500 MHz, CDCl₃) δ 8.12 (s, 1H), 7.62 (d, J=8.3 Hz, 1H), 7.02 (s, 1H), 6.81 (d, J=7.2 Hz, 1H), 4.93 (dd, J=12.3, 5.3 Hz, 1H), 4.51 (s, 1H), 3.21 (t, J=7.2 Hz, 2H), 3.09 (d, J=6.4 Hz, 2H), 2.90 (dd, J=18.3, 15.3 Hz, 1H), 2.82-2.68 (m, 2H), 2.16-2.08 (m, 1H), 1.66 (p, J=7.2 Hz, 2H), 1.37 (d, J=62.3 Hz, 20H).

LCMS 501.41 (M+H)⁺.

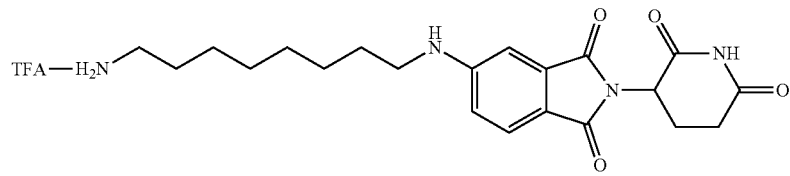

5-((8-Aminooctyl)amino)-2-(2,6-dioxopiperidin-3-yl)isoindoline-1,3-dione trifluoroacetate salt tert-Butyl (8-((2-(2,6-dioxopiperidin-3-yl)-1,3-dioxoisoindolin-5-yl)amino)octyl) carbamate (334.5 mg, 0.668 mmol, 1 eq.) was dissolved in TFA (6.7 mL) and heated to 50° C. After 50 minutes, the mixture was cooled to room temperature, diluted with DCM and concentrated under reduced pressure, triturated with Et₂O, and dried under high vacuum to yield a dark yellow foam (253 mg, 0.492 mmol, 74%) that was used without further purification.

¹H NMR (500 MHz, MeOD) δ 7.56 (d, J=8.4 Hz, 1H), 6.97 (d, J=2.1 Hz, 1H), 6.83 (dd, J=8.4, 2.2 Hz, 1H), 5.04 (dd, J=12.6, 5.5 Hz, 1H), 3.22 (t, J=7.1 Hz, 2H), 2.94-2.88 (m, 2H), 2.85-2.68 (m, 3H), 2.09 (ddd, J=10.4, 5.4, 3.0 Hz, 1H), 1.70-1.61 (m, 4H), 1.43 (d, J=19.0 Hz, 8H).

LCMS 401.36 (M+H)⁺.

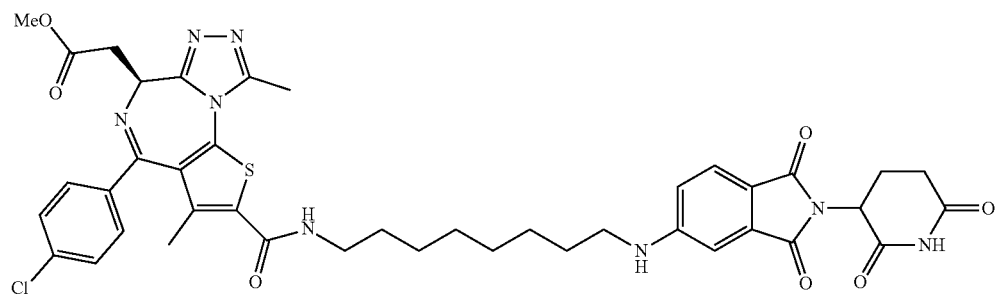 [SMILES: COC(=O)C[C@@H]1N=C(c2ccc(Cl)cc2)c2c(sc(C(=O)NCCCCCCCCNc3ccc4c(c3)C(=O)N(C3CCC(=O)NC3=O)C4=O)c2C)-n2c(C)nnc21]

dBET72

5-((8-aminooctyl)amino)-2-(2,6-dioxopiperidin-3-yl) isoindoline-1,3-dione trifluoroacetate salt (10.3 mg, 0.020 mmol, 1 eq.) in DMF (200 microliters) was added to (S)-4-(4-chlorophenyl)-6-(2-methoxy-2-oxoethyl)-3,9-dimethyl-6H-thieno[3,2-f][1,2,4]triazolo [4,3-a][1,4]diazepine-2-carboxylic acid (8.9 mg, 0.020 mmol, 1 eq.) at room temperature. DIPEA (10.5 microliters, 0.060 mmol, 3 eq.) was added, followed by HATU (7.6 mg, 0.020 mmol, 1 eq.). After 27 hours, the mixture was diluted with EtOAc then washed with saturated sodium bicarbonate, water and brine. The organic layer was dried over sodium sulfate, filtered and concentrated under reduced pressure. The mixture was purified by column chromatography (ISCO, 4 g column, 0-10% MeOH/DCM, 25 minute gradient) to give the desired product as a yellow solid (4.98 mg, 0.00602 mmol, 30%).

¹H NMR (500 MHz, MeOD) δ 7.54 (d, J=8.4 Hz, 1H), 7.49-7.40 (m, 4H), 6.96 (d, J=2.1 Hz, 1H), 6.82 (dd, J=8.4, 2.1 Hz, 1H), 5.02 (dd, J=12.7, 5.5 Hz, 1H), 4.67 (t, J=7.1 Hz, 1H), 3.76 (s, 3H), 3.54 (d, J=7.2 Hz, 2H), 3.41-3.33 (m, 2H), 3.20 (t, J=7.0 Hz, 2H), 2.85 (ddd, J=19.2, 14.0, 5.3 Hz, 1H), 2.77-2.65 (m, 5H), 2.11-2.04 (m, 1H), 1.99 (s, 3H), 1.64 (dt, J=19.3, 7.1 Hz, 4H), 1.43 (d, J=21.8 Hz, 8H).

LCMS 827.46 (M+H)⁺.

Example 24: Synthesis of (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid

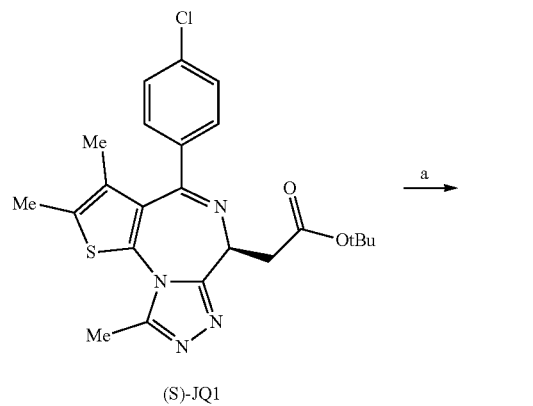

(S)-JQ1

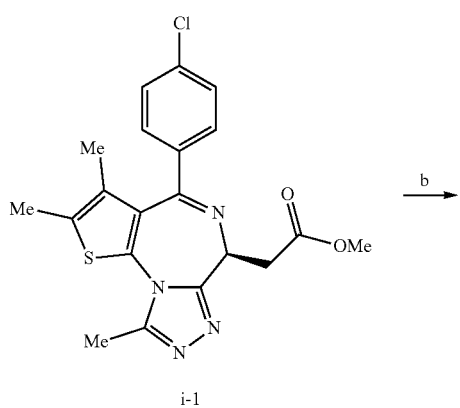

i-1

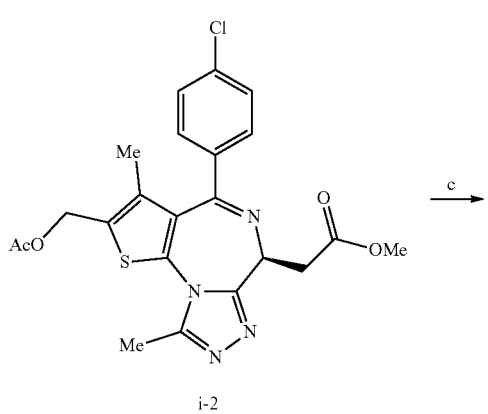

i-2

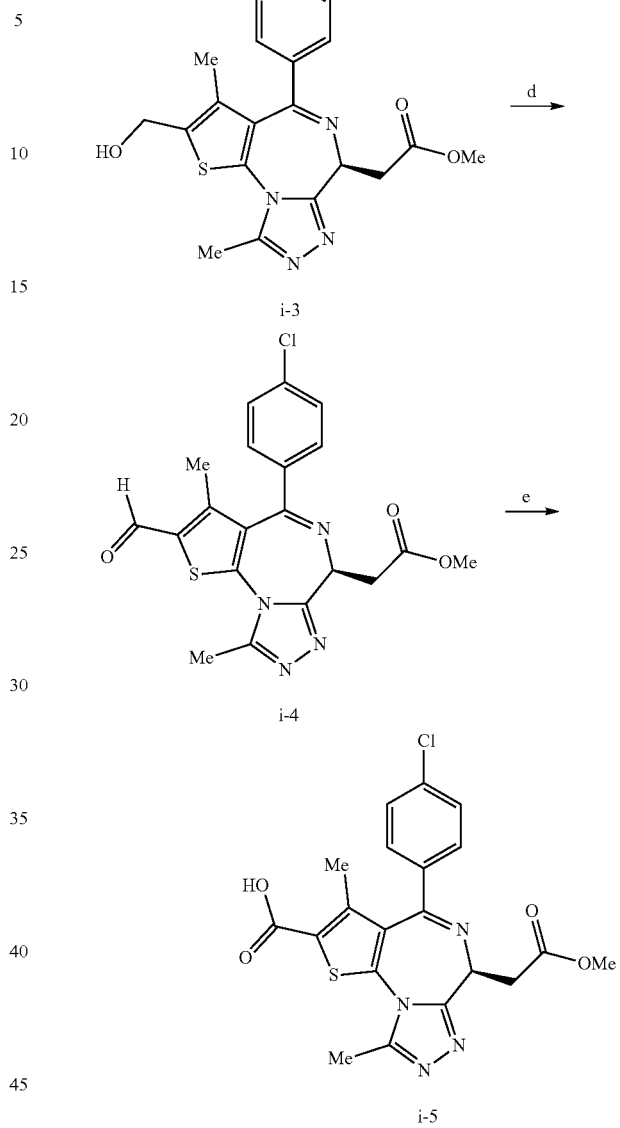

a) MeOH, H₂SO₄; b) Mn(OAc)₃·2H₂O, Ac₂O, H₂SO₄(s), AcOH; c) K₂CO₃, MeOH; d) Dess-Martin, CH₂Cl₂; e) NaClO₂, H₂O₂, NaH₂PO₄, CH₃CN Compound i-1

(S)-JQ1 (4.57 g, 10 mmol) was dissolved in MeOH (0.25 M). conc.H₂SO₄ (50 drops) was added to the solution. The mixture was refluxed overnight. The mixture was concentrated in vacuo, poured into water, extracted with AcOEt, and washed with brine. The organic layer was dried over Na₂SO₄, filtered, and concentrated in vacuo. The residue was purified by flash column chromatography (AcOEt/MeOH) to give title compound 3.93 g (95%).

Compound i-2

To a mixture of acetic acid (52 mL) and acetic anhydride (30 mL) was added dropwise concentrated sulfuric acid (8 mL). Compound i-1 (6.04 g, 14.6 mmol) was added, and manganese acetate (III)*dihydrate (8 g, 29.4 mmol) was further added. The mixture was stirred at room temperature for 3 days. The reaction mixture was poured into ice water, and extracted twice with ethyl acetate (300 mL). The organic layer was washed twice with saturated brine (300 mL). The residue was dried over Na₂SO₄, and the solvent was evaporated to give an oil (5 g), which was used without further purification.

Compound i-3

Compound i-2 (6.0 g, 12.7 mmol) and K₂CO₃ (1.2 eq.) were suspended in MeOH (0.1 M). The mixture was stirred at room temperature for 2 hours. The mixture was neutralized with 1N HCl, then concentrated in vacuo. The residue was poured into water, and extracted with DCM. The organic layer was dried over Na₂SO₄, filtrated, and concentrated in vacuo. The residue was purified with flash column chromatography (AcOEt/MeOH) to give title compound 2 g (32% over 2 steps).

Compound i-4

Compound i-3 (867 mg, 2.01 mmol) was dissolved in DCM (20 mL). Dess-Martin periodinane (1.2 eq.) was added to the solution at 0° C. The mixture was stirred at room temperature for 2 hours. The mixture was diluted with DCM, washed with saturated NaHCO₃ solution, dried over Na₂SO₄, and concentrated in vacuo to give an oil (850 mg). The crude product was used directly without further purification.

Compound i-5

Compound i-4 (850 mg, 1.98 mmoL) was suspended in CH₃CN (8 mL). Sodium phosphate monobasic (0.97 eq.) in H₂O (3 mL) solution was added to the suspension. Hydrogen peroxide (5 eq.) was added to the solution dropwise. Sodium chlorite (1.4 eq.) in H₂O (2 mL) solution was added to the suspension. The mixture was stirred for 3 hours. The mixture was diluted with EtOAc, quenched with Na₂S₂O₃ aq, then, acidified with 1N HCl (pH<4). The mixture was extracted with EtOAc, washed with brine. The organic layer was dried over Na₂SO₄, filtered, and concentrated in vacuo. The residue was purified by prep-HPLC to give compound i-5 (667 mg, 75%).

¹H NMR (400 MHz, Methanol-d₄) δ 7.44 (q, J=8.8 Hz, 4H), 4.68 (t, J=7.2 Hz, 1H), 3.76 (s, 3H), 3.54 (d, J=7.2 Hz, 2H), 2.74 (s, 3H), 2.09 (s, 3H).

Example 25: Synthesis of ZXH-2-42

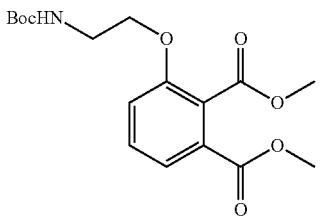 [SMILES: COC(=O)c1cccc(OCCNC(=O)OC(C)(C)C)c1C(=O)OC]

Dimethyl 3-(2-((tert-butoxycarbonyl)amino)ethoxy)phthalate tert-butyl (2-bromoethyl)carbamate (280 mg, 1.25 mmol, 1 eq.) and dimethyl 3-hydroxyphthalate (263 mg, 1.25 mmol, 1 eq.) were dissolved in DMF (6.25 mL, 0.2 M) followed by potassium carbonate (345 mg, 2.5 mmol, 2 eq.). The mixture was stirred at 50° C. After the reaction completed, the mixture was cooled down to room temperature, diluted with EtOAc and washed with water and brine. The organic layer was dried over sodium sulfate, filtered and concentrated under reduced pressure. Purification by column chromatography (ISCO, 12 g silica column, 0-40% EtOAc/hexane) gave the desired product as a white solid (268 mg, 61%).

LCMS 354 (M+H)⁺.

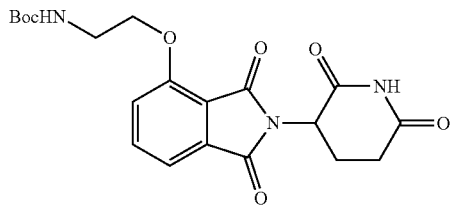 [SMILES: CC(C)(C)OC(=O)NCCOc1cccc2c1C(=O)N(C1CCC(=O)NC1=O)C2=O]

tert-Butyl (2-((2-(2,6-dioxopiperidin-3-yl)-1,3-dioxoisoindolin-4-yl)oxy)ethyl) carbamate Dimethyl 3-(2-((tert-butoxycarbonyl)amino)ethoxy)phthalate (268 mg, 0.76 mmol, 1 eq.) was dissolved in EtOH (3.8 mL, 0.2 M) followed by aqueous 3M NaOH (760 μL, 2.28 mmol, 3 eq.). The mixture was heated to 80° C. for 4 hours. The mixture was then cooled down to room temperature, diluted with DCM (14 mL) and 0.5M HCl (5.5 mL). The organic layer was washed with 7 mL of water. The aqueous layers were combined and extracted three times with 14 mL of chloroform. The combined organic layers were dried over sodium sulfate, filtered and concentrated to give the material that was used in the next step.

LCMS 326 (M+H)⁺.

The resultant material and 3-aminopiperidine-2,6-dione hydrochloride (125 mg, 0.76 mmol, 1 eq.) were dissolved in pyridine (3.8 mL, 0.2 M) and heated to 110° C. overnight. Then the mixture was cooled to room temperature and concentrated under reduced pressure, purified by column chromatography (ISCO, 12 g silica column, 0-6% MeOH/DCM) to give the desired product (152 mg, 48% for two steps).

LCMS 417 (M+H)⁺.

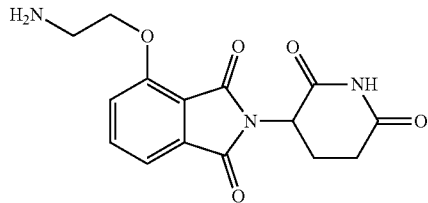 [SMILES: NCCOc1cccc2c1C(=O)N(C1CCC(=O)NC1=O)C2=O]

4-(2-Aminoethoxy)-2-(2,6-dioxopiperidin-3-yl)isoindoline-1,3-dione tert-Butyl (2-((2-(2,6-dioxopiperidin-3-yl)-1,3-dioxoisoindolin-4-yl)oxy)ethyl) carbamate (152 mg, 0.37 mmol) was dissolved in TFA (3.7 mL, 0.1 M) and heated to 50° C. for 3 hours. The mixture was cooled to room temperature, diluted with methanol and concentrated under reduced pressure. The material was purified by column chromatography (ISCO, 4 g silica column, 0-20% 1.75N NH₃.MeOH/DCM) to give the free base product (101 mg, 86%).

LCMS 317 (M+H)⁺.

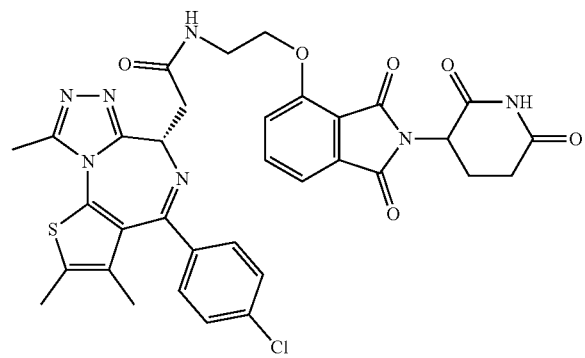 [SMILES: Cc1sc2c(c1C)C(c1ccc(Cl)cc1)=N[C@@H](CC(=O)NCCOc1cccc3c1C(=O)N(C1CCC(=O)NC1=O)C3=O)c1nnc(C)n1-2]

ZXH-2-42

To a solution of (S)-2-(4-(4-chlorophenyl)-2,3,9-trimethyl-6H-thieno[3,2-f] [1,2,4]triazolo[4,3-a][1,4]diazepin-6-yl)acetic acid (24 mg, 0.06 mmol, 1 eq.) and 4-(2-aminoethoxy)-2-(2,6-dioxopiperidin-3-yl)isoindoline-1,3-dione (19 mg, 0.06 mmol, 1 eq.) in DMF (1 ml) were added DIEA (30 μL, 0.18 mmol, 3 eq.) and HATU (27 mg, 0.072 mmol, 1.2 eq.). The mixture was stirred at room temperature overnight and then purified by HPLC to give the product as TFA salt (3.8 mg, 8%).

LCMS 700 (M+H)⁺.

¹H NMR (500 MHz, DMSO-d₆) δ 11.10 (s, 1H), 8.51 (s, 1H), 7.83 (t, J=7.8 Hz, 1H), 7.59 (d, J=8.6 Hz, 1H), 7.51-7.48 (m, 1H), 7.45-7.39 (m, 4H), 5.09 (s, 1H), 4.57-4.49 (m, 1H), 4.30 (t, J=5.8 Hz, 2H), 3.35 (s, 3H), 3.18-3.13 (m, 2H), 2.86 (s, 1H), 2.60 (s, 3H), 2.42 (s, 2H), 1.62 (s, 3H), 1.27 (s, 2H).

Example 26: Synthesis of ZXH-2-43

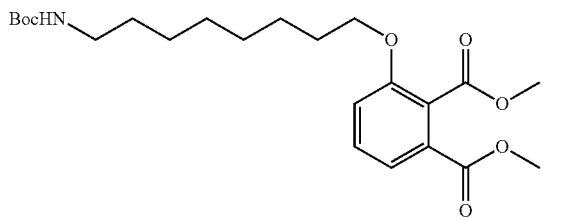 [SMILES: COC(=O)c1cccc(OCCCCCCCCNC(=O)OC(C)(C)C)c1C(=O)OC]

Dimethyl 3-((8-((tert-butoxycarbonyl)amino)octyl)oxy)phthalate tert-Butyl (8-bromooctyl)carbamate (308 mg, 1 mmol, 1 eq.) and dimethyl 3-hydroxyphthalate (210 mg, 1 mmol, 1 eq.) were dissolved in DMF (5 mL, 0.2 M) followed by potassium carbonate (276 mg, 2 mmol, 2 eq.). The mixture was stirred at 50° C. After the reaction reached completion, the mixture was allowed to cool down to room temperature, diluted with EtOAc and washed with water and brine. The organic layer was dried over sodium sulfate, filtered and concentrated under reduced pressure. Purification by column chromatography (ISCO, 12 g silica column, 0-25% EtOAc/hexane) gave the desired product as a white solid (315 mg, 72%).

LCMS 438 (M+H)⁺.

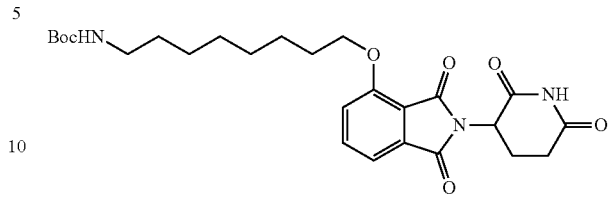

tert-Butyl (8-(2-(2,6-dioxopiperidin-3-yl)-1,3-dioxoisoindolin-4-yl)oxy)octyl) carbamate Dimethyl 3-((8-((tert-butoxycarbonyl)amino)octyl)oxy) phthalate (315 mg, 0.72 mmol, 1 eq.) was dissolved in EtOH (3.6 mL, 0.2 M) followed by aqueous 3M NaOH (720 μL, 2.16 mmol, 3 eq.), then the mixture was heated to 80° C. for 4 hours. The mixture was then cooled down to room temperature, diluted with DCM (13 mL) and 0.5M HCl (0.5 mL). The layers were separated and the organic layer was washed with water (6.5 mL). The aqueous layers were combined and extracted three times with chloroform (13 ml). The combined organic layers were dried over sodium sulfate, filtered and condensed to give the material that was directly used in next step.

LCMS 410 (M+H)⁺.

The resultant material and 3-aminopiperidine-2,6-dione hydrochloride (118 mg, 0.72 mmol, 1 eq.) were dissolved in pyridine (3.6 mL, 0.2 M) and heated to 110° C. overnight. Then the mixture was cooled to room temperature and concentrated under reduced pressure, purified by column chromatography (ISCO, 12 g silica column, 0-5% MeOH/DCM) to give the desired product (217 mg, 54% for two steps).

LCMS 502 (M+H)⁺.

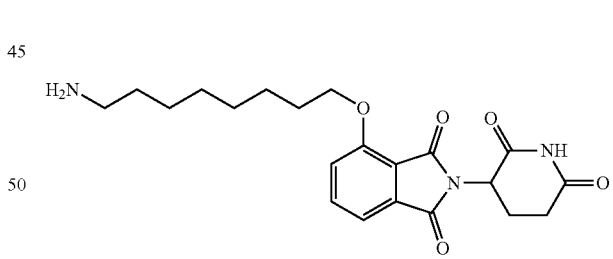

4-((8-Aminooctyl)oxy)-2-(2,6-dioxopiperidin-3-yl)isoindoline-1,3-dione tert-butyl (8-((2-(2,6-dioxopiperidin-3-yl)-1,3-dioxoisoindolin-4-yl)oxy)octyl) carbamate (217 mg, 0.43 mmol) was dissolved in TFA (4.3 mL, 0.1 M) and heated to 50° C. for 3 hours. The mixture was cooled to room temperature, diluted with MeOH and concentrated under reduced pressure. The material was purified by column chromatography (ISCO, 4 g silica column, 0-20% 1.75N NH₃.MeOH/DCM) to give the free base product (152 mg, 88%).

LCMS 402 (M+H)⁺.

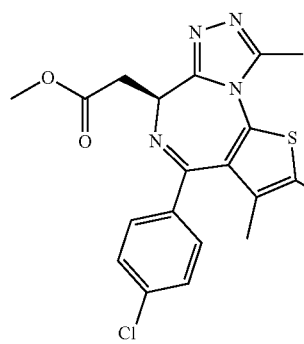

ZXH-2-43

To a solution of (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (20 mg, 0.045 mmol, 1 eq.) and 4-((8-aminooctyl)oxy)-2-(2,6-dioxopiperidin-3-yl)isoindoline-1,3-dione (19 mg, 0.045 mmol, 1 eq.) in DMF (1 mL) were added DIEA (23 µL, 0.14 mmol, 3 eq.) and HATU (21 mg, 0.05 mmol, 1.2 eq.). The mixture was stirred at room temperature overnight and then purified by HPLC, then by column chromatography (ISCO, 4 g silica column, 0-8% 1.75 N NH$_3$ in Methanol/DCM) to give the free base product (22.1 mg, 59%).

LCMS 828 (M+H)$^+$.

$^1$H NMR (500 MHz, DMSO-d$_6$) δ 11.10 (s, 1H), 8.30 (t, J=5.7 Hz, 1H), 7.80 (dd, J=8.5, 7.2 Hz, 1H), 7.51 (d, J=2.6 Hz, 1H), 7.50 (d, J=2.7 Hz, 2H), 7.48-7.43 (m, 3H), 5.08 (dd, J=12.8, 5.5 Hz, 1H), 4.58 (dd, J=7.7, 6.6 Hz, 1H), 4.20 (t, J=6.4 Hz, 2H), 3.68 (s, 3H), 3.47 (qd, J=16.6, 7.2 Hz, 2H), 3.34 (s, 1H), 3.29-3.20 (m, 2H), 2.89 (ddd, J=16.9, 13.9, 5.4 Hz, 1H), 2.65 (s, 3H), 2.06-1.99 (m, 1H), 1.91 (s, 3H), 1.76 (p, J=6.6 Hz, 2H), 1.50 (dt, J=33.3, 7.3 Hz, 4H), 1.33 (s, 6H).

Example 27: Synthesis of ZXH-2-45

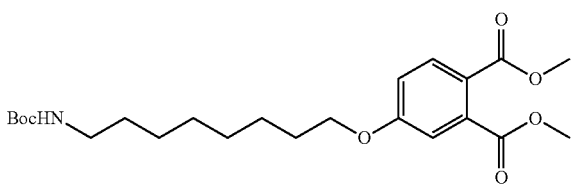 [SMILES: COC(=O)c1ccc(OCCCCCCCCNC(=O)OC(C)(C)C)cc1C(=O)OC]

Dimethyl 4-((8-(((tert-butoxycarbonyl)amino)octyl)oxy)phthalate tert-Butyl (8-bromoethyl)carbamate (182 mg, 0.87 mmol, 1 eq.) and dimethyl 4-hydroxyphthalate (267 mg, 0.87 mmol, 1 eq.) were dissolved in DMF (4.4 mL) followed by potassium carbonate (239 mg, 1.73 mmol, 2 eq.). The mixture was stirred at 50° C. After the reaction reached completion, the mixture was allowed to cool to room temperature, diluted with EtOAc and washed with water and brine. The organic layer was dried over sodium sulfate, filtered and concentrated under reduced pressure. Purification by column chromatography (ISCO, 12 g silica column, 0-30% EtOAc/hexane) gave the desired product as a white solid (296 mg, 78%).

LCMS 438 (M+H)$^+$.

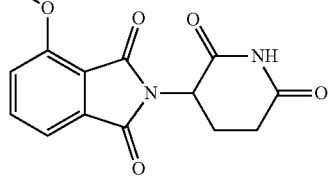

tert-Butyl (8-((2-(2,6-dioxopiperidin-3-yl)-1,3-dioxoisoindolin-5-yl)oxy)octyl) carbamate Dimethyl 4-((8-((tert-butoxycarbonyl)amino)octyl)oxy)phthalate (296 mg, 0.68 mmol, 1 eq.) was dissolved in EtOH (3.4 mL, 0.2 M) followed by aqueous 3M NaOH (680 µL, 2.04 mmol, 3 eq.). The mixture was heated to 80° C. for 4 hours. The mixture was allowed to cool to room temperature, diluted with DCM (12 mL) and 0.5 M HCl (4.7 mL). The layers were separated and the organic layer was washed with 6.2 mL water. The aqueous layers were combined and extracted three times with chloroform (12 mL). The combined organic layers were dried over sodium sulfate, filtered and condensed to give the material that was used in next step.

LCMS 410 (M+H)$^+$.

The resultant material and 3-aminopiperidine-2,6-dione hydrochloride (112 mg, 0.68 mmol, 1 eq.) were dissolved in pyridine (3.4 mL, 0.2 M) and heated to 110° C. overnight. Then the mixture was cooled to room temperature and concentrated under reduced pressure, purified by column chromatography (ISCO, 12 g silica column, 0-7% Methanol/DCM) to give the desired product (170 mg, 50% for two steps).

LCMS 502 (M+H)$^+$.

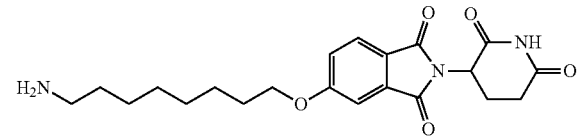 [SMILES: NCCCCCCCCOc1ccc2c(c1)C(=O)N(C1CCC(=O)NC1=O)C2=O]

5-((8-Aminooctyl)oxy)-2-(2,6-dioxopiperidin-3-yl)isoindoline-1,3-dione tert-Butyl (8-((2-(2,6-dioxopiperidin-3-yl)-1,3-dioxoisoindolin-5-yl)oxy)octyl) carbamate (170 mg, 0.34 mmol, 1 eq.) was dissolved in TFA (3.4 mL, 0.1 M) and then heated to 50° C. for 3 hours. The mixture was allowed to cool to room temperature, diluted with MeOH and concentrated under reduced pressure. The material was purified by column chromatography (ISCO, 4 g silica column, 0-20% 1.75N NH$_3$.MeOH/DCM) to give the free base product (111 mg, 82%).

LCMS 402 (M+H)$^+$.

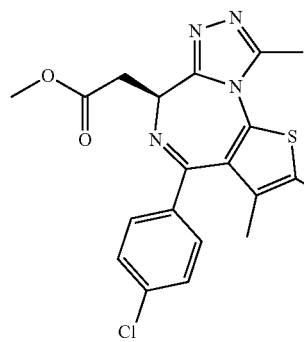

ZXH-2-45

To a solution of (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (24 mg, 0.054 mmol, 1 eq.) and 5-((8-aminooctyl)oxy)-2-(2,6-dioxopiperidin-3-yl)isoindoline-1,3-dione (22 mg, 0.054 mmol, 1 eq.) in DMF (1 mL) were added DIEA (27 µL, 0.16 mmol, 3 eq.) and HATU (25 mg, 0.065 mmol, 1.2 eq.). The mixture was stirred at room temperature overnight and then purified by HPLC to give the product as TFA salt (18.3 mg, 36%).

LCMS 828 (M+H)$^+$.

$^1$H NMR (500 MHz, DMSO-d$_6$) δ 11.11 (s, 1H), 8.33 (t, J=5.7 Hz, 1H), 7.82 (d, J=8.3 Hz, 1H), 7.50 (d, J=8.8 Hz, 2H), 7.46 (d, J=8.6 Hz, 2H), 7.41 (d, J=2.2 Hz, 1H), 7.34 (dd, J=8.4, 2.3 Hz, 1H), 5.12 (dd, J=12.8, 5.4 Hz, 1H), 4.58 (dd, J=7.7, 6.6 Hz, 1H), 4.17 (t, J=6.5 Hz, 2H), 3.68 (s, 3H), 3.47 (qd, J=16.6, 7.3 Hz, 2H), 3.25 (dq, J=17.2, 6.7 Hz, 2H), 3.17 (s, 1H), 2.90 (ddd, J=16.8, 13.8, 5.4 Hz, 1H), 2.65 (s, 3H), 2.09-2.01 (m, 1H), 1.91 (s, 3H), 1.75 (p, J=6.8 Hz, 2H), 1.53 (t, J=6.9 Hz, 2H), 1.42 (q, J=7.0 Hz, 2H), 1.33 (d, J=3.8 Hz, 6H).

Example 28: Synthesis of ZXH-2-145

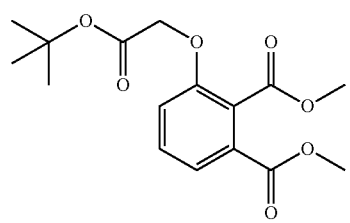 [SMILES: COC(=O)c1cccc(OCC(=O)OC(C)(C)C)c1C(=O)OC]

Dimethyl 3-(2-(tert-butoxy)-2-oxoethoxy)phthalate

To a solution of 3-Hydroxyphthalic anhydride (1260 mg, 6 mmol, 1 eq.) and tert-butyl 2-bromoacetate (1172 mg, 6 mmol, 1 eq.) in DMF (10 mL) was added K$_2$CO$_3$ (1656 mg, 12 mmol, 2 eq.). The mixture was stirred at room temperature until the reaction completed. And then the mixture was diluted with EtOAc and washed with water and brine. The organic layer was dried over sodium sulfate, filtered and concentrated under reduced pressure. Purification by column chromatography (ISCO, 24 g silica column, 0-25% EtOAc/hexane) gave the desired product (1408 mg, 72%).

LCMS 325 (M+H)$^+$.

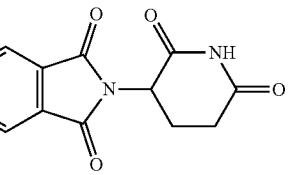

2-(2,3-Bis (methoxycarbonyl)phenoxy)acetic acid

To a solution of dimethyl 3-(2-(tert-butoxy)-2-oxoethoxy) phthalate (972 mg, 3 mmol) in DCM (6 mL) was added TFA (2 mL). The mixture was then stirred at room temperature until the reaction completed. And then the mixture was concentrated under reduced pressure, purification by column chromatography (ISCO, 24 g silica column, 0-6% MeOH/DCM) gave the desired product as TFA salt (734 mg, 64%).

LCMS 269 (M+H)$^+$.

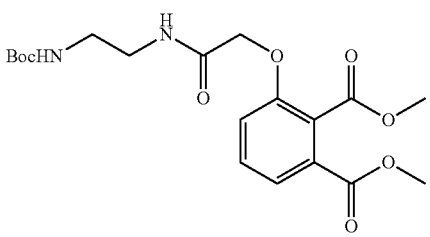 [SMILES: COC(=O)c1cccc(OCC(=O)NCCNC(=O)OC(C)(C)C)c1C(=O)OC]

Dimethyl 3-(2-((2-((tert-butoxycarbonyl)amino)ethyl)amino)-2-oxoethoxy) phthalate To a solution of 2-(2,3-bis (methoxycarbonyl)phenoxy) acetic acid with TFA (382 mg, 1 mmol, 1 eq.) and tert-butyl (2-aminoethyl)carbamate (160 mg, 1 mmol, 1 eq.) in DMF (5 mL) were added HATU (456 mg, 1.2 mmol, 1.2 eq.) and DIPEA (495 μL, 3 mmol, 3 eq.), and then the mixture was stirred at room temperature until the reaction completed. The mixture was then diluted with EtOAc and washed with water and brine. The organic layer was dried over sodium sulfate, filtered and concentrated under reduced pressure. The crude product was used in next step without further purification.

LCMS 411 (M+H)+.

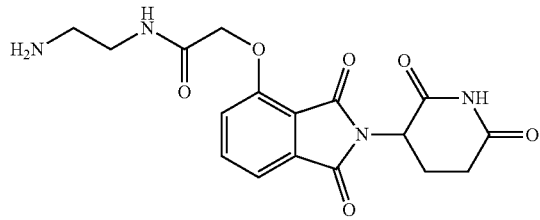 [SMILES: NCCNC(=O)COc1cccc2c1C(=O)N(C1CCC(=O)NC1=O)C2=O]

N-(2-Aminoethyl)-2-((2-(2,6-dioxopiperidin-3-yl)-1,3-dioxoisoindolin-4-yl)oxy)acetamide To a solution of dimethyl 3-(2-((2-((tert-butoxycarbonyl)amino)ethyl)amino)-2-oxoethoxy)phthalate (410 mg, 1 mmol, 1 eq.) in EtOH (5 mL) was added aqueous 3M NaOH (1 mL, 3 mmol, 3 eq.), then the mixture was heated to 80° C. for 4 hours. The mixture was allowed to cool to room temperature, diluted with DCM (18 mL) and 0.5M HCl (7.2 mL). The layers were separated and the organic layer was washed with water (9 mL). The aqueous layers were combined and extracted three times with chloroform (18 mL). The combined organic layers were dried over sodium sulfate, filtered and concentrated to give N-(2-aminoethyl)-2-((2-(2,6-dioxopiperidin-3-yl)-1,3-dioxoisoindolin-4-yl)oxy)acetamide without further purification.

LCMS 383 (M+H)+.

N-(2-aminoethyl)-2-((2-(2,6-dioxopiperidin-3-yl)-1,3-dioxoisoindolin-4-yl)oxy)acetamide and 3-aminopiperidine-2,6-dione hydrochloride (164 mg, 1 mmol, 1 eq.) were dissolved in pyridine (5 mL, 0.2 M) and heated to 110° C. overnight. The mixture was cooled to room temperature, concentrated under reduced pressure, and purified by column chromatography (ISCO, 12 g silica column, 0-4% MeOH/DCM) to give the desired product.

LCMS 473 (M+H)+.

To a solution of the resultant material (1 mmol, 1 eq.) in DCM (6 mL) was added TFA (2 mL). The mixture was stirred at room temperature until the reaction completed. The mixture was concentrated under reduced pressure and purified by column chromatography (ISCO, 12 g silica column, 0-30% 1.75N NH₃.MeOH/DCM) to give the free base product (103 mg, 28% for 4 steps).

LCMS 373 (M+H)+.

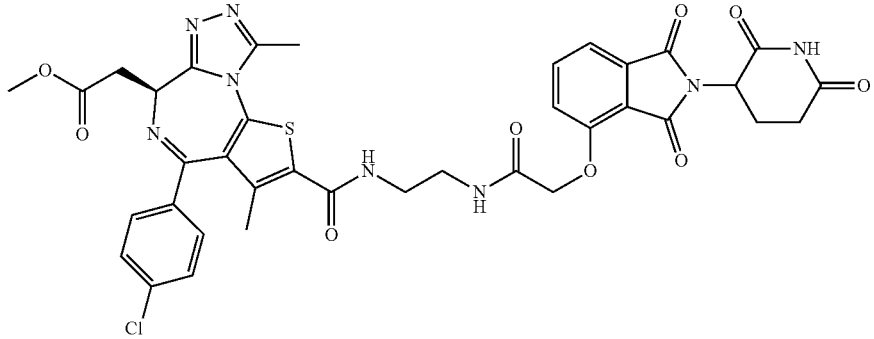 [SMILES: COC(=O)C[C@@H]1N=C(c2ccc(Cl)cc2)c2c(sc(C(=O)NCCNC(=O)COc3cccc4c3C(=O)N(C3CCC(=O)NC3=O)C4=O)c2C)-n2c(C)nnc21]

ZXH-2-145

To a solution of (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (20 mg, 0.045 mmol, 1 eq.) and N-(2-aminoethyl)-2-((2-(2,6-dioxopiperidin-3-yl)-1,3-dioxoisoindolin-4-yl)oxy)acetamide (17 mg, 0.045 mmol, 1 eq.) in DMF (1 mL) were added HATU (21 mg, 0.054 mmol, 1.2 eq.) and DIPEA (22 μL, 0.135 mmol, 3 eq.). The mixture was stirred at room temperature overnight and then purified by HPLC to give the product as TFA salt (5 mg, 12%).

LCMS 801 (M+H)+.

¹H NMR (500 MHz, DMSO-d₆) δ 11.11 (s, 1H), 8.32 (d, J=5.5 Hz, 1H), 8.18-8.13 (m, 1H), 7.74 (t, J=7.9 Hz, 1H), 7.52-7.44 (m, 5H), 7.37 (dd, J=8.5, 2.9 Hz, 1H), 5.14-5.08 (m, 1H), 4.62-4.55 (m, 1H), 3.97 (s, 2H), 3.68 (s, 3H), 3.54-3.36 (m, 6H), 2.94-2.86 (m, 1H), 2.64 (s, 3H), 2.60 (d, J=18.0 Hz, 1H), 2.06-1.98 (m, 1H), 1.88 (s, 3H).

Example 29: Synthesis of ZXH-2-147

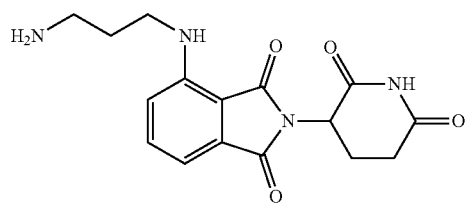 [SMILES: NCCCNc1cccc2c1C(=O)N(C1CCC(=O)NC1=O)C2=O]

4-((3-Aminopropyl)amino)-2-(2,6-dioxopiperidin-3-yl)isoindoline-1,3-dione

To a stirred solution of 2-(2,6-dioxopiperidin-3-yl)-4-fluoroisoindoline-1,3-dione (277 mg, 1 mmol, 1 eq.) in DMF (5 mL) were added DIPEA (330 μL, 2 mmol, 2 eq.) and tert-butyl (3-aminopropyl)carbamate (191 mg, 1.1 mmol, 1.1 eq.). The reaction mixture was heated to 90° C. overnight. Cooled to room temperature, the mixture was diluted with EtOAc and washed with water and brine, dried over Na$_2$SO$_4$ and then concentrated in vacuo give the product that was used in next step.

LCMS 431 (M+H)$^+$.

To a solution of 4-((3-Aminopropyl)amino)-2-(2,6-dioxopiperidin-3-yl)isoindoline-1,3-dione (1 mmol, 1 eq.) in DCM (6 mL) was added TFA (2 mL). The mixture was stirred at room temperature until the reaction completed. And then the mixture was concentrated under reduced pressure, purified by column chromatography (ISCO, 12 g silica column, 0-15% 1.75N NH$_3$.MeOH/DCM) to give the free base product (236 mg, 72% for 2 steps).

LCMS 331 (M+H)$^+$.

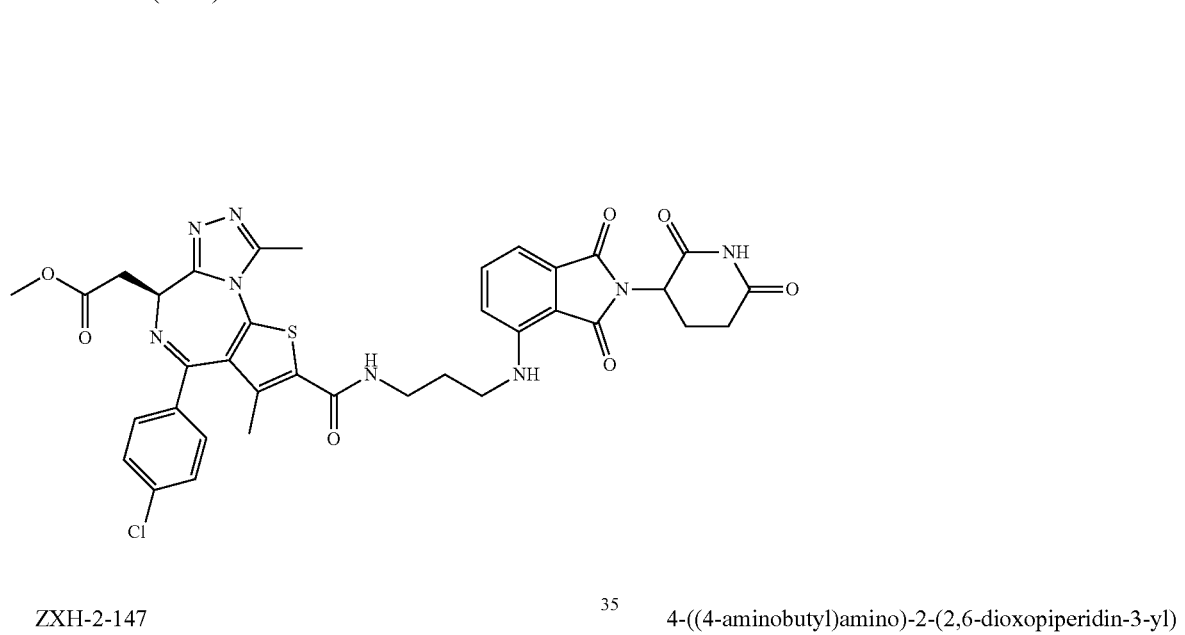

ZXH-2-147

To a solution of (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (25 mg, 0.056 mmol, 1 eq.) and 4-((3-aminopropyl)amino)-2-(2,6-dioxopiperidin-3-yl)isoindoline-1,3-dione (19 mg, 0.056 mmol, 1 eq.) in DMF (1 mL) were added HATU (25 mg, 0.067 mmol, 1.2 eq.) and DIPEA (28 μL, 0.168 mmol, 3 eq.). The mixture was stirred at room temperature overnight and then purified by HPLC to give the product as TFA salt (3.5 mg, 8%).

LCMS 757 (M+H)$^+$.

$^1$H NMR (500 MHz, DMSO-$d_6$) δ 11.09 (s, 1H), 8.43-8.36 (m, 1H), 7.61-7.44 (m, 5H), 7.17-7.11 (m, 1H), 7.06 (dd, J=20.6, 7.8 Hz, 1H), 6.73 (d, J=19.8 Hz, 1H), 5.06 (dd, J=12.7, 5.5 Hz, 1H), 4.58 (ddd, J=8.0, 6.6, 1.3 Hz, 1H), 4.53-4.48 (m, 1H), 3.68 (s, 3H), 3.50-3.44 (m, 3H), 3.34 (d, J=11.6 Hz, 2H), 2.93-2.84 (m, 1H), 2.66 (s, 3H), 2.59 (d, J=19.8 Hz, 1H), 2.42-2.36 (m, 1H), 2.31-2.25 (m, 2H), 2.03 (d, J=7.0 Hz, 1H), 1.93 (s, 3H), 1.82 (p, J=6.8 Hz, 2H).

Example 30: Synthesis of ZXH-2-184

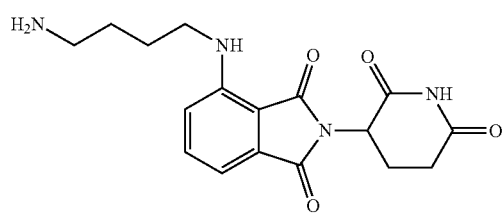 [SMILES: NCCCCNc1cccc2c1C(=O)N(C1CCC(=O)NC1=O)C2=O]

4-((4-aminobutyl)amino)-2-(2,6-dioxopiperidin-3-yl)isoindoline-1,3-dione

To a stirred solution of 2-(2,6-dioxopiperidin-3-yl)-4-fluoroisoindoline-1,3-dione (277 mg, 1 mmol, 1 eq.) in DMF (5 mL) were added DIPEA (330 μL, 2 mmol, 2 eq.) and tert-butyl (4-aminopropyl)carbamate (207 mg, 1.1 mmol, 1.1 eq.). The reaction mixture was heated to 90° C. overnight. Cooled to room temperature, the mixture was diluted with EtOAc and washed with water and brine, dried over Na$_2$SO$_4$ and concentrated in vacuo to give the product that was used in next step.

LCMS 445 (M+H)$^+$.

To a solution of 4-((4-aminobutyl)amino)-2-(2,6-dioxopiperidin-3-yl)isoindoline-1,3-dione (1 mmol, 1 eq.) in DCM (6 mL) was added TFA (2 mL), then the mixture was stirred at room temperature until the reaction completed. The mixture was concentrated under reduced pressure and purified by column chromatography (ISCO, 12 g silica column, 0-20% 1.75N NH$_3$.MeOH/DCM) to give the free base product (224 mg, 65% for 2 steps).

LCMS 345 (M+H)$^+$.

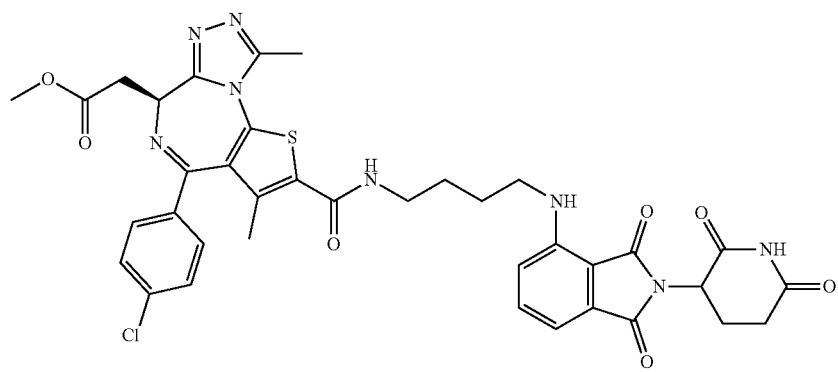 [SMILES: COC(=O)C[C@@H]1N=C(c2ccc(Cl)cc2)c2c(sc(C(=O)NCCCCNc3cccc4c3C(=O)N(C3CCC(=O)NC3=O)C4=O)c2C)-n2c(C)nnc21]

ZXH-2-184

To a solution of (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (37 mg, 0.08 mmol, 1 eq.) and 4-((4-aminobutyl)amino)-2-(2,6-dioxopiperidin-3-yl)isoindoline-1,3-dione (28 mg, 0.08 mmol, 1 eq.) in DMF (1 mL) were added HATU (37 mg, 0.1 mmol, 1.2 eq.) and DIPEA (40 μL, 0.24 mmol, 3 eq.). The mixture was stirred at room temperature overnight and then purified by HPLC to give the product as TFA salt (4.8 mg, 7%).

LCMS 771 (M+H)$^+$.

$^1$H NMR (500 MHz, DMSO-d$_6$) δ 11.09 (s, 1H), 8.37 (t, J=5.7 Hz, 1H), 7.56 (dd, J=8.6, 7.1 Hz, 1H), 7.51 (d, J=8.7 Hz, 2H), 7.46 (d, J=8.6 Hz, 2H), 7.12 (d, J=8.6 Hz, 1H), 7.01 (d, J=7.0 Hz, 1H), 6.59 (t, J=6.1 Hz, 1H), 5.05 (dd, J=12.8, 5.5 Hz, 1H), 4.58 (dd, J=7.7, 6.6 Hz, 1H), 3.68 (s, 3H), 3.47 (qd, J=16.5, 7.2 Hz, 2H), 3.31 (d, J=5.6 Hz, 2H), 2.89 (ddd, J=17.0, 13.8, 5.4 Hz, 1H), 2.64 (s, 3H), 2.59 (ddd, J=17.0, 4.4, 2.4 Hz, 1H), 2.03 (ddd, J=10.0, 6.2, 2.2 Hz, 1H), 1.90 (s, 3H), 1.61 (q, J=2.8, 2.4 Hz, 4H), 1.24 (s, 2H).

Example 31: Synthesis of ZXH-3-26

4-((5-Aminopentyl)amino)-2-(2,6-dioxopiperidin-3-yl)isoindoline-1,3-dione

To a stirred solution of 2-(2,6-dioxopiperidin-3-yl)-4-fluoroisoindoline-1,3-dione (219 mg, 0.8 mmol, 1 eq.) in DMF (4 mL) were added DIPEA (264 μL, 1.6 mmol, 2 eq.) and tert-butyl (5-aminopropyl)carbamate (177 mg, 0.88 mmol, 1.1 eq.). The reaction mixture was heated to 90° C. overnight. Cooled to room temperature, the mixture was diluted with EtOAc and EtOAc and washed with water and brine, dried over Na$_2$SO$_4$ and concentrated in vacuo to obtain 4-((5-aminopentyl)amino)-2-(2,6-dioxopiperidin-3-yl)isoindoline-1,3-dione that was used directly in next step.

LCMS 458 (M+H)$^+$.

To a solution of 4-((5-aminopentyl)amino)-2-(2,6-dioxopiperidin-3-yl)isoindoline-1,3-dione (0.8 mmol, 1 eq.) in DCM (6 mL) was added TFA (2 mL). The mixture was stirred at room temperature until the reaction completed. The mixture was concentrated under reduced pressure and purified by column chromatography (ISCO, 12 g silica column, 0-20% 1.75N NH$_3$.MeOH/DCM) to give the free base product (194 mg, 68% for 2 steps).

LCMS 359 (M+H)$^+$.

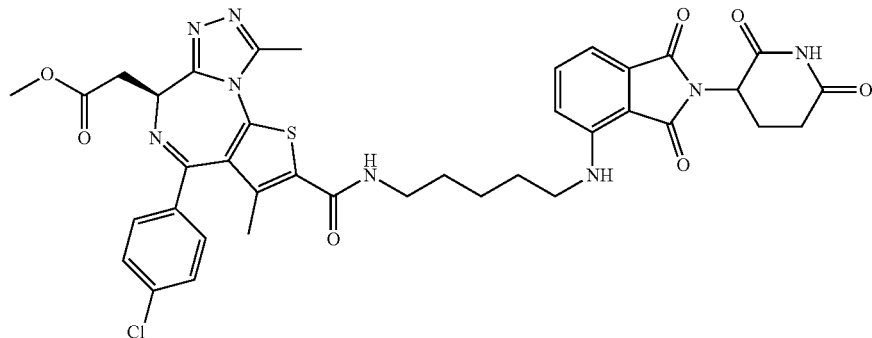 [SMILES: COC(=O)C[C@@H]1N=C(c2ccc(Cl)cc2)c2c(sc(C(=O)NCCCCCNc3cccc4c3C(=O)N(C3CCC(=O)NC3=O)C4=O)c2C)-n2c(C)nnc21]

ZXH-3-26

To a solution of (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (62 mg, 0.14 mmol, 1 eq.) and 4-((5-aminopentyl)amino)-2-(2,6-dioxopiperidin-3-yl)isoindoline-1,3-dione (50 mg, 0.14 mmol, 1 eq.) in DMF (1 mL) were added HATU (64 mg, 0.168 mmol, 1.2 eq.) and DIPEA (70 μL, 0.42 mmol, 3 eq.). The mixture was stirred at room temperature overnight and then purified by HPLC to give the product as TFA salt (18.4 mg, 15%).

LCMS 785 (M+H)+.

$^1$H NMR (500 MHz, DMSO-$d_6$) δ 11.09 (s, 1H), 8.32 (t, J=5.7 Hz, 1H), 7.57 (dd, J=8.6, 7.1 Hz, 1H), 7.51 (d, J=8.8 Hz, 2H), 7.46 (d, J=8.6 Hz, 2H), 7.10 (d, J=8.6 Hz, 1H), 7.02 (d, J=7.0 Hz, 1H), 6.55 (t, J=6.0 Hz, 1H), 5.04 (ddd, J=12.8, 5.5, 1.1 Hz, 1H), 4.58 (dd, J=7.7, 6.6 Hz, 1H), 3.68 (s, 3H), 3.47 (qd, J=16.6, 7.3 Hz, 2H), 3.31-3.23 (m, 4H), 2.89 (ddd, J=16.9, 13.8, 5.5 Hz, 1H), 2.65 (s, 3H), 2.59 (ddd, J=17.0, 4.4, 2.5 Hz, 1H), 2.05-1.99 (m, 1H), 1.90 (s, 3H), 1.60 (dp, J=21.6, 7.2 Hz, 4H), 1.40 (h, J=7.4, 6.5 Hz, 2H).

Example 32: Synthesis of ZXH-3-27

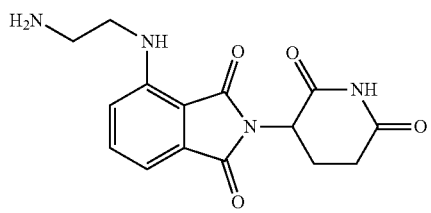 [SMILES: NCCNc1cccc2c1C(=O)N(C1CCC(=O)NC1=O)C2=O]

4-((2-Aminoethyl)amino)-2-(2,6-dioxopiperidin-3-yl)isoindoline-1,3-dione

To a stirred solution of 2-(2,6-dioxopiperidin-3-yl)-4-fluoroisoindoline-1,3-dione (180 mg, 0.65 mmol, 1 eq.) in DMF (4 mL) were added DIPEA (214 μL, 1.3 mmol, 2 eq.) and tert-butyl (2-aminopropyl)carbamate (114 mg, 0.72 mmol, 1.1 eq.). The reaction mixture was heated to 90° C. overnight. Cooled to room temperature, the mixture was diluted with EtOAc and washed with water and brine, dried over Na$_2$SO$_4$ and concentrated in vacuo and then used in next step without further purification.

LCMS 417 (M+H)+.

To a solution of 4-((2-aminoethyl)amino)-2-(2,6-dioxopiperidin-3-yl)isoindoline-1,3-dione (0.65 mmol, 1 eq.) dissolved in DCM (6 mL) was added TFA (2 mL), then the mixture was stirred at room temperature until the reaction completed. The mixture was concentrated under reduced pressure and purified by column chromatography (ISCO, 12 g silica column, 0-15% 1.75N NH$_3$.MeOH/DCM) to give the free base product (100 mg, 49% for 2 steps).

LCMS 317 (M+H)+.

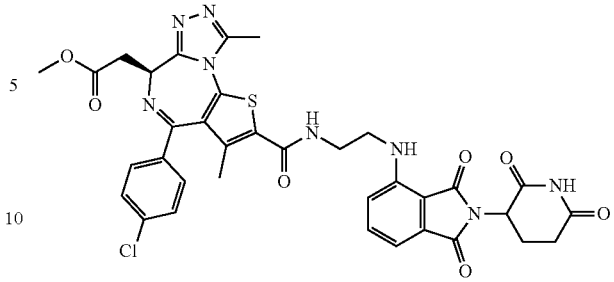

ZXH-3-27

To a solution of (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (44 mg, 0.1 mmol, 1 eq.) and 4-((2-aminoethyl)amino)-2-(2,6-dioxopiperidin-3-yl)isoindoline-1,3-dione (31 mg, 0.1 mmol, 1 eq.) in DMF (1 mL) were added HATU (46 mg, 0.12 mmol, 1.2 eq.) and DIPEA (50 μL, 0.3 mmol, 3 eq.). The mixture was stirred at room temperature overnight and then purified by HPLC to give the product as TFA salt (6.6 mg, 8%).

LCMS 743 (M+H)+.

$^1$H NMR (500 MHz, DMSO-$d_6$) δ 11.09 (s, 1H), 8.49 (dt, J=5.7, 2.9 Hz, 1H), 7.61 (ddd, J=8.6, 7.0, 1.6 Hz, 1H), 7.54-7.48 (m, 2H), 7.45 (d, J=8.4 Hz, 2H), 7.24 (d, J=8.6 Hz, 1H), 7.04 (d, J=7.1 Hz, 1H), 6.83 (t, J=6.0 Hz, 1H), 5.05 (ddd, J=12.8, 5.5, 1.4 Hz, 1H), 4.58 (ddd, J=7.6, 6.6, 0.9 Hz, 1H), 3.68 (s, 3H), 3.57-3.42 (m, 6H), 2.89 (ddd, J=17.8, 13.9, 5.4 Hz, 1H), 2.64 (d, J=1.1 Hz, 3H), 2.59 (ddd, J=15.0, 4.7, 2.4 Hz, 1H), 2.01 (dtd, J=12.5, 5.2, 2.2 Hz, 1H), 1.90 (d, J=2.6 Hz, 3H).

Example 33: Synthesis of ZXH-3-028

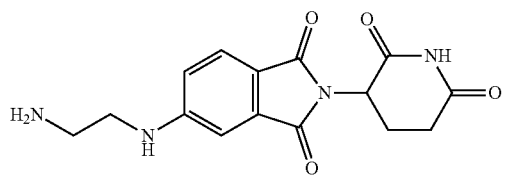 [SMILES: NCCNc1ccc2c(c1)C(=O)N(C1CCC(=O)NC1=O)C2=O]

5-((2-aminoethyl)amino)-2-(2,6-dioxopiperidin-3-yl)isoindoline-1,3-dione

To a solution of 2-(2,6-dioxopiperidin-3-yl)-5-fluoroisoindoline-1,3-dione (50 mg, 0.18 mmol) in DMF (1 mL) were added tert-butyl (2-aminoethyl)carbamate (29 mg, 0.18 mmol) and DIEA (89 μL, 0.54 mmol). The mixture was stirred at 120° C. for 1 h, and the crude product was purified by HPLC (MeOH/H$_2$O, 0.035% TFA) to give intermediate 5-((2-aminoethyl)amino)-2-(2,6-dioxopiperidin-3-yl)isoindoline-1,3-dione. The intermediate was dissolved in TFA/DCM (4 mL, v/v=1/3), stirred for 1 h, and then concentrated in vacuo to give the product as TFA salt (46 mg, 80% for 2 steps).

LCMS: 317 (M+H)+.

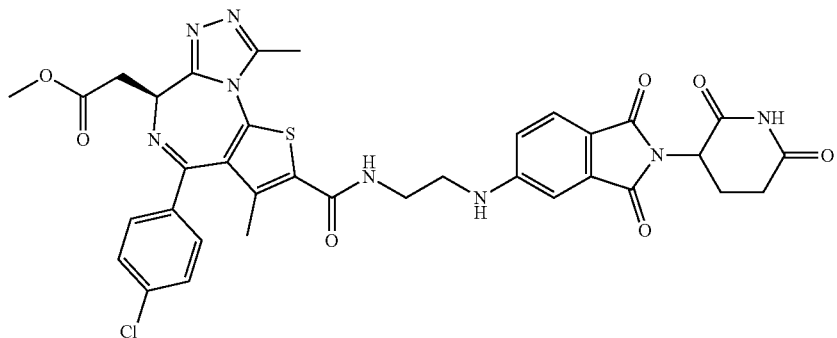 [SMILES: COC(=O)C[C@@H]1N=C(c2ccc(Cl)cc2)c2c(sc(C(=O)NCCNc3ccc4c(c3)C(=O)N(C3CCC(=O)NC3=O)C4=O)c2C)-n2c(C)nnc21]

ZXH-3-028

To a solution of (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (73 mg, 0.16 mmol) and 5-((2-aminoethyl)amino)-2-(2,6-dioxopiperidin-3-yl)isoindoline-1,3-dione (TFA salt, 46 mg, 0.11 mmol) in DMF (1 mL) were added 1-ethyl-3-(3-dimethylaminopropyl)carbodiimide (EDCI) (32 mg, 0.16 mmol), 1-hydroxybenzotriazole (HOBt) (22 mg, 0.16 mmol) and DMAP (20 mg, 0.16 mmol). The mixture was stirred at room temperature overnight and then purified by HPLC (MeOH/H₂O, 0.035% TFA) to give ZXH-3-028 as TFA salt (3 mg, 3%).

LCMS: 743 (M+H)⁺.

5-((5-Aminopentyl)amino)-2-(2,6-dioxopiperidin-3-yl)isoindoline-1,3-dione

To a solution of 2-(2,6-dioxopiperidin-3-yl)-5-fluoroisoindoline-1,3-dione (83 mg, 0.3 mmol) in DMF (1 mL) were added tert-butyl (5-aminopentyl)carbamate (61 mg, 0.3 mmol) and DIEA (148 µL, 0.9 mmol). The mixture was stirred at 120° C. for 1 h, and the crude was purified by HPLC (MeOH/H₂O, 0.035% TFA) to give the intermediate. The intermediate was dissolved in TFA/DCM (4 mL, v/v=1/3) and then concentrated in vacuo to give the product as TFA salt (79 mg, 56% for 2 steps).

LCMS: 359 (M+H)⁺.

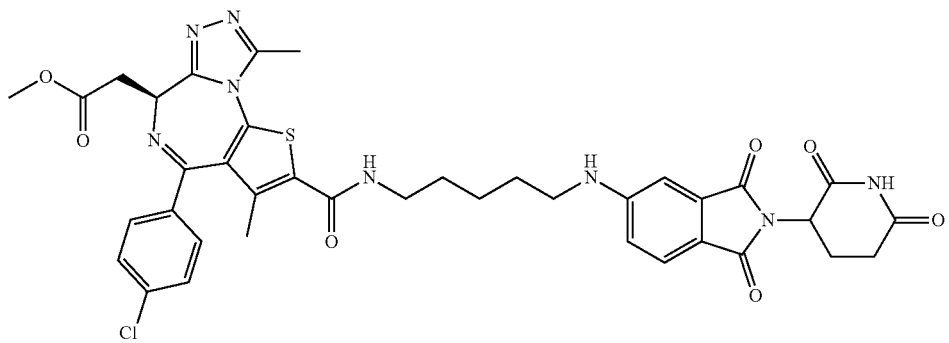

¹H NMR (500 MHz, DMSO-d₆) δ 11.05 (d, J=4.5 Hz, 1H), 8.40 (s, 1H), 7.59 (d, J=8.3 Hz, 1H), 7.51 (d, J=8.9 Hz, 1H), 7.45 (d, J=8.5 Hz, 2H), 7.27 (s, 1H), 7.05 (d, J=2.1 Hz, 1H), 6.92 (dd, J=8.4, 2.1 Hz, 1H), 5.03 (ddd, J=12.8, 5.5, 2.4 Hz, 1H), 4.58 (t, J=7.2 Hz, 1H), 3.68 (s, 3H), 3.51-3.44 (m, 2H), 2.92-2.83 (m, 1H), 2.65 (d, J=1.9 Hz, 3H), 2.61-2.55 (m, 1H), 2.55 (s, 1H), 2.19 (t, J=7.4 Hz, 1H), 2.02-1.96 (m, 1H), 1.93 (d, J=2.8 Hz, 3H), 1.48 (t, J=7.4 Hz, 1H).

Example 34: Synthesis of ZXH-3-195

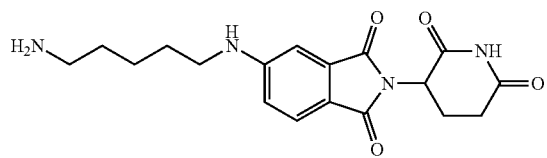

ZXH-3-195

To a solution of (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (13 mg, 0.03 mmol) and 5-((5-aminopentyl)amino)-2-(2,6-dioxopiperidin-3-yl)isoindoline-1,3-dione (14 mg, 0.03 mmol) in DMF (1 mL) were added HATU (14 mg, 0.036 mmol) and DIPEA (25 µL, 0.15 mmol). The mixture was stirred at room temperature for 1 h and then purified by HPLC (MeOH/H₂O, 0.035% TFA) to give ZXH-3-195 as TFA salt (7.9 mg, 29%).

LCMS: 785 (M+H)⁺.

¹H NMR (500 MHz, DMSO-d₆) δ 11.06 (s, 1H), 8.31 (dt, J=6.1, 3.0 Hz, 1H), 7.55 (d, J=8.4 Hz, 1H), 7.51 (d, J=8.8 Hz, 2H), 7.46 (d, J=8.6 Hz, 2H), 7.11 (t, J=5.4 Hz, 1H), 6.95 (d, J=2.1 Hz, 1H), 6.84 (dd, J=8.4, 2.1 Hz, 1H), 5.03 (dd, J=12.8, 5.4 Hz, 1H), 4.58 (dd, J=7.8, 6.6 Hz, 1H), 3.68 (s, 3H), 3.53-3.43 (m, 2H), 3.30-3.26 (m, 2H), 3.17 (q, J=6.4, 5.2 Hz, 2H), 2.88 (ddd, J=16.8, 13.7, 5.4 Hz, 1H), 2.65 (s, 3H), 2.61-2.54 (m, 1H), 2.03-1.95 (m, 1H), 1.91 (s, 3H), 1.60 (dp, J=21.4, 7.1 Hz, 4H), 1.43 (dt, J=11.8, 7.3 Hz, 2H).

Example 35: Synthesis of ZXH-3-142

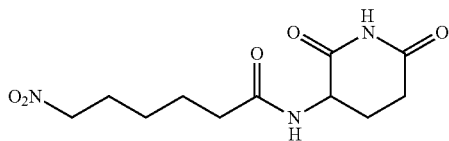

N-(2,6-Dioxopiperidin-3-yl)-6-nitrohexanamide

A solution of 6-nitrohexanoic acid (260 mg, 1.61 mmol) in thionyl chloride (3 mL) was stirred at 90° C. for 1 h and then was concentrated in vacuo to obtain the intermediate 6-nitrohexanoyl chloride. The intermediate was then dissolved in DCM (2 mL), and then added into the solution of 3-aminopiperidine-2,6-dione hydrochloride salt (266 mg, 1.61 mmol) and DIEA (1.3 mL, 8.05 mmol) in DCM (2 mL) at 0° C. The mixture was then stirred at room temperature for 3 h, and then purified by HPLC (MeOH/H$_2$O, 0.035% TFA) to give the product as TFA salt.

LCMS: 272 (M+H)$^+$.

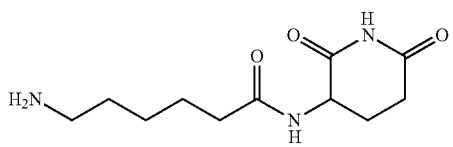

6-Amino-N-(2,6-dioxopiperidin-3-yl)hexanamide

N-(2,6-Dioxopiperidin-3-yl)-6-nitrohexanamide from last step was dissolved in MeOH and then hydrogenation was conducted to give the product (111 mg, 29% for 2 steps).

LCMS: 242 (M+H)$^+$.

ZXH-3-142

To a solution of perfluorophenyl (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylate (73 mg, 0.12 mmol) and 6-amino-N-(2,6-dioxopiperidin-3-yl)hexanamide (30 mg, 0.12 mmol) in DMF (1 mL) was added 4-pyrrolidinopyridine (71 mg, 0.48 mmol), the mixture was stirred at room temperature for 3 h, and then purified by HPLC (MeOH/H$_2$O, 0.035% TFA) to give the product as TFA salt (1.7 mg, 2%).

LCMS: 668 (M+H)$^+$.

Example 36: Synthesis of ZXH-3-052

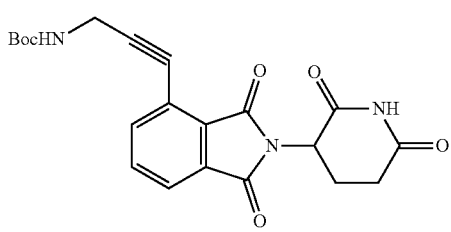

tert-Butyl (3-(2-(2,6-dioxopiperidin-3-yl)-1,3-dioxoisoindolin-4-yl)prop-2-yn-1-yl)carbamate To a solution of 4-bromo-2-(2,6-dioxopiperidin-3-yl)isoindoline-1,3-dione (758 mg, 2.26 mmol) and tert-butyl prop-2-yn-1-ylcarbamate (700 mg, 4.5 mmol) in DMF (10 mL) were added CuI (86 mg, 0.45 mmol), Pd(pph3)2Cl$_2$ (158 mg, 0.226 mmol) and Et3N (5.6 mL). The mixture was then stirred at 70° C. for 3 h. The reaction was allowed to cool to room temperature and then filtered. The filtrate was concentrated in vacuo and then purified by flash column

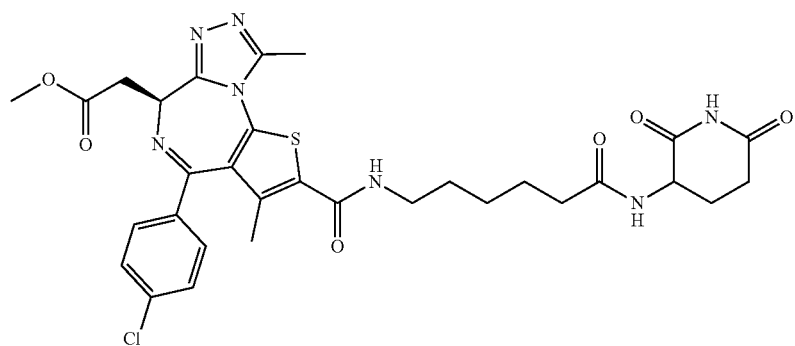

chromatography with silica gel (MeOH/DCM, 0-4%) to obtain the desired product with trace DMF.

LCMS: 412 (M+H)+.

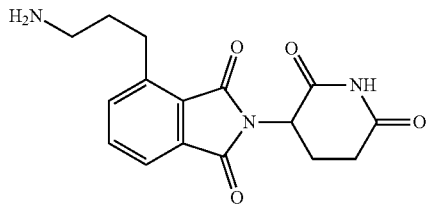 [SMILES: NCCCc1cccc2c1C(=O)N(C1CCC(=O)NC1=O)C2=O]

4-(3-Aminopropyl)-2-(2,6-dioxopiperidin-3-yl)isoindoline-1,3-dione tert-Butyl (3-(2-(2,6-dioxopiperidin-3-yl)-1,3-dioxoisoindolin-4-yl)prop-2-yn-1-yl)carbamate from last steps was dissolved in MeOH, and then hydrogenation was conducted to obtain the intermediate. The intermediate was then dissolved in TFA/DCM (4 mL, v/v=1/3), stirred at room temperature for 3 h, and then purified by HPLC (MeOH/H2O, 0.035% TFA) to give product as TFA salt (300 mg, 31% for 3 steps).

LCMS: 315 (M+H)+.

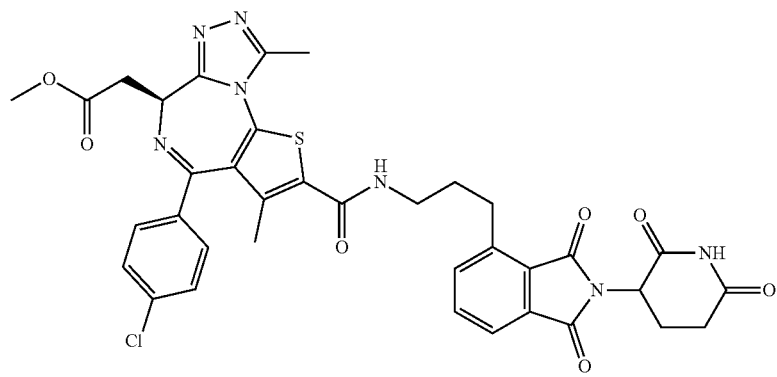

ZXH-3-052

To a solution of (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (22 mg, 0.05 mmol) and 4-(3-aminopropyl)-2-(2,6-dioxopiperidin-3-yl)isoindoline-1,3-dione (20 mg, 0.045 mmol) in DMF (1 mL) were added HATU (21 mg, 0.054 mmol) and DIEA (22 uL, 0.135 mmol). The mixture was stirred at room temperature for 1 h, and the crude product was purified by HPLC (MeOH/H2O, 0.035% TFA) to give ZXH-3-052 as TFA salt (19.5 mg, 51%).

LCMS: 742 (M+H)+.

$^1$H NMR (500 MHz, DMSO-d$_6$) δ 11.12 (s, 1H), 8.38 (dt, J=6.3, 3.1 Hz, 1H), 7.87-7.80 (m, 2H), 7.75 (dd, J=7.7, 1.5 Hz, 1H), 7.51 (d, J=8.8 Hz, 2H), 7.46 (d, J=8.6 Hz, 2H), 5.14 (dd, J=12.8, 5.5 Hz, 1H), 4.58 (dd, J=7.8, 6.7 Hz, 1H), 3.68 (s, 3H), 3.47 (qd, J=16.6, 7.1 Hz, 2H), 3.33-3.25 (m, 2H), 2.95-2.88 (m, 1H), 2.88-2.80 (m, 2H), 2.66 (s, 3H), 2.64-2.58 (m, 1H), 2.55 (s, 1H), 2.05 (dtd, J=12.9, 5.3, 2.2 Hz, 1H), 1.93 (d, J=1.1 Hz, 3H), 1.92-1.88 (m, 2H).

Example 37: Synthesis of Methyl 2-((6S)-4-(4-chlorophenyl)-2-((5-((2-(2,6-dioxopiperidin-3-yl)-6-fluoro-1-oxoisoindolin-4-yl)amino)pentyl)carbamoyl)-3,9-dimethyl-6H-thieno[3,2-f][1,2,4]triazolo[4,3-a][1,4]diazepin-6-yl)acetate (BJG-01-174)

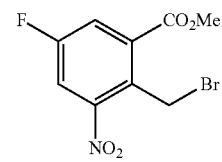 [SMILES: COC(=O)c1cc(F)cc([N+](=O)[O-])c1CBr]

Methyl 2-(bromomethyl)-5-fluoro-3-nitrobenzoate

Methyl 2-methyl-5-fluoro-3-nitrobenzoate (500 mg, 2.35 mmol, 1 eq.), N-bromosuccinimide (NBS) (520 mg, 2.85 mmol, 1.2 eq.), and Azobisisobutyronitrile (AIBN) (54.6 mg, 0.33 mmol, 0.15 eq.) were dissolved in benzene (6 mL, 0.4 M). The reaction was sparged with nitrogen for 15 minutes, and then heated to 80° C. for 21 hours. The reaction was cooled to room temperature and diluted with EtOAc (50 mL). The organic layer was washed sequentially with water, saturated NaHCO3, and brine. The organic layer was dried over magnesium sulfate, filtered, and concentrated under reduced pressure to provide a clear, yellow oil. NMR analysis showed a 4:1 mixture of methyl 2-(bromomethyl)-5-fluoro-3-nitrobenzoate and remaining starting material (RSM) 2-methyl-5-fluoro-3-nitrobenzoate. The inseparable mixture was subjected directly to the lactamization reaction.

$^1$H NMR: (500 MHz, CDCl$_3$) δ 7.85 (dd, J=8.1, 2.8 Hz, 1H), 7.71 (dd, J=7.3, 2.8 Hz, 1H), 5.12 (s, 2H), 4.01 (s, 3H).

LC-MS: 314.07/316.07 (M+H)+.

TLC: R$_f$=0.6, 2:1 hexanes/EtOAc.

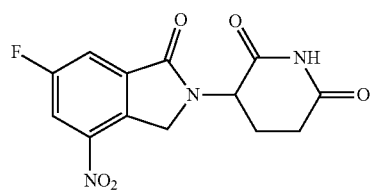 [SMILES: Nc1cc(F)cc2c1CN(C1CCC(=O)NC1=O)C2=O]

3-(6-Fluoro-4-nitro-1-oxoisoindolin-2-yl)piperidine-2,6-dione

To the crude mixture of methyl 2-(bromomethyl)-5-fluoro-3-nitrobenzoate and methyl 2-methyl-5-fluoro-3-nitrobenzoate (2.35 mmol, 1 eq.) were added $K_2CO_3$ (816 mg, 5.88 mmol, 2.5 eq.), 3-aminopiperidine-2,6-dione hydrochloride (580 mg, 3.55 mmol, 1.5 eq.), and DMF (4.0 mL, 0.7 M). The reaction was heated to 60° C. for 14 hours, and then cooled to room temperature. Water (4 mL) was added to precipitate the product, and the suspension was stirred for 1 hour. The product was collected by suction filtration, washed with water (25 mL) and DCM (10 mL), and dried under vacuum to provide a blue-gray solid (331 mg, 45% yield over 2 steps). The crude product was pure by $^1$H-NMR and LC-MS analyses and did not require additional purification.

$^1$H NMR: (500 MHz, DMSO-$d_6$) δ 11.03 (s, 1H), 8.33 (dd, J=8.8, 2.4 Hz, 1H), 8.06 (dd, J=6.9, 2.3 Hz, 1H), 5.18 (dd, J=13.3, 5.2 Hz, 1H), 4.87 (d, J=19.0 Hz, 1H), 4.78 (d, J=19.0 Hz, 1H), 2.96-2.85 (m, 1H), 2.65-2.58 (m, 1H), 2.53 (m, 1H), 2.03 (ddd, J=11.6, 6.2, 4.2 Hz, 1H).

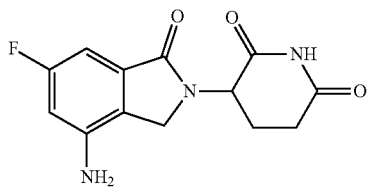

3-(4-Amino-6-fluoro-1-oxoisoindolin-2-yl)piperidine-2,6-dione

A suspension of 3-(6-Fluoro-4-nitro-1-oxoisoindolin-2-yl)piperidine-2,6-dione (277 mg, 0.90 mmol, 1 eq.) and palladium on charcoal (10 wt %; 98.2 mg, 0.09 mmol, 0.10 eq.) in THF (5 mL, 0.18 M) was sparged with $H_2$ for 10 minutes. The reaction was stirred overnight under a $H_2$ balloon. After 14 hours, the reaction was diluted with methanol (25 mL), filtered through Celite, and concentrated under reduced pressure to provide the desired product as a gray solid (131.2 mg, 52% yield). The material was 95% pure by $^1$H-NMR and did not require further purification.

$^1$H NMR: (500 MHz, DMSO-$d_6$) δ 10.99 (s, 1H), 6.59 (dd, J=7.7, 2.2 Hz, 1H), 6.54 (dd, J=11.8, 2.3 Hz, 1H), 5.71 (s, 2H), 5.09 (dd, J=13.3, 5.1 Hz, 1H), 4.17 (d, J=16.9 Hz, 1H), 4.09 (d, J=16.8 Hz, 1H), 2.90 (ddd, J=17.4, 13.9, 5.4 Hz, 1H), 2.61 (d, J=17.3 Hz, 1H), 2.29 (qd, J=13.3, 4.5 Hz, 1H), 2.04 (m, 1H).

LC-MS: 278.17 (M+H).

tert-Butyl (5-((2-((2,6-dioxopiperidin-3-yl)-6-fluoro-1-oxoisoindolin-4-yl)amino)pentyl)carbamate 3-(4-Amino-6-fluoro-1-oxoisoindolin-2-yl)piperidine-2,6-dione (84.5 mg, 0.30 mmol, 1.2 eq.), tert-butyl (5-bromopentyl)carbamate (66.2 mg, 0.25 mmol, 1.0 eq.), and $K_2CO_3$ (67.0 mg, 0.50 mmol, 2.0 eq.) were dissolved in DMF (1.25 mL, 0.2 M) and the mixture was heated to 50° C. After 14 hours, the reaction was cooled and quenched with EtOAc and water (3 mL each). The aqueous layer was extracted three times with EtOAc (3 mL). The combined organic layers were washed with water and then brine, dried over magnesium sulfate, filtered, and concentrated under reduced pressure. Purification by column chromatography (ISCO, 12 g silica column, 0-15% MeOH/DCM, 10 minute gradient) provided the desired product as a clear yellow oil (40.5 mg, 35% yield).

$^1$H NMR: (500 MHz, MeOH-$d_4$) δ 6.74 (dd, J=7.7, 2.6 Hz, 1H), 6.61 (dd, J=11.4, 2.4 Hz, 1H), 5.12 (dd, J=13.2, 5.5 Hz, 1H), 4.28 (d, J=16.8 Hz, 1H), 4.22 (d, J=16.6 Hz, 1H), 3.82-3.70 (m, 2H), 3.02 (q, J=6.6 Hz, 2H), 2.96-2.88 (m, 1H), 2.42 (qd, J=13.0, 6.0 Hz, 1H), 2.16 (m, 1H), 1.53 (quint, J=7.8 Hz, 2H), 1.48 (m, 1H), 1.42 (s, 9H), 1.34-1.27 (m, 2H).

LC-MS: 485.28 (M+Na)$^+$, 463.28 (M+H)$^+$, 363.17 (M−Boc)$^+$.

TLC: $R_f$=0.4, 10% MeOH/DCM.

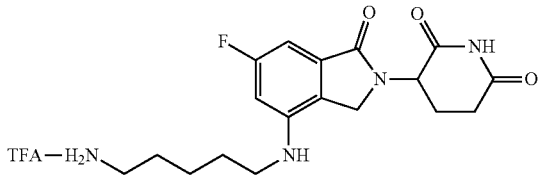

3-(4-((5-Aminopentyl)amino)-6-fluoro-1-oxoisoindolin-2-yl)piperidine-2,6-dione trifluoroacetate salt tert-Butyl (5-((2-(2,6-dioxopiperidin-3-yl)-6-fluoro-1-oxoisoindolin-4-yl)amino)pentyl)carbamate (40.5 mg, 0.088 mmol, 1 eq.) was dissolved in 1:1 DCM/TFA (1.0 mL) and stirred at 50° C. After 2 hours, solvents were removed under reduced pressure. The product was lyophilized to give a tan solid (46.9 mg, quantitative yield). LC-MS analysis showed full Boc-deprotection.

LC-MS: 363.27 (M+H)$^+$.

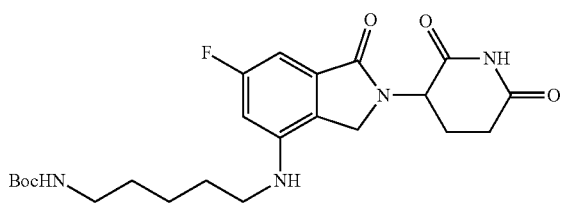 [SMILES: CC(C)(C)OC(=O)NCCCCCNc1cc(F)cc2c1CN(C1CCC(=O)NC1=O)C2=O]

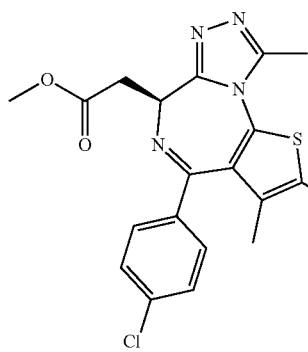
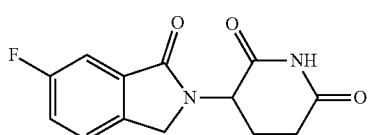

BJG-01-174

3-(4-((5-aminopentyl)amino)-6-fluoro-1-oxoisoindolin-2-yl)piperidine-2,6-dione trifluoroacetate salt (16.7 mg, 0.036 mmol, 1.2 eq.), (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (13.1 mg, 0.030 mmol, 1.0 eq.), and HATU (13.4 mg, 0.036 mmol, 1.2 eq.) were dissolved in DMSO (0.50 mL, 0.06 M). DIPEA (20.70 µL, 0.119 mmol, 4 eq.) was added. The reaction was stirred at room temperature for 4 hours, and then diluted with MeOH (1 mL) and purified by reverse-phase prep HPLC (100-0% H$_2$O/MeOH, 45 minute gradient). The product was lyophilized from H$_2$O/MeCN to provide a white powder (7.9 mg, TFA salt, 29% yield).

$^1$H NMR: (500 MHz, DMSO-d$_6$) δ 8.31 (t, J=5.7 Hz, 1H), 7.49 (d, J=8.4 Hz, 2H), 7.45 (d, J=8.4 Hz, 2H), 6.61 (d, J=7.7, 1H), 6.56 (d, J=11.7 Hz, 1H), 5.79 (s, 1H), 5.15 (dd, J=13.6, 5.1 Hz, 1H), 4.56 (td, J=7.2, 2.1 Hz, 1H), 4.18 (dd, J=16.9, 5.9 Hz, 1H), 4.06 (dd, J=16.9, 2.2 Hz, 1H), 3.67 (s, 3H), 3.62 (m, 2H), 3.52-3.42 (m, 3H), 3.26-3.19 (m, 2H), 2.99 (ddd, J=18.1, 13.5, 5.4 Hz, 1H), 2.75 (d, J=17.7, Hz, 1H), 2.63 (s, 3H), 2.26 (m, 1H), 2.09-2.00 (m, 1H), 1.90 (s, 3H), 1.51 (quint, J=7.5 Hz, 2H), 1.46 (quint, J=7.6 Hz, 2H), 1.27 (m, 2H).

LC-MS: 789.31 (M+H)$^+$.

Example 38: Synthesis of Methyl 2-((6S)-4-(4-chlorophenyl)-2-((5-((2-(2,6-dioxopiperidin-3-yl)-7-fluoro-1,3-dioxoisoindolin-4-yl)amino)pentyl)carbamoyl)-3,9-dimethyl-6H-thieno[3,2f][1,2,4]triazolo[4,3-a][1,4]diazepin-6-yl)acetate (BJG-02-119)

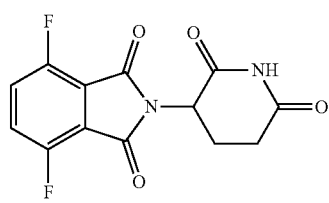 [SMILES: O=C1CCC(N2C(=O)c3c(F)ccc(F)c3C2=O)C(=O)N1]

2-(2,6-Dioxopiperidin-3-yl)-4,7-difluoroisoindoline-1,3-dione 3,6-Difluorophthalic anhydride (77.3 mg, 0.40 mmol, 1.0 eq.), potassium acetate (120.8 mg, 1.24 mmol, 3.1 eq.), and 3-aminopiperidine-2,6-dione hydrochloride (80.4 mg, 0.48 mmol, 1.2 eq.) were dissolved in glacial acetic acid (1.2 mL, 0.33 M), and then the mixture was heated to 120° C. After 16 hours, the reaction was cooled to room temperature and the excess acetic acid was removed by rotary evaporation. The residue was dissolved in EtOAc and water (20 mL each), and the aqueous layer was extracted 4 times with EtOAc (15 mL). The combined organic layers were washed with water and then brine, dried over magnesium sulfate, filtered, and concentrated under reduced pressure to provide the desired product as a tan solid (94.0 mg, 80% yield).

$^1$H NMR: (500 MHz, DMSO-d$_6$) δ 11.14 (s, 1H), 7.79 (t, J=5.7 Hz, 2H), 5.15 (dd, J=12.9, 5.4 Hz, 1H), 2.88 (ddd, J=17.1, 13.8, 5.5 Hz, 1H), 2.60 (d, J=17.3 Hz, 1H), 2.55-2.45 (m, 1H), 2.05 (m, 1H).

LC-MS: 295.17 (M+H)$^+$.

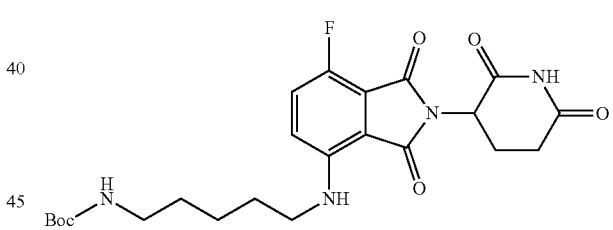

tert-Butyl (5-((2-(2,6-dioxopiperidin-3-yl)-7-fluoro-1,3-dioxoisoindolin-4-yl)amino)pentyl)carbamate 2-(2,6-Dioxopiperidin-3-yl)-4,7-difluoroisoindoline-1,3-dione (58.8 mg, 0.20 mmol, 1.0 eq.) and tert-butyl (5-aminopentyl)carbamate (44.4 mg, 0.22 mmol, 1.1 eq.) were dissolved in DMSO (0.7 mL, 0.3 M). DIPEA (0.070 mL, 0.40 mmol, 2.0 eq.) was added at room temperature, and the solution was heated to 130° C. for 2 hours. The reaction was then cooled to room temperature and quenched with water (3 mL). The aqueous layer was extracted 4 times with EtOAc (15 mL). The combined organic layers were washed three times with water, then once with brine, dried over magnesium sulfate, filtered, and concentrated under reduced pressure. The crude material, a dark green oil, was carried on directly to the Boc-deprotection reaction.

LC-MS: 499.28 (M+Na)$^+$, 377.27 (M−Boc)$^+$.

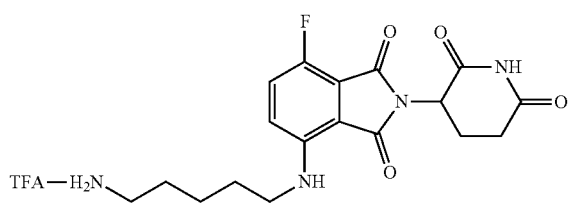

4-((5-aminopentyl)amino)-2-(2,6-dioxopiperidin-3-yl)-7-fluoroisoindoline-1,3-dione trifluoroacetate salt Crude tert-butyl (5-((2-(2,6-dioxopiperidin-3-yl)-7-fluoro-1,3-dioxoisoindolin-4-yl)amino)pentyl)carbamate (0.20 mmol) was dissolved in 4:1 DCM/TFA (2.5 mL, 0.08 M) and heated to 50° C. After 2 hours, the reaction was cooled to room temperature and concentrated under reduced pressure. Reverse-phase prep HPLC (100-40% H$_2$O/MeCN, 60-minute gradient), followed by lyophilization from MeCN/water provided the desired product as a forest-green powder (53.7 mg, 54% yield over 2 steps).

LC-MS: 377.07 (M+H)$^+$.

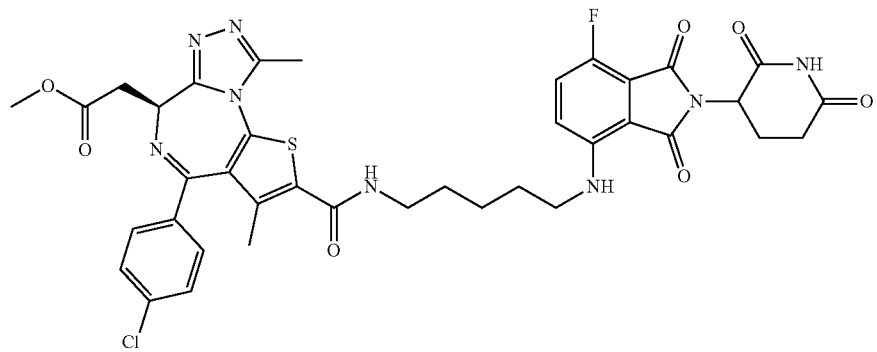 [SMILES: COC(=O)C[C@@H]1N=C(c2ccc(Cl)cc2)c2c(sc(C(=O)NCCCCCNc3ccc(F)c4c3C(=O)N(C3CCC(=O)NC3=O)C4=O)c2C)-n2c(C)nnc21]

(BJG-02-119)

4-((5-aminopentyl)amino)-2-(2,6-dioxopiperidin-3-yl)-7-fluoroisoindoline-1,3-dione trifluoroacetate salt (18.1 mg, 0.033 mmol, 1.1 eq.), (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (13.4 mg, 0.030 mmol, 1.0 eq.), and HATU (12.9 mg, 0.033 mmol, 1.1 eq.) were dissolved in DMSO (0.60 mL, 0.05 M). DIPEA (16.00 µL, 0.092 mmol, 3 eq.) was added. The reaction was stirred at room temperature overnight, and then diluted with DMSO (1 mL). The crude product purified by reverse-phase prep HPLC (100-0% H$_2$O/MeCN, 45 minute gradient). The product was lyophilized from H$_2$O/MeCN to provide a yellow powder (15.6 mg, TFA salt, 56% yield).

$^1$H NMR: (500 MHz, DMSO-d$_6$) δ 11.10 (s, 1H), 8.31 (t, J=5.7 Hz, 1H), 7.50 (d, J=8.8 Hz, 2H), 7.47-7.42 (m, 3H), 7.16 (dd, J=9.4, 3.3 Hz, 1H), 6.50 (s, 1H), 5.04 (dd, J=12.8, 5.4 Hz, 1H), 4.57 (t, J=7.2 Hz, 1H), 3.67 (s, 3H), 3.50 (dd, J=16.6, 6.7 Hz, 1H), 3.43 (dd, J=16.6, 7.8 Hz, 1H), 3.33-3.19 (m, 4H), 2.87 (ddd, J=17.1, 13.9, 5.4 Hz, 1H), 2.64 (s, 3H), 2.62-2.55 (m, 1H), 2.05-1.97 (m, 1H), 1.90 (d, J=1.2 Hz, 3H), 1.57 (m, 4H), 1.42-1.33 (m, 2H).

$^{19}$F NMR: (471 MHz, DMSO-d$_6$) δ −130.4 (aryl fluoride), −74.7 (TFA).

LC-MS: 803.51 (M+H)$^+$.

Example 39: Synthesis of Methyl 2-((6S)-4-(4-chlorophenyl)-2-((5-((2-(2,6-dioxopiperidin-3-yl)-1,3-dioxoisoindolin-4-yl)oxy)pentyl)carbamoyl)-3,9-dimethyl-6H-thieno[3,2-f][1,2,4]triazolo[4,3-a][1,4]diazepin-6-yl)acetate (BJG-02-030)

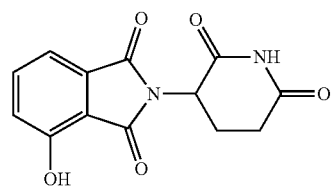 [SMILES: O=C1CCC(N2C(=O)c3cccc(O)c3C2=O)C(=O)N1]

2-(2,6-dioxopiperidin-3-yl)-4-hydroxyisoindoline-1,3-dione

3-Hydroxyphthalic anhydride (329 mg, 2.0 mmol, 1.0 eq.), potassium acetate (617 mg, 6.2 mmol, 3.1 eq.), and 3-aminopiperidine-2,6-dione hydrochloride (375 mg, 2.3 mmol, 1.15 eq.) were dissolved in glacial acetic acid (6.0 mL, 0.33 M), and then the mixture was heated to 120° C. After 16 hours, the reaction was cooled to room temperature and acetic acid was removed by rotary evaporation. The residue was dissolved in EtOAc and water (20 mL each), and the aqueous layer was extracted 5 times with EtOAc (40 mL). The combined organic layers were washed twice with water and then brine, dried over magnesium sulfate, filtered, and concentrated to provide the desired product as a red powder (390 mg, 71% yield). The material was >95% pure by 1H-NMR and did not require further purification.

$^1$H NMR: (500 MHz, DMSO-d$_6$) δ 11.16 (s, 1H), 11.08 (s, 1H), 7.65 (t, J=7.8 Hz, 1H), 7.32 (d, J=7.2 Hz, 1H), 7.25 (d, J=8.4 Hz, 1H), 5.07 (dd, J=12.8, 5.4 Hz, 1H), 2.88 (ddd, J=16.9, 13.8, 5.5 Hz, 1H), 2.58 (d, J=18.4 Hz, 1H), 2.53 (m, 1H), 2.06-1.98 (m, 1H).

LC-MS: 275.07 (M+H)$^+$.

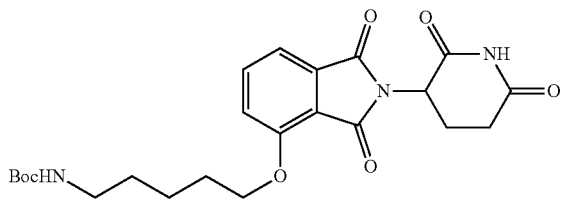 [SMILES: CC(C)(C)OC(=O)NCCCCCOc1cccc2c1C(=O)N(C1CCC(=O)NC1=O)C2=O]

tert-Butyl (5-((2-(2,6-dioxopiperidin-3-yl)-1,3-dioxoisoindolin-4-yl)oxy)pentyl) carbamate 2-(2,6-Dioxopiperidin-3-yl)-4-hydroxyisoindoline-1,3-dione (54.7 mg, 0.20 mmol, 1.0 eq.), tert-butyl (5-bromopentyl)carbamate (64.0 mg, 0.24 mmol, 1.2 eq.), and K₂CO₃ (54.6 mg, 0.40 mmol, 2.0 eq.) were dissolved in DMF (0.5 mL, 0.4 M) and heated to 50° C. After 18 hours, the reaction was cooled and quenched with EtOAc and water (3 mL each). The aqueous layer was extracted 4 times with EtOAc (10 mL). The combined organic layers were washed with water and then brine, dried over magnesium sulfate, filtered, and concentrated under reduced pressure. Purification by column chromatography (ISCO, 12 g silica column, 0-15% MeOH/DCM, 10 minute gradient) provided the desired product as a viscous yellow oil in quantitative yield.

LC-MS: 482.28 (M+Na)⁺, 360.27 (M−Boc)⁺.

TLC: $R_f$=0.33, 5% MeOH/DCM

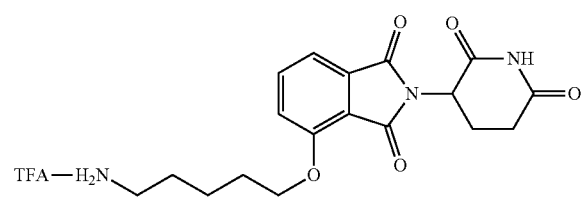

4-((5-Aminopentyl)oxy)-2-(2,6-dioxopiperidin-3-yl)isoindoline-1,3-dione trifluoroacetate salt tert-Butyl (5-((2-(2,6-dioxopiperidin-3-yl)-1,3-dioxoisoindolin-4-yl)oxy)pentyl)carbamate (0.20 mmol) was dissolved in 1.5:1 DCM/TFA (1.25 mL, 0.16 M) and heated to 50° C. After 2 hours, the reaction was cooled to room temperature and concentrated under reduced pressure. Lyophilization from MeCN/water provided the desired product as a sticky, colorless oil (82.4 mg, 87% yield).

¹H NMR: (500 MHz, DMSO-d₆) δ 11.13 (s, 1H), 7.88-7.82 (m, 1H), 7.54 (t, J=8.9 Hz, 1H), 7.48 (d, J=7.3 Hz, 1H), 5.10 (dd, J=12.8, 5.4 Hz, 1H), 4.24 (t, J=6.1 Hz, 2H), 3.05-2.94 (m, 1H), 2.90-2.77 (m, 2H), 2.69-2.60 (m, 1H), 2.12-2.00 (m, 2H), 1.83 (p, J=6.6 Hz, 2H), 1.65 (p, J=7.4 Hz, 2H), 1.60-1.51 (m, 2H).

LC-MS: 360.27 (M+H)⁺.

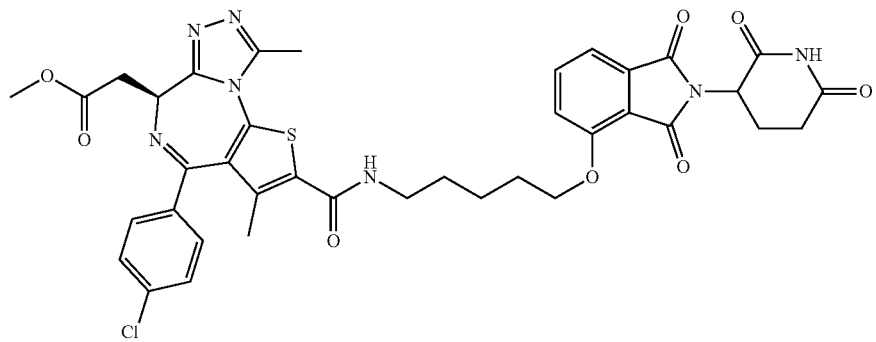 [SMILES: COC(=O)C[C@@H]1N=C(c2ccc(Cl)cc2)c2c(sc(C(=O)NCCCCCOc3cccc4c3C(=O)N(C3CCC(=O)NC3=O)C4=O)c2C)-n2c(C)nnc21]

BJG-02-030

4-((5-aminopentyl)oxy)-2-(2,6-dioxopiperidin-3-yl)isoindoline-1,3-dione trifluoroacetate salt (17.2 mg, 0.036 mmol, 1.2 eq.), (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (14.1 mg, 0.030 mmol, 1.0 eq.), and HATU (15.0 mg, 0.039 mmol, 1.3 eq.) were dissolved in DMSO (0.50 mL, 0.06 M). DIPEA (18.00 μL, 0.103 mmol, 3.4 eq.) was added. The reaction was stirred at room temperature overnight, and then diluted with DMSO (1 mL) and purified by reverse-phase prep HPLC (100-0% H₂O/MeCN, 45 minute gradient). The product was lyophilized from H₂O/MeCN to provide a white powder (7.9 mg, TFA salt, 29% yield).

¹H NMR: (500 MHz, DMSO-d₆) δ 11.09 (s, 1H), 8.33 (t, J=5.7 Hz, 1H), 7.80 (t, J=7.9 Hz, 1H), 7.53-7.48 (m, 3H), 7.46-7.41 (m, 3H), 5.06 (dd, J=12.8, 5.4 Hz, 1H), 4.57 (t, J=7.2 Hz, 1H), 4.21 (t, J=6.4 Hz, 2H), 3.46 (qd, J=16.6, 7.2 Hz, 2H), 3.28 (dp, J=19.7, 6.5 Hz, 2H), 2.87 (ddd, J=17.1, 13.8, 5.4 Hz, 1H), 2.64 (s, 3H), 2.58 (d, J=17.6 Hz, 1H), 2.07-1.97 (m, 1H), 1.90 (s, 3H), 1.80 (p, J=6.7 Hz, 2H), 1.61 (p, J=7.1 Hz, 2H), 1.51 (p, J=8.0 Hz, 2H).

LC-MS: 786.41 (M+H)⁺.

Tables

TABLE 1

Data collection and refinement statistics.

| | DDB1ΔB-CRBN-dBET6-BRD4BD1 | DDB1ΔB-CRBN-dBET23-BRD4BD1 | DDB1ΔB-CRBN-dBET55-BRD4BD1 D145A |
|---|---|---|---|
| Data collection | | | |
| Space group | P 65 2 2 | P 65 2 2 | P 65 2 2 |
| Cell dimensions | | | |
| a, b, c (Å) | 115.40, 115.40, 588.14 | 115.57, 115.57, 596.32 | 115.204, 115.20, 597.14 |
| α, β, γ (°) | 90, 90, 120 | 90, 90, 120 | 90, 90, 120 |
| Resolution (Å) | 49.7-3.3 | 49.9-3.5 | 99.8-3.9 |
| | (3.4-3.3) | (3.6-3.5) | (4.1-4.0) |
| $R_{merge}$ | 0.0201 (0.6794) | 0.0263 (0.7619) | 0.3213 (2.743) |
| I/σ I | 17.83 (0.96) | 12.73 (0.88) | 8.20 (0.86) |
| Completeness (%) | 99.48 (95.66) | 97.82 (88.45) | 99.95 (99.71) |
| Redundancy | 2.0 (2.0) | 2.0 (2.0) | 17.4 (16.2) |
| Refinement | | | |
| Resolution (Å) | 3.3 | 3.5 | 3.9 |
| No. reflections | 35240 (3287) | 30444 (2658) | 21193 (2038) |
| $R_{work}$ | 0.2167 (0.3428) | 0.2292 (0.3561) | 0.2888 (0.3749) |
| $R_{free}$ | 0.2441 (0.3725) | 0.2506 (0.4034) | 0.3087 (0.3917) |
| No. atoms | | | |
| Protein | 1289 | 10267 | 10256 |
| Ligand/ion | 60 | 63 | 1 |
| Water | 0 | 0 | 0 |
| B-factors | | | |
| Protein | 182.91 | 208.13 | 226.95 |
| Ligand/ion | 143.02 | 208.40 | 131.82 |
| Water | — | — | — |
| R.m.s. deviations | | | |
| Bond lengths (Å) | 0.015 | 0.014 | 0.012 |
| Bond angles (°) | 1.81 | 1.84 | 1.75 |

Each dataset was collected from one crystal.
Values in parentheses are for highest-resolution shell.

TABLE 2

Data collection and refinement statistics.

| | DDB1ΔB-CRBN-dBET57-BRD4BD1 | DDB1ΔB-CRBN-dBET70-BRD4BD1 |
|---|---|---|
| Data collection | | |
| Space group | I 4 2 2 | P 65 2 2 |
| Cell dimensions | | |
| a, b, c (Å) | 313.60, 313.60, 166.09 | 115.779, 115.779, 593.505 |
| α, β, γ (°) | 90, 90, 90 | 90 90 120 |
| Resolution (Å) | 49.4-6.8 | 98.8-4.3 |
| | (7.0-6.8) | (4.4-4.3) |
| $R_{merge}$ | 0.1501 (4.422) | 0.4852 (2.183) |
| I/σI | 18.37 (0.77) | 8.75 (1.66) |
| Completeness (%) | 98.94 (96.59) | 99.98 (100.00) |
| Redundancy | 26.0 (26.5) | 36.9 (36.7) |
| Refinement | | |
| Resolution (Å) | 6.8 | 4.3 |
| No. reflections | 7315 | 17739 |
| $R_{work}$ | 0.3351 | 0.2600 |
| $R_{free}$ | 0.4133 | 0.3148 |
| No. atoms | | |
| Protein | 1267 | 1298 |
| Ligand/ion | 1 | 1 |
| Water | 0 | 0 |
| B-factors | | |
| Protein | 276.28 | 197.19 |
| Ligand/ion | 94.22 | 91.93 |
| Water | — | — |
| R.m.s. deviations | | |
| Bond lengths (Å) | 0.011 | 0.008 |
| Bond angles (°) | 1.43 | 1.13 |

Each dataset was collected from one crystal.
Values in parentheses are for highest-resolution shell.

CITATIONS OF PUBLICATIONS REFERENCED IN THE EXAMPLES

1. Abdulrahman, W., M. Uhring, I. Kolb-Cheynel, J.-M. Garnier, D. Moras, N. Rochel, D. Busso and A. Poterszman (2009). "A set of baculovirus transfer vectors for screening of affinity tags and parallel expression strategies." Analytical Biochemistry 385 (2): 383-385.
2. Afonine, P. V., R. W. Grosse-Kunstleve, N. Echols, J. J. Headd, N. W. Moriarty, M. Mustyakimov, T. C. Terwilliger, A. Urzhumtsev, P. H. Zwart and P. D. Adams (2012).

"Towards automated crystallographic structure refinement with phenix.refine." Acta Crystallographica Section D 68 (4): 352-367.
3. Bricogne G, Blanc E, Brandl M, Flensburg C, Keller P, Paciorek P, Roversi P, Sharff A, Smart O, Vonrhein C and W. T (2011). BUSTER version 2.10.2. Cambridge, United Kingdom, Global Phasing Ltd.
4. Buchdunger, E., C. L. Cioffi, N. Law, D. Stover, S. Ohno-Jones, B. J. Druker and N. B. Lydon (2000). "Abl protein-tyrosine kinase inhibitor ST1571 inhibits in vitro signal transduction mediated by c-kit and platelet-derived growth factor receptors." J Pharmacol Exp Ther 295 (1): 139-145.
5. Chau, N. G., S. Hurwitz, C. M. Mitchell, A. Aserlind, N. Grunfeld, L. Kaplan, P. Hsi, D. E. Bauer, C. S. Lathan, C. Rodriguez-Galindo, R. B. Tishler, R. I. Haddad, S. E. Sallan, J. E. Bradner and C. A. French (2016). "Intensive treatment and survival outcomes in NUT midline carcinoma of the head and neck." Cancer 122 (23): 3632-3640.
6. Chen, V. B., W. B. Arendall, III, J. J. Headd, D. A. Keedy, R. M. Immormino, G. J. Kapral, L. W. Murray, J. S. Richardson and D. C. Richardson (2010). "MolProbity: all-atom structure validation for macromolecular crystallography." Acta Crystallographica Section D 66 (1): 12-21.
7. Douglass, E. F., Jr., C. J. Miller, G. Sparer, H. Shapiro and D. A. Spiegel (2013). "A comprehensive mathematical model for three-body binding equilibria." J Am Chem Soc 135 (16): 6092-6099.
8. Filippakopoulos, P., S. Picaud, M. Mangos, T. Keates, J. P. Lambert, D. Barsyte-LoveJoy, I. Felletar, R. Volkmer, S. Muller, T. Pawson, A. C. Gingras, C. H. Arrowsmith and S. Knapp (2012). "Histone recognition and large-scale structural analysis of the human bromodomain family." Cell 149 (1): 214-231.
9. Filippakopoulos, P., J. Qi, S. Picaud, Y. Shen, W. B. Smith, O. Fedorov, E. M. Morse, T. Keates, T. T. Hickman, I. Felletar, M. Philpott, S. Munro, M. R. McKeown, Y. Wang, A. L. Christie, N. West, M. J. Cameron, B. Schwartz, T. D. Heightman, N. La Thangue, C. A. French, O. Wiest, A. L. Kung, S. Knapp and J. E. Bradner (2010). "Selective inhibition of BET bromodomains." Nature 468 (7327): 1067-1073.
10. Fischer, E. S., K. Bohm, J. R. Lydeard, H. Yang, M. B. Stadler, S. Cavadini, J. Nagel, F. Serluca, V. Acker, G. M. LingaraJu, R. B. Tichkule, M. Schebesta, W. C. Forrester, M. Schirle, U. Hassiepen, J. Ottl, M. Hild, R. E. J. Beckwith, J. W. Harper, J. L. Jenkins and N. H. Thoma (2014). "Structure of the DDB1-CRBN E3 ubiquitin ligase in complex with thalidomide." Nature 512 (7512): 49-53.
11. Kabsch, W. (2010). "XDS." Acta Crystallographica Section D 66 (2): 125-132.
12. Krissinel, E. and K. Henrick (2007). "Inference of macromolecular assemblies from crystalline state." J Mol Biol 372 (3): 774-797.
13. Krissinel, E. and K. Henrick (2007). "Inference of Macromolecular Assemblies from Crystalline State." Journal of Molecular Biology 372 (3): 774-797.
14. Kuriyan, J. and D. Eisenberg (2007). "The origin of protein interactions and allostery in colocalization." Nature 450 (7172): 983-990.
15. Marks, B. D., N. Qadir, H. C. Eliason, M. S. Shekhani, K. Doering and K. W. Vogel (2005). "Multiparameter Analysis of a Screen for Progesterone Receptor Ligands: Comparing Fluorescence Lifetime and Fluorescence Polarization Measurements." ASSAY and Drug Development Technologies 3 (6): 613-622.
16. Matyskiela, M. E., G. Lu, T. Ito, B. Pagarigan, C. C. Lu, K. Miller, W. Fang, N. Y. Wang, D. Nguyen, J. Houston, G. Carmel, T. Tran, M. Riley, L. Nosaka, G. C. Lander, S. Gaidarova, S. Xu, A. L. Ruchelman, H. Handa, J. Carmichael, T. O. Daniel, B. E. Cathers, A. Lopez-Girona and P. P. Chamberlain (2016). "A novel cereblon modulator recruits GSPT1 to the CRL4 (CRBN) ubiquitin ligase." Nature 535 (7611): 252-257.
17. McAlister, G. C., D. P. Nusinow, M. P. Jedrychowski, M. Wuhr, E. L. Huttlin, B. K. Erickson, R. Rad, W. Haas and S. P. Gygi (2014). "MultiNotch MS3 enables accurate, sensitive, and multiplexed detection of differential expression across cancer cell line proteomes." Anal Chem 86 (14): 7150-7158.
18. McCoy, A. J., R. W. Grosse-Kunstleve, P. D. Adams, M. D. Winn, L. C. Storoni and R. J. Read (2007). "Phaser crystallographic software." Journal of Applied Crystallography 40 (4): 658-674.
19. Moriarty, N. W., R. W. Grosse-Kunstleve and P. D. Adams (2009). "Electronic Ligand Builder and Optimization Workbench (eLBOW): a tool for ligand coordinate and restraint generation." Acta Crystallographica Section D 65 (10): 1074-1080.
20. Morin, A., B. Eisenbraun, J. Key, P. C. Sanschagrin, M. A. Timony, M. Ottaviano and P. Sliz (2013). "Collaboration gets the most out of software." Elife 2: e01456.
21. Petzold, G., E. S. Fischer and N. H. Thoma (2016). "Structural basis of lenalidomide-induced CKlalpha degradation by the CRL4 ubiquitin ligase." Nature 532 (7597): 127-130.
22. Petzold, G., E. S. Fischer and N. H. Thoma (2016). "Structural basis of lenalidomide-induced CK1α degradation by the CRL4CRBN ubiquitin ligase." Nature 532 (7597): 127-130.
23. Ritchie, M. E., B. Phipson, D. Wu, Y. Hu, C. W. Law, W. Shi and G. K. Smyth (2015). "Limma powers differential expression analyses for RNA-sequencing and microarray studies." Nucleic Acids Res 43 (7): e47.
24. Sircar, A., S. Chaudhury, K. P. Kilambi, M. Berrondo and J. J. Gray (2010). "A generalized approach to sampling backbone conformations with RosettaDock for CAPRI rounds 13-19." Proteins 78 (15): 3115-3123.
25. Stathis, A., E. Zucca, M. Bekradda, C. Gomez-Roca, J. P. Delord, T. de La Motte Rouge, E. Uro-Coste, F. de Braud, G. Pelosi and C. A. French (2016). "Clinical Response of Carcinomas Harboring the BRD4-NUT Oncoprotein to the Targeted Bromodomain Inhibitor OTX015/MK-8628." Cancer Discov 6 (5): 492-500.
26. Team, R. C. (2013). "R: A language and environment for statistical computing." R Foundation for Statistical Computing, Vienna, Austria.
27. Winn, M. D., C. C. Ballard, K. D. Cowtan, E. J. Dodson, P. Emsley, P. R. Evans, R. M. Keegan, E. B. Krissinel, A. G. W. Leslie, A. McCoy, S. J. McNicholas, G. N. Murshudov, N. S. Pannu, E. A. Potterton, H. R. Powell, R. J. Read, A. Vagin and K. S. Wilson (2011). "Overview of the CCP4 suite and current developments." Acta Crystallographica Section D 67 (4): 235-242.
28. Winter, G. E., D. L. Buckley, J. Paulk, J. M. Roberts, A. Souza, S. Dhe-Paganon and J. E. Bradner (2015). "DRUG DEVELOPMENT. Phthalimide conjugation as a strategy for in vivo target protein degradation." Science 348 (6241): 1376-1381.
29. Zakeri, B., J. O. Fierer, E. Celik, E. C. Chittock, U. Schwarz-Linek, V. T. Moy and M. Howarth (2012).

"Peptide tag forming a rapid covalent bond to a protein, through engineering a bacterial adhesin." Proceedings of the National Academy of Sciences 109 (12): E690-E697.

Zuber, J., J. Shi, E. Wang, A. R. Rappaport, H. Herrmann, E. A. Sison, D. Magoon, J. Qi, K. Blatt, M. Wunderlich, M. J. Taylor, C. Johns, A. Chicas, J. C. Mulloy, S. C. Kogan, P. Brown, P. Valent, J E. Bradner, S. W. Lowe and C. R. Vakoc (2011). "RNAi screen identifies Brd4 as a therapeutic target in acute myeloid leukaemia." Nature 478 (7370): 524-528.

What is claimed is:

1. A compound of Formula (I):

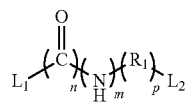

(I) or a pharmaceutically acceptable salt or stereoisomer thereof, wherein n is 0 or 1; m is 0 or 1; p is 0 or 1; and $R_1$ is an ether, an alkyl ether,

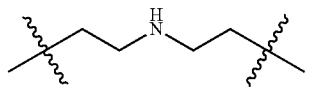 [SMILES: *CCNCC*]

$C_1$ alkyl, $C_2$ alkyl, $C_3$ alkyl, $C_4$ alkyl, $C_5$ alkyl, $C_6$ alkyl, or a 5- or 6-member cyclic group; wherein $L_1$ binds a target protein and at least one other protein and is represented by structure 1-a or 2:

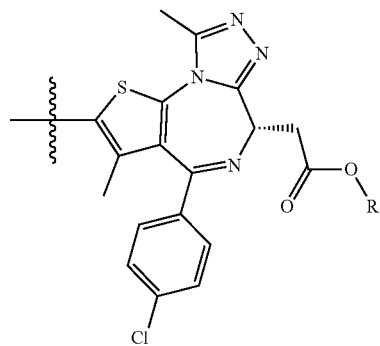

(Structure 1-a), wherein R is methyl or tBu, or

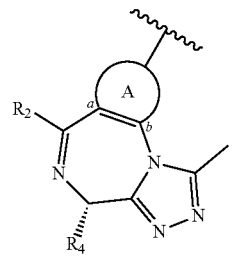

(structure 2), wherein

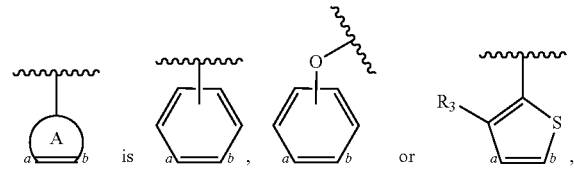

wherein $R_3$ is methyl or

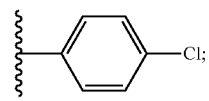 [SMILES: *c1ccc(Cl)cc1]

$R_2$ is

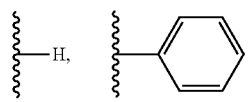 or 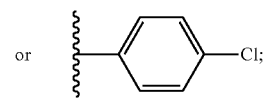

and $R_4$ is

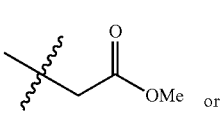 or 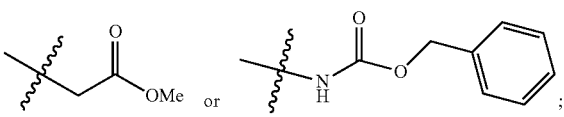 [SMILES: *CC(=O)OC ; *NC(=O)OCc1ccccc1]

and wherein $L_2$ is a moiety that binds an E3 ubiquitin ligase or a component of an E3 ubiquitin ligase which is cereblon, and is represented by any one of structures:

L2-a
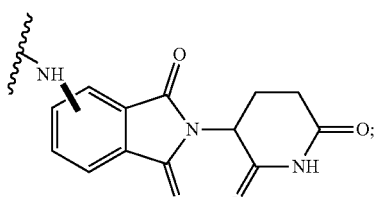

L2-b
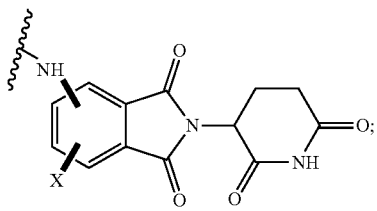

L2-c
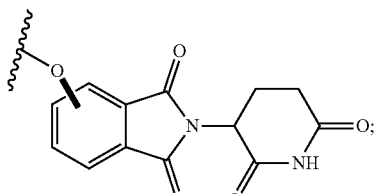

-continued
L2-d
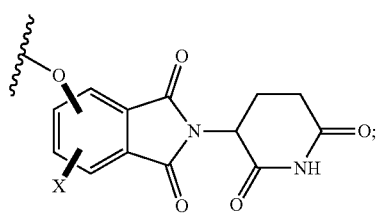
L2-e
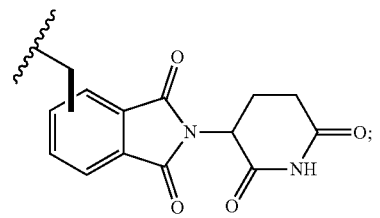
L2-f
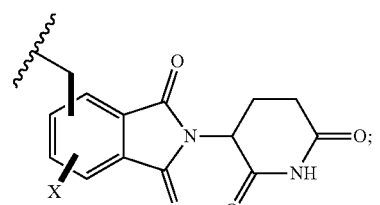
L2-g
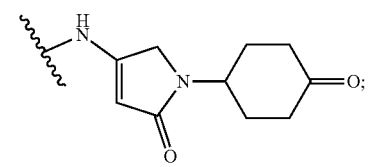
L2-h
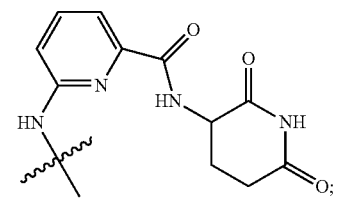
L2-I
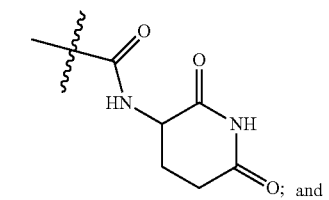
and
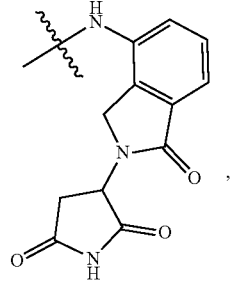
wherein X is F and the compound selectively degrades the target protein relative to the at least one other protein to which L₁ binds.
2. The compound of claim 1, wherein R₁ is a polyethylene glycol chain ranging from 1 to 2 ethylene glycol units.
3. The compound of claim 1, wherein
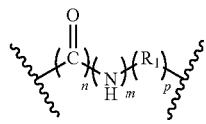
is selected from the structures:
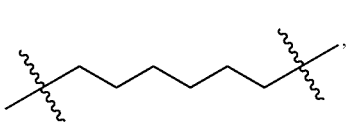 (C1-a)
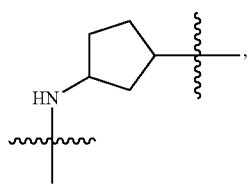 (C1-b)
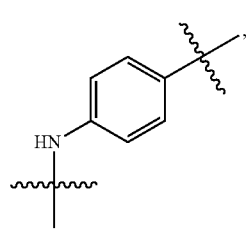 (C1-c)
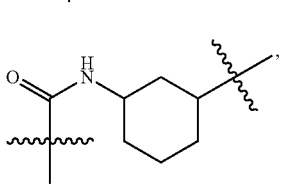 (C1-d)
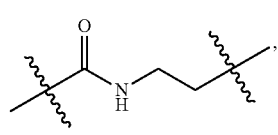 (C1-e)
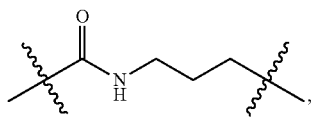 (C1-f)
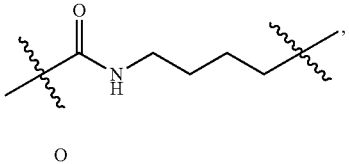 (C1-g)
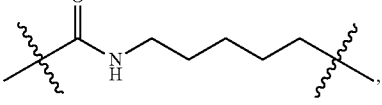 (C1-h)

-continued

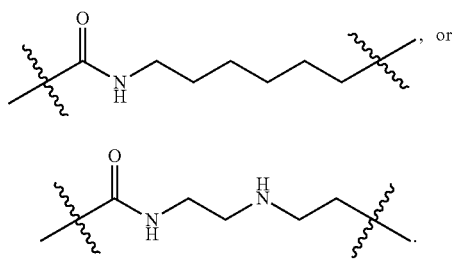

(C1-i), or (C1-J)

4. The compound of claim 1, wherein the at least one other protein to which $L_1$ binds is homologous to the target protein.

5. The compound of claim 4, wherein the target protein to which $L_1$ binds is BRD4 and the at least one other protein to which $L_1$ binds is a bromo extra-terminal domain (BET) protein, wherein
the targeting ligand $L_1$ binds the target protein with greater affinity than the at least one other BET protein,
the targeting ligand $L_1$ binds the target protein with lesser affinity than the at least one other BET protein, or
the targeting ligand L1 binds the target protein with substantially equal affinity than the at least one other BET protein.

6. The compound of claim 5, wherein $L_1$ also binds BRD2 and BRD3.

7. The compound of claim 6, wherein $L_1$ is

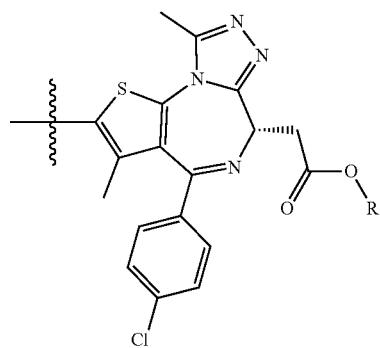

(Structure 1-a) and the target protein is BRD4.

8. The compound of claim 1, wherein $L_1$ is selected from the structures:

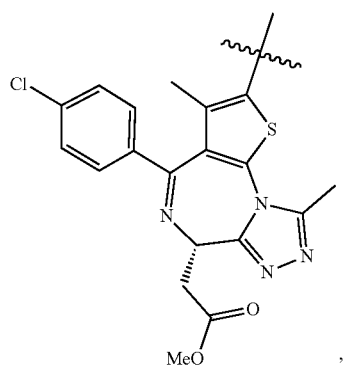

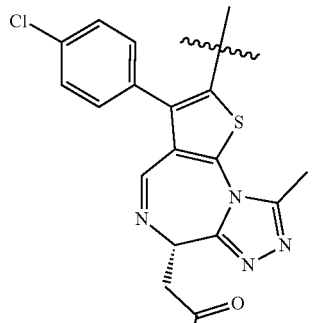

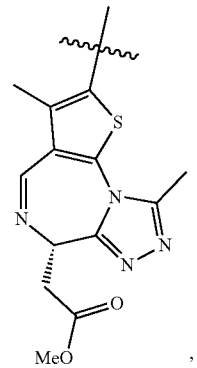

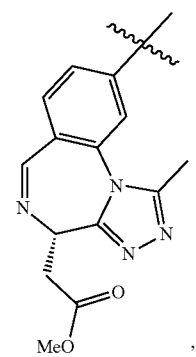

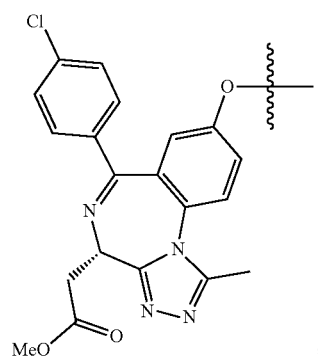

, and

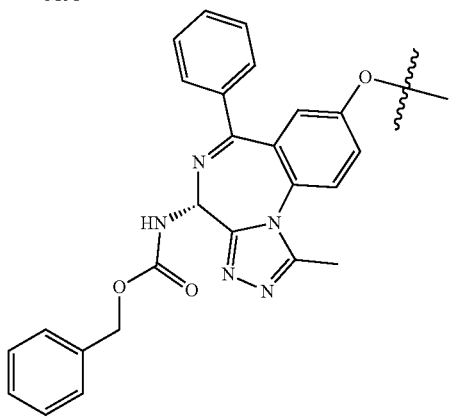

9. A compound, which is represented by any one of the following structures:

113                                    114
ZXH-3-26
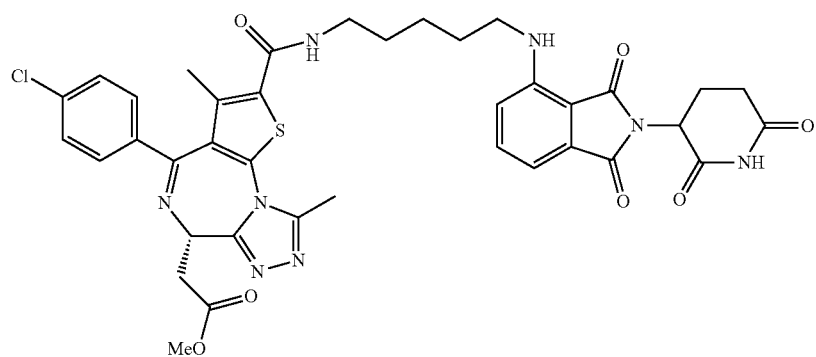
ZXH-2-147                              ZXH-2-184
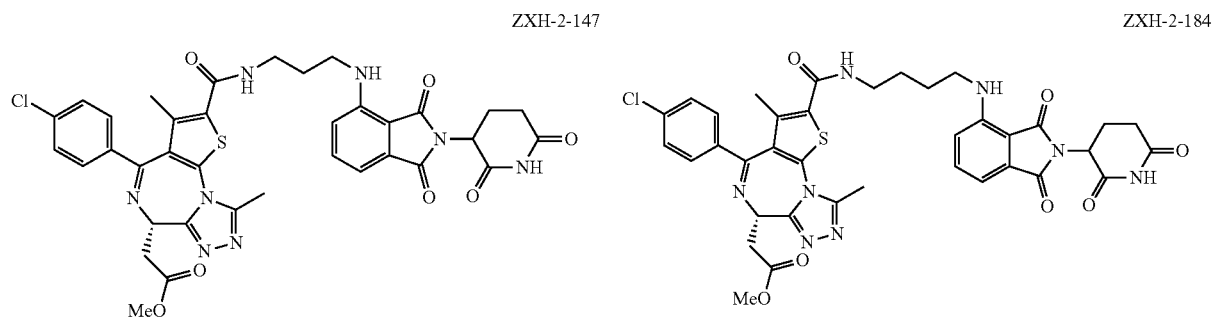
ZXH-3-82
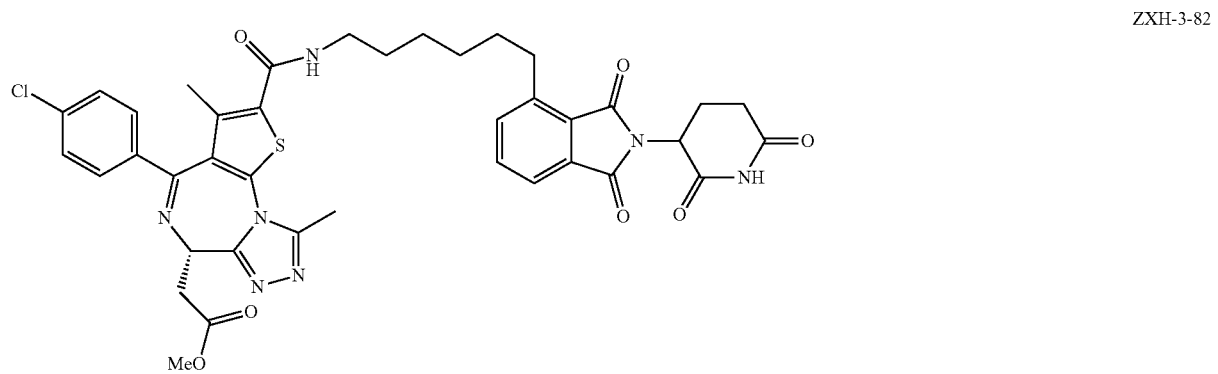
ZXH-3-028
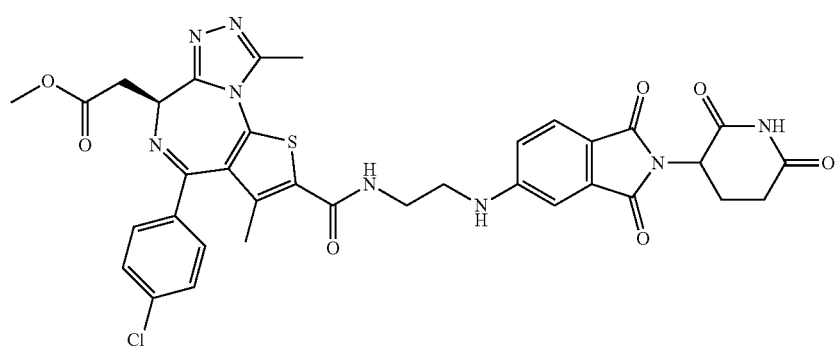

ZXH-3-195
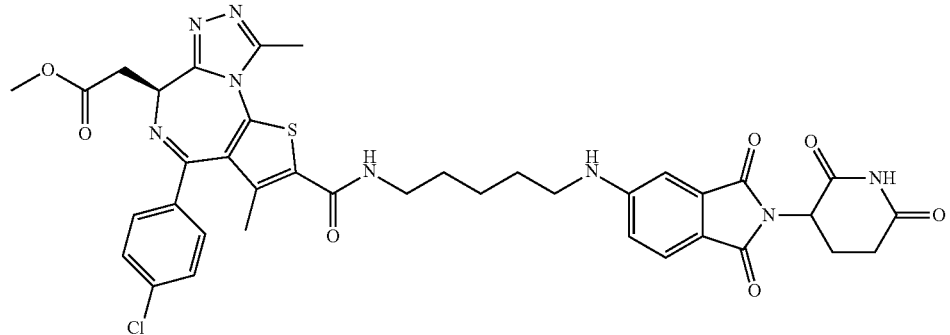
ZXH-3-142
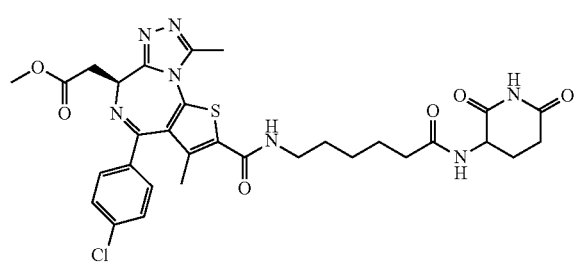
ZXH-3-052
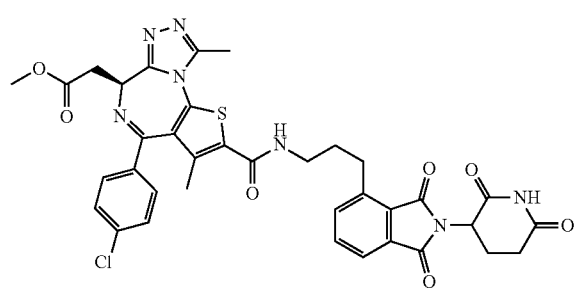
BJG-02-119
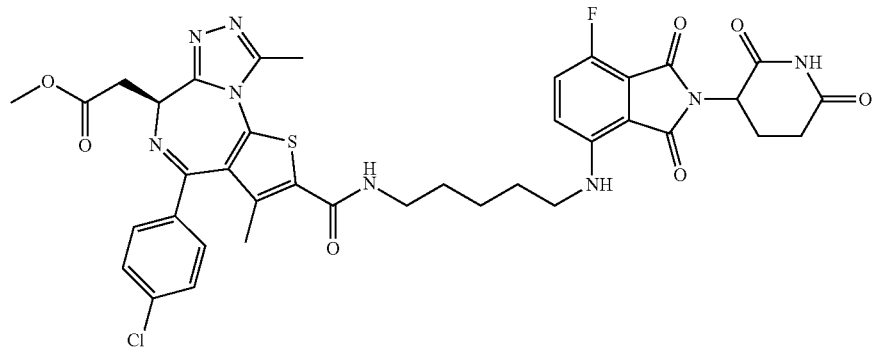
BJG-02-030
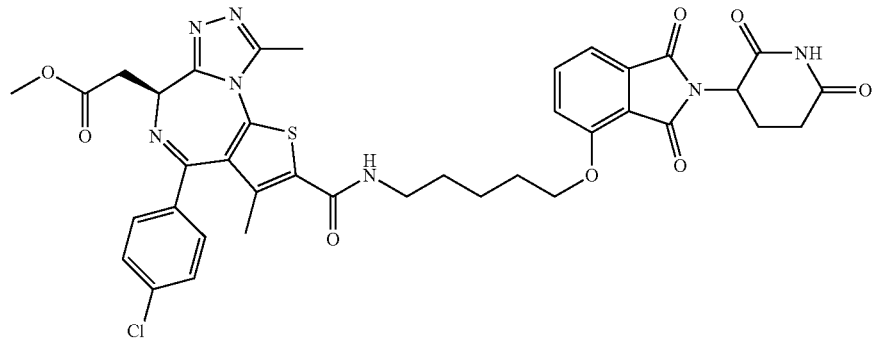

-continued
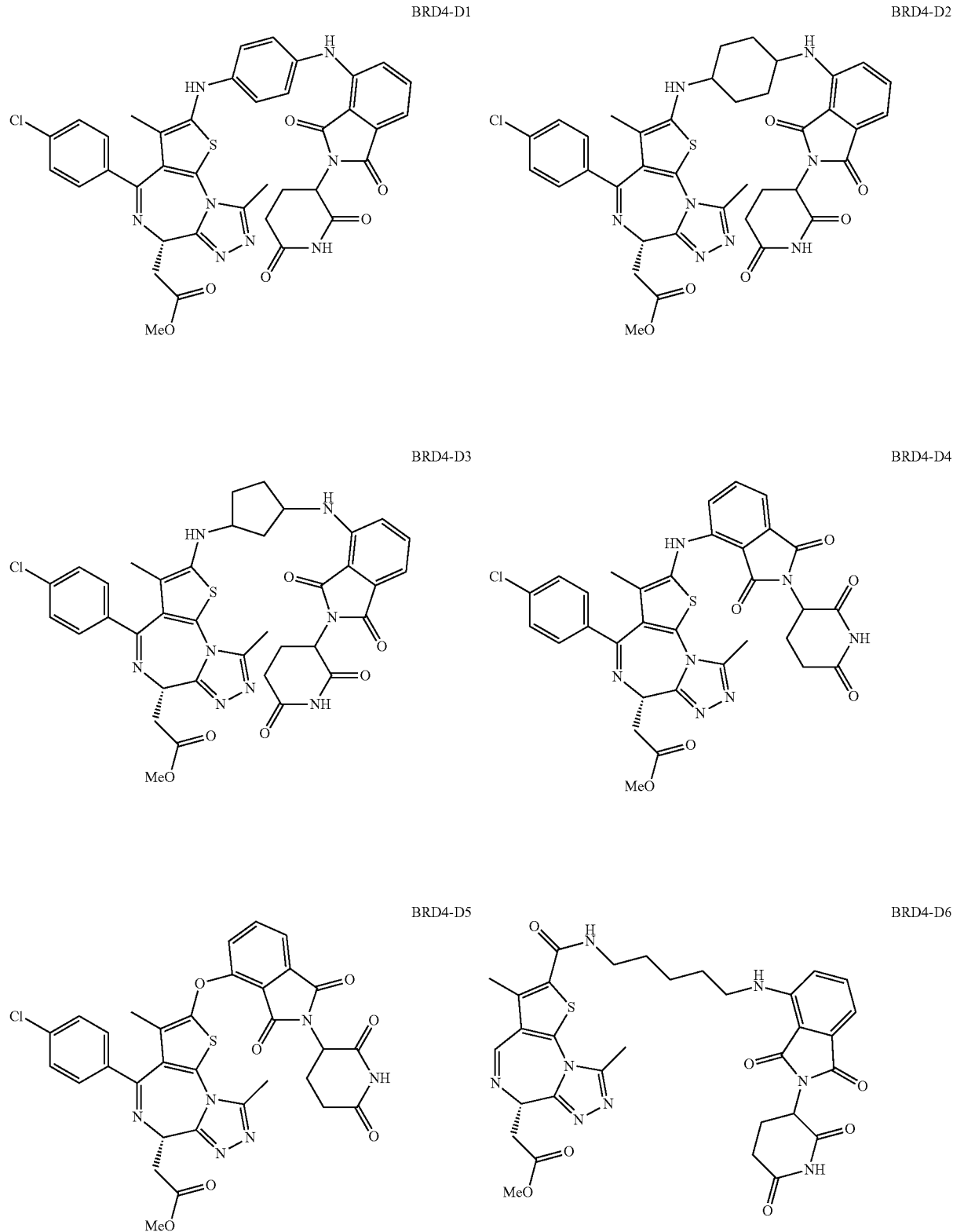

-continued
BRD4-D7
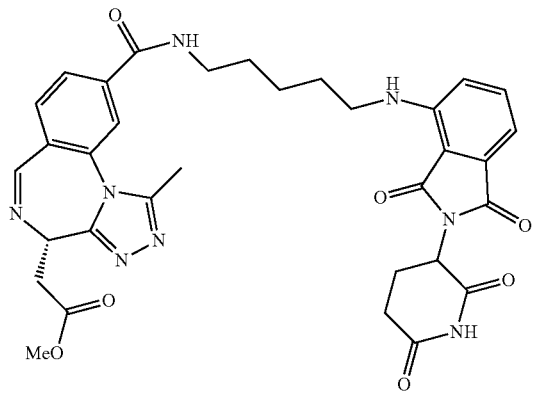
BRD4-D8
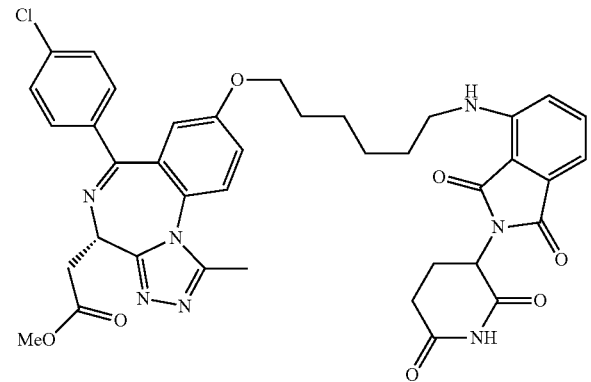
BRD4-D9
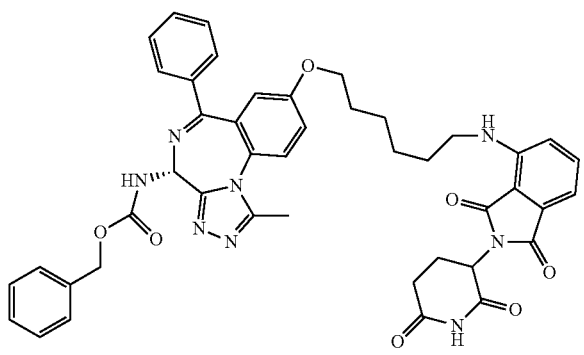
BRD4-D10
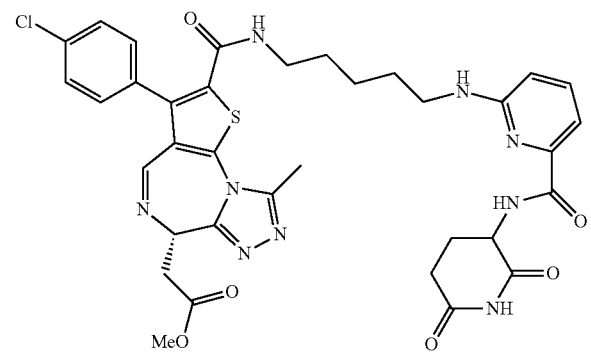
BRD4-D11
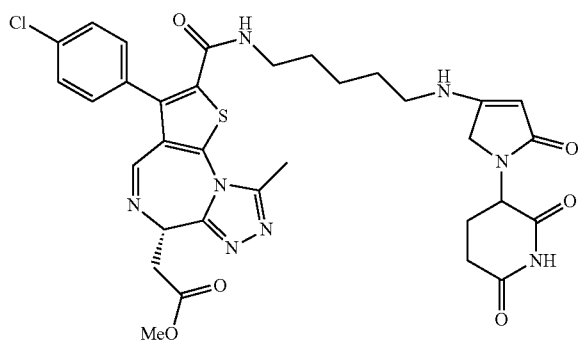
BRD4-D12
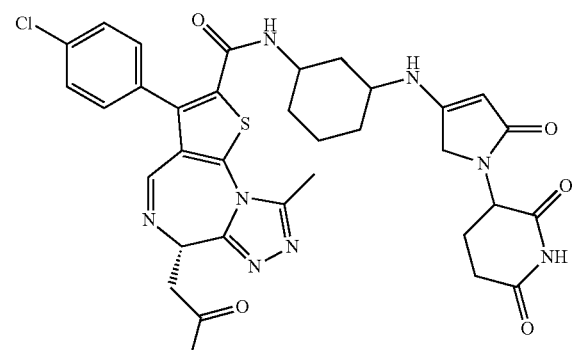
BRD4-D13
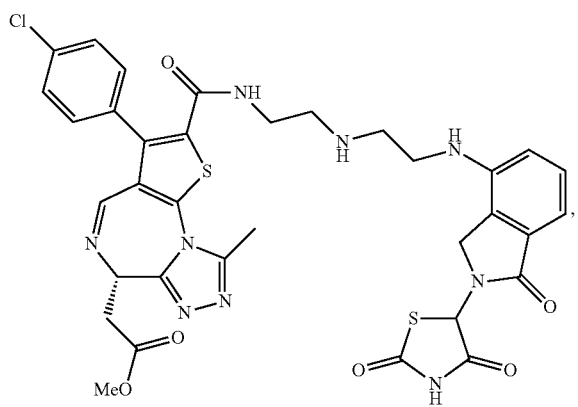

or a pharmaceutically acceptable salt and stereoisomer thereof.

10. A pharmaceutical composition, comprising a therapeutically effective amount of the compound or pharmaceutically acceptable salt or stereoisomer of claim 1 or claim 9, and a pharmaceutically acceptable carrier.

11. A method of treating a disease or disorder mediated by dysfunctional or dysregulated proteins activities comprising administering to a subject in the need thereof the compound or pharmaceutically acceptable salt or stereoisomer of claim 1 or claim 9.

12. The method of claim 11, wherein the subject has cancer.

13. The method of claim 12, wherein the subject has a NUT midline carcinoma.

14. A method of selectively degrading a target protein that is a member of a family of homologous proteins, the method comprising contacting a cell with the compound or pharmaceutically acceptable salt or stereoisomer of claim 1 or claim 9 for a period of time sufficient to result in selective degradation of the target protein.

15. The method of claim 14, wherein the cell is a human cell or a mouse cell.

16. The method of claim 14, wherein the cell is HEK293, HEK293T, MM.1S, MOLM-13, MV4:11, or a THP-1 cell.

* * * * *

UNITED STATES PATENT AND TRADEMARK OFFICE
CERTIFICATE OF CORRECTION

PATENT NO. : 11,505,560 B2  
APPLICATION NO. : 16/755502  
DATED : November 22, 2022  
INVENTOR(S) : Nowak et al.

Page 1 of 2

It is certified that error appears in the above-identified patent and that said Letters Patent is hereby corrected as shown below:

In the Claims

In Column 109, Lines 30-35:
Delete the following structure:

"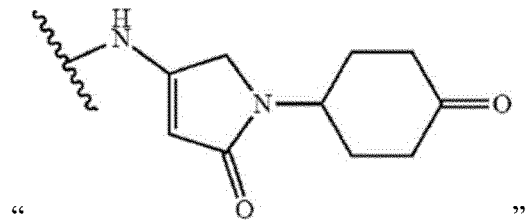"

Replace with the following structure:

--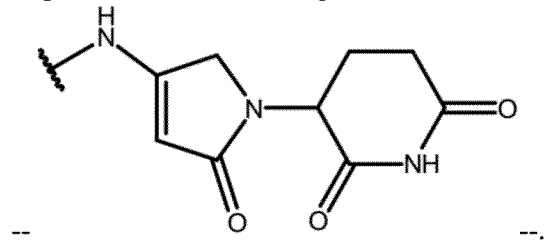--.

In Column 109, Lines 52-63:

Signed and Sealed this  
Twenty-first Day of February, 2023

Katherine Kelly Vidal  
*Director of the United States Patent and Trademark Office*

CERTIFICATE OF CORRECTION (continued)
U.S. Pat. No. 11,505,560 B2

Delete the following structure:

"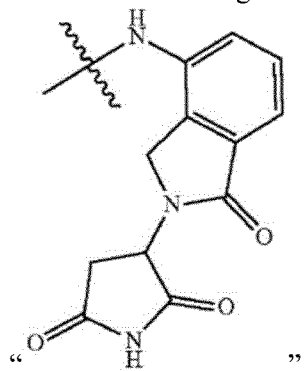"

Replace with the following structure:

--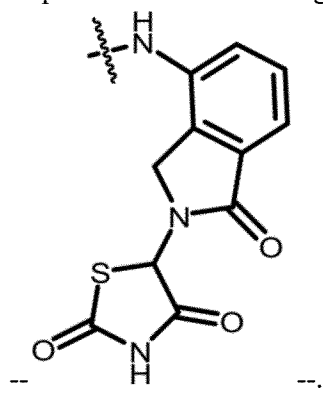--.